US007910554B2

(12) United States Patent
McKerracher

(10) Patent No.: US 7,910,554 B2
(45) Date of Patent: *Mar. 22, 2011

(54) TREATMENT OF MACULAR DEGENERATION WITH ADP-RIBOSYL TRANSFERASE FUSION PROTEIN THERAPEUTIC COMPOSITIONS

(75) Inventor: Lisa McKerracher, Hallandale Beach, FL (US)

(73) Assignee: Bioaxone Therapeutique Inc., Montréal (CA)

(*) Notice: Subject to any disclaimer, the term of this patent is extended or adjusted under 35 U.S.C. 154(b) by 0 days.

This patent is subject to a terminal disclaimer.

(21) Appl. No.: 12/219,179

(22) Filed: Oct. 14, 2008

(65) Prior Publication Data

US 2009/0053190 A1 Feb. 26, 2009

Related U.S. Application Data

(60) Division of application No. 10/902,959, filed on Aug. 2, 2004, now Pat. No. 7,442,686, which is a continuation-in-part of application No. 10/118,079, filed on Apr. 9, 2002, now Pat. No. 6,855,688.

(60) Provisional application No. 60/506,162, filed on Sep. 29, 2003.

(30) Foreign Application Priority Data

Apr. 12, 2001 (CA) .................................... 2342970
Nov. 13, 2001 (CA) .................................... 2362004
Jan. 15, 2002 (CA) .................................... 2367636

(51) Int. Cl.
*A61K 38/00* (2006.01)
*A61K 38/43* (2006.01)
*C12N 15/00* (2006.01)

(52) U.S. Cl. .................... 514/20.8; 514/13.3; 424/94.5; 435/69.7

(58) Field of Classification Search ....................... None
See application file for complete search history.

(56) References Cited

U.S. PATENT DOCUMENTS 5,393,739 A 2/1995 Bentz et al.
5,652,122 A 7/1997 Frankel et al.
5,670,617 A 9/1997 Frankel et al.
5,674,980 A 10/1997 Frankel et al.
5,747,641 A 5/1998 Frankel et al.
5,804,604 A 9/1998 Frankel et al.
5,945,290 A 8/1999 Cowsert
6,855,688 B2 2/2005 McKerracher
7,442,686 B2 10/2008 Lasko et al.
2002/0032148 A1 3/2002 Uehata et al.
2002/0077283 A1 6/2002 Sessa
2003/0103957 A1 6/2003 McKerracher et al.
2005/0059595 A1 3/2005 Lasko et al.
2007/0270340 A1 11/2007 McKerracher et al.
2008/0269120 A1 10/2008 McKerracher et al.

FOREIGN PATENT DOCUMENTS

CA 2300878 2/1999
CA 2304981 5/1999
CA 2301157 A1 11/1999
CA 2342970 AA 10/2002
EP 585168 A2 3/1994
EP 1177796 A 6/2002
WO WO 97/23236 7/1997
WO WO 99/23113 5/1999
WO 2005030248 4/2005
WO WO 2005/030248 4/2005
WO 2008022182 2/2008

OTHER PUBLICATIONS

Wilde et al., Toxicon, 2001, vol. 39(11):1647-1660.*
Borras, Exp. Eye Res., 2003, vol. 76, pp. 643-652.*
Kimura et al., Adv. Drug Deliv. Rev., 2001, vol. 52(1):79-91.*
ISR, Jul. 3, 2008.
ISR, Mar. 21, 2003.
Adler et al., Cell death in age-related macular degeneration, Molecular Vision, 1999: 5:31, pp. 31-36.
Curcio et al., Photoreceptor loss in age-related macular degeneration, Invest Ophthalmol Vis Sci, Jun. 1996;37 (7):1236-49 (Abstract only).
Fan et al., Differential regulation of A beta42-induced neuronal Clq synthesis and microglial activation,J. Neuroinflammation, 2005, 2:1, pp. 1-13.
Hahn et al., Disruption of ceruloplasmin and hephaestin in mice causes retinal iron overload and . . . , PNAS, 2004, 101:38, pp. 13850-13855.
Klaver et al., Genetic Association of Apolipoprotein E with Age-Related Macular Degeneration, Am. J. Hum Genet.. 1998, 63:200-206.
Medeiros et al., Preservation of Ganglion Cell Layer Neurons in Age-related Macular Degeneration, Investigative Ophthalmology & Visual Science, 2001, 42:3, pp. 795-803.
Vander et al., Growth rate of subretinal newvascularization in age-related macumar degeneration, Ophthalmology, 1989, 96(9), pp. 1422-1426. (Abstract only).
E.I. Pecheur et al., Peptides and Membrane Fusion: Towards an Understanding of the Molecular Mechanism of Protein-Induced Fusion, J. Membrane Biol., 1999, 167:1-17, Springer-Verlag New York Inc.
Kazmierczak et al., Rho GTPase activity modulates Pseudomonas aeruginosa internalization by epithelial cells, Cellular Microbiology, 2001, 3:2, pp. 85-98.
Sauzeau et al., Human urotensin II-induced contraction and arterial smooth muscle cell proliferation are mediated by RhoA and Rho-kinase, Circulation Research, 2001, 88:11, pp. 1102-1104.

(Continued)

*Primary Examiner* — Elizabeth C. Kemmerer
*Assistant Examiner* — Xiaozhen Xie
(74) *Attorney, Agent, or Firm* — Ogilvy Renault LLP

(57) ABSTRACT

The Rho family of GTPases regulates axon growth and regeneration. Inactivation of Rho with C3, a toxin from *Clostridium botulinum*, can stimulate regeneration and sprouting of injured axons. The present invention provides novel chimeric C3-like Rho antagonists. These new antagonists are a significant improvement over C3 compounds because they are 3-4 orders of magnitude more potent to stimulate axon growth on inhibitory substrates than recombinant C3. The invention further provides methods of treating a disease of the eye by administering the compounds of the invention.

20 Claims, 13 Drawing Sheets

OTHER PUBLICATIONS

Winton et al., A novel group of permeable Rho antagonists that promote axon regeneration on growth inhibitory substances. Society for Neuroscience Abstracts, 2001, 27:2, p. 2120. (Abstract only).
Lehmann et al., Inactivation of Rho signaling pathway promotes CNS axon regeneration, Journal of Neuroscience, 1999, 19:17, pp. 7537-7547.
Folkman et al., J. Biol. Chem. (1992), pp. 10931-10934, vol. 267.
Rojas et al., Nature Biotechnology (1998), pp. 370-375, vol. 16.
Vives et al., The Journal of Biological Chemistry (1997), pp. 16010-16017, vol. 272, No. 25.
Wender et al., Proc. Nat'l Acad. Sci, USA (2000), pp. 13003-13008, vol. 97, No. 24.
Derossi et al., The Journal of Biological Chemistry (1996), pp. 18188-18193, vol. 271, No. 30.
Wilde et al., The Journal of Biological Chemistry (2001), pp. 9537-9542, vol. 276, No. 12.
Aullo et al., The EMBO Journal (1993), pp. 921-931, vol. 12, No. 3.
Bloch-Gallego et al., The Journal of Cell Biological Chemistry (1993), pp. 485-492, vol. 120, No. 2.
Derossi et al., The Journal of Biological Chemistry (1994), pp. 10444-10450, vol. 269, No. 14.
Verschuren, H. et al., European Journal of Cell Biology (1997), pp. 182-187, vol. 73.
Imamura, F. et al., Jpn. J. Cancer Res. (2000), pp. 811-816, vol. 91.
Yoshioka, K. et al., FEBS Letters (1995), pp. 25-28, vol. 372.
Van Aelst, L. et al., Genes & Development (1997), pp. 2295-2322, vol. 11.
Wilde, C. et al., Journal of Biological Chemistry (2000), pp. 16478-16483, vol. 275, No. 22.
Aktories, K. et al., Trends in Cell Biology (1995), pp. 441-443, vol. 5.
Kemp, C.M. et al., Investigative Ophthalmology & Visual Science (1994), pp. 3154-3162, vol. 35. No. 8.
Dalke, C. et al., Experimental Eye Research (2005), pp. 503-512, vol. 81.
Winton, M.J. et al., Journal of Biological Chemistry (2002), pp. 32820-32829, Vo. 277.
Hirai, F. et al., Biochemical and Biophysical Research Communications (2007), vol. 356: 279-285.
Singh, A.T., et al., Endocrinology (2005), vol. 146(5): 2171-2175.
Majumder et al., J. Biol. Chem (1998), vol. 273(17), pp. 10099-10106.
Van Golen, et al., Neoplasia (2000), vol. 2(5), pp. 418-425.
Park, et al., Circ. Res. (2002), vol. 91(2), pp. 143-50.
Cleverly, et al., Oncogene (2000), vol. 19, pp. 13-20.
Moorman, et al., J. Immunol. (1996). vol. 156(1), pp. 4146-4153.
Burger, J. Neuro-Oncology (1995), vol. 24, pp. 3-7.
Classification of Cancer—Grading, Staging, www.oncologychannel.com—published Sep. 1, 2002.
Fawell, et al., PNAS USA (1994), vol. 91, pp. 664-668.
Busca, et al., Mol. Biol. Chem. (1998), vol. 9, pp. 1367-1378.
Forget, et al., Clin. Exp. Metastasis (2002), vol. 19(1), pp. 9-15.
Pecheur, E. I., et al., J. Membrane Biol. (1999), 167:1-17, Springer-Verlag New York Inc.
Adler, et al., Molecular Vision (1999), 5:31, pp. 31-36.
Curcio, et al., Invest. Ophthalmol. Vis. Sci. (1996), Jun.; 37(7): 1236-49 (Abstract only).
Fan, et al., J. Neuroinflammation (2005), 2:1, pp. 1-13.
Hahn, et al., PNAS (2004), 101:38, pp. 13850-13855.
Klaver, et al., AM. J. Hum. Genet. (1998), 63:200-206.
Medeiros, et al., Investigative Ophthalmology & Visual Science (2001), 42:3, pp. 795-803.
Vander, et al., Ophthalmology (1989), 96(9), pp. 1422-1426 (Abstract only).
Ciardella, et al., Ophthalmol. Clin. N. Am. 15 (2002), pp. 453-458.
Borras T. et al., Experimental Eye Research 76 (2003), pp. 643-652.
Wenzel A., et al., Progress in Retinal and Eye Research 24 (2005), pp. 275-306.
Bertrand J., et al., Neurobiology of Disease (2006), doi:10.1016/j.nbd.2006.08.008.
Bertrand J., et al., The Journal of Neuroscience (2005), 25(5), pp. 1113-1121.
Flannery J. G., et al., ILAR Journal (1999), vol. 40(2).

* cited by examiner

TREATMENT OF MACULAR DEGENERATION WITH ADP-RIBOSYL TRANSFERASE FUSION PROTEIN THERAPEUTIC COMPOSITIONS

CROSS-REFERENCE TO RELATED APPLICATIONS

This application is a divisional of application Ser. No. 10/902,959 filed Aug. 2, 2004, now U.S. Pat. No. 7,442,686, which is a continuation in part of application Ser. No. 10/118,079 filed Apr. 9, 2002, now U.S. Pat. No. 6,855,688, which claims priority on Canadian Applications 2,342,970; 2,362,004; and 2,367,636 filed Apr. 12, 2001, Nov. 13, 2001 and Jan. 15, 2002, and claims priority of U.S. Provisional Application 60/506,162 filed Sep. 29, 2003 respectively. The entire content of these applications is hereby incorporated by reference.

FIELD OF THE INVENTION

The present invention relates to conjugate or fusion type proteins (polypeptides) comprising, for example, C3-like fusion proteins, C3 chimeric fusion proteins. Although, in the following, fusion-type proteins of the present invention will be particularly discussed in relation to the use to facilitate regeneration of axons and neuroprotection, it is to be understood that the fusion proteins may be exploited in other contexts.

The present invention in particular pertains to the field of mammalian nervous system repair (e.g. repair of a central nervous system (CNS) lesion site or a peripheral nervous system (PNS) lesion site), axon regeneration and axon sprouting, neurite growth and protection from neurodegeneration and ischemic damage.

The retina is part of the CNS, and this invention pertains to repair of the retina, neuroprotection in the retina, retinal trauma and disease, and ischemic damage to the retina. The invention in particular pertains to compositions and methods useful to treat diseases of the eye such as macular degeneration (such as wet macular degeneration and dry macular degeneration), Stargardt's Disease, Retinitis Pigmentosa, diabetic retinopathy, hypertensive retinopathy, occlusive retinopathy, and other diseases of the retina, including diseases comprising abnormal blood and fluid flow.

BACKGROUND OF THE INVENTION

Traumatic injury of the spinal cord results in permanent functional impairment. Most of the deficits associated with spinal cord injury result from the loss of axons that are damaged in the central nervous system (CNS). Similarly, other diseases of the CNS are associated with axonal loss and retraction, such as stroke, human immunodeficiency virus (HIV) dementia, prion diseases, Parkinson's disease, Alzheimer's disease, multiple sclerosis and glaucoma. Common to all of these diseases is the loss of axonal connections with their targets, and cell death. The ability to stimulate growth of axons from the affected or diseased neuronal population would improve recovery of lost neurological functions, and protection from cell death can limit the extent of damage. For example, following a white matter stroke, axons are damaged and lost, even though the neuronal cell bodies are alive, and stroke in grey matter kills many neurons and non-neuronal (glial) cells. Treatments that are effective in eliciting sprouting from injured axons are equally effective in treating some types of stroke (Boston life sciences, Sep. 6, 2000 Press release). Neuroprotective agents often tested as potential compounds that can limit damage after stroke. Compounds which show both growth-promotion and neuroprotection are especially good candidates for treatment of stroke and neurodegenerative diseases. Similarly, although the following discussion will generally relate to delivery of Rho antagonists, etc. to a traumatically damaged nervous system, this invention may also be applied to damage from unknown causes, such as during stroke, multiple sclerosis, HIV dementia, Parkinson's disease, Alzheimer's disease, prion diseases or other diseases of the CNS were axons are damaged in the CNS environment. Also, Rho is an important target for treatment of cancer and metastasis (Clark et al (2000) Nature 406:532-535), and hypertension (Uehata et al. (1997) Nature 389:990) and RhoA is reported to have a cardioprotective role (Lee et al. FASEB J. 15:1886-1884). Therefore, the new C3-like proteins are expected to be useful for a variety of diseases were inhibition of Rho activity is required.

It has been proposed to use various Rho antagonists as agents to stimulate regeneration of (cut) axons, i.e. nerve lesions; please see, for example, Canadian Patent application nos. 2,304,981 (McKerracher et al) and 2,300,878 (Strittmatter). These patent application documents propose the use of known Rho antagonists such as for example C3, chimeric C3 proteins, etc. (see blow) as well as substances selected from among known trans-4-amino (alkyl)-1-pyridylcarbamoylcyclohexane compounds (also see below) or Rho kinase inhibitors for use in the regeneration of axons. C3 inactivates Rho by ADP-ribosylation and is fairly non-toxic to cells (Dillon and Feig (1995) Methods in Enzymology: Small GTPases and their regulators Part. B.256:174-184).

While the following discussion will generally relate or be directed at repair in the CNS, the techniques described herein may be extended to use in many other diseases including, but not restricted to, cancer, metastasis, hypertension, cardiac disease, stroke, diabetic neuropathy, and neurodegenerative disorders such as stroke, Alzheimer's disease, Parkinson's disease, amyotrophic lateral sclerosis (ALS). Treatment with Rho antagonists would be used to enhance the rate of axon growth of peripheral nerves and thereby be effective for repair of peripheral nerves after surgery, for example after reattaching severed limbs. Also, treatment with our fusion compounds (proteins) is expected to be effective for the treatment of various peripheral neuropathies because of their axon growth promoting effects.

As mentioned above, traumatic injury of the spinal cord results in permanent functional impairment. Axon regeneration does not occur in the adult mammalian CNS because substrate-bound growth inhibitory proteins block axon growth. Many compounds, such as trophic factors, enhance neuronal differentiation and stimulate axon growth in tissue culture. However, most factors that enhance growth and differentiation are not able to promote axon regenerative growth on inhibitory substrates. To demonstrate that a compound known to stimulate axon growth in tissue culture most accurately reflects the potential for therapeutic use in axon regeneration in the CNS, it is important for the cell culture studies to include the demonstration that a compound can permit axon growth on growth inhibitory substrates. An example of trophic and differentiation factors that stimulate growth on permissive substrates in tissue culture, are neurotrophins such as nerve growth factor (NGF) and brain-derived growth factor. NGF, however, does not promote growth on inhibitory substrates (Lehmann, et al. (1999) 19: 7537-7547) and it has not been effective in promoting axon regeneration in vivo. Brain derived neurotrophic factor (BDNF) is not effective to promote regeneration in vivo either (Mansour-Robaey, et al.

J. Neurosci. (1994) 91: 1632-1636). BDNF does not promote neurite growth on growth inhibitory substrates (Lehmann et al supra).

Targeting intracellular signaling mechanisms involving Rho and the Rho kinase for promoting axon regeneration has been proposed (see, for example, the above-mentioned Canadian Patent application nos. 2,304,981 (McKerracher et al)). For demonstration that inactivation of Rho promotes axon regeneration on growth inhibitory substrates, recombinant C3, a protein that inactivates Rho by ADP ribosylation of the effector domain was used. While such a C3 protein can effectively promote regeneration, it has been noted that such a C3 protein does not easily penetrate into cells, and high doses must therefore be applied for it to be effective. The high dose of recombinant C3 needed to promote functional recovery presents a practical constraint or limitation on the use of C3 in vivo to promote regeneration (Lehmann, et al. (1999) J. Neurosci. 19: 7537-7547; Morii, N and Narumiya, S. (1995) Methods in Enzymology, Vol 256 part B, pg. 196-206. In tissue culture studies, it has, for example, been determined that the minimum amount of C3 that can be used to induce growth on inhibitory substrates is 25 ug/ml (Lehmann, et al. (1999) J. Neurosci. 19: 7537-7547; Morii, N and Narumiya, S. (1995) Methods in Enzymology, Vol 256 part B, pg. 196-206. If the cells are not triturated, even this dose is ineffective. It has been estimated, for example, that at least 40 µg of C3 per 20 g mouse needs to be applied to injured mouse spinal cord or rat optic nerve (McKerracher, Canadian patent application No.: 2,325,842). Calculating doses that would be required to treat an adult human on an equivalent dose per weight scale up used for rat and mice experiments, it would be necessary to apply 120 mg/kg of C3 (i.e. alone) to the injured human spinal cord. The large amount of recombinant C3 protein needed creates significant problems for manufacturing, due to the large-scale protein purification and cost. It also limits the dose ranging that can be tested because of the large amount of protein needed for minimal effective doses.

Another related limitation with respect to the use of C3 to promote repair in the injured CNS is that it does not easily penetrate the plasma membrane of living cells. In tissue culture studies when C3 is applied to test biological effects it has been microinjected directly into the cell (Ridley and Hall (1992) Cell 70: 389-399), or applied by trituration of the cells to break the plasma membrane (Lehmann, et al. (1999) J. Neurosci. 19: 7537-7547, Jin and Strittmatter (1997) J. Neurosci. 17: 6256-6263). In the case of axon injury in vivo, the C3 protein is likely able to enter the cell because injured axons readily take up substances from their environment. However, C3-like proteins of the present invention are likely to act also on surrounding undamaged neurons and help them make new connections as well, thus facilitating recovery. After incomplete SCI, there is plasticity of motor systems attributed to cortical and subcortical levels, including spinal cord circuitry (Raineteau, O., and Schwab, M. E. (2001) Nat Rev Neurosci 2: 263-73). This plasticity may be attributed to axonal or dendritic sprouting of collaterals and synaptic strengthening or weakening. Additionally, it has been shown that sparing of a few ventrolateral fibers may translate into significant differences in locomotor performance since these fibers are important in the initiation and control of locomotor pattern through spinal central pattern generators (Brustein, E., and Rossignol, S. (1998) J Neurophysiol 80: 1245-67). It is well documented that reorganization of spared collateral cortical spinal fibers occurs after spinal cord injury and this contributes to functional recovery (Weidner et al, 2001 Proc. Natl. Acad. Sci. 98: 3513-3518). The process of reorganization and sprouting of spared fibers would be enhanced by treatment with C3-like proteins able to enter non-injured neurons. This would enhances spontaneous plasticity of axons and dendritic remodeling known to help functional recovery.

Other methods of delivery of C3 in vitro have been to make a recombinant protein that can be taken up by a receptor-mediated mechanism (Boquet, P. et al. (1995) Meth. Enzymol. 256: 297-306). The disadvantage of this method is that the cells needing treatment must express the necessary receptor. Lastly, addition of a C2II binding protein to the tissue culture medium, along with a C21N-C3 fusion toxin allows uptake of C3 by receptor-mediated endocytosis (Barthe et al. (1998) Infection and Immunity 66:1364). The disadvantage of this system is that much of the C3 in the cell will be restrained within a membrane compartment. More importantly, two different proteins must be added separately for transport to occur (Wahl et al. 2000. J. Cell Biol. 149:263), which make this system difficult to apply to for treatment of disease in vivo.

Retinitis pigmentosa is a retinal degeneration disease which manifests as night blindness, progressive loss of visual field and peripheral vision, eventually leading to total blindness; opthalmoscopic changes can consist in dark mosaic-like retinal pigmentation, attenuation of the retinal vessels, waxy pallor of the optic disc, and in the advanced forms, macular degeneration. In some cases there can be a lack of pigmentation. This disease is hereditary and the degeneration of retinal photoreceptor cell proceeds with increasingly narrower retinochoroidal blood vessel and circulatory disorders.

Diabetic retinopathy, a leading cause of blindness in type 1 and type 2 diabetics, is a complication of diabetes which produces damage to the blood vessels inside the retina. Diabetic retinopathy can have four stages: (1) mild nonproliferative retinopathy, wherein microaneurysms in the retina's blood vessels occur; (2) moderate nonproliferative retinopathy, wherein some blood vessels feeding the retina become blocked; (3) severe nonproliferative retinopathy, wherein many blood vessels to the retina are blocked, depriving several areas of the retina with their blood supply; and (4) proliferative retinopathy, wherein new, abnormal, thin-and fragile-walled blood vessels grow to supply blood to the retina, but which new blood vessels may leak blood to produce severe vision loss and blindness. Hemorrhages can occur more than once, often during sleep. Fluid can also leak into the center of the macula at any stage of diabetic retinopathy and cause macular edema and blurred vision. About 40 to 45 percent of Americans diagnosed with diabetes have some stage of diabetic retinopathy, and about half of the people with proliferative retinopathy also have macular edema.

Stargardt's disease, or fundus flavimaculatus, is a hereditary macular degenerative disorder. Most patients with the condition present in the teenage years with complaints of bilaterally reduced vision. Vision is commonly in the 20/40 range upon first presentation, but frequently falls to the 20/100 level within 4 or 5 years. Vision usually progressively, but gradually, declines beyond 20 years of age, perhaps to the 20/200 level, or worse. Patients will invariably have characteristic flecks in the retina, and these may occupy the macular area in early life. With progression of the disorder, the macula shows atrophy that is not unlike some cases of age related macular degeneration. However, this degree of atrophy is often present in the teens or early 20's. Some patients will develop choroidal neovascular membranes or vessels beneath the retina which may leak fluid or bleed. There is no known treatment that will delay or halt the progression of the disease. Hypertensive retinopathy involves damage to the retina caused by high blood pressure which produces narrowing of and excess fluid oozing from blood vessels in the retina. The degree of retina damage (retinopathy) is graded on a scale of I to IV, wherein Group I comprises minimal narrowing of the retinal arteries; Group II comprises narrowing of the retinal arteries in conjunction with regions of focal narrowing and arteriovenous nicking; Group III comprises abnormalities seen in groups I and II, as well as retinal hemorrhages, hard exudation, and cotton-wool spots; and Group IV hypertensive retinopathy comprises abnormalities encountered in groups I through III, as well as swelling of the optic nerve head and macula, which can cause decreased vision. Control of high blood pressure (hypertension) is the only treatment for hypertensive retinopathy. Some patients with grade IV hypertensive retinopathy will have permanent damage to the optic nerve or macula. Hypertensive choroidopathy frequently accompanies hypertensive retinopathy when the changes of group IV, and sometimes those of group III, are present. In the acute phase, yellow spots are visible at the level of the retinal pigment epithelium. They are known as Elshnig Nodules. They are hyperfluorescent on fluorescein angiography and appear to occur secondary to fibrinoid necrosis within the choriocapillaris, leading to damage to the overlying retinal pigment epithelium. In severe cases, the intense leakage of plasma from these foci contributes to serous retinal detachment. Over a period of weeks, these spots become pigmented or depigmented. When the spots occur in a linear fashion, they are referred to as Siegrist's streaks.

Occlusive retinopathy or retinal vein occlusion, second only to diabetic retinopathy as a cause of visual loss due to retinal vascular disease, comprises both branch and central retinal vein occlusion in which a portion of the circulation that drains the retina of blood becomes blocked, causing back-up pressure in the capillaries, dilated blood vessels, hemorrhages, swelling (edema), and leakage of fluid and other constituents of blood in the distribution of the vein. An occlusion of the central retinal vein involves the entire retina. Complete vein blockage leads to intense hemorrhages and edema, and involved capillaries can cease to function and close off (ischemia or capillary non-perfusion). Complications of branch retinal vein occlusion include macular edema, macular ischemia (non-perfusion) and neovacularization (growth of new abnormal blood vessels). When the distribution of the vein involves the macula, bleeding and exudation or leakage occurs there to produce macular edema with blurred vision and loss of portions of the field of vision. Scar tissue may form on the surface of the retina to produce a macular pucker or an epiretinal membrane may result in distorted vision (metamorphopsia). With significant closure of capillaries, abnormal vessels may grow (neovascularization) and bleed into the overlying ocular cavity in the posterior part of the eye (vitreous hemorrhage) leading to retinal detachment. Central retinal vein occlusion is closure of the retinal vein located at the optic nerve; the occlusion can be non-ischemic or ischemic. Some central retinal vein occlusions are associated with a significant obstruction of capillaries or non-perfusion, and predisposition to neovascularization that occurs in front of the eye on the iris (rubeosis irides). These eyes may develop a very high pressure (neovascular glaucoma) due to obstruction of the fluid outflow channels, and experience severe vision loss, pain, and loss of the eye. Central retinal vein occlusion can produce macular edema and neovascularization in the back of the eye leading to vitreous hemorrhage and retinal detachment.

The Rho family GTPases regulates axon growth and regeneration. Inactivation of Rho with *Clostridium botulinum* C3 exotransferase (hereinafter simply referred to as C3) can stimulate regeneration and sprouting of injured axons; C3 is a toxin purified from *Clostridium botulinum* (see Saito et al., 1995, FEBS Lett 371:105-109; Wilde et al 2000. J. Biol. Chem. 275:16478). Compounds of the C3 family from *Clostridium botulinum* inactivate Rho by ADP-ribosylation and thus act as antagonists of Rho effect or function (Rho antagonists).

Degeneration of components of the retina can lead to partial or total blindness. Macular degeneration is a degeneration of the macular region of the retina in the eye. Degeneration of the macula causes a decrease in acute vision and can lead to eventual loss of acute vision. The wet form of macular degeneration is related to abnormal growth of blood vessels in the retina that can leak blood and can cause damage to photoreceptor cells.

Age-related macular degeneration (AMD) is a collection of clinically recognizable ocular findings that can lead to blindness.

Macular degeneration is a group of diseases that affect the central retina, or macula. There are two basic types of macular degeneration: "wet" and "dry". In wet macular degeneration, there is an abnormal growth of new blood vessels. These new blood vessels break and leak fluid, causing damage to the central retina. This form of macular degeneration is often associated with aging. Approximately 90% of macular degeneration cases are dry macular degeneration. Vision loss can result from the accumulation of deposits in the retina called drusen, and from the death of photoreceptor cells. This process can lead to thinning and drying of the retina.

The findings of AMD include the presence of drusen, retinal pigment epithelial disturbance, including pigment clumping and/or dropout, retinal pigment epithelial detachment, geographic atrophy, subretinal neovascularization and disciform scar. Age-related macular degeneration is a leading cause of presently incurable blindness, particularly in persons over 55 years of age. Approximately one in four persons age 65 or over have signs of age-related maculopathy, and about 7% of persons age 75 or over have advanced macular degeneration with vision loss.

Drusen are opthalmoscopically visible, yellow-white hyaline excrescences or nodules of Bruch's membrane. Bruch's membrane lies beneath the retina and the adjacent retina pigment epithelium layer. Fat accumulates in Bruch's membrane with age and may contribute to the formation of drusen.

Drusen can occur in two forms. One form comprises hard, small (less than about 60 micrometers in diameter) drusen which do not increase with age and which do not predispose to macular degeneration. Another form comprises soft, large (more than about 63 micrometers in diameter) drusen which enlarge and become confluent with age. The soft, large drusen may predispose to macular degeneration, and are commonly seen in eyes of people with advanced macular degeneration in at least their other eye.

Drusen may be metabolic waste products from various layers of the retina such as from the retina, retina pigment epithelium, and choriocapillaris. Drusen may be yellow, white, gray, refractile, and/or pink. Drusen may be small, medium or large in size. Drusen may be regular or irregular, or symmetrical or asymmetrical in shape. A patient who has drusen and who suffers complications in one eye may suffer no complications in the other eye. Complications may comprise one or more conditions selected from the group consisting of retina pigment epithelium atrophy, choroid neovascularization, retina detachment serous, and retina detachment hemorrhagic. Drusen may affect contrast sensitivity, and may reduce the eye's ability to see adequately to allow a person to read in dim light or to see sufficient detail to permit a person to drive an automobile safely at night.

Not all these manifestations are needed for AMD to be considered present, and drusen alone are not directly associated with vision loss. The amount of opthalmoscopically or photographically identifiable drusen increases with age. Most definitions of AMD include drusen as a requisite because of the association of drusen with vision-threatening lesions of AMD such as geographic atrophy, retinal pigment epithelial detachment and subretinal neovascularization.

While the exact causes of macular degeneration are not known, contributing factors have been identified. The collective result of the contributing factors is a disturbance between the photoreceptor cells and the tissues under the retina which nourish the photoreceptor cells, including the retinal pigment epithelium, which directly underlies and supports the photoreceptor cells, and the choroid, which underlies and nourishes the retinal pigment epithelium.

The retina and macula may be subjected to oxidative damage by oxidants such as free-radicals and singlet oxygen, $^1O_2$. The macula contains polyunsaturated fatty acids and is exposed to light, including in the visible and near ultraviolet light spectrum high-energy blue light, which can photosensitize the conversion of triplet oxygen to singlet oxygen, an oxidizing agent capable of damaging the polyunsaturated fatty acids, DNA, proteins, lipids, and carbohydrates in the macula. Reaction products resulting from oxidative interactions between components of the retina and oxidizing agents may accumulate in the retinal pigment epithelium and contribute to macular degeneration. Certain antioxidant nutrients may reduce the risk of developing macular degeneration by reducing the formation of radicals and reactive oxygen by decomposition of hydrogen peroxide without generating radicals, by quenching active singlet oxygen, and by trapping and quenching radicals before they reach a cellular target.

Another factor which may be involved in the pathology of macular degeneration comprises an elevated serum concentration of low density cholesterol lipoprotein (LDL). Low density lipoprotein cholesterol can be oxidized by an oxidizing agent to form oxidized LDL, which is found in atherosclerotic plaques. These oxidized products may accumulate as deposits in healthy retinal pigment epithelium and cause necrosis or death of functioning tissue. LDL cholesterol may also form atherosclerotic plaques in the blood vessels of the retinal and subretinal tissue, inducing hypoxia in the tissue, resulting in neovascularization. Postmenopausal women given unopposed estrogen replacement therapy can have a reduced risk of neovascular age-related macular degeneration. Estrogen can increase the amount of high density lipoprotein cholesterol (HDL) in the blood, which may produce changes in the transport and metabolism of lipid-soluble antioxidants, and limit the accumulation of oxidized LDL cholesterol in the retinal and subretinal tissues and blood vessels.

A contributing and indicating factor of advanced macular degeneration is neovascularization of the choroid tissue underlying the photoreceptor cells in the macula. Healthy mature ocular vasculature is normally quiescent and exists in a state of homeostasis in which a balance is maintained between positive and negative mediators of angiogenisis in development of new vasculature. Macular degeneration, particularly in its advanced stages, is characterized by the pathological growth of new blood vessels in the choroid underlying the macula. Angiogenic blood vessels in the subretinal choroid can leak vision obscuring fluids, leading to blindness.

Angiogenisis in the choroid can be induced by the presence of cytokine growth factors such as basic fibroblast growth factor (bFGF). Hypoxia of retinal cells may induce the expression of such growth factors, wherein the hypoxia may be induced by cellular debris or drusen accumulated in the retinal pigment epithelium, by oxidative damage of retinal and subretinal tissue, or by deposits of oxidized LDL cholesterol.

Existing retinal and subretinal vascular endothelial cells can be activated by interaction of the cytokine growth factors, such as bFGF, with tyrosine kinase mediated receptors of the endothelial cells. The activated endothelial cells can increase in cellular proliferation and express several molecular agents, such as the integrin $\alpha_v\beta_3$, adhesion molecules, and proteolytic enzymes, which enable newly developed endothelial cells to extend through the surrounding tissue. The newly extended endothelial cells can form into vascular cords and eventually differentiate into mature blood vessels.

Currently, no treatment has been shown to be of benefit to the majority of people who have AMD. There is no therapy that can significantly slow the degenerative progression of macular degeneration, or which can inhibit or substantially reduce the rate of subretinal neovascularization and proliferation of neovascular tissue in the choroids under the macula of the eye. Most experimental forms of treatment address the wet form of AMD, and target specifically neovascularization. Laser photocoagulation of the subretinal neovascular membranes that occur in 10-15% of affected patients can benefit individuals with macular degeneration who develop acute, extrafoveal choroidal neovascularization. For dry AMD, high daily doses of antioxidants such vitamin C (500 mg), vitamin E (400 IU), beta carotene (15 mg), as well as zinc oxide (80 mg; high concentrations of zinc occur in ocular tissues, particularly the retina, pigment epithelium and choroid) may modestly reduce risk of progression of those who have intermediate-sized drusen, large drusen, or non-central geographic atrophy, or advanced macular degeneration in one eye.

A number of techniques have been disclosed for administration of drugs to the eye including the posterior region of the eye. For example, U.S. Pat. No. 5,707,643 relates to a biodegradable scleral plug that is inserted through an incision in the sclera into the vitreous body. For administration of a drug to the eye, the plug releases a drug into the vitreous body for treating the retina by diffusion through the vitreous body.

Another technique for administration of a drug to the eye is disclosed in U.S. Pat. No. 5,443,505 which discloses implants which can be placed in the suprachoroidal space over an avascular region of the eye such as the pars plana or a surgically induced avascular region. Another embodiment involves forming a partial thickness scleral flap over an avascular region, inserting an implant onto the remaining scleral bed, optionally with holes therein, and suturing closed the flap. The drug can diffuse into the vitreous region and the intraocular structure.

Another delivery approach for administration of a drug to the eye is direct injection. For the posterior segment of the eye, an intravitreal injection has been used to deliver drugs into the vitreous body. In this regard, U.S. Pat. No. 5,632,984 relates to a treatment of macular degeneration with various drugs by intraocular injection. For administration of a drug to the eye, drugs are preferably injected as microcapsules. Intraocular injection into the posterior segment of the eye can allow diffusion of the drug throughout the vitreous, the entire retina, the choroid and the opposing sclera. Additionally, U.S. Pat. No. 5,770,589 relates to treating macular degeneration by intravitreally injecting an anti-inflammatory into the vitreous humor for administration of a drug to the eye. Injections can be administered through the pars plana in order to minimize the damage to the eye while drug is delivered to the posterior segment.

Another delivery approach is by surgical procedure. For example, U.S. Pat. No. 5,767,079 relates to the treatment of ophthalmic disorders including macular holes and macular degeneration, by administration of TGF-β for example by placing an effective amount of the growth factor on the ophthalmic abnormality. In treating the macula and retina, for administration of a drug to the eye a surgical procedure involving a core vitrectomy or a complete pars plana vitrectomy is performed before the growth factor can be directly applied, presumably by administration to the sclera on the anterior segment of the eye at an avascular region or by administration to the sclera behind the retina via a surgical procedure through the vitreous body, retina, and choroids, a dramatic, highly invasive, technique usually suitable only where partial vision loss has already occurred or was imminently threatened.

Another delivery approach for administration of a drug to the eye is by use of a device and a cannula. For example, U.S. Pat. No. 5,273,530 relates to the intraretinal delivery and withdrawal of samples and a device therefor. Unlike direct intraocular injection techniques, the method disclosed in this patent avoids the use of a pars plana incision and instead uses an insertion path around the exterior of the orbit. The device, having a curved handle and a tip with collar, allows a cannula to be inserted through the posterior sclera and down into the subretinal space without passing through the vitreous body. The collar is stated to regulate the penetration to the desired depth. The device is taught to be adjustable to any part of the eye including the scleral area, the choroidal area, the subretinal area, the retinal area and the vitreous area.

Another delivery approach for administration of a drug to the eye is by intrascleral injection. For example, U.S. Pat. No. 6,397,849, the contents of which is hereby incorporated by reference in its entirety, discloses a method of intrascleral injection which comprises injecting into the scleral layer of an eye through a location on the exterior surface of the sclera which overlies retinal tissue an effective amount of a therapeutic or diagnostic material. Depending on the injection conditions, the material can form a depot within the scleral layer and diffuse into the underlying tissue layers such as the choroid and/or retina, and/or the material can be propelled through the scleral layer and into the underlying layers. Because the sclera moves with the entire eye including the retina, the site of deposit on the sclera remains constant relative to a point on the underlying retina, even as the eye moves within the eye socket to permit site specific delivery by depositing material into the sclera at a site overlying the macula, thereby allowing material to be delivered to the macula and surrounding tissues. The injection procedure employs a cannula or needle as well as needle-less particle/solution techniques. In a preferred embodiment, a cannula is inserted into the sclera in a rotational direction relative to the eye and not orthogonal to the surface of the sclera.

Another delivery approach for administration of a drug to the eye is disclosed in U.S. Pat. No. 6,299,895 which discloses a method for delivering a biologically active molecule to the eye comprising implanting a capsule periocularly in the sub-Tenon's space, the capsule comprising a core containing a cellular source of the biologically active molecule and a surrounding biocompatible jacket, the jacket permitting diffusion of the biologically active molecule into the eye, wherein the dosage of the biologically active molecule delivered is between 50 pg and 1000 ng per eye per patient per day. The biologically active molecule can be an anti-angiogenic factor, and a second biologically active molecule or peptide can be co-delivered from the capsule to the eye. The method is disclosed to be useful treating ophthalmic disorders including macular degeneration.

Other delivery approaches for administration of a drug to the eye which can be useful with compositions of the current invention are well known in the art. For example, U.S. Pat. No. 5,399,163 discloses a method of providing a jet injection by pressurizing a fluid injectant; U.S. Pat. No. 5,383,851 discloses a needleless injection device; U.S. Pat. No. 5,312,335 discloses a needleless injection system; U.S. Pat. No. 5,064,413 discloses an injection device; U.S. Pat. No. 4,941,880 discloses an ampule for non-invasive injecting of a medication; U.S. Pat. No. 4,790,824 discloses a non-invasive hypodermic injection device; U.S. Pat. No. 4,596,556 discloses a pressure-operated hypodermic injection apparatus; U.S. Pat. No. 4,487,603 discloses an implantable micro-infusion pump for dispensing medication at a controlled rate; U.S. Pat. No. 4,486,194 discloses a therapeutic device for administering medicants through the skin; U.S. Pat. No. 4,447,233 discloses a medication infusion pump for delivering medication at a precise infusion rate; U.S. Pat. No. 4,447,224 discloses a variable flow implantable infusion apparatus for continuous drug delivery; U.S. Pat. No. 4,439,196 discloses an osmotic drug delivery system having multi-chamber compartments; and U.S. Pat. No. 4,475,196 discloses an osmotic drug delivery system.

SUMMARY OF THE INVENTION

In accordance with the present invention a conjugate, drug delivery construct, or fusion protein comprising a therapeutically active agent is provided whereby the active agent may be delivered across a cell wall membrane, the conjugate or fusion protein comprising at least a transport subdomain(s) or moiety(ies) (i.e., transport agent region) in addition to an active agent moiety(ies) (i.e., active agent region). More particularly, as discussed herein, in accordance with the present invention a conjugate or fusion protein is provided wherein the therapeutically active agent is one able to facilitate (for facilitating) axon (or dendrite, or neurite) growth (e.g. regeneration) i.e. a conjugate or fusion protein in the form of a conjugate Rho antagonist.

The present invention also relates to methods of treatment of macular degeneration associated with subretinal neovascularization and a proliferation of neovascular tissue in the eye of a mammalian host, and to methods of inhibiting or substantially reducing the rate of subretinal neovascularization and proliferation of neovascular tissue in the eye associated with macular degeneration, and to pharmaceutical compositions useful therein comprising a cell-permeable fusion protein conjugate comprising a polypeptidic cell-membrane transport agent and an active agent having ADP-ribosyl transferase activity.

The present invention also relates to methods of treatment of diabetic neuropathy, especially diabetic retinopathy associated with the damage to blood vessels caused by diabetes that leads to macular edema in the eye and neovascularization, and to methods of inhibiting or substantially reducing the rate of blood vessel damage and proliferation of neovascular tissue in the eye associated with diabetic neuropathy, and to pharmaceutical compositions useful therein comprising a cell-permeable fusion protein conjugate comprising a polypeptidic cell-membrane transport agent and an active agent having ADP-ribosyl transferase activity The present invention also relates to methods of treatment of retinitis pigmentosa, a group of hereditary retinal diseases associated with degeneration of the retinal neurons, specifically the photoreceptor neurons (also referred to as photoreceptor cells), and to method of inhibiting photoreceptor degeneration in the eye of a mammalian host, and to methods of inhibiting or substantially reducing the rate of photoreceptor cell death associated with retinitis pigmentosa, and to pharmaceutical compositions useful therein comprising a cell-permeable fusion protein conjugate comprising a polypeptidic cell-membrane transport agent and an active agent having ADP-ribosyl transferase activity.

The present invention in particular relates to a means of intracellular delivery of C3 protein (e.g. C3 itself or other active analogues such as C3-like transferases—see below) or other Rho antagonists to repair damage in the nervous system, to prevent ischemic cell death, and to treat various disease where the inactivation of Rho is required. The means of delivery may take the form of chimeric (i.e. conjugate) C3-like Rho antagonists. These conjugate antagonists provide a significant improvement over C3 compounds (alone) because they are 3 to 4 orders of magnitude more potent with respect to the stimulation of axon growth on inhibitory substrates than recombinant C3 alone. Examples of these Rho antagonists have been made as recombinant proteins created to facilitate penetration of the cell membrane (i.e. to enhance cell uptake of the antagonists), improve dose-response when applied to neurons to stimulate growth on growth inhibitory substrates, and to inactivate Rho. Examples of these conjugate Rho antagonists are described below in relation to the designations C3APL, C3APLT, C3APS, C3-TL, C3-TS, C3Basic1, C3Basic2 and C3Basic3.

The present invention in accordance with an aspect thereof provides a drug delivery construct or conjugate [e.g. able to (for) suppress(ing) the inhibition of neuronal axon growth at a central nervous system (CNS) lesion site or a peripheral nervous system (PNS) lesion site] comprising at least one transport agent region and an active agent region not naturally associated with the active agent region, wherein the transport agent region is able to facilitate (i.e. facilitates) the uptake of the active agent region into a mammalian (i.e. human or animal) tissue or cell, and wherein the active agent region is an active therapeutic agent region able (i.e. has the capacity or capability) to facilitate axon growth for example on growth inhibitory substrates (e.g. regeneration), either in vivo (in a mammal (e.g., human or animal)) or in vitro (in cell culture), including a derivative or homologue thereof (i.e. pharmaceutically acceptable chemical equivalents thereof—pharmaceutically acceptable derivative or homologue).

In accordance with the present invention the active agent region may be an ADP-ribosyl transferase C3 region. In accordance with the present invention the ADP-ribosyl transferase C3 may be selected from the group consisting of ADP-ribosyl transferase (e.g., ADP-ribosyl transferase C3) derived from *Clostridium botulinum* and a recombinant ADP-ribosyl transferase (e.g., recombinant ADP-ribosyl transferase C3) that includes the entire C3 coding region, or only a part (fragment) of the C3 coding region that retains the ADP-ribosyl transferase activity, or analogues (derivatives) of C3 that retains the ADP-ribosyl transferase activity, or enough of the C3 coding region to be able to effectively inactivate Rho. The active agent could also be selected from other known ADP-ribosyl transferases that act on Rho (Wilde et al. 2000 J. Biol. Chem. 275-16478-16483; Wilde et al 2001. J. Biol. Chem. 276:9537-9542).

In accordance with another aspect the present invention provides a drug conjugate consisting of a transport polypeptide moiety (e.g. rich in basic amino acids e.g. arginine, lysine, histidine, asparagine, glutamine) covalently linked to an active cargo moiety (e.g. by a peptide bond or a labile bond (i.e. a bond readily cleavable or subject to chemical change in the interior target cell environment)) wherein the transport polypeptide moiety is able to or has the capability to facilitate(s) the uptake of the active cargo moiety into a mammalian (e.g. human or animal) tissue or cell (for example, a transport subdomain of HIV (e.g., HIV-1) Tat protein, a homeoprotein transport sequence (referred also as a transport homeoprotein) (e.g. the homeodomain of antennapedia), a Histidine tag (ranging in length from 4 to 30 histidine repeat) or a variation derivative or homologue thereof, (i.e. pharmaceutically acceptable chemical equivalents thereof)) [by a receptor independent process] and wherein the active cargo moiety is an active therapeutic moiety able (i.e. has the capacity or capability) to facilitate (i.e. for facilitating) axon growth (e.g. regeneration, budding) or neuroprotection (prevention of cell death) either in vivo (in a mammal (e.g., human or animal)) or in vitro (in cell culture).

In accordance with the present invention the transport polypeptide moiety may be selected from the group consisting of SEQ ID NO.: 48, a transport subdomain of HIV (e.g., HIV-1) Tat protein such as for example SEQ ID NO.: 46, SEQ ID NO.:47, a homeodomain of antennapedia, such as for example SEQ ID NO.: 44, SEQ ID NO.: 45, a Histidine tag and a functional derivative and analogues thereof (e.g., SEQ ID NO.: 21, SEQ ID NO.: 26, SEQ ID NO.: 31) [i.e. by the addition of polyamine, or any random sequence enriched in basic amino acids]—[i.e. pharmaceutically acceptable chemical equivalents thereof] and wherein the active cargo moiety is selected from the group consisting of C3 protein able (i.e. has the capacity or capability) to facilitate (i.e. for facilitating) axon growth (e.g. regeneration, budding) or neuroprotection (prevention of cell death) either in vivo (in a mammal (e.g., human or animal)) or in vitro (in cell culture).

In accordance with the present invention the C3 protein may be selected from the group consisting of ADP-ribosyl transferase C3 and ADP-ribosyl transferase C3 analogue. In accordance with the present invention the ADP-ribosyl transferase C3 may be selected from the group consisting of ADP-ribosyl transferase (e.g., ADP-ribosyl transferase C3) derived from *Clostridium botulinum* and a recombinant ADP-ribosyl transferase (e.g., recombinant ADP-ribosyl transferase C3). The ADP-ribosyl transferase may be a protein with a C3-like activity, such as that derived from *Staphylococcus aureus* (Wilde et al 2001. J. Biol. Chem. 276:9537-9542). The ADP-ribosyl transferase may be any other transferase that acts to inactivate RhoA, RhoB and/or RhoC such as those derived from *Clostridium limosum*, and *Bacillus cereus* (Wilde et al 2000. J. Biol. Chem. 275:16478-16483). In accordance with the present invention the transport polypeptide moiety may include an active contiguous amino acid sequence as described herein.

In accordance with an additional aspect the present invention provides a fusion protein (polypeptide) [e.g. able to (for) suppress(ing) the inhibition of neuronal axon growth at a central nervous system (CNS) lesion site or a peripheral nervous system (PNS) lesion site] consisting of a carboxy terminal active cargo moiety and an amino terminal transport moiety, wherein the amino terminal transport moiety is selected from the group consisting of a transport subdomain of HIV (e.g., HIV-1) Tat protein, homeoprotein transport sequence (referred also as a transport homeoprotein) (e.g. the homeodomain of antennapedia), a Histidine tag and a functional derivatives and analogues thereof (i.e. pharmaceutically acceptable chemical equivalents thereof) and wherein the active cargo moiety consists of a C3 protein.

The present invention in particular provides a fusion protein (polypeptide) (e.g. able to (for) suppressing the inhibition of neuronal axon growth at a central nervous system (CNS) lesion site or a peripheral nervous system (PNS) lesion site) consisting of a carboxy terminal active cargo moiety and an amino terminal transport moiety, wherein the amino terminal transport moiety consists of the homeodomain of antennapedia and the active cargo moiety consists of a C3 protein (i.e. as described herein). The present invention also in particular provides a fusion protein (polypeptide) (e.g. able to (for) suppressing the inhibition of neuronal axon growth at a central nervous system (CNS) lesion site or a peripheral nervous system (PNS) lesion site) consisting of a carboxy terminal active cargo moiety and an amino terminal transport moiety, wherein the amino terminal transport moiety consists of a transport subdomain of (e.g., HIV-1) Tat protein and the active cargo moiety consists of a C3 protein (i.e. as described herein).

In accordance with the present invention the C3 protein may be selected from the group consisting of ADP-ribosyl transferase C3 and ADP-ribosyl transferase C3 analogues. In accordance with the present invention the ADP-ribosyl transferase C3 is selected from the group consisting of ADP-ribosyl transferase (e.g., ADP-ribosyl transferase C3) derived from *Clostridium botulinum* and a recombinant ADP-ribosyl transferase (e.g., recombinant ADP-ribosyl transferase C3).

In accordance with an additional aspect the present invention provides a fusion protein (polypeptide) [e.g. able to (for) suppress(ing) the inhibition of neuronal axon growth at a central nervous system (CNS) lesion site or a peripheral nervous system (PNS) lesion site] consisting of an amino terminal active cargo moiety and a carboxy terminal transport moiety, wherein the carboxy terminal transport moiety is selected from the group consisting of a transport subdomain of HIV Tat protein, a homeoprotein transport sequence (referred also as a transport homeoprotein) (e.g. the homeodomain of antennapedia), a Histidine tag and a functional derivatives and analogues thereof (i.e. pharmaceutically acceptable chemical equivalents thereof) and wherein the active cargo moiety consists of a C3 protein.

The present invention in particular provides a fusion protein (polypeptide) (e.g. able to (for) suppressing the inhibition of neuronal axon growth at a central nervous system (CNS) lesion site or a peripheral nervous system (PNS) lesion site) consisting of an amino terminal active cargo moiety and a carboxy terminal transport moiety, wherein the carboxy terminal transport moiety consists of the homeodomain of antennapedia and the active cargo moiety consists of a C3 protein (i.e. as described herein).

The present invention also in particular provides a fusion protein (polypeptide) (e.g. able to (for) suppressing the inhibition of neuronal axon growth at a central nervous system (CNS) lesion site or a peripheral nervous system (PNS) lesion site) consisting of an amino terminal active cargo moiety and a carboxy terminal transport moiety, wherein the carboxy terminal transport moiety consists of a transport subdomain of HIV Tat protein and the active cargo moiety consists of a C3 protein (i.e. as described herein).

In accordance with the present invention the C3 protein may be selected from the group consisting of ADP-ribosyl transferase C3 and ADP-ribosyl transferase C3 analogues. In accordance with the present invention the ADP-ribosyl transferase C3 is selected from the group consisting of ADP-ribosyl transferase C3 derived from *Clostridium botulinum* and a recombinant ADP-ribosyl transferase C3.

The present invention in a further aspect provides for the use of a member selected from the group consisting of a drug delivery construct as described herein, a drug conjugate as described herein and a fusion protein (polypeptide) as described herein (e.g. including pharmaceutically acceptable chemical equivalents thereof) for suppressing the inhibition of neuronal axon growth.

The present invention in a further aspect relates to a pharmaceutical composition (e.g. for suppressing the inhibition of neuronal axon growth), the pharmaceutical composition comprising a pharmaceutically acceptable diluent or carrier and an effective amount of an active member selected from the group consisting of a drug delivery construct as described herein, a drug conjugate as described herein, and a fusion protein (polypeptide) as described herein (e.g. including pharmaceutically acceptable chemical equivalents thereof).

The present invention further provides for the use of a member selected from the group consisting of a drug delivery construct as described herein, a drug conjugate as described herein, and a fusion protein (polypeptide) as described herein (e.g. including pharmaceutically acceptable chemical equivalents thereof) for the manufacture of a pharmaceutical composition (e.g. for suppressing the inhibition of neuronal axon growth).

The present invention also relates to a method for preparing a drug delivery construct, a conjugate or fusion protein (polypeptide) as defined above comprising
 cultivating a host cell (bacterial or eukaryotic) under conditions which provide for the expression of the drug delivery construct, the conjugate or fusion protein (polypeptide) within the cell; (the drug delivery construct, conjugate or fusion protein (polypeptide), could also be expressed to be produced in an animals, such as, for example, the production of recombinant proteins in the milk of farm animals) and,
 recovering the drug delivery construct, conjugate or fusion protein (polypeptide) by a purification step.

The purification of the drug delivery construct, conjugate or fusion protein (polypeptide) may be done by affinity methods, ion exchange chromatography, size exclusion chromatography, hydrophobicity or any other purification technique typically used for protein purification. Preferably, the purification step would be performed under non-denaturating conditions. On the other hand, if a denaturating step is required, the protein may be renatured using techniques known in the art.

The present invention also relates to the expression of the drug delivery construct, conjugate or fusion protein (polypeptide) in a mammalian cell, which when used with a signal sequence, will allow expression and secretion of the fusion protein into the extracellular milieu. Other system of expression (yeast cells, bacterial cells, insect cells, etc.) may be suitable to express (produce) the drug delivery construct, conjugate or fusion protein (polypeptide) of the present invention as discussed herein.

The present invention in particular provides a fusion protein (polypeptide) selected from the group consisting of C3APL (SEQ ID NO.: 4), C3APLT (SEQ ID NO.: 37), C3APS (SEQ ID NO.:6), C3-TL (SEQ ID NO.:14), C3-TS (SEQ ID NO.: 18), C3Basic1 (SEQ ID NO.:25), C3Basic2 (SEQ ID NO.: 30), C3Basic3 (SEQ ID NO.:35), SEQ ID NO.: 20, and SEQ ID NO.: 43 and pharmaceutically acceptable chemical equivalents thereof.

In accordance with an additional aspect, the present invention provides a pharmaceutical composition comprising a polypeptide selected from the group consisting of C3APL (SEQ ID NO.:4), C3APLT (SEQ ID NO.:37), C3APS (SEQ ID NO.:6), C3-TL (SEQ ID NO.: 14), C3-TS (SEQ ID NO.: 18), C3Basic1 (SEQ ID NO.:25), C3Basic2 (SEQ ID NO.: 30), C3Basic3 (SEQ ID NO.:35), SEQ ID NO.: 20 and SEQ ID NO.: 43, and a pharmaceutically acceptable carrier.

In accordance with the present invention, the pharmaceutical composition may further comprise a biological adhesive, such as, for example, fibrin (fibrin glue).

In a further aspect the present invention provides a pharmaceutical composition comprising a polypeptide comprising at least one (one or more) transport agent region and an active agent region, said active agent region being selected from the group consisting of ADP-ribosyl transferase C3 and ADP-ribosyl transferase C3 analogues, and a pharmaceutically acceptable carrier.

In accordance with the present invention, the transport agent region may be at the carboxy-terminal end of said polypeptide and the active agent region may be at the amino terminal end of said polypeptide.

In accordance with the present invention, the pharmaceutical composition may further comprise a biological adhesive, such as, for example, fibrin (fibrin glue).

In an additional aspect, the present invention provides a polypeptide comprising at least one (one or more) transport agent region and an active agent region, said active agent region being selected from the group consisting of ADP-ribosyl transferase C3 and ADP-ribosyl transferase C3 analogues (wherein the transport agent region is able to facilitate the uptake of the active agent region into (inside the cell or in the cell membrane) a cell).

In an additional aspect, the present invention provides a polypeptide consisting of a carboxy-terminal active agent moiety and an amino-terminal transport moiety region (wherein the transport agent region is able to facilitate the uptake of the active agent region into (inside the cell or in the cell membrane) a cell) and wherein said carboxy-terminal active agent moiety may be selected from the group consisting of ADP-ribosyl transferase C3 and ADP-ribosyl transferase C3 analogues thereof.

In accordance with the present invention, the carboxy-terminal transport moiety region may be selected from the group consisting of a basic amino acid rich region and a proline rich region.

In a further aspect, the present invention relates to a polypeptide consisting of an amino-terminal active agent moiety and a carboxy-terminal transport moiety region, wherein said amino-terminal active agent moiety may be selected from the group consisting of ADP-ribosyl transferase C3 and ADP-ribosyl transferase C3 analogues thereof.

In accordance with the present invention, the carboxy-terminal transport moiety region may be selected from the group consisting of a basic amino acid rich region and a proline rich region.

In yet a further aspect, the present invention relates to a conjugate comprising at least one transport agent region (including one, two, three or more transport agent region) and an active agent region, said active agent region being selected from the group consisting of ADP-ribosyl transferase C3 and ADP-ribosyl transferase C3 analogues, wherein said transport agent region is covalently linked to said active agent region.

In accordance with the present invention, the transport agent region may be cross-linked (e.g., chemically cross-linked, UV cross-linked) to the active agent region (C3-like proteins of the present invention and analogues thereof).

In accordance with the present invention, the transport agent region may be fused to ADP-ribosyl transferase C3 and ADP-ribosyl transferase C3 analogues according to recombinant DNA technology (e.g., cloning the DNA sequence of the transport agent region in frame with the DNA sequence of the ADP-ribosyl transferase C3 or an ADP-ribosyl transferase C3 analogue comprising or not a spacer DNA sequence (multiple cloning site, linker) or any other DNA sequence that would not interfere with the activity of the C3-like protein once expressed).

In an additional aspect, the present invention relates to the use of a polypeptide selected from the group consisting of C3APL (SEQ ID NO.: 4), C3APLT (SEQ ID NO.:37), C3APS (SEQ ID NO.:6), C3-TL (SEQ ID NO.: 14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43, for the manufacture of a pharmaceutical composition.

In other aspects, the present invention relates to the use of a polypeptide comprising at least one (one or more) transport agent region and an active agent region, for the manufacture of a pharmaceutical composition, or to facilitate (for facilitating) axon growth or for treating (in the treatment of) nerve injury (e.g., nerve injury arising from traumatic nerve injury or nerve injury caused by disease), or for preventing (diminishing, inhibiting (partially or totally)) cell apoptosis (cell death, such as following ischemia in the CNS), or for suppressing (diminishing) the inhibition of neuronal axon growth, or for the treatment of ischemic damage related to stroke, or for suppressing (diminishing) Rho activity, or to regenerate (for regenerating) injured axon (helping injured axon to recover, partially or totally, their function), or to help (for helping) neurons to make new connections (developing axon, dendrite, neurite) with other (surrounding) cells (neuronal cells), in a mammal, (e.g., human, animal), wherein said active agent region being selected from the group consisting of ADP-ribosyl transferase C3 and ADP-ribosyl transferase C3 analogues.

A cell-permeable fusion protein conjugate comprising a polypeptidic cell-membrane transport agent covalently linked to an active agent having ADP-ribosyl transferase activity can be used to treat diseases of the eye selected from the group consisting of macular degeneration (wet AMD and dry AMD), retinitis pigmentosa, Stargardt's Disease, diabetic retinopathy, hypertensive retinopathy, and occlusive retinopathy and related diseases of the retina. Cell permeable fusion protein Rho antagonists are expected to prevent both neovascularization and photoreceptor cell death, unlike other treatments that only target the neovascularization present in the disease. This can be particularly advantageous for the treatment of wet macular degeneration.

In one aspect, a therapeutically effective amount of a pharmaceutical composition comprising a cell-permeable fusion protein conjugate comprising a polypeptidic cell-membrane transport moiety and a *Clostridium botulinum* C3 exotransferase unit, or a functional analog thereof, for example a fusion protein such as C3APLT, can exhibit anti-angiogenic activity and is useful in the treatment of a disease of the eye selected from the group consisting of macular degeneration, retinitis pigmentosa, Stargardt's Disease, diabetic retinopathy, hypertensive retinopathy, and occlusive retinopathy. A therapeutically effective amount can be about 1 microgram per milliliter to about 10 micrograms per milliliter or from about 10 micrograms to about 50 micrograms per milliliter.

Administration of a pharmaceutical composition of this invention can be selected from the group consisting of intrarticular, intraocular, intranasal, intraneural, intradermal, intraosteal, sublingual, oral, topical, intravesical, intrathecal, intravenous, intraperitoneal, intracranial, intramuscular, subcutaneous, inhalation, atomization and inhalation, application directly into a tissue of or proximal to the eye or CNS, application directly into a disease site especially into a blood vessel that supplies blood to the retina or to a cell or tissue or structure of an eye, application directly on or into the margins remaining after an operative resection such as a resuction of a tumor, enteral, enteral together with a gastroscopic procedure, and ECRP.

Administration of a pharmaceutical composition of this invention is preferably by injection, such as by injection into an eye, preferably into a blood vessel that supplies blood to the eye or by microinjection into the macula by first penetrating the sclera, by topical application such as to a tissue of the eye such as the cornea or sclera, or by implantation such as by controlled release from a depot or implant comprising a fusion protein of this invention optionally in the presence of a pharmaceutically acceptable matrix or pharmaceutically acceptable carrier, which depot or implant is located proximal to the tissue of the eye, preferably proximal to or embedded into tissue comprising the posterior portion of the eye. A therapeutically effective amount of a fusion protein of this invention can be delivered to the choroid and retina proximal to the macula of the eye to prevent (such as in a prophylactic treatment) or retard the growth of blood vessels that lead to macular degeneration in the eye.

In one aspect, therapeutic compositions of this invention can be administered to the eye by a number of techniques including by use of medical devices and methods of administration known in the art, such as for example those described in U.S. Pat. Nos. 6,397,849; 6,299,895; 5,770,589; 5,767,079; 5,707,643; 5,632,984; 5,443,505; 5,399,163; 5,383,851; 5,273,530; 5,064,413; 4,941,880; 4,790,824; 4,596,556; 4,487,603; 4,486,194; 4,475,196; 4,447,224; 4,447,233; and 4,439,196 cited hereinabove, which patents are incorporated herein by reference. Many other methods of administration such as a single or multiple implant comprising a poorly water soluble and/or biodegradable matrix composition for controlled release of a protein of this invention, an implantable hydrogel matrix which can be biodegradable and comprising a drug, an injectable delivery system such as a liposome suspension comprising a protein of this invention entrapped in the interior and/or membrane portion of the liposome which liposome is suspended in an aqueous medium, injection methods such as comprising a needleless syringe or cannula or needle and syringe, nanoparticulate implantation methods comprising a protein of this invention and a poorly water soluble and biodegradable carrier, and delivery routes that are applicable to administer a drug to the eye and to blood vessels that feed blood to the eye can be used with the compositions of this invention.

The fusion proteins and pharmaceutical compositions of fusion proteins of the present invention can be delivered by a variety of techniques to the macula region of the eye, preferably to the posterior segment of the eye proximal to the macula. Examples of such techniques include:

a) use of a sterile, pharmaceutically acceptable biodegradable scleral plug which comprises a fusion protein of this invention and optionally a pharmaceutically acceptable biodegradable matrix such as a polylactic acid or polyglycolic acid or a copolymer of lactic acid and glycolic acid, which plug can be inserted into the eye via an incision in the sclera;

b) use of an implant comprising a fusion protein of this invention and optionally a pharmaceutically acceptable biodegradable matrix wherein the sclera is cut to expose the suprachoroid and wherein the implant is placed into a suprachoroidal space form which implant the fusion protein is released for example into the vitreous region of the eye;

c) use of intravitreal injection into the vitreous body of a pharmaceutical composition comprising a fusion protein of this invention and a sterile aqueous carrier, wherein the fusion protein comprises a submicron-to about 4 micron-sized pharmaceutically acceptable particulate composition;

d) injection or infusion via a flexible cannula that can be inserted through the posterior sclera and down into the subretinal space at the posterior region of the eye; and e) by injection of a pharmaceutical composition comprising a fusion protein of this invention and a pharmaceutically acceptable carrier into an avascular region of the sclera to form a depot comprising a fusion protein of this invention within the scleral layer and from which the fusion protein can diffuse to the macula, choroid layer, and/or retina.

In one aspect, a pharmaceutical composition of this invention can comprise a pharmaceutically acceptable carrier selected from the group consisting of poly(ethylene-co-vinyl acetate), PVA, partially hydrolyzed poly(ethylene-co-vinyl acetate), poly(ethylene-co-vinyl acetate-co-vinyl alcohol), a cross-linked poly(ethylene-co-vinyl acetate), a cross-linked partially hydrolyzed poly(ethylene-co-vinyl acetate), a cross-linked poly(ethylene-co-vinyl acetate-co-vinyl alcohol), poly-D,L-lactic acid, poly-L-lactic acid, polyglycolic acid, PGA, copolymers of lactic acid and glycolic acid, polycaprolactone, polyvalerolactone, poly(anhydrides), copolymers of polycaprolactone with polyethylene glycol, copolymers of polylactic acid with polyethylene glycol, polyethylene glycol; fibrin, Gelfoam (which is a water-insoluble, off-white, nonelastic, porous, pliable gel foam prepared from purified gelatin such as pork skin gelatin and water for injection), and combinations and blends thereof. Copolymers can comprise from about 1% to about 99% by weight of a first monomer unit such as ethylene oxide and from 99% to about 1% by weight of a second monomer unit such as propylene oxide. Blends of a first polymer such as gelatin and a second polymer such as poly-L-lactic acid or polyglycolic acid can comprise from about 1% to about 99% by weight of the first polymer and from about 99% to about 1% of the second polymer.

A fusion protein of this invention can be prepared as a solution or as a suspension in an aqueous medium such as a buffered saline or phosphate solution in water for injection, sterilized such as by filtration through a 0.2 micron or smaller pore size filter and injected in to an implanted matrix proximal to the tissue of the eye such as in a sterile gel foam (Gelfoam) matrix which can be absorbed completely. This absorption is dependent on several factors, including the amount used, degree of saturation with blood or other fluids, and the site of use. When placed in soft tissues, Gelfoam can be absorbed completely for example in from four to six weeks, without inducing excessive scar tissue. When applied to bleeding nasal, rectal or vaginal mucosa, it can liquefy within two to five days.

In another aspect, a pharmaceutical composition of this invention comprises a pharmaceutically acceptable carrier. For example, the carrier can be selected from the group consisting of water, a pharmaceutically acceptable buffer salt, a pharmaceutically acceptable buffer solution, a pharmaceutically acceptable antioxidant such as ascorbic acid, one or more low molecular weight pharmaceutically acceptable polypeptide such as a pharmaceutically acceptable peptide comprising about 2 to about 10 amino acid residues, one or more pharmaceutically acceptable protein such as albumin, one or more pharmaceutically acceptable amino acid such as an essential-to-human amino acid, one or more pharmaceutically acceptable carbohydrate, one or more pharmaceutically acceptable acetylated or otherwise esterified carbohydrate material obtained for example by esterification with a 2 to 20 carbon pharmaceutically acceptable carboxylic acid, a non-reducing sugar, glucose, sucrose, sorbitol, trehalose, mannitol, maltodextrin, dextrins, cyclodextrin, a pharmaceutically acceptable chelating agent, EDTA which is ethylenediamine tertraacetic acid, DTPA, a chelating agent for a divalent metal ion such as zinc ion, a chelating agent for a trivalent metal ion, glutathione, pharmaceutically acceptable nonspecific serum albumin, an antibody to a growth factor, and combinations thereof.

The pharmaceutical compositions of this invention can be sterile, sterilizable, and sterilized. A preferred method of sterilization comprises filtration of a pharmaceutical composition through a 0.2 micron filter in a sterile environment. The sterile filtered composition can be filled in a vial, preferably into a sterile vial, in a unit dosage volume amount (comprising a therapeutically effective amount of fusion protein of this invention) or in an integral multiple of a unit dosage amount (e.g., as 2 unit dosage amount, 3 unit dosage amounts, 4 unit dosage amounts, et cetera), preferably under an inert atmosphere such as sterile nitrogen or argon, and the vials sealed with a pharmaceutically acceptable stopper, optionally with a crimp cap. In another aspect, pharmaceutical composition is dried by removal of water, for example the aqueous medium can be removed from each vial by a drying process such as by lyophilization or evaporation to leave a dried or dehydrated matrix comprising the fusion protein of this invention, before sealing and capping of the vial. In another aspect, the carrier can comprise a sterile or sterilizable hypertonic solution of a pharmaceutically acceptable matrix-forming material or excipient that is compatible with the fusion protein, for example, such as a pharmaceutically acceptable non-reducing carbohydrate, together with a compound or fusion protein of the invention, which hypertonic solution can be placed in a vial and dried (e.g., by lyophilization) to provide a matrix comprising the fusion protein and the matrix-forming excipient, which can be sealed in the vial with a cap. Prior to use, sterile water can be added to the vial, for example via sterile syringe or cannula, which water can dissolve the matrix to provide a solution or suspension of the fusion protein. Sufficient water can be added to provide the reconstituted solution or suspension as an isotonic solution suitable for injectable or implantable use.

The pharmaceutical compositions provided herein may be placed within containers along with packaging material which provides instructions regarding the use of such materials. Generally, such instructions will include a description of the concentration of the active agent, as well as within certain embodiments, relative amounts or identities of excipient ingredients or diluents (e.g., water, saline or PBS). In addition, it may be necessary to reconstitute the pharmaceutical composition to a pharmaceutically acceptable solution or suspension by the addition of water and optionally also with shaking or sonication.

A pharmaceutical composition of the present invention in a therapeutically effective amount (e.g., in the form of a spray or an aerosol) may be delivered via an endoscopic procedure, wherein the composition is sprayed or aerosolized inside a patient to provide a coating comprising a fusion protein of this invention on a tissue inside a patient. In another aspect, coating of a pharmaceutical composition on to a tissue proximal to an eye and preferably accessible to the chorioid of the eye can inhibit angiogenesis in the region of tissue that is coated by the pharmaceutical composition.

Optionally, the pharmaceutical composition can be packaged in a vial or syringe for injection. The vial or syringe can contain a unit dosage amount of the pharmaceutical composition or of the fusion protein in lyophilized form which can be rehydrated by the addition of water such as water for injection. Optionally, the vial can contain two or more such as three or four or five unit dosage amounts of the fusion protein or a pharmaceutical composition thereof. Optionally, the pharmaceutical composition can by lyophilized. Preferably, the pharmaceutical composition is prepared in the presence of an inert or non-oxidizing or substantially oxygen-free gas or atmosphere such as nitrogen, argon, carbon dioxide, or a fluorocarbon or fluorohydrocarbon gas.

Preferably, a pharmaceutically acceptable solution of this invention is substantially isotonic with blood.

In one aspect, the fusion protein can be formed into a sterile aqueous pharmaceutically acceptable solution or nanoparticulate suspension in the presence of a substantially water-insoluble gas such fluorocarbon such as perfluoropropane and optionally in the presence of a pharmaceutically acceptable surface active agent such as a phospholipids or a polyethylene oxide-containing surfactant such as Pluronic F68 or F108, and subjected to vibration such as ultrasonic vibration or rapid shaking, wherein microbubbles comprising the fusion protein and the gas are obtained, preferably having a mean diameter of less than about 2 microns, which microbubbles can be injected by microinjection into the blood vessel which supplies blood to the eye to deliver a therapeutically effective amount of the fusion protein to the corroid and retina proximal to the macula.

Compositions of the present invention useful for treatment of a disease of the eye selected from the group consisting of macular degeneration, retinitis pigmentosa, Stargardt's Disease, diabetic retinopathy, hypertensive retinopathy, and occlusive retinopathy may be formulated in a variety of forms. For example, in one embodiment, a pharmaceutical composition comprising a therapeutically effective amount of a cell-permeable fusion protein conjugate comprising a polypeptidic cell-membrane transport moiety and a *Clostridium botulinum* C3 exotransferase unit, or a functional analog thereof, can comprise a microsphere, wherein the fusion protein is blended with or embibed into a matrix comprising a pharmaceutically acceptable polymeric carrier, optionally in the presence of water (wherein the blend comprises from about 0.1% to about 50% of a fusion protein of this invention in one embodiment; alternatively, a microsphere comprising a fusion protein of this invention and a polymeric carrier can be suspended in a sterile pharmaceutically acceptable aqueous medium which is preferably isotonic with blood, in another embodiment), a pharmaceutically acceptable buffer salt, a pharmaceutically acceptable surface active agent, a pharmaceutically acceptable carbohydrate, a pharmaceutically acceptable emollient, and the like.

In another embodiment, a pharmaceutical composition of this invention can comprise a therapeutically effective amount of a cell-permeable fusion protein conjugate comprising a polypeptidic cell-membrane transport moiety and a *Clostridium botulinum* C3 exotransferase unit, or a functional analog thereof, and can comprise a paste, a cream, an ointment, a suspension, for example in a pharmaceutically acceptable oil such as a pharmaceutically acceptable triglyceride, and the like.

In another embodiment, a pharmaceutical composition comprising a therapeutically effective amount of a cell-permeable fusion protein conjugate comprising a polypeptidic cell-membrane transport moiety and a *Clostridium botulinum* C3 exotransferase unit, or a functional analog thereof, can comprise a film, for example wherein the fusion protein is blended or mixed together with a pharmaceutically acceptable carrier such as an aqueous gelatin or an aqueous protein or a polymeric carrier or a combination thereof, optionally by injection in vivo proximal to the eye or proximal to the blood vessels of the eye, optionally in the presence of a pharmaceutically acceptable cross-linking agent species which can crosslink the carrier. In one embodiment, the blend can be injected. In another embodiment, the blend can be coated into a film or laminate, optionally in the present of a film base or a support or matrix, and dried or dehydrated, optionally by the addition of heat or by lyophilization. Films can be prepared in unit dosage forms or in bulk and divided and cut into unit dosage forms.

In another embodiment, a pharmaceutical composition comprising a therapeutically effective amount of a cell-permeable fusion protein conjugate comprising a polypeptidic cell-membrane transport moiety and a *Clostridium botulinum* C3 exotransferase unit, or a functional analog thereof, can comprise an aerosol or sprayable or aerosolizable composition such as a suspension or solution of the fusion protein in a pharmaceutically acceptable fluid such as an aqueous solution of a buffer, optionally with a tonicity modifier; in a pharmaceutically acceptable fluid such as a supercritical or liquefied gas such as carbon dioxide or propane or a low molecular weight fluorocarbon or fluorohydrocarbon or bromofluorocarbon or chlorofluorocarbon and the like, each of which is a gas at 37° C. and ambient pressure, the composition suitable for use, for example, as an aerosol. An aerosol can be used to apply a fusion protein of this invention to the surface of a tissue proximal to the eye or into a tissue of the eye.

In another aspect, the compositions of the present invention may be formulated to contain a variety of additional compounds, in order to provide the formulated fusion protein formulations with certain physical properties (e.g., elasticity related to incorporation of a pharmaceutically acceptable plasticizing agent, a particular melting point such as about 30° C. such as by use of a polyethylene glycol, or a specified release rate which may be related to degree of crosslinking or rate of hydration in a matrix or to solubilization of a matrix, or to preferential solublization of one component of a matrix which can leave pores in the matrix through which a carrier fluid such a water can assist in transport of the fusion protein out of the matrix and into or onto a desired site such as tissue proximal to or a part of the eye in the body of a mammal.

A chemical modification of a drug molecule which can produce a lengthening of the half life of the drug molecule in bodily fluids such as blood and in tissue in vivo is PEGylation. PEGylation comprises a covalent attachment of one or more PEG-containing group to a drug molecule such as a protein or a peptide drug molecule. PEG is sometimes known referred to as poly(ethylene glycol) or polyoxyethylene or polyethylene glycol. A PEG-containing group is sometimes referred to as a "PEG" group or as a "MPEG" group where PEG refers to a hydroxy-terminated poly(ethylene glycol) or omega-hydroxy-PEG- or HO-PEG- and MPEG- refers to a methoxy-terminated poly(ethylene glycol) or omega-methoxy-PEG- or CH$_3$O-PEG- or MeO-PEG-. Useful PEG and MPEG molecular weights are often from about 1000 Daltons to about 20,000 Daltons or more, preferably from about 2000 to about 20000 Daltons, and more preferably from about 5000 to about 20000 Daltons in average molecular weight. PEGylation can be achieved by chemically reacting an activated PEG or MPEG group (e.g., an MPEG that is terminally substituted with a chemically reactive functional group) with a chemically reactive site of a drug molecule (e.g., an epsilon-amino group of a lysine in a peptide or protein, a terminal amino group of a peptide or protein, a sulfhydryl group, and the like), in a suitable medium such as an aqueous buffer solution. Examples of a chemically reactive functional group on a PEG-containing reagent include an alpha-active ester of a PEG or MPEG such as an alpha-N-hydroxysuccinamidyl PEG or MPEG ester, an alpha-p-nitrophenyl PEG or MPEG ester, a vinyl sulfone group, a chlorotriazinyl group, and the like. The active functional group is usually separated from the PEG group by a spacing group which is, for example, covalently attached by a first covalent bond (e.g, amide bond formed by reaction of an active ester group with an amine; a thioether bond formed by reaction of a sulfhydryl group with a iodomethylcarbonyl group) to the PEG or MPEG group and by a second covalent bond to the chemically reactive functional group. Examples of useful spacing groups include a succinate ester spacing group, a methylenecarbonyl group, an ethylenecarbonyl group, a triazine group, an ethylenesulfonyl group, and the like. Useful pegylation reagents including low-diol pegylation reagents can be obtained commercially, for example, from Nektar Therapeutics, Huntsville, Ala. A useful family of PEG reagents and methods is described in U.S. Pat. No. 5,672,662, the disclosure of which is herein incorporated by reference. PEGylation is often associated with reduction of dose of drug and with lowered toxicity) and in some cases can interfere with generation of an immune response is PEGylation. PEGylation is believed to work by changing the size of the molecule and by changing interactions with other molecules such as antibodies by steric hindrance. PEGylation has been found to be effective for some therapeutic enzymes, peptides and antibodies.

A useful embodiment of a PEGylated fusion protein of the current invention can comprise a PEG-containing group (e.g., one or two or three or four or five molecules of 20,000 molecular weight PEG-containing group) covalently linked (e.g., by an amide bond or a thioether bond) to a fusion protein of the invention, wherein the cell permeation ability of the transport agent moiety in said PEGylated fusion protein is in the range of about 1% to about 100% (e.g., 10%, 20%, 25%, 30%, 40%, 50%, 60%, 70%, 75%, 80%, 80%, 95%, 99%) of the cell permeation ability of said transport agent in said fusion protein that is not PEGylated, and wherein the ADP-ribosyl transferase activity of said PEGylated fusion protein is in the range of about 1% to about 100% (e.g., 10%, 20%, 25%, 30%, 40%, 50%, 60%, 70%, 75%, 80%, 80%, 95%, 99%) of the ADP-ribosyl transferase activity of said fusion protein that is not PEGylated when the properties of the PEGylated fusion protein and the corresponding non-PEGylated fusion protein are compared under identical reference experimental conditions.

Within certain embodiments of the invention, compositions may be combined in order to achieve a desired effect (e.g., two or more compositions such as a first composition of microspheres comprising an amount (e.g., 15% by weight) of a fusion protein of this invention in a gelatin matrix together with 0.1% of a crosslinking agent such as succinaldehye and a second composition of microspheres comprising an amount (e.g., 25% by weight) of a fusion protein of this invention in a gelatin matrix together with about 2% of a crosslinking agent such as succinaldehye may be combined in order to achieve a modified net release rate of a fusion protein of this invention such as both a rapid release plus a slow or prolonged release.

In one aspect, a rapid release can comprise release of about 50% of the fusion protein in a composition in less than about 8 hours. In another aspect, a slow or prolonged release can comprise release of about 50% of the amount of fusion protein in about 2 weeks.

Within yet other aspects of the present invention, a pharmaceutical composition of this invention can be coated onto the surface of an implantable device such as a sterile surgical mesh, wire, stent, prosthetic device, and the like, to form a coated device, the coating comprising a fusion protein of this invention and optionally a carrier such as a polymeric carrier, which coated device may be implanted in a tissue or organ in a patient such as tissue proximal to the eye or part of the eye, or in a blood vessel which feeds blood to the eye, as part of a surgical treatment, which pharmaceutical composition is delivered in a therapeutically effective amount which can prevent or inhibit or delay or retard growth of neovascularization proximal to the location of the device such as retard neovascularization proximal to the macula.

In another aspect, a therapeutically effective amount of fusion protein can prevent or inhibit or delay or retard growth of blood vessels proximal to the macula which is remote from the site of the implanted device.

The concentration of the fusion protein can be from 0.01% to about 20% by weight of the carrier that forms a coating on the device, and the thickness of the coating can be from about 20 micrometers to about 1 millimeter. The coating can be applied by coating means known in the art of coating devices. For example, a coating comprising a pharmaceutical composition of this invention can be applied to the surface of a device by means of a spray or aerosol applicator in which the pharmaceutical composition as a solution in a liquid or fluid comprising a solvent or as a suspension in a liquid or fluid, which liquid or fluid can evaporate during and after application as a spray or an aerosol, is sprayed or aerosolized onto the surface of a device. Optionally, the coated composition can comprise reactive chemical functional groups such as olefins or anhydride groups or active esters or Michael reaction acceptors such as a carbon-carbon double bond conjugated to a carbonyl group, which double bond can react with an amine of a protein or peptide or gelatin such as a carrier protein, which reactive chemical functional groups can chemically or photochemically form crosslinks in the carrier, which can prevent solubilization or limit or modify or control swelling (as a function of concentration of the number of reactive functional groups or the time of exposure to crosslinking conditions such as ultraviolet or gamma irradiation of the coated device) of the coated carrier by aqueous fluid in the tissue of blood vessel in which the device is implanted. Control of swelling can be useful to control the rate at which a therapeutically effective amount of the fusion protein of this invention migrates from the device into the tissue proximal to the device and further into the body of the patient. A wide variety of crosslinking chemistry known in the art can be useful in this aspect of the invention as long as the biological activity of the fusion protein is not negated or eliminated. If an organic solvent or supercritical fluid or liquefied gas is used in the coating process, then a pharmaceutically acceptable carrier can be selected which does not immediately dissolve in the aqueous medium present in tissue proximal to the site of implantation but permits permeation of a therapeutically effective amount of the fusion protein into the aqueous medium.

Other methods of coating a device can be used such as dip coating of a composition, painting, curtain coating, and lamination of a pharmaceutical composition of this invention. In one embodiment, the surface of a device can be first coated with a first coating layer or primer layer such as gelatin or polyvinyl alcohol, which is then subsequently optionally crosslinked, and then coated with a pharmaceutical composition of this invention as a second coating layer. The primer layer can be selected to adhere to the surface of the metal or polymeric device and to adhere to the carrier of the second coating layer such as gelatin. The primer layer can also comprise immobilized chemical functional groups (e.g., which can be attached to a polymer in the primer layer) and which can form crosslinking bonds with the second layer. The primer layer can optionally contain relatively mobile molecules comprising for example two or more reactive functional groups such as a dialdehyde such as succinaldehye, which molecules can migrate into the second layer and react with chemical functional groups therein to form crosslinking molecular bridges.

In another embodiment, a pharmaceutically acceptable third layer can be overcoated on the second layer on the device, the third layer optionally void of a fusion protein of this invention. The third layer (e.g., a gelatin layer) can serve to control or modify the release rate of the fusion protein from the device, for example by being able to dissolve or swell or increase its permeability with respect to water or the fusion protein as a function of time to expose the second layer comprising the pharmaceutical composition of this invention to aqueous media from the tissue.

Within one embodiment of the invention a surgical mesh device comprising a pharmaceutical composition of the present invention coated on the surface of a wire or polymer mesh may be utilized or implanted in a patient such as during a surgical procedure on the eye of a patient. The coated mesh device can release a therapeutically effective amount of the active component (such as C3APLT or an active mutant or truncated form thereof) of the pharmaceutical composition sufficient to prevent neovascularization in Bruch's membrane proximal to the macula and proximal to the site of implantation of the coated device. The fusion protein can migrate from the device at a rate sufficient to provide a therapeutically effective concentration range in the tissue proximal to the device.

A currently preferred concentration range is about 0.0001 micrograms of fusion protein per cubic centimeter (cc) of tissue to about 100 micrograms per cubic centimeter of tissue can be useful. A currently more preferred therapeutically effective concentration range is about 0.001 micrograms per cc to about 50 micrograms per cc of tissue.

In one embodiment of the invention, the fusion protein can have molecular weight of from about 240,000 daltons to about 300,000 daltons.

Another aspect of the invention comprises a pharmaceutical composition of this invention in a kit of parts such as a kit comprising a container and a pharmaceutical composition of this invention; a kit comprising a sealed vial and a pharmaceutical composition of this invention; a kit comprising a sterile syringe and a pharmaceutical composition of this invention; a kit comprising a sterile syringe containing a pharmaceutical composition of this invention; a kit comprising a spray or aerosol applicator and a pharmaceutical composition of this invention; a kit comprising a brush applicator and a pharmaceutical composition of this invention; a kit comprising a cannula and a pharmaceutical composition of this invention; a kit comprising a powder applicator and a pharmaceutical composition of this invention (which powder applicator can be used to administer a pharmaceutical dosage form of this invention as a powder by sprinkle application of a dried (e.g., lyophilized) powder in a topical application to a tissue; a kit comprising a coated implantable device and a pharmaceutical composition of this invention, wherein administration is by implantation.

In accordance with the present invention, the transport agent region may be at the amino-terminal end of the polypeptide (i.e., protein) and the ADP-ribosyl transferase C3 or ADP-ribosyl transferase C3 analogue may be at the carboxy-terminal end of the polypeptide (i.e., protein).

In accordance with the present invention, the transport agent region may be at the carboxy-terminal end of the polypeptide (i.e., protein) and the ADP-ribosyl transferase C3 or ADP-ribosyl transferase C3 analogue may be at the amino-terminal end of the polypeptide (i.e., protein).

In a further aspect, the present invention provides a method of (for) suppressing the inhibition of neuronal axon growth (e.g., in a mammal, (e.g., human, animal)) comprising administering (e.g., delivering) a member selected from the group consisting of a drug delivery construct, a drug conjugate, a fusion protein and a polypeptide (e.g. including pharmaceutically acceptable chemical equivalents thereof), said polypeptide comprising at least one (one or more) transport agent region and an active agent region selected from the group consisting of ADP-ribosyl transferase C3 and ADP-ribosyl transferase C3 analogues (directly) at (to) a central nervous system (CNS) lesion site or a peripheral nervous system (PNS) lesion site (of a patient), in an amount effective to counteract said inhibition. Such application could be useful for treatment of a wide variety of peripheral neuropathies, such as diabetic neuropathy.

The present invention, for example, provides recombinant Rho antagonists comprising C3 enzymes with basic stretches of amino acids (e.g., a basic amino acid rich region) or a proline rich region added to the C3 coding sequence to facilitate the uptake thereof into tissue or cells for the repair and/or promotion of repair or promotion of growth in the CNS, even in the lack of traumatic axon damage. Examples of basic amino acid rich regions and proline rich regions are given below.

In yet a further aspect, the present invention provides a method of (for) facilitating axon growth (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site, in an amount effective to facilitate said growth.

In an additional aspect, the present invention provides a method of (for) treating nerve injury (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at (to) a central nervous system (CNS) lesion site or a peripheral nervous system (PNS) lesion site.

In yet an additional aspect, the present invention provides a method of (for) preventing cell apoptosis (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site.

In another aspect, the present invention provides a method of (for) treating ischemic damage related to stroke (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site (to said mammal).

In yet another aspect, the present invention provides a method of (for) suppressing Rho activity comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site, in an amount effective to suppress said activity.

In accordance with an additional aspect, the present invention provides a method of (for) regenerating injured axon (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site (e.g., in a mammal), in an amount effective to regenerate said injured axon.

In accordance with a further aspect, the present invention provides a method of (for) helping neurons to make new cell connection (developing axon, dendrite, neurite with other (surrounding) cells (neuronal cells) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site.

In an additional aspect, the present invention provides a method for (of) preparing a polypeptide comprising at least one (one or more) transport agent region and an active agent region, wherein said transport agent region may be selected from the group consisting of SEQ ID NO.: 21, SEQ ID NO.: 26, SEQ ID NO.: 31, SEQ ID NO.: 44, SEQ ID NO.: 45, SEQ ID NO.: 46, SEQ ID NO.: 47, SEQ ID NO.: 48 and analogues thereof, and wherein said active agent region may be selected from the group consisting of ADP-ribosyl transferase C3 and ADP-ribosyl transferase C3 analogues, said method comprising:

a) cultivating a host cell under conditions which provide for the expression of the polypeptide within the cell; and b) recovering the polypeptide by a purification step.

In accordance with the present invention, the purification of polypeptide may be done by affinity methods, ion exchange chromatography, size exclusion chromatography, hydrophobicity or any other purification technique typically used for protein purification. Preferably, the purification step would be performed under non-denaturing conditions. On the other hand, if a denaturating step is required, the protein may be renatured using techniques known in the art.

In another aspect, the present invention provides a polypeptide consisting of a basic amino acid rich region and an active agent region, wherein, amino acids from said basic rich region comprises amino acids selected from the group consisting of Histidine, Asparagine, Glutamine, Lysine and Arginine and wherein the active agent region is ADP-ribosyl transferase C3.

In yet another aspect, the present invention relates to the use of a polypeptide comprising at least one transport agent region and an active agent region, said active agent region being selected from the group consisting of ADP-ribosyl transferase C3 and ADP-ribosyl transferase C3 analogues for the manufacture of a medicament (or a pharmaceutical composition) for suppressing the inhibition of neuronal axon growth.

In accordance with the present invention, the polypeptide may be selected from the group consisting of C3APL (SEQ ID NO.: 4), C3APL (SEQ ID NO.:37), C3APS (SEQ ID NO.:6), C3-TL (SEQ ID NO.:14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43.

In a further aspect, the present invention relates to the use of a polypeptide comprising at least one transport agent region and an active agent region, said active agent region being selected from the group consisting of ADP-ribosyl transferase C3 and ADP-ribosyl transferase C3 analogues for the manufacture of a medicament (or pharmaceutical composition) for facilitating axon growth.

In accordance with the present invention, the polypeptide may be selected from the group consisting of C3APL (SEQ ID NO.: 4), C3APLT (SEQ ID NO.:37), C3APS (SEQ ID NO.:6), C3-TL (SEQ ID NO.:14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43.

In yet a further aspect the present invention relates to the use of a polypeptide comprising at least one (one or more) transport agent region and an active agent region, said active agent region being selected from the group consisting of ADP-ribosyl transferase C3 and ADP-ribosyl transferase C3 analogues for the manufacture of a medicament (or pharmaceutical composition) for treating nerve injury (e.g., in a mammal, (e.g., human, animal)).

In accordance with the present invention, the polypeptide may be selected from the group consisting of C3APL (SEQ ID NO.: 4), C3APLT (SEQ ID NO.:37), C3APS (SEQ ID NO.:6), C3-TL (SEQ ID NO.:14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43.

In accordance with the present invention, the transport agent region discussed herein may be selected from the group consisting of a basic amino acid rich region (region comprising basic amino acid (e.g., arginine, lysine, histidine, glutamine, and/or asparagine)) and a proline rich region (e.g. region comprising prolines).

In accordance with the present invention, the basic amino acid rich region discussed herein may be selected from the group consisting of SEQ ID NO.: 48, a subdomain of HIV Tat protein (e.g., SEQ ID NO.: 46, SEQ ID NO.: 47, or any other subdomain of Tat, that could act as a transport sequence), a homeodomain of antennapedia (e.g., SEQ ID NO.: 44, SEQ ID NO.: 45, or any other domain of antennapedia, that could act as a transport sequence), a homeoprotein transport sequence, a Histidine tag, and analogues thereof (e.g., SEQ ID NO.: 21, SEQ ID NO.: 26, SEQ ID NO.:31).

In accordance with the present invention, the basic amino acid region discussed herein may be selected from the group consisting of SEQ ID NO.: 21 (Basic 1), SEQ ID NO.: 26 (Basic2), SEQ ID NO.: 31 (Basic3), SEQ ID NO.: 44 (APL), SEQ ID NO.: 45 (APS) SEQ ID NO.: 46 (TL), SEQ ID NO.: 47 (TS), and analogues thereof.

In accordance with the present invention, the proline rich region discussed herein may be selected from the group consisting of SEQ ID NO.: 48 (APLT) and analogues thereof.

In another aspect, the present invention provides an isolated polynucleotide comprising at least the polynucleotide sequence (for example the polynucleotide sequence disclosed herein in addition with (or in some cases without) a suitable (DNA) backbone (e.g., plasmid, viral vector)) selected from the group consisting of SEQ ID NO.: 3, SEQ ID NO.: 5, SEQ ID NO.: 13, SEQ ID NO.: 17, SEQ ID NO.: 19, SEQ ID NO.: 24, SEQ ID NO.: 29, SEQ ID NO.: 34, SEQ ID NO.: 36, and SEQ ID NO.: 42.

In yet another aspect, the present invention provides a cell transformed (transfected, transduced, infected, electroporated, micro-injected, etc.) with an isolated polynucleotide comprising at least the polynucleotide sequence (for example the polynucleotide sequence disclosed herein in addition with (or in some cases without) a suitable backbone (e.g., plasmid, viral vector)) selected from the group consisting of SEQ ID NO.: 3, SEQ ID NO.: 5, SEQ ID NO.: 13, SEQ ID NO.: 17, SEQ ID NO.: 19, SEQ ID NO.: 24, SEQ ID NO.: 29, SEQ ID NO.: 34, SEQ ID NO.: 36, and SEQ ID NO.: 42.

In a further aspect, the present invention provides a delivery agent consisting of a cargo moiety in combination with a transport moiety, wherein the transport moiety is selected from the group consisting of SEQ ID NO: 48 and analogues thereof. SEQ ID NO: 48 and analogues thereof act as a transport moiety which facilitate penetration of the cell membrane. Any cargo moiety (e.g., protein, chemicals) linked (e.g. attached) to SEQ ID NO: 48 or to some analogues thereof are encompassed by the present invention. For example, SEQ ID NO: 48 and analogues thereof may be fused to an anticancer agent, a therapeutic agent, an apoptotic agent, an anti-apoptotic agent, a reporter protein, an antibody, an antibody fragment, a dye, a probe, a marker etc. In one aspect, the polypeptidic cell-membrane transport moiety can comprise a peptide containing from about 5 to about 50 amino acids.

In accordance with the present invention, the cargo moiety may retain biological activity following transport moiety-dependent intracellular delivery. Biological activity may include for example, biological properties (e.g. enzymatic activity) as well as its immunological properties. The cargo moiety may have a direct biological effect on the cell, such as for example killing the cell following its internalization or may have an indirect biological effect, for example, the cargo moiety may be a pro-drug that is inactive by itself but becomes active following modification (e.g., cleavage, phosphorylation, etc.) or when a second molecules is introduced inside the cell. The cargo moiety may also be a biologically inactive (i.e., inert) compound such as a labeling molecule (e.g., chemicals, proteins), an imaging molecule etc.

In accordance with the present invention, the agent may be a fusion protein having an amino-terminal that is the cargo moiety and having a carboxy-terminal that is the transport moiety.

In accordance with the present invention the cargo moiety may be selected from the group consisting of analytical molecules (e.g., molecules used in tissue culture experiments, markers, probes, dyes, reporter proteins) therapeutic molecules (e.g., toxin, drug, pro-drug), prophylactic molecules and diagnostic molecules (i.e., molecules used in in vivo or in vitro detection of a specific condition, metabolite, other molecule). Examples of analytical molecules, therapeutic molecules, prophylactic molecules and diagnostic molecules includes proteins (e.g., enzymes (e.g., nucleases, proteases, kinases, etc.), cytokines, chemokines, antigen, antibodies, antibody fragments, reporter proteins such as horseradish peroxidase, beta-galactosidase, fluorescent proteins (e.g., green fluorescent protein)), nucleic acids, polysaccharides, dyes, isotopes (e.g., radioisotope), markers, probes, and other types of chemicals. Transport polypeptides of the present invention may be advantageously attached to cargo molecules by chemical cross-linking or by genetic fusion.

In accordance with the present invention the cargo moiety may be selected from the group consisting of ADP-ribosyl transferase C3 and ADP-ribosyl transferase C3 analogues thereof.

In an additional aspect, the present invention relates to the polypeptide set forth in SEQ ID NO: 48 and analogues thereof.

In yet an additional aspect, the present invention provides a polypeptide as set forth in SEQ ID NO: 48 and analogues thereof, wherein said polypeptide and analogues may be able to act as a transport agent for the intracellular delivery of a cargo agent selected from the group consisting of analytical molecules, therapeutic molecules, prophylactic molecules, and diagnostic molecules.

In accordance with the present invention, the cargo agent may be selected from the group consisting of ADP-ribosyl transferase C3 and ADP-ribosyl transferase C3 analogues thereof.

The transport of a cargo moiety across the cellular membrane (intracellular delivery) may be facilitated (increased) when linked (e.g., genetically fused, chemically cross-linked, etc.) to SEQ ID NO: 48 and analogues thereof. Therefore it is an object of the present invention to provide a method for the intracellular delivery of a cargo moiety, the method comprising exposing the cell to a delivery agent comprising a cargo moiety and a transport moiety, said transport moiety being selected from the group consisting of SEQ ID NO: 48 and analogues thereof and wherein said transport moiety enables the delivery agent to be delivered inside the cell (i.e., across cellular membranes). An example of a cargo moiety that may be delivered across the cell membrane is ADP-ribosyl transferase C3 and analogues thereof. Other examples of a cargo moiety are mentioned herein. The method also comprise bringing the delivery agent comprising a cargo moiety and a transport moiety (SEQ ID NO: 48 and analogues thereof) in the surrounding of a target cell in a manner (e.g., concentration) sufficient to permit the uptake of the delivery agent by the cell. For example, in the case of in vitro (e.g., cell culture) delivery, the delivery agent (in a pharmaceutically acceptable carrier, diluent, excipient, etc.) may be added directly to the extracellular milieu (e.g., cell culture media) of adherent cells (i.e., cell lines or primary cells) or cells in suspension. Alternatively, cells may be harvested and concentrated before being put in contact with the delivery agent. Intracellular delivery may be monitored by techniques known in the art, such as for example, immunofluorescence, immunohistochemistry or by the intrinsic properties of the cargo moiety (e.g., its enzymatic activity).

In vivo delivery (in a mammal) may be performed for example, by exposing (i.e., contacting) a tissue, a nerve injury site, an open wound, etc. with the delivery agent (in a pharmaceutically acceptable carrier, diluent, excipient, fibrin gel etc.) of the present invention in an amount sufficient to promote the biological effect of the cargo moiety (e.g., recovery, healing of the wounded tissue, etc.). In addition, in vivo delivery may be performed by other methods known in the art such as for example, injection via the intramuscular (IM), subcutaneous (SC), intra-dermal (ID), intra-venous (IV) or intra-peritoneal (IP) routes or administration at the mucosal membranes including the oral and nasal cavity membranes using any suitable means. Alternatively, cells may be isolated from a mammal and treated (exposed) ex-vivo (e.g., in gene therapy techniques) with the delivery agent of the present invention before being re-infused in the same individual or in a compatible individual.

The term "Rho antagonists" as used herein includes, but is not restricted to, (known) C3, including C3 chimeric proteins, and like Rho antagonists.

The term "C3 protein" refers to ADP-ribosyl transferase C3 isolated from *Clostridium botulinum* or a recombinant ADP-ribosyl transferase.

The term "C3-like protein", "ADP-ribosyl transferase C3-like protein", "ADP-ribosyl transferase C3 analogue", "C3-like transferase" or "C3 chimeric proteins" as used herein refers to any protein (polypeptide) having a biological activity similar (e.g., the same, substantially similar), to ADP-ribosyl transferase C3. Examples of such C3-like protein include, for example, but are not restricted to C3APL, C3APLT, C3APS, C3-TL, C3-TS, C3Basic1, C3Basic2 and C3Basic3 and the protein defined in SEQ ID NO.: 20.

The term "nerve injury site" refers to a site of traumatic nerve injury or nerve injury caused by disease. The nerve injury site may be a single nerve (eg sciatic nerve) or a nerve tract comprised of many nerves (eg. damaged region of the spinal cord). The nerve injury site may be in the central nervous system or peripheral nervous system or in any region needing repair. The nerve injury site may form as a result of damage caused by stroke. The nerve injury site may be in the brain as a result of surgery, brain tumour removal or therapy following a cancerous lesion. The nerve injury site may result from stroke, Parkinson's disease, Alzheimer's disease, amyotrophic lateral sclerosis (ALS), diabetes or any other type of neurodegenerative disease.

The term "cargo" refers to a molecule other than the transport moiety and that is either (1) not inherently capable of entering a cell (e.g., cell compartment) or (2) not inherently capable of entering a cell (e.g., cell compartment) at a useful rate. The term "cargo" as used herein refers either to a molecule per se, i.e., before conjugation, or to the cargo moiety of a transport polypeptide-cargo conjugate. Examples of "cargo" include, but are not limited to, small molecules and macromolecules such as polypeptides, nucleic acids (polynucleotides), polysaccharides and chemicals.

As used herein, the term "delivery agent" relates to an agent comprising a cargo moiety and a transport moiety. Examples of cargo moiety are discussed above and includes for example ADP-ribosyl transferase C3 and ADP-ribosyl transferase C3 analogues. Examples of transport moiety comprise for example SEQ ID NO: 48 and analogues thereof.

"Polynucleotide" generally refers to any polyribonucleotide or polydeoxyribonucleotide, which may be unmodified RNA or DNA, or modified RNA or DNA. "Polynucleotides" include, without limitation single-and double-stranded DNA, DNA that is a mixture of single-and double-stranded regions, single-and double-stranded RNA, and RNA that is a mixture of single-and double-stranded regions, hybrid molecules comprising DNA and RNA that may be single-stranded or, more typically, double-stranded or a mixture of single-and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

"Polypeptides" refers to any peptide or protein comprising two or more amino acids joined to each other by peptide bonds or modified peptide bonds (i.e., peptide isosteres). "Polypeptide" refers to both short chains, commonly referred as peptides, oligopeptides or oligomers, and to longer chains generally referred to as proteins. As described above, polypeptides may contain amino acids other than the 20 gene-encoded amino acids.

As used herein the term "analogues" relates to mutants, variants, chimeras, fusions, deletions, additions and any other type of modifications made relative to a given polypeptide.

The term "analogue" is synonym of homologue, derivative and chemical equivalent or biological equivalent.

As used herein, the term "homologous" sequence relates to nucleotide or amino acid sequence derived from the DNA sequence or polypeptide sequence of C3APL, C3APLT, C3APS, C3-TL, C3-TS, C3Basic1, C3Basic2 and C3Basic3.

As used herein, the term "heterologous" sequence relates to DNA sequence or amino acid sequence of a heterologous polypeptide and includes sequence other than that of C3APL, C3APLT, C3APS, C3-TL, C3-TS, C3Basic1, C3Basic2 and C3Basic3.

As used herein the term "basic amino acid rich region" relates to a region of a protein with a high content of the basic amino acids such as Arginine, Histidine, Asparagine, Glutamine, Lysine (Lys). A "basic amino acid rich region" may have, for example 15% or more (up to 100%) of basic amino acids. In some instance, a "basic amino acid rich region" may have less than 15% of basic amino acids and still function as a transport agent region. More preferably, a basic amino acid region will have 30% or more (up to 100%) of basic amino acids.

As used herein the term "proline rich region" refers to a region of a protein with 5% or more (up to 100%) of proline in its sequence. In some instance a "proline rich region" may have between 5% and 15% of prolines. Additionally, a "proline rich region" refers to a region, of a protein containing more prolines than what is generally observed in naturally occurring proteins (e.g., proteins encoded by the human genome). "Proline rich region" of the present invention function as a transport agent region.

The term "proline-rich region" can further refer to any linear sequence of 10 amino acids linked together by peptide amide bonds within a molecule comprising a peptide or protein, wherein at least 3 out of the 10 amino acids in the linear sequence are proline residues, wherein each proline is covalently linked in a peptide amide bond at its nitrogen and in another peptide amide bond at its carboxylic (carbonyl) site. A proline-rich region in any 10 amino acid sequence within a peptide can comprise 2 or more proline residues and 8 or fewer non-proline amino acids. For example, in one aspect, a proline-rich region in a peptide comprising a 10 amino acid sequence within a peptide comprising 10 or more amino acids can comprise 2 proline residues and 8 non-proline amino acid residues distributed in any combination among the 10 amino acids. In another aspect, a proline-rich region in a peptide comprising a 10 amino acid sequence within a peptide comprising 10 or more amino acids can comprise 3 proline residues and 7 non-proline amino acid residues distributed in any combination among the 10 amino acids. In another aspect, a proline-rich region in a peptide comprising a 10 amino acid sequence within a peptide comprising 10 or more amino acids can comprise 4 proline residues and 6 non-proline amino acid residues distributed in any combination among the 10 amino acids. In another aspect, a proline-rich region in a peptide comprising a 10 amino acid sequence within a peptide comprising 10 or more amino acids can comprise 5 proline residues and 5 non-proline amino acid residues distributed in any combination among the 10 amino acids. In another aspect, a proline-rich region in a peptide comprising a 10 amino acid sequence within a peptide comprising 10 or more amino acids can comprise 6 proline residues and 4 non-proline amino acid residues distributed in any combination among the 10 amino acids. In another aspect, a proline-rich region in a peptide comprising a 10 amino acid sequence within a peptide comprising 10 or more amino acids can comprise 7 proline residues and 3 non-proline amino acid residues distributed in any combination among the 10 amino acids. In another aspect, a proline-rich region in a peptide comprising a 10 amino acid sequence within a peptide comprising 10 or more amino acids can comprise 8 proline residues and 2 non-proline amino acid residues distributed in any combination among the 10 amino acids. In another aspect, a proline-rich region in a peptide comprising a 10 amino acid sequence within a peptide comprising 10 or more amino acids can comprise 9 proline residues and 1 non-proline amino acid residue distributed in any combination among the 10 amino acids. In another aspect, a proline-rich region in a peptide comprising a 10 amino acid sequence within a peptide comprising 10 or more amino acids can comprise 10 proline residues.

In another aspect, a "proline-rich region" refers to an amino acid sequence region of a protein containing more prolines than that which is generally observed in naturally occurring proteins (e.g., proteins encoded by the human genome).

A "proline-rich region" of a peptide in a composition of the present invention can function to enhance the rate of transport of a fusion protein of this invention through a cell membrane.

A non-proline-rich region of a peptide or protein can comprise a sequence of 10 amino acids covalently linked by peptide bonds, which region contains zero or one proline residues.

A cell membrane transport-enhancing peptide of a composition of this invention can comprise one or more than one proline-rich regions, each of which can be the same or different sequence of amino acids, and each of which is covalently linked together by a peptide bond or by the peptide bonds comprising one or more non-proline-rich amino-acid sequence which may each be the same or different when the non-proline-rich amino-acid sequence comprises more than 10 amino acids.

In one aspect of this invention, a preferred composition comprises a cell-permeable fusion protein conjugate comprising a proline-rich polypeptidic cell-membrane transport moiety comprising a proline-rich amino acid sequence added to the C-terminal region of a *Clostridium botulinum* C3 exotransferase unit, or a functional analog thereof, in a fusion protein conjugate. An especially preferred composition is a fusion protein designated C3APLT. In another aspect of this invention, a preferred composition comprises a cell-permeable fusion protein conjugate comprising a proline-rich polypeptidic cell-membrane transport moiety comprising a proline-rich amino acid sequence added to the N-terminal region of a *Clostridium botulinum* C3 exotransferase unit, or a functional analog thereof, in a fusion protein conjugate. Fusion protein compositions comprising a proline-rich amino acid sequence added to the N-terminal region of a *Clostridium botulinum* C3 exotransferase unit, or a functional analog thereof, are sometimes referred to herein as analogs or variants of C3APLT.

Fusion protein functional analogs of a *Clostridium botulinum* C3 exotransferase unit can comprise polypeptides such as biologically active fragments and altered-amino-acid-sequence analogs of a fusion protein such as C3APLT, wherein the biological activity of such fragments and altered-amino-acid-sequence analogs of C3APLT derives from a mechanism of action essentially similar to that of C3APLT. Such fragments can comprise or encompass amino acid sequences having truncations of one or more amino acids relative to that in C3APLT. Such fragments comprise or encompass amino acid sequences having truncations (or eliminations) of one or more amino acids relative to the sequence of amino acids in C3APLT, wherein a truncation may originate from the amino or N-terminus, from the carboxy or C-terminus, or from the interior of the protein sequence. Analogs and variants of a fusion protein such as C3APLT of the invention can comprise an insertion or a substitution of one or more amino acids.

Compositions of this invention comprising fragments, analogs and variants useful in this invention have the biological property of C3APLT and C3 that is capable of inactivation a Rho GTPase by ADP-ribosylation. Preferably a fusion protein of this invention is capable of inactivation of more than one Rho GTPase. Preferably the activity of a fusion protein of this invention with respect to ADP-ribosylation of a Rho GTPase is in the range of 0.5 to 10 times the activity of *Clostridium botulinum* C3 in inactivation of a Rho GTPase, more preferably 0.5 to 100 times the activity of *Clostridium botulinum* C3 in inactivation of a Rho GTPase, and most preferably 0.8 to 1000 times the activity of *Clostridium botulinum* C3 in inactivation of a Rho GTPase.

With respect to inactivation of a Rho GTPase by ADP-ribosylation, the activity provided by the presence of the $Glu^{173}$ residue in *Clostridium botulinum* C3 exoenzyme is present in fusion proteins of this invention. Preferably, the amino acid sequence of a fusion protein of this invention comprises the $Glu^{173}$ amino acid residue in *Clostridium botulinum* C3 exoenzyme and the fusion protein of this invention exhibits ADP-ribosylation activity in the range of 0.5 to 10 times the ADP-ribosylation activity of *Clostridium botulinum* C3, more preferably 0.5 to 100 times the ADP-ribosylation activity of *Clostridium botulinum* C3, and most preferably 0.8 to 1000 times the ADP-ribosylation activity of *Clostridium botulinum* C3. The particular portion of the structure of *Clostridium botulinum* C3 that must be conserved to retain ADP-ribosylation activity can be found in Saito et al., FEBS Letters, 371:105-109, 1995, the entire contents of which is hereby incorporated by reference.

As used herein the term "to help neuron make new connections with other cells" or "helping neurons to make new cell connection" means that upon treatment of cells (e.g., neuron(s)) or tissue with a drug delivery construct, a conjugate, a fusion-protein, a polypeptide or a pharmaceutical compositions of the present invention, neurons may grow (develop) for example new dendrite, new axon or new neurite (i.e., cell bud), or already existing dendrite(s), axon or neurite (i.e., cell bud) are induce to grow to a greater extent.

As used herein, the term "vector" refers to an autonomously replicating DNA or RNA molecule into which foreign DNA or RNA fragments are inserted and then propagated in a host cell for either expression or amplification of the foreign DNA or RNA molecule. The term "vector" comprises and is not limited to a plasmid (e.g., linearized or not) that can be used to transfer DNA sequences from one organism to another.

The term "pharmaceutically acceptable carrier" or "adjuvant" and "physiologically acceptable vehicle" and the like are to be understood as referring to an acceptable carrier or adjuvant that may be administered to a patient, together with a compound of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

As used herein, "pharmaceutical composition" means therapeutically effective amounts (dose) of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral routes. In one embodiment the pharmaceutical composition is administered parenterally, paracancerally, transmucosally, transdermally, intramuscularly, intravenously, intradermally, subcutaneously, intraperitonealy, intraventricularly, intracranially intratumorally or more preferably, directly at a central nervous system (CNS) lesion site or a peripheral nervous system (PNS) lesion site.

In addition, the term "pharmaceutically effective amount" or "therapeutically effective amount" refers to an amount (dose) effective in treating a patient, having, for example, a nerve injury. It is also to be understood herein that a "pharmaceutically effective amount" may be interpreted as an amount giving a desired therapeutic effect, either taken into one dose or in any dosage or route or taken alone or in combination with other therapeutic agents. In the case of the present invention, a "pharmaceutically effective amount" may be understood as an amount of ADP-ribosyl transferase C3 or ADP-ribosyl transferase C3 analogues (e.g., fusion proteins) of the present invention which may for example, suppress (e.g., totally or partially) the inhibition of neuronal axon growth, facilitate axon growth, prevent cell apoptosis, suppress Rho activity, help regenerate injured axon, or which may help neurons to make new connections with other cells.

As may be appreciated, a number of modifications may be made to the polypeptides of the present invention, such as for example the active agent region (e.g., ADP-ribosyl transferase C3 or ADP-ribosyl transferase C3 analogue) or the transport agent region (e.g., a subdomain of HIV Tat protein, or a homeodomain of antennapedia) and fragments thereof without deleteriously affecting the biological activity of the polypeptides or fragments. Polypeptides of the present invention comprises for example, those containing amino acid sequences modified either by natural processes, such as post-translational processing, or by chemical modification techniques which are known in the art. Modifications may occur anywhere in a polypeptide including the polypeptide backbone, the amino acid side-chains and the amino or carboxy termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, $2^{nd}$ Ed., T. E. Creighton, W.H. Freeman and Company, New-York, 1993).

Other type of polypeptide modification may comprises for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide. Polypeptides of the present invention comprise for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may have the biological properties of polypeptides of the present invention which comprise for example (without being restricted to the present examples) to facilitate neuronal axon growth, to suppress the inhibition of neuronal axon growth, to facilitate neurite growth, to inhibit apoptosis, to treat nerve injury, to regenerate injured axon and/or to act as a Rho antagonist.

As it may be exemplified (Example 13: reverse Tat sequence), in some instance, the order of the amino acids in a particular polypeptide is not critical. As for the transport agent region described herein, the transport function of this region may be preserved even if the amino acids are not in their original (as it is found in nature) order (sequence).

Example of substitutions may be those, which are conservative (i.e., wherein a residue is replaced by another of the same general type). As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same group as that of the amino acid being replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA may also be made. For example, alternative residues include the omega amino acids of the formula $NH_2(CH_2)_n COOH$ wherein n is 2-6. These are neutral nonpolar amino acids, as are sarcosine, t-butyl alanine, t-butyl glycine, N-methyl isoleucine, and norleucine. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that mutants or variants may be generated by substitutional mutagenesis and retain the biological activity of the polypeptides of the present invention. These variants have at least one amino acid residue in the protein molecule removed and a different residue inserted in its place (one or more nucleotide in the DNA sequence is changed for a different one using known molecular biology techniques, giving a different amino acid upon translation of the corresponding messenger RNA to a polypeptide). For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as "conservative substitutions" are shown in Table 1. If such substitutions result in a change not desired, then other type of substitutions, denominated "exemplary substitutions" in Table 1, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

i. hydrophobic: norleucine, methionine (Met), Alanine (Ala), Valine (Val), Leucine (Leu), Isoleucine (Ile)
 ii. neutral hydrophilic: Cysteine (Cys), Serine (Ser), Threonine (Thr)
 iii. acidic: Aspartic acid (Asp), Glutamic acid (Glu)

iv. basic: Asparagine (Asn), Glutamine (Gln), Histidine (His), Lysine (Lys), Arginine (Arg)
v. residues that influence chain orientation: Glycine (Gly), Proline (Pro); and
vi. aromatic: Tryptophan (Trp), Tyrosine (Tyr), Phenylalanine (Phe)

Non-conservative substitutions will entail exchanging a member of one of these classes for another.

TABLE 1

Preferred amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Amino acids sequence insertions (e.g., additions) include amino and/or carboxyl-terminal fusions ranging in length from one residue to polypeptides containing a hundred or more residues, as well as intrasequence insertions of single or multiple amino acid residues. Other insertional variants include the fusion of the N-or C-terminus of the protein to a homologous or heterologous polypeptide forming a chimera. Chimeric polypeptides (i.e., chimeras, polypeptide analogue) comprise sequence of the polypeptides of the present invention fused to homologous or heterologous sequence. Said homologous or heterologous sequence encompass those which, when formed into a chimera with the polypeptides of the present invention retain one or more biological or immunological properties.

Other type of chimera generated by homologous fusion includes new polypeptides formed by the repetition of two or more polypeptides of the present invention. The number of repeat may be, for example, between 2 and 50 units (i.e., repeats). In some instance, it may be useful to have a new polypeptide with a number of repeat greater than 50. For example, it may be useful to fuse (using cross-linking techniques or recombinant DNA technology techniques) polypeptides such as C3APL, C3APLT, C3APS, C3-TL, C3-TS, C3Basic1, C3Basic2 and C3Basic3 either to themselves (e.g., C3APLT fused to C3APLT) or to another polypeptide of the present invention (e.g., C3APLT fused to C3APL).

In addition, a transport agent such as for example, a sub-domain of HIV Tat protein, and a homeodomain of antennapedia may be repeated more than one time in a polypeptide comprising the ADP-ribosyl transferase C3 or ADP-ribosyl transferase C3 analogues. The transport agent region may be either at the amino-terminal region of an ADP-ribosyl transferase C3 or ADP-ribosyl transferase C3 analogues or at its carboxy-terminal region or at both regions. The repetition of a transport agent region may affect (e.g., increase) the uptake of the ADP-ribosyl transferase C3 or ADP-ribosyl transferase C3 analogues by a desired cell.

Heterologous fusion includes new polypeptides made by the fusion of polypeptides of the present invention with heterologous polypeptides. Such polypeptides may include but are not limited to bacterial polypeptides (e.g., betalactamase, glutathione-S-transferase, or an enzyme encoded by the *E. coli* trp locus), yeast protein, viral proteins, phage proteins, bovine serum albumin, chemotactic polypeptides, immunoglobulin constant region (or other immunoglobulin regions), albumin, or ferritin.

Other type of polypeptide modification includes amino acids sequence deletions (e.g., truncations). Those generally range from about 1 to 30 residues, more preferably about 1 to 10 residues and typically about 1 to 5 residues.

Mutants, Variants and Analogues Proteins

Mutant polypeptides will possess one or more mutations, which are deletions (e.g., truncations), insertions (e.g., additions), or substitutions of amino acid residues. Mutants can be either naturally occurring (that is to say, purified or isolated from a natural source) or synthetic (for example, by performing site-directed mutagenesis on the encoding DNA or made by other synthetic methods such as chemical synthesis). It is thus apparent that the polypeptides of the invention can be either naturally occurring or recombinant (that is to say prepared from the recombinant DNA techniques).

A protein at least 50% identical, as determined by methods known to those skilled in the art (for example, the methods described by Smith, T. F. and Waterman M. S. (1981) Ad. Appl. Math., 2:482-489, or Needleman, S. B. and Wunsch, C. D. (1970) J. Mol. Biol., 48: 443-453), to those polypeptides of the present invention, for example C3APL, C3APLT, C3APS, C3-TL, C3-TS, C3Basic1, C3Basic2 and C3Basic3 are included in the invention, as are proteins at least 70% or 80% and more preferably at least 90% identical to the protein of the present invention. This will generally be over a region of at least 5, preferably at least 20 contiguous amino acids.

"Variant" as the term used herein, is a polynucleotide or polypeptide that differs from reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion and truncations in the polypeptide encoded by the reference sequence, as discussed herein. A typical variant of a polypeptide differs in amino acid sequence from another, reference polypeptide. Generally, differences are limited so that the sequence of the reference polypeptide and the variant are closely similar overall and, in many regions, identical. A variant and reference polypeptide may differ in amino acid by one or more substitutions, additions, deletions, or any combination therefore. A substituted or inserted amino acid residue may or may not be one encoded by the genetic code. A variant polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

Amino acid sequence variants may be prepared by introducing appropriate nucleotide changes into DNA, or by in vitro synthesis of the desired polypeptide. Such variant include, for example, deletions, insertions, or substitutions of residues within the amino acid sequence. A combination of deletion, insertion and substitution can be made to arrive at the final construct, provided that the final protein product possesses the desired biological activity, or characteristics. The amino acid changes also may alter posttranslational processes such as changing the number or position of the glycosylation sites, altering the membrane anchoring characteristics, altering the intra-cellular location by inserting, deleting or otherwise affecting the transmembrane sequence of the native protein, or modifying its susceptibility to proteolytic cleavage.

Unless otherwise indicated, the recombinant DNA techniques utilized in the present invention are standard procedures, known to those skilled in the art. Example of such techniques are explained in the literature in sources such as J. Perbal, A Practical Guide to Molecular Cloning, John Wiley and Sons (1984), J. Sambrook et al., Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present) and are incorporated herein by reference.

It is to be understood herein, that if a "range" or "group of substances" is mentioned with respect to a particular characteristic (e.g. amino acid groups, temperature, pressure, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, a) with respect to a sequence comprising up to 50 base units it is to be understood as specifically incorporating herein each and every individual unit, as well as sub-range of units;
b) with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;
c) with respect to polypeptides, a polypeptide analogue comprising a particular sequence and having an addition of at least one amino acid to its amino-terminus or to its carboxy terminus is to be understood as specifically incorporating each and every individual possibility, such as for example one, two, three, ten, eighteen, forty, etc.;
d) with respect to polypeptides, a polypeptide analogue having at least 90% of its amino acid sequence identical to a particular amino acid sequence is to be understood as specifically incorporating each and every individual possibility (excluding 100%), such as for example, a polypeptide analogue having 90%, 90.5%, 91%, 93.7%, 97%, 99%, etc., of its amino acid sequence identical to a particular amino acid sequence;
e) with respect to polypeptides, a polypeptide analogue having at least 70% of its amino acid sequence identical to a particular amino acid sequence is to be understood as specifically incorporating each and every individual possibility (excluding 100%), such as for example, a polypeptide analogue having 70%, 72.3%, 73%, 88.6%, 98% etc., of its amino acid sequence identical to a particular amino acid sequence;
f) with respect to polypeptides, a polypeptide analogue having at least 50% of its amino acid sequence identical to a particular amino acid sequence is to be understood as specifically incorporating each and every individual possibility (excluding 100%), such as for example, a polypeptide analogue having 50%, 54%, 66.7%, 70.2%, 84%, 93% etc., of its amino acid sequence identical to that particular amino acid sequence;
g) with respect to polypeptide, a polypeptide comprising at least one transport agent region is to be understood as specifically incorporating each and every individual possibility, such as for example a polypeptide having one, two, five, ten, etc., transport agent region; and
h) similarly with respect to other parameters such as low pressures, concentrations, elements, etc.

It is also to be understood herein that "g" or "gm" is a reference to the gram weight unit; and that "C", or "° C." is a reference to the Celsius temperature unit.

TABLE 2

Abbreviations

| Abbreviation | Full name |
|---|---|
| C3 | ADP-ribosyl transferase C3 |
| NGF | Nerve growth factor |
| BDNF | Brain-derived neurotrophic factor |
| C. or ° C. | Degree Celcius |
| ml | milliliter |
| µl or ul | microliter |
| µM or uM | micromolar |
| mM | millimolar |
| M | molar |
| N | normal |
| CNS | Central nervous system |
| PNS | Peripheral nervous system |
| HIV | Human immunodeficiency virus |
| HIV-1 | Human immunodeficiency virus type-1 |
| kDa | kilodalton |
| GST | Glutathione S-transferase |
| MTS | Membrane transport sequence |
| SDS-PAGE | Sodium dodecyl sulfte polyacrylamide gel electrophoresis |
| PBS | Phosphate buffered saline |
| U | unit |
| BBB | Basso, Beattie Breshnahan behavior recovery scale |
| IPTG | Isopropyl.beta.-D-thiogalactopyranoside |
| rpm | Rotation per minutes |
| DTT | dithiothreitol |
| PMSF | Phenylmethylsulfonyl fluoride |
| NaCl | Sodium chloride |
| MgCl$_2$ | Magnesium chloride |
| HBSS | Hank's balanced salt solution |
| NaOH | Sodium hydroxide |
| CSPG | chondroitin sulfate proteoglycan |
| PKN | Protein kinase N |
| RSV | Rous sarcoma virus |
| MMTV | Mouse mammary tumor virus |
| LTR | Long terminal repeat |
| HL | Hind limb |
| FL | Fore limb |
| neo | neomycin |
| hygro | hygromycin |
| IN-1 | monoclonal antibody called IN-1 |
| ADP | Adenosine di-phosphate |
| ATP | Adenosine tri-phosphate |
| $^{32}$P | Isotope 32 of phosphorus |
| DHFR | Dihydrofolate reductase |
| PCR | Polymerase chain reaction |

The invention in particular provides C3-like proteins, which may have additional amino acids added to the carboxy terminal end of the C3 proteins. Examples of such proteins includes:

C3APL: (C3 antennapedia-long) created by annealing sequences from the antennapedia transcription factor to the 3' end of the sequence encoding C3 cDNA. The long antennapedia sequence of 60 amino acids containing the homeodomain of antennapedia, was used;

C3APLT: (C3 antennapedia-truncated) created by annealing sequences from the antennapedia transcription factor to the 3' end of the sequence encoding C3 cDNA. This clone with a frameshift mutation gives a proline-rich transport peptide with good transport activity. This sequence is truncated i.e. shorter than C3APL.

C3APS: A short 11 amino acid sequence of antennapedia that has transmembrane transport properties was fused to the carboxy terminal of C3 to create C3APS;

C3-TL: C3 Tat-long created by fusing amino acids 27 to 72 of Tat to the carboxy terminal of C3 protein;

C3-TS: C3 Tat-short created by fusing the amino acids YGRKKRRQRRR (SEQ ID NO:49) to the C3 protein;

C3Basic1 a random basic charge sequence added to the C-terminal of C3;

C3Basic2: a random basic charge sequence added to the C-terminal of C3;

C3Basic3: C3 Tat-short created by fusing the reverse sequence of Tat amino acids RRQRRKKR (SEQ ID NO:50) to the C3 protein.

C3-07: The sequence of C3APLT modified to remove the GST sequence used for purification, and with silent amino acid changes induced when cloned into the pEt expression vector, but which silent amino acid changes maintaining ADP-ribosylation activity of the protein.

C3-07Q189A: The sequence of C3-07 with an amino acid substitution of Glu 189 to Gln 189 in the catalytic domain that removes ADP-ribosylation activity to create an inactive construct.

It has been found that conjugates or fusion proteins (C3-like proteins) Rho antagonists of the present invention are effective to stimulate repair in the CNS after spinal cord injury. The increased cell permeability of new Rho antagonist (new chimeric C3) would now allow treatment of victims of stroke and neurodegenerative disease because Rho signaling pathway is important in repair after stroke (Hitomi, et al. (2000) 67: 1929-39. Trapp et al 2001. Mol. Cell. Neurosci. 17: 883-84). Treatment with Rho antagonists in the adhesive delivery system could be used to enhance the rate of axon growth in the PNS. Also, evidence in the literature now links Rho signaling with formation of Alzheimer's disease tangles through its ability to activate PKN which then phosphorylates tau and neurofilaments (Morissette, et al. (2000) 278: H1769-74., Kawamata, et al. (1998) 18: 7402-10., Amano, et al. (1996) 271: 648-50., Watanabe, et al. (1996) 271: 645-8.). Therefore, Rho antagonists are expected to be useful in the treatment of Alzheimer's disease. The new chimeric C3 drugs should be able to diffuse readily and therefore can promote repair for diseases that are neurodegenerative. Examples include, but are not limited to stroke, traumatic brain injury, Parkinson's disease, Alzheimer's disease and ALS. Moreover, it is now well established that Rho signaling antagonists are effective in the treatment of other diseases. These include, but are not limited to eye diseases such as glaucoma (Honjo, et al. (2001) 42: 137-44., Rao, et al. (2001) 42: 1029-1037) eye diseases such as macular degeneration, retinitis pigmentosa, Stargardt's Disease, diabetic retinopathy, hypertensive retinopathy, and occlusive retinopathy, cancer cell migration and metastasis (Sahai, et al. (1999) 9: 136-45., Takamura, et al. (2001) 33: 577-81., Imamura, et al. (2000) 91: 811-6). The effects of the Rho signaling pathway on smooth muscle relaxation are well established. This has led to the identification of Rho signaling antagonists as effective in treatment of hypertension (Chitaley, et al. (2001) 3: 139-144., Somlyo (1997) 389: 908-911, Uehata, et al. (1997) 389: 990-994), asthma (Nakahara, et al. (2000) 389: 103-6., Ishizaki, et al. (2000) 57: 976-83), and vascular disease (Miyata, et al. (2000) 20: 2351-8., Robertson, et al. (2000) 131: 5-9.) as well as penile erectile dysfunction (Chitaley, et al. (2001) 7: 119-22.). Rho is also important as a cardioprotective protein (Lee et al. 2001. FASEB J. 15:1886-1894).

Rho GTPases include members of the Rho, Rac and Cdc42 family of proteins. Our invention concerns Rho family members of the Rho class. Rho proteins consist of different variants encoded by different genes. For example, PC-12 cells express RhoA, RhoB and RhoC (Lehmann et al 1999 supra); PC-12 cells: Pheochromocytom cell line (Greene A and Tischler, A S PNAS 73:2424 (1976). To inactivate Rho proteins inside cells, Rho antagonists of the C3 family type are effective because they inactivate all forms of Rho (e.g. RhoA, Rho B etc). In contrast, gene therapy techniques, such as introduction of a dominant negative RhoA family member into a diseased cell, will only inactivate that specific RhoA family member.

Recombinant C3 proteins, or C3 proteins that retain the ribosylation activity are also effective in our delivery system and are covered by this invention. In addition, Rho kinase is a well-known target for active Rho, and inactivating Rho kinase has the same effect as inactivating Rho, at least in terms of neurite or axon growth (Kimura and Schubert (1992) Journal of Cell Biology. 116:777-783, Keino-Masu, et al. (1996) Cell. 87:175-185, Matsui, et al. (1996) EMBO J. 15:2208-2216, Matsui, et al. (1998) J. Cell Biol. 140:647-657, Ishizaki (1997) FEBS Lett. 404: 118-124), the biological activity that concerns this invention.

The C3 polypeptides of the present invention include biologically active fragments and analogues of C3; fragments encompass amino acid sequences having truncations of one or more amino acids, wherein the truncation may originate from the amino terminus, carboxy terminus, or from the interior of the protein. Fragments containing Glu(173) of C3 are included in this invention (Saito et al. 1995. FEBS Lett. 371-105). Analogues of the invention involve an insertion or a substitution of one or more amino acids. Fragments and analogues will have the biological property of C3 that is capable of inactivating Rho GTPase on Asn(41) on Rho. Also encompassed by the invention are chimeric polypeptides comprising C3 amino acid sequences fused to heterologous amino acid sequences. Said heterologous sequences encompass those which, when formed into a chimera with C3 retain one or more biological or immunological properties of C3. A host cell transformed or transfected with nucleic acids encoding C3 protein or C3 chimeric protein are also encompassed by the invention. Any host cell which produces a polypeptide having at least one of the biological properties of C3 may be used. Specific examples include bacterial, yeast, plant, insect or mammalian cells. In addition, C3 protein may be produced in transgenic animals. Transformed or transfected host cells and transgenic animals are obtained using materials and methods that are routinely available to one skilled in the art. Host cells may contain nucleic acid sequences having the full-length gene for C3 protein including a leader sequence and a C-terminal membrane anchor sequence (see below) or, alternatively, may contain nucleic acid sequences lacking one or both of the leader sequence and the C-terminal membrane anchor sequence. In addition, nucleic acid fragments, variants and analogues which encode a polypeptide capable of retaining the biological activity of C3 may also be resident in host expression systems.

C3 is produced as a 26 kDa protein. The full length C3 protein inactivates Rho by ADP-ribosylating asparagine 41 of Rho A (Han et al. (2001) J. Mol. Biol. 305: 95). Truncated, elongated or altered C3 proteins or C3-derived peptides that retain the ability to ribosylate Rho are included in this invention and can be used to make fusion proteins. The crystal structure of C3 has been determined giving insight to elements of the C3 protein that could be changed without affecting ribosylating activity (Han et al. (2001) J. Mol. Biol. 305: 95).

The Rho antagonist that is a recombinant proteins can be made according to methods present in the art. The proteins of the present invention may be prepared from bacterial cell extracts, or through the use of recombinant techniques. In general, C3 proteins according to the invention can be produced by transformation (transfection, transduction, or infection) of a host cell with all or part of a C3-encoding DNA fragment in a suitable expression vehicle. Suitable expression vehicles include: plasmids, viral particles, and phages. For insect cells, baculovirus expression vectors are suitable. The entire expression vehicle, or a part thereof, can be integrated into the host cell genome. In some circumstances, it is desirable to employ an inducible expression vector.

Those skilled in the field of molecular biology will understand that any of a wide variety of expression systems can be used to provide the recombinant protein. The precise host cell used is not critical to the invention. The C3 and C3-like proteins may be produced in a prokaryotic host (e.g., *E. coli* or *B. subtilis*) or in a eukaryotic host (e.g., *Saccharomyces* or *Pichia*; mammalian cells, e.g., COS, NIH 3T3, CHO, BHK, 293, or HeLa cells; or insect cells).

To determine the relative and effective Rho antagonist activity of the compositions of this invention, a tissue culture bioassay system can be used. A fusion protein such as C3APLT at a concentration range of from about 0.01 to about 10 µg/ml (microgram per milligram) is useful and is not toxic to cells.

Proteins and polypeptides may also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.). The methods of transformation or transfection and the choice of expression vehicle will depend on the host system selected.

The host cells harboring the expression vehicle can be cultured in conventional nutrient media adapted as need for activation of a chosen gene, repression of a chosen gene, selection of transformants, or amplification of a chosen gene. One expression system is the mouse 3T3 fibroblast host cell transfected with a pMAMneo expression vector (Clontech, Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a C3 or C3-like protein would be inserted into the pMAMneo vector in an orientation designed to allow expression. The recombinant C3 or C3-like protein would be isolated as described below. Other preferable host cells that can be used in conjunction with the pMAMneo expression vehicle include COS cells and CHO cells (ATCC Accession Nos. CRL 1650 and CCL 61, respectively).

C3 polypeptides can be produced as fusion proteins. For example, expression vectors may be used to create lacz fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Another strategy to make fusion proteins is to use the His tag system.

In an insect cell expression system, *Autographa californica* nuclear polyhedrosis virus AcNPV), which grows in *Spodoptera frugiperda* cells, is used as a vector to express foreign genes. A C3 coding sequence can be cloned individually into non-essential regions (for example the polyhedrin gene) of the virus and placed under control of an AcNPV promoter, e.g., the polyhedrin promoter. Successful insertion of a gene encoding a C3 or C3-like protein (polypeptide) will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed (see, Lehmann et al for an example of making recombinant MAG protein).

In mammalian host cells, a number of viral-based expression systems can be utilized. In cases where an adenovirus is used as an expression vector, the C3 nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a C3 gene product in infected hosts.

Specific initiation signals may also be required for efficient translation of inserted nucleic acid sequences. These signals include the ATG initiation codon and adjacent sequences. In cases where an entire native C3 gene or cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, W138, and in particular, choroid plexus cell lines.

Alternatively, a C3 protein can be produced by a stably-transfected mammalian cell line. A number of vectors suitable for stable transfection of mammalian cells are available to the public; methods for constructing such cell lines are also publicly available. In one example, cDNA encoding the C3 protein may be cloned into an expression vector that includes the dihydrofolate reductase (DHFR) gene. Integration of the plasmid and, therefore, the C3 or C3-like protein-encoding gene into the host cell chromosome is selected for by including 0.01-300 µM (micromole) methotrexate in the cell culture medium (as described in Ausubel et al., supra). This dominant selection can be accomplished in most cell types. Recombinant protein expression may be increased by DHFR-mediated amplification of the transfected gene. Methods for selecting cell lines bearing gene amplifications are known in the art; such methods generally involve extended culture in medium containing gradually increasing levels of methotrexate. DHFR-containing expression vectors commonly used for this purpose include pCVSEII-DHFR and pAdD26SV(A). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

A number of other selection systems may be used, including but not limited to the herpes simplex virus thymidine kinase, hypoxanthine-guanine phosphoribosyltransferase, and adenine phosphoribosyltransferase genes can be employed in tk, hgprt, or aprt cells, respectively. In addition, gpt, which confer resistance to mycophenolic acid; neo, which confers resistance to the aminoglycoside G-418; and hygro, which confers resistance to hygromycin may be used.

Alternatively, any fusion protein can be readily purified by utilizing an antibody specific for the fusion protein being expressed. For example, a system described in Janknecht et al. (1981) Proc. Natl. Acad. Sci. USA 88, 8972, allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni2+nitriloacetic acid-agarose columns, and histidine-tagged proteins are selectively eluted with imidazole-containing buffers.

Alternatively, C3, C3-like protein or a portion (fragment) thereof, can be fused to an immunoglobulin Fc domain. Such a fusion protein can be readily purified using a protein A column.

To test Rho antagonists for activity, a tissue culture bioassay system was used. This bioassay is used to define activity of Rho antagonists that will be effective in promoting axon regeneration in spinal cord injury, stroke or neurodegenerative disease.

Neurons do not grow neurites on inhibitory myelin substrates. When neurons are placed on inhibitory substrates in tissue culture, they remain rounded. When an effective Rho antagonist is added, the neurons are able to grow neurites on myelin substrates. The time that it takes for neurons to growth neurites upon the addition of a Rho antagonist is the same as if neurons had been plated on growth permissive substrate such as laminin or polylysine, typically 1 to 2 days in cell culture. The results can be scored visually. If needed, a quantitative assessment of neurite growth can be performed. This involved measuring the neurite length in a) control cultures where neurons are plated on myelin substrates and left untreated b) in positive control cultures, such as neurons plated on polylysine c) or treating cultures with different concentrations of the test antagonist.

To test C3 in tissue culture, it has been found that the best concentration is 25-50 ug/ml. (Lehmann et al, 1999. J. Neurosci. 19: 7537-7547; Jin & Strittmatter, 1997. J. Neurosci. 17: 6256-6263). Thus, high concentrations of this Rho antagonist are needed as compared to the growth factors used to stimulate neurite outgrowth. Growth factors, such as nerve growth factor (NGF) are used at concentrations of 1-100 ng/ml in tissue culture. However, growth factors are not able to overcome growth inhibition by myelin. Our tissue culture experiments are all performed in the presence of the growth factor BDNF for retinal ganglion cells, or NGF for PC-12 cells. When growth factors have been tested in vivo, typically the highest concentrations possible are used, in the ug/ml range. Also they are often added to the CNS with the use of pumps for prolonged delivery (e.g. Ramer et al, supra). For in vivo experiments the highest concentrations possible was used when working with C3 stored as a frozen 1 mg/ml solution.

The Rho antagonist C3 is stable at 37° C. for at least 24 hours. The stability of C3 was tested in tissue culture with the following experiment. The C3 was diluted in tissue culture medium, left in the incubator at 37° C. for 24 hours, then added to the bioassay system described above, using retinal ganglion cells as the test cell type. These cells were able to extend neurites on inhibitory substrates when treated with C3 stored for 24 hours at 37° C. Therefore, the minimum stability is 24 hours. This is in keeping with the stability projection based on amino acid composition (see sequence data, below).

A compound can be confirmed as a Rho antagonist in one of the following ways:
 a. Cells are cultured on a growth inhibitory substrate as above, and exposed to the candidate Rho antagonist;
 b. Cells of step a) are homogenized and a pull-down assay is performed. This assay is based on the capability of GST-Rhotektin to bind to GTP-bound Rho. Recombinant GST-Rhotektin or GST rhotektin binding domain (GST-RBD) is added to the cell homogenate made from cells cultured as in a). It has been found that inhibitory substrates activate Rho, and that this activated Rho is pulled down by GST-RBD. Rho antagonists will block activation of Rho, and therefore, an effective Rho antagonist will block the detection of Rho when cell are cultured as described by a) above; or
 c. An alternate method for this pull-down assay would be to use the GTPase activating protein, Rho-GAP as bait in the assay to pull down activated Rho, as described (Diekmann and Hall, 1995. In Methods in Enzymology Vol. 256 part B 207-215).

Another method to confirm that a compound is a Rho antagonist is as follows: When added to living cells antagonists that inactivate Rho by ADP-ribosylation of the effector domain can be identified by detecting a molecular weight shift in Rho (Lehmann et al, 1999 supra). The molecular weight shift can be detected after treatment of cells with Rho antagonist by homogenizing the cells, separating the proteins in the cellular homogenate by SDS polyacrylamide gel electrophoresis. The proteins are transferred to nitrocellulose paper, then Rho is detected with Rho-specific antibodies by a Western blotting technique.

Another method to confirm that compound is a Rho-kinase antagonist is as follows:

a. Recombinant Rho kinase tagged with myc epitope tag, or a GST tag or any suitable tag is expressed in Hela cells or another suitable cell type by transfection;
b. The kinase is purified from cell homogenates by immunoprecipitation using antibodies directed against the specific tag (e.g., myc tag or the GST tag); and
c. The recovered immunoprecipitates from b) are incubated with [$^{32}$P] ATP and histone type 2 as a substrate in the presence or absence of the Rho kinase inhibitor. In the absence of Rho kinase inhibitor activity, the Rho kinase phosphorylated histone. In the presence of Rho kinase inhibitor the phosphorylation activity of Rho kinase (i.e. phosphorylation of histone) is blocked, and as such identified the compound as a Rho kinase antagonist.

Turning now to the transport side of the conjugates of the present invention, known methods are available to add transport sequences that allow proteins to penetrate into the cell; examples include membrane translocating sequence (Rojas (1998) 16: 370-375), Tat-mediated protein delivery (Vives (1997) 272: 16010-16017), polyargine sequences (Wender et al. 2000, PNAS 24: 13003-13008) and antennapedia (Derossi (1996) 271: 18188-18193). Examples of known transport agents, moities, subdomains and the like are also shown for example in Canadian patent document no. 2,301,157 (conjugates containing homeodomain of antennapedia) as well as in U.S. Pat. Nos. 5,652,122, 5,670,617, 5,674,980, 5,747,641, and 5,804,604 (conjugates containing amino acids of Tat HIV protein (hereinafter Tat HIV protein is sometimes simply referred to as Tat); the entire contents of each of these patent documents is incorporated herein by reference.

A 16 amino acid region of the third alpha-helix of antennapedia homeodomain has been shown to enable proteins (made as fusion proteins) to cross cellular membranes (PCT international publication number WO 99/11809 and Canadian application No.: 2,301,157 (Crisanti et al,) incorporated herein as references). Here we have generated fusion-proteins comprising C3 and having an antennapedia homeodomain sequence located at the carboxy-terminal end of the fusion-protein. The biological activity (e.g., promoting axon growth) of these fusion proteins was demonstrated on primary mammalian cells such as neurons. Similarly, HIV Tat protein was shown to be able to cross cellular membranes (Frankel A. D. et al., Cell, 55: 1189). We have shown here using a sequence spanning amino acid 27 to 72 of HIV Tat, that Tat-mediated delivery of biologically active C3 protein is possible in neuronal cells and more specifically, in primary neuronal cells.

In addition to HIV Tat and antennapedia-mediated transport of C3 proteins and analogs, new transport sequences (i.e., transport polypeptide moiety, transport agent region, etc.) are presented herein.

Several receptor-mediated transport strategies have been used to try and improve function of ADP ribosylases: these methods include fusing C2 and C3 sequences (Wilde, et al. (2001) 276: 9537-9542.) and use of receptor-mediated transport with the diphtheria toxin receptor (Aullo, et al. (1993) 12: 921-31; Boquet, P. et al. (1995) Meth. Enzymol. 256: 297-306).). These methods have not been demonstrated to dramatically increase the potency of C3. Moreover, these proteins require receptor-mediated transport. This means that the cells must express the receptor, and must express sufficient quantities of the receptor to significantly improve transport. Moreover, when C3 enters the cell by endocytosis, it will be locked within a membrane compartment, and therefore most of it will not be available to inactivate Rho. In the case of diphtheria toxin, not all cells express the appropriate receptor, limiting its potential use. The clinical importance for any of these has not been tested or shown. A C2/C3 fusion protein has also been made to try and improve the effectiveness of C3. In this case, the addition of a C211 binding protein to the tissue culture medium is needed, along with the C2-C3 fusion toxin to allow uptake of C3 by receptor-mediated endocytosis (Barthe et al. (1998) Infection and Immunity 66:1364). The disadvantage of this system is that much of the C3 in the cell will be restrained within a membrane compartment. More importantly, two different proteins must be added separately for transport to occur (Wahl et al. 2000. J. Cell Biol. 149:263), which make this system difficult to apply to in vivo for treatment of disease. Moreover, none of the methods to inactivate Rho with C3 or C3 analogues (C3-like protein) have been demonstrated to be sufficient to overcome growth inhibition in tissue culture, or to promote recovery after CNS damage in vivo.

One strategy which may be used in accordance with the present invention is to exploit the antennapedia homeodomain that is able to transport proteins across the plasma membrane by a receptor-independent mechanism (Derossi (1996) 271: 18188-18193); an alternate strategy is to exploit Tat-mediated delivery (Vives (1997) 272: 16010-16017, Fawell (1994) 91: 664-668, Frankel (1988) 55: 1189-1193).

The Antennapedia strategy has been used for protein translocation into neurons (Derossi (1996) 271: 18188-18193). Antennapedia has, for example, been used to transport biotin-labeled peptides in order to demonstrate the efficacy of the technique; see U.S. Pat. No. 6,080,724 (the entire contents of this patent are incorporated herein by reference). Antennapedia enhances growth and branching of neurons in vitro (Bloch-Gallego (1993) 120: 485-492). Homeoproteins are transcription factors that regulate development of body organization, and antennapedia is a *Drosophila* homeoprotein. Tat on the other hand is a regulatory protein from human immunodeficiency virus (HIV). It is a highly basic protein that is found in the nucleus and can transport reporter genes into cell. Moreover, Tat-linked proteins can penetrate cells after intraperitoneal injection, and it can even cross the blood brain barrier to enter cells within the brain (Schwarze, et al. (1999) 285: 1569-72).

Other transport sequences that have been tested in other contexts, (i.e., to show that they work through the use of reporter sequences), are known. One transport peptide, a 12 mer, AAVLLPVLLAAP (SEQ ID NO:51), is rich in proline. It was made as a GST-MTS fusion protein and is derived from the h region of the Kaposi FGF signal sequence (Royas et al. 1998 Nature Biotech. 16: 370-375. Another example is the sperm fertiline alpha peptide, HPIQIAAFLARIPPIS-SIGTCILK (SEQ ID NO:52) (This is reviewed in Pecheur, J. Sainte-Marie, A. Bienvenuie, D. Hoekstra. 1999. J. Membrane Biol. 167: 1-17). It must be noted however that the alpha helix-breaking propensity of proline (Pro) residues is not a general rule, since the putative fusion peptide of sperm fertilin alpha displays a high alpha helical content in the presence of liposomes. However, the Pro-Pro sequence is required for efficient fusion properties of fertilin. The C3APLT fusion protein that we tested fits the requirement of having a two prolines for making an effective transport peptide. Therefore, proline-rich sequences and random sequences that have helix-breaking propensity that act as effective transporters would also be effective if fused to C3.

In the context of axon growth on inhibitory substrates, axon regeneration after injury, or axon regeneration in the brain or spinal cord, no method using these transport sequences has been devised. In particular, it should be noted that the ability of antennapedia to enhance growth was tested with neurons placed on laminin-coated coverslips. Laminin supports axon growth and overrides growth inhibition (David, et al. (1995) 42: 594-602) thus, it is not a suitable substrate to test the potential for regeneration. There is an enormous wealth of literature over the last 20 years on substances that promote axon growth under such favorable tissue culture conditions, but none of these has lead to clinical advances in the treatment of spinal cord injury. The effect of antennapedia was shown to act as similar to a growth factors. Growth factors do not overcome growth inhibition by CNS growth inhibitory substrates (Lehmann, et al. (1999) 19: 7537-7547, Cai, et al. (1999) 22: 89-101). Growth factors applied in vivo do not support regeneration, only sprouting (Schnell, et al. (1994) 367: 170-173).

The transport sequence may be added to the N-terminal (amino-terminal) sequence of the C3 protein. Alternatively, the transport sequence may be added on the C-terminal (carboxy-terminal) end of the C3 protein; because the C-terminal is already quite basic, this should enhance further the transport properties. This is likely one of the reasons that C3APLT shows activity in addition to its basic charge and the proline-rich sequences.

The new chimeric C3 may be used to treat spinal cord injury to promote functional repair. We have demonstrated that both C3APLT and C3APS can overcome growth inhibition on complex inhibitory substrates that include myelin and mixed chondroitin sulfate proteoglycans. Further, we demonstrate that C3APLT can promote functional recovery after application to injured spinal cord in adult mice. The new chimeric protein may be used to promote axon regeneration and reduce scarring after CNS injury. Scarring is a barrier to nerve regeneration.

The advantage of the new chimeric C3 is the ability to treat the injured axons after a significant delay between the injury and the treatment. Also, the new recombinant protein may be useful in the treatment of chronic injury. The chimeric C3 can also be used to treat neurodegenerative diseases such as Alzheimer's disease and Parkinson's disease where penetration of the Rho antagonist to the affected neuronal population is required for effective treatment. The chimeric C3 (fusion proteins) will also be of benefit for the treatment of stroke and traumatic brain injury. Moreover, much evidence suggests efficacy in the treatment of cancer cell migration. Rho antagonists are also useful in the treatment of disease involving smooth muscle, such as vascular disease, hypertension, asthma, and penile dysfunction.

For treatment of spinal cord injury, the conjugate Rho antagonists of the present invention may be used in conjunction with cell transplantation. Many different cell transplants have been extensively tested for their potential to promote regeneration and repair, including, but not restricted to, Schwann cells, fibroblasts modified to express growth factors, fetal spinal cord transplants, macrophages, embryonic or adult stem cells, and olfactory ensheathing glia. C3 fusion proteins may be used in conjunction with neurotrophins, apoptosis inhibitors, or other agents that prevent cell death. They may be used in conjunction with cell adhesion molecules such as L1, laminin, and artificial growth matrices that promote axon growth. The chimeric C3 constructs of the present invention may also be used in conjunction with the use of antibodies that block growth inhibitory protein substrates to promote axon growth. Examples of such antibody methods are the use of IN-1 or related antibodies (Schnell and Schwab (1990) 343: 269-272) or through the use of therapeutic vaccine approaches (Huang (1999) 24: 639-647).

The compositions of this invention can be administered to the eye, for example by intravenous delivery to the eye, by implantation of a depot comprising a composition of the invention, by injection into the eye or into tissues proximal to the eye.

The bulb of the eye is imbedded in the fat of the orbit from which it is separated by a thin membrane, the fascia bulbi, which envelops the bulb from the optic nerve to the ciliary region. The smooth inner surface of the facia is separated from the outer surface of the sclera by the periscleral lymph space which is continuous with the subdural and subarachnoid cavities. The fascia is perforated by the ciliary vessels and nerves, and fuses with the sheath of the optic nerve and with the sclera around the entrance of the optic nerve. The optic nerve enters its eyeball about 3 millimeters to the nasal side and a little below the level of the central point of the posterior curvature of the eye. Optic nerve fiber growth is centripetal, and during their formation, most optic nerve fibers grow backward into the optic stalk from nerve cells of the retina, but some optic nerve fibers extend and are derived from nerve cells in the brain. The optic nerve fiber layer is composed principally of axons of the retinal ganglion cells that project to the brain through the optic nerve and the supporting glial cells.

The outer layer of the eye comprises the sclera and cornea. The sclera is an opaque, firm membrane, as much as 1 millimeter thick, and constitutes the posterior five-sixths of the eye. The sclera is formed of white fibrous tissue intermixed with fine elastic fibers; flattened connective-tissue corpuscles, some of which are pigmented, are contained in cell spaces between the fibers. Compositions of this invention can be administered for example by injection into and/or through the sclera or by formation of a depot proximal to and/or in the sclera, preferably in the posterior of the eye.

The inner surface of the sclera is separated from the outer surface of the choroid by an extensive lymph space or spatium perichorioideale which is traversed by fine cellular tissue, the lamina suprachorioidea. The sclera is pierced by the optic nerve, and is continuous through the fibrous sheath of this nerve with the dura mater. Where the optic nerve passes through the sclera, the sclera forms a thin cribriform lamina, the lamina cribrosa sclerx. Minute orifices in this lamina serve for the transmission of nervous filaments, and the retinal ganglion cell axons distal to the lamina cribrosa are myelinated by oligodedrocytes. The fibrous septa dividing them from one another are continuous with the membranous processes which separate the bundles of nerve fibers. One of these openings, larger than the rest, occupies the center of the lamina; it transmits the central artery and vein of the retina. Around the entrance of the optic nerve are numerous small apertures for the transmission of the ciliary vessels and nerves. About midway between this entrance and the sclerocorneal junction are four or five large apertures for the transmission of veins, the venæ vorticosæ. Compositions of this invention can be administered, for example by injection or perfusion or from a depot such as an implanted matrix comprising a composition of the invention, into a blood vessel which delivers blood to the retina, preferably to the region proximal to the macula.

The vascular tunic of the eye comprises the choroid, the ciliary body, and the iris. The choroid invests the posterior five-sixths of the bulb of the eye proximal to the retina, and extends forward to the ora serrata of the retina. The ciliary body connects the choroid to the circumference of the iris.

The choroid comprises a thin spongy layer between the sclera and the retina; the choroid is filled with blood vessels. The choroid is a thin, highly vascular, dark brown membrane investing the posterior five-sixths of the globe of the eye; it is pierced behind by the optic nerve, and in this situation is firmly adherent to the sclera. It is thicker behind than in front. Its outer surface is loosely connected by the lamina suprachorioidea with the sclera; its inner surface is attached to the pigmented layer of the retina. Compositions of this invention can be administered, for example by injection or perfusion or from a depot such as an implanted matrix comprising a composition of the invention, into a blood vessel which delivers blood to the choroid, preferably to the region proximal to the macula.

The choroid consists mainly of a dense capillary plexus, and of small arteries and veins carrying blood to and returning it from this plexus. On its external surface is a thin membrane, the lamina suprachorioidea, composed of delicate non-vascular lamellæ. Each lamella consists of a network of fine elastic fibers among which are branched pigment cells. The spaces between the lamellæ are lined by endothelium, and open freely into the perichoroidal lymph space, which communicates with the periscleral space by the perforations in the sclera through which the vessels and nerves are transmitted. Internal to this lamina is the choroid proper which consists of two layers: an outer layer, composed of small arteries and veins, with pigment cells interspersed between them; and an inner layer, consisting of a capillary plexus. The outer layer, or lamina vasculosa, consists, in part, of the larger branches of the short ciliary arteries which run forward between the veins before they bend inward to end in capillaries. The venæ vorticosæ is formed principally of veins which converge to four or five equidistant trunks, which pierce the sclera about midway between the sclero-corneal junction and the entrance of the optic nerve. Interspersed between the vessels are dark star-shaped pigment cells, the processes of which, communicating with those of neighboring cells, form a delicate network or stroma, which toward the inner surface of the choroid loses its pigmentary character. The inner layer of the choroid, or lamina choriocapillaris, consists of an exceedingly fine capillary plexus formed by the short ciliary vessels. This network is closer and finer in the posterior than in the anterior part of the choroid. About 1.25 centimeters behind the cornea its meshes become larger, and are continuous with those of the ciliary processes. These two laminæare connected by a stratum intermedium consisting of fine elastic fibers. On the inner surface of the lamina choriocapillaris is a very thin, structureless or faintly fibrous membrane, the lamina basalis, which is closely connected with the stroma of the choroid, and separates it from the pigmentary layer of the retina.

The retina is a nervous tissue in the eye, and contains millions of rod and cone cells which convert light energy into chemical electrical or neural signals which are sent to the brain via the optic nerve. The outer surface of the retina is in contact with the choroid. The inner surface of the retina is in contact with the hyaloid membrane of the vitreous body. The retina is continuous with the optic nerve, and gradually diminishes in thickness from the posterior of the eye forward, extending nearly as far as the ciliary body, where it appears to end in a jagged margin, the ora serrata. At the ora serrata, the nervous tissues of the retina end, but a thin prolongation of the membrane extends forward over the back of the ciliary processes and iris, forming the pars ciliaris retinæ and pars iridica retina. The retina is soft, semitransparent, and purple in tint due to the presence of rhodopsin.

The macula lutea resides at the center of the posterior part of the retina at a point corresponding to the axis of the eye where the sense of vision is most acute, i.e., where finer or higher resolution visual detail and visual focus occurs to provide the greatest degree of visual acuity. The macula comprises an oval yellowish area in which the color is deepest toward the center, and is about 6 by 7 millimeters (mm) in size. The fovea centralis comprises a central depression in the macula, wherein the retina is exceedingly thin. The fovea is about 1.5 mm in diameter and located just behind the macula, where the highest concentration of cone photoreceptors are concentrated. Light rays are focused in the eye by the lens onto the fovea for straight ahead vision and fine detail.

The ganglionic layer (retinal ganglion layer (RGC layer)) of the macula lutea consists of several strata of cells. There are no rod cells, but only cone cells which are longer and narrower than in other parts of the retina. In the outer nuclear layer there are only cone-cells, the processes of which are very long and arranged in curved lines. The layers of the fovea centralis comprise cone cells plus the outer nuclear layer, the cone-fibers of which are almost horizontal in direction, plus a thin inner plexiform layer.

About 3 millimeters to the nasal side of the macula lute is the entrance of the optic nerve, i.e., the optic disk, the circumference of which is slightly raised to form an eminence or colliculus nervi optici; the arteria centralis retinæ pierces the center of the disk. This part of the surface of the retina, termed the blind spot is insensitive to light. The optic nerve and the central retinal blood vessels enter the back of the eye at the disc comprising the blind spot.

The arteria centralis retina and its accompanying vein pierce the optic nerve, and enter the bulb of the eye through the porus opticus. The artery immediately bifurcates into an upper and a lower branch, and each of these again divides into a medial or nasal and a lateral or temporal branch, which at first run between the hyaloid membrane and the nervous layer before entering the latter to pass forward, dividing dichotomously. From these branches a minute capillary plexus is given off, which does not extend beyond the inner nuclear layer. The macula receives two small branches, which are the superior and inferior macular arteries, from the temporal branches and small arterial twigs directly from the central artery. These do not reach as far as the fovea centralis, which has no blood vessels. The branches of the arteria centralis retina do not anastomose with each other, i.e., they are terminal arteries.

The nervous structures of the retina are supported by a series of non-nervous or sustentacular fibers and the retina consist of seven layers: the stratum opticum or fiber layer which is composed of axons of the retinal ganglion cells (RGC); the ganglionic layer or RGC layer composed of cell bodies of RGCs and some displaced amacrine cells; the inner plexiform layer composed of dendrites of the RGCs and amacrine cells; the inner nuclear layer, or layer with cell bodies of the interneurons of the retina; the outer plexiform layer, a layer with dentrites; the outer nuclear layer composed of cell bodies of the photoreceptor cells; and the layer of rods and cones.

The stratum opticum is formed by the RGC axons that extend to the optic nerve. As the nerve fibers pass through the lamina cribrosa sclera toward the eye they lose their myelinated sheaths and are continued onward through the choroid and retina as simple unmylinated axons. When they reach the internal surface of the retina they radiate from their point of entrance over this surface grouped in bundles, and in many places are arranged in plexuses. Most of the fibers are centripetal, and are the direct continuations of the axis-cylinder processes of the cells of the RGC layer, but a few of them are centrifugal and ramify in the inner plexiform and inner nuclear layers, where they end in enlarged extremities.

The RGC layer consists of a single layer of large ganglion cells, except in the macula lutea, where there are several strata of ganglion cells. The ganglion cells rest on and each sends off a prolonged axon into the stratum opticum. Numerous dendrites extend into the inner plexiform layer, where they branch and form flattened arborizations at different levels. The ganglion cells vary in size, and the dendrites of the smaller ones arborize in the inner plexiform layer as soon as they enter it; while the dendrites of the larger cells ramify close to the inner nuclear layer.

The inner plexiform layer is made up of a dense reticulum of minute fibrils formed by the interlacement of the dendrites of the ganglion cells with those of the cells of the inner nuclear layer; within this reticulum a few branched spongioblasts are sometimes imbedded.

The inner nuclear layer or layer of inner granules (cells) comprises three varieties of closely packed cells: bipolar cells, horizontal cells, and amacrine cells. The bipolar cells are the most numerous, and are round or oval in shape. Each is prolonged into an inner and an outer process. They are divisible into rod bipolars and cone bipolars. The inner processes of the rod bipolars run through the inner plexiform layer and arborize around the bodies of the cells of the ganglionic layer; their outer processes end in the outer plexiform layer in tufts of fibrils around the ends of the inner processes of the rod cells. The inner processes of the cone bipolars ramify in the inner plexiform layer in contact with the dendrites of the ganglionic cells. The horizontal cells have flattened cell bodies and lie in the outer part of the inner nuclear layer. Their dendrites divide into numerous branches in the outer plexiform layer, while their axons run horizontally for some distance and finally ramify in the same layer. The amacrine cells are found in the inner part of the inner nuclear layer. Their dendrites undergo extensive ramification in the inner plexiform layer.

The outer plexiform layer is thinner than the inner plexiform layer, and consists of a dense network of minute fibrils derived from the processes of the horizontal cells of the preceding layer. The outer processes of the rod and cone bipolar cells, which ramify in it, form arborizations around the enlarged ends of the rod fibers and with the branched foot plates of the cone fibers.

The outer nuclear layer, like the inner nuclear layer, contains cell bodies which are of two kinds: rod and cone cells, which are respectively connected with the rods and cones of the next layer. The rods are much more numerous than the cones, and are placed at different levels throughout the layer. Prolonged from either extremity of each rod cell is a fine process, one of which is continuous with a single rod of the layer of rods and cones, while the other ends in the outer plexiform layer in an enlarged extremity, and is imbedded in the tuft into which the outer processes of the rod bipolar cells break up. The cones are close to the membrana limitans externa through which they are continuous with the cones of the layer of rods and cones. From one extremity of the cone a thick process passes into the outer plexiform layer where it expands into a pyramidal enlargement or foot plate, from which are given off numerous fine fibrils, that come in contact with the outer processes of the cone bipolar cells.

The layer of rods and cones comprises rods and cones (photoreceptor cells), the former being much more numerous than the latter except in the macula lutea. The rods are cylindrical, of nearly uniform thickness, and are arranged perpendicularly to the surface. Each rod consists of two segments, an outer and inner, of about equal lengths. The outer segment is marked by transverse striæ, and tends to break up into a number of thin disks superimposed on one another. The deeper part of the inner segment is granular; its more superficial part presents a longitudinal striation, being composed of fine, highly refracting fibrils. Rhodopsin is found only in the outer segments. The cones are conical shaped, with their broad ends resting upon the membrana limitans externa, and the narrow extremity being turned to the choroid. Like the rods, each is made up of two segments, outer and inner; the outer segment is a short conical process, which, like the outer segment of the rod, exhibits transverse striæ. The inner segment resembles the inner segment of the rods in structure, presenting a superficial striated and deep granular part, but differs from it by being bulged out laterally and flask-shaped. The chemical and optical characters of the two portions are identical with those of the rods.

The term retinal cell can refer herein to any of the cell types that comprise the retina, such as retinal ganglion cells, amacrine cells, horizontal cells, bipolar cells, and photoreceptor cells including rods and cones, Muller glial cells, and retinal pigmented epithelium.

Advanced wet macular degeneration is a disease of the eye which comprises neovascularization of the choroid tissue underlying the photoreceptor cells in the macula. Macular degeneration, particularly in its advanced stages, is characterized by the pathological growth of new blood vessels in the choroid underlying the macula. Angiogenic blood vessels in the subretinal choroid can leak vision obscuring fluids, leading to blindness.

In one aspect, diseases of the eye which exhibit neovascularization proximal to the retina such as wet macular degeneration, retinitis pigmentosa, Stargardt's Disease, diabetic retinopathy, hypertensive retinopathy, and occlusive retinopathy can be treated to reduce the rate of neovascularization by administration of a composition of this invention comprising a fusion protein of this invention having angiogenesis inhibiting activity.

In another aspect, diseases of the eye which exhibit neovascularization proximal to the retina such as wet macular degeneration, retinitis pigmentosa, Stargardt's Disease, diabetic retinopathy, hypertensive retinopathy, and occlusive retinopathy can be treated to prevent or reduce the rate of photoreceptor cell death by administration of a composition of this invention comprising a fusion protein of this invention.

The compositions of the present invention when administered to the eye or to blood vessels that feed into the eye of a patient can be useful to treat diseases such as wet macular degeneration, retinitis pigmentosa, Stargardt's Disease, diabetic retinopathy, hypertensive retinopathy, and occlusive retinopathy by reducing the rate of formation of neovascularization and thereby slow the progress of the disease. The rate of neovascularization which occurs in such a disease in a patient is preferably reduced by administration of a fusion protein of this invention to at most 90%, more preferably to at most 50%, even more preferably to at most 25%, even more preferably to at most 10%, even more preferably to at most 5%, even more preferably to at most 1%, and most preferably to at most 0.1% of (times) the rate of neovascularization which occurs in such a disease in the absence of administration of a fusion protein of this invention (i.e., in an untreated patient).

The compositions of the present invention when administered to the eye or to blood vessels that feed into the eye of a patient can be useful to treat diseases such as wet macular degeneration, retinitis pigmentosa, Stargardt's Disease, diabetic retinopathy, hypertensive retinopathy, and occlusive retinopathy by reducing the rate of photoreceptor cell death and thereby slow the progress of the disease. The rate of photoreceptor cell death which occurs in such a disease in a patient is preferably reduced by administration of a fusion protein of this invention to at most 90%, more preferably to at most 50%, even more preferably to at most 25%, even more preferably to at most 10%, even more preferably to at most 5%, even more preferably to at most 1%, and most preferably to at most 0.1% of (times) the rate of photoreceptor cell death which occurs in such a disease in the absence of administration of a fusion protein of this invention (i.e., in an untreated patient).

Neovascularization proximal to the retina as a result of a disease, especially neovascularization proximal to the macula, can lead to photoreceptor cell death in the retina of a patient. Photoreceptor cell death in the retina can be produced as a consequence of a disease of the retina as a result of neovascularization as well as other mechanisms of cell death.

Advanced dry macular degeneration comprises the deposition of drusen and death of photoreceptor cells. The mechanism of drusen deposition is unknown, but exocytosis from cells is one likely mechanism of release into the extracellular space. Another embodiment of the present invention comprises the inhibition of drusen deposition and prevention of photoreceptor cell death by a cell-permeable fusion protein conjugate comprising a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating cellular uptake of the active agent, for example a fusion protein such as C3APLT. In one aspect, the functional analog of a *Clostridium botulinum* C3 exotransferase unit comprises a protein exhibiting an ADP-ribosyl transferase activity in the range of 50% to 500% of the ADP-ribosyl transferase activity of *Clostridium botulinum* C3 exotransferase. Inactivation of Rho in a cell by a fusion protein of this invention after penetration of the cell membrane can block or inhibit exocytosis and thereby block or inhibit the release from the cell of cellular debris or cellular-derived material that can form drusen. A fusion protein of this invention can also prevent injury-induced cell death of a cell in the CNS.

Angiogenesis in neovascularization is the complex process of blood vessel formation. The process involves both biochemical and cellular events, including (1) activation of endothelial cells (ECs) by an angiogenic stimulus; (2) degradation of the extracellular matrix, invasion of the activated endothelial cells into the surrounding tissues, and migration toward the source of the angiogenic stimulus; and (3) proliferation and differentiation of endothelial cells to form new blood vessels (Folkman et al., 1991, J. Biol. Chem. 267: 10931-10934).

The control of angiogenesis is a highly regulated process involving angiogenic stimulators and inhibitors. In healthy humans and animals, angiogenesis occurs under specific, restricted situations. For example, angiogenesis is normally observed in fetal and embryonal development, development and growth of normal tissues and organs, wound healing, and the formation of the corpus luteum, endometrium and placenta. Another embodiment of the present invention comprises the inhibition of angiogenesis by a cell-permeable fusion protein conjugate comprising a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating cellular uptake of the active agent, for example a fusion protein such as C3APLT. In one aspect, the functional analog of a *Clostridium botulinum* C3 exotransferase unit comprises a protein exhibiting an ADP-ribosyl transferase activity in the range of 50% to 500% or more of the ADP-ribosyl transferase activity of *Clostridium botulinum* C3 exotransferase.

Another embodiment of the present invention comprises the inhibition of angiogenesis by an effective amount of a pharmaceutical composition comprising a cell-permeable fusion protein conjugate comprising a polypeptidic cell-membrane transport moiety and a *Clostridium botulinum* C3 exotransferase unit, or a functional analog thereof retaining an ADP-ribosyl transferase activity, for example a fusion protein such as C3APLT.

In one embodiment, this invention discloses a method of treatment of a disease of the eye selected from the group consisting of macular degeneration, retinitis pigmentosa, Stargardt's Disease, diabetic retinopathy, hypertensive retinopathy, and occlusive retinopathy, the method comprising administration to a patient in need of such treatment a therapeutically effective amount of a pharmaceutical composition comprising: a) a polypeptide consisting of SEQ ID NO:43 and; b) a pharmaceutically acceptable carrier. In one aspect of this embodiment, the carrier comprises a biological adhesive. In one aspect of this embodiment, the carrier comprises fibrin. In one aspect of this embodiment, the administration comprises injection.

In another embodiment, this invention discloses a method of treatment of a disease of the eye selected from the group consisting of macular degeneration, retinitis pigmentosa, Stargardt's Disease, diabetic retinopathy, hypertensive retinopathy, and occlusive retinopathy, the method comprising administration to a patient in need of such treatment a therapeutically effective amount of a pharmaceutical composition comprising: a) a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating uptake of the active agent by a receptor-independent mechanism and being selected from the group consisting of a subdomain of HIV Tat protein, a homeodomain of antennapedia, and a Histidine tag, said polypeptide having ADP-ribosyl transferase activity, and; b) a pharmaceutically acceptable carrier. In one aspect of this embodiment, the amino acid sequence of the transport agent is at the carboxy-terminal end of said polypeptide and the amino acid sequence of the active agent is at the amino terminal end of said polypeptide. In one aspect of this embodiment, the carrier comprises a biological adhesive. In one aspect of this embodiment, the carrier comprises fibrin. In one aspect of this embodiment, the administration comprises injection.

In another embodiment, this invention discloses a method of treatment of a disease of the eye selected from the group consisting of macular degeneration, retinitis pigmentosa, Stargardt's Disease, diabetic retinopathy, hypertensive retinopathy, and occlusive retinopathy, the method comprising administration to a patient in need of such treatment a therapeutically effective amount of a pharmaceutical composition comprising: a) a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating uptake of the active agent by a receptor-independent mechanism and being selected from the group consisting of SEQ ID NO: 21, SEQ ID NO: 26, SEQ ID NO: 31, SEQ ID NO: 44, SEQ ID NO: 45, SEQ ID NO: 46, SEQ ID NO: 47, and SEQ ID NO: 48, said polypeptide having ADP-ribosyl transferase activity, and; b) a pharmaceutically acceptable carrier. In one aspect of this embodiment, the amino acid sequence of the transport agent is at the carboxy-terminal end of said polypeptide and the amino acid sequence of the active agent is at the amino terminal end of said polypeptide. In one aspect of this embodiment, the carrier comprises a biological adhesive. In one aspect of this embodiment, the carrier comprises fibrin. In one aspect of this embodiment, the administration comprises injection.

In another embodiment, this invention discloses a method of treatment of a disease of the eye selected from the group consisting of macular degeneration, retinitis pigmentosa, Stargardt's Disease, diabetic retinopathy, hypertensive retinopathy, and occlusive retinopathy, the method comprising administration to a patient in need of such treatment a therapeutically effective amount of a pharmaceutical composition comprising: a) a polypeptide comprising an amino acid sequence of a transport agent covalently linked to an amino acid sequence of an active agent, said amino acid sequence of said active agent consisting of ADP-ribosyl transferase C3 or an amino acid sequence having at least 90% sequence identity with the amino acid sequence of SEQ ID NO: 43 and retaining ADP-ribosyl transferase activity, said amino acid sequence of said transport agent facilitating facilitating uptake of the active agent by a receptor-independent mechanism and being selected from the group consisting of a subdomain of HIV Tat protein, a homeodomain of antennapedia, and a Histidine tag, said polypeptide having ADP-ribosyl transferase activity, and; b) a pharmaceutically acceptable carrier. In one aspect of this embodiment, the carrier comprises a biological adhesive. In one aspect of this embodiment, the carrier comprises fibrin. In one aspect of this embodiment, the administration comprises injection. In one aspect of this embodiment, the amino acid sequence of the transport agent is at the carboxy-terminal end of said polypeptide and the amino acid sequence of the active agent is at the amino terminal end of said polypeptide.

In another embodiment, this invention discloses a method of treatment of a disease of the eye selected from the group consisting of macular degeneration, retinitis pigmentosa, Stargardt's Disease, diabetic retinopathy, hypertensive retinopathy, and occlusive retinopathy, the method comprising administration to a patient in need of such treatment a therapeutically effective amount of a pharmaceutical composition comprising: a) a polypeptide comprising an amino acid sequence of a transport agent covalently linked to an amino acid sequence of an active agent, said amino acid sequence of said active agent consisting of ADP-ribosyl transferase C3 or an amino acid sequence having at least 90% sequence identity with the amino acid sequence of SEQ ID NO: 43 and retaining ADP-ribosyl transferase activity, said amino acid sequence of said transport agent facilitating uptake of the active agent by a receptor-independent mechanism and being selected from the group consisting of SEQ ID NO: 21, SEQ ID NO: 26, SEQ ID NO: 31, SEQ ID NO: 44, SEQ ID NO: 45, SEQ ID NO: 46, SEQ ID NO: 47, and SEQ ID NO: 48, and; b) a pharmaceutically acceptable carrier. In one aspect of this embodiment, the carrier comprises a biological adhesive. In one aspect of this embodiment, the carrier comprises fibrin. In one aspect of this embodiment, the administration comprises injection. In one aspect of this embodiment, the amino acid sequence of the transport agent is at the carboxy-terminal end of said polypeptide and the amino acid sequence of the active agent is at the amino terminal end of said polypeptide.

In another embodiment, this invention discloses a method of inhibiting or substantially reducing the rate of subretinal neovascularization and proliferation of neovascular tissue, preventing drusen deposition and protecting retinal photoreceptors from cell death (i.e., reducing the rate of drusen deposition and reducing the rate of retinal photoreceptor cell death) in the eye of a mammalian host comprising administration to said host a therapeutically effective amount of a pharmaceutical composition comprising: a) a polypeptide consisting of SEQ ID NO:43 and; b) a pharmaceutically acceptable carrier. In one aspect of this embodiment, the carrier comprises a biological adhesive. In one aspect of this embodiment, the carrier comprises fibrin. In one aspect of this embodiment, the administration comprises injection.

In another embodiment, this invention discloses a method of inhibiting or substantially reducing the rate of subretinal neovascularization and proliferation of neovascular tissue preventing drusen deposition and protecting retinal photoreceptors from cell death (i.e., reducing the rate of drusen deposition and reducing the rate of retinal photoreceptor cell death) in the eye of a mammalian host comprising administration to said host a therapeutically effective amount of a pharmaceutical composition comprising: a) a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating uptake of the active agent by a receptor-independent mechanism and being selected from the group consisting of a subdomain of HIV Tat protein, a homeodomain of antennapedia, and a Histidine tag, said polypeptide having ADP-ribosyl transferase activity, and; b) a pharmaceutically acceptable carrier.

In one aspect of this embodiment, the amino acid sequence of the transport agent is at the carboxy-terminal end of said polypeptide and the amino acid sequence of the active agent is at the amino terminal end of said polypeptide. In one aspect of this embodiment, the carrier comprises a biological adhesive. In one aspect of this embodiment, the carrier comprises fibrin. In one aspect of this embodiment, the administration comprises injection.

In another embodiment, this invention discloses a method of inhibiting or substantially reducing the rate of subretinal neovascularization and proliferation of neovascular tissue, preventing drusen deposition and protecting retinal photoreceptors from cell death (i.e., reducing the rate of drusen deposition and reducing the rate of retinal photoreceptor cell death) in the eye of a mammalian host comprising administration to said host a therapeutically effective amount of a pharmaceutical composition comprising: a) a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating uptake of the active agent by a receptor-independent mechanism and being selected from the group consisting of SEQ ID NO: 21, SEQ ID NO: 26, SEQ ID NO: 31, SEQ ID NO: 44, SEQ ID NO: 45, SEQ ID NO: 46, SEQ ID NO: 47, and SEQ ID NO: 48, said polypeptide having ADP-ribosyl transferase activity, and; b) a pharmaceutically acceptable carrier. In one aspect of this embodiment, the amino acid sequence of the transport agent is at the carboxy-terminal end of said polypeptide and the amino acid sequence of the active agent is at the amino terminal end of said polypeptide. In one aspect of this embodiment, the carrier comprises a biological adhesive. In one aspect of this embodiment, the carrier comprises fibrin. In one aspect of this embodiment, the administration comprises injection.

In another embodiment, this invention discloses a method of inhibiting or substantially reducing the rate of subretinal neovascularization and proliferation of neovascular tissue, preventing drusen deposition and protecting retinal photoreceptors from cell death (i.e., reducing the rate of drusen deposition and reducing the rate of retinal photoreceptor cell death) in the eye of a mammalian host comprising administration to said host a therapeutically effective amount of a pharmaceutical composition comprising: a) a polypeptide comprising an amino acid sequence of a transport agent covalently linked to an amino acid sequence of an active agent, said amino acid sequence of said active agent consisting of ADP-ribosyl transferase C3 or an amino acid sequence having at least 90% sequence identity with the amino acid sequence of SEQ ID NO: 43 and retaining ADP-ribosyl transferase activity, said amino acid sequence of said transport agent facilitating facilitating uptake of the active agent by a receptor-independent mechanism and being selected from the group consisting of a subdomain of HIV Tat protein, a homeodomain of antennapedia, and a Histidine tag, said polypeptide having ADP-ribosyl transferase activity, and; b) a pharmaceutically acceptable carrier. In one aspect of this embodiment, the carrier comprises a biological adhesive. In one aspect of this embodiment, the carrier comprises fibrin. In one aspect of this embodiment, the administration comprises injection. In one aspect of this embodiment, the amino acid sequence of the transport agent is at the carboxy-terminal end of said polypeptide and the amino acid sequence of the active agent is at the amino terminal end of said polypeptide.

In another embodiment, this invention discloses a method of inhibiting or substantially reducing the rate of subretinal neovascularization and proliferation of neovascular tissue, preventing drusen deposition and protecting retinal photoreceptors from cell death (i.e., reducing the rate of drusen deposition and reducing the rate of retinal photoreceptor cell death) in the eye of a mammalian host comprising administration to said host a therapeutically effective amount of a pharmaceutical composition comprising: a) a polypeptide comprising an amino acid sequence of a transport agent covalently linked to an amino acid sequence of an active agent, said amino acid sequence of said active agent consisting of ADP-ribosyl transferase C3 or an amino acid sequence having at least 90% sequence identity with the amino acid sequence of SEQ ID NO: 43 and retaining ADP-ribosyl transferase activity, said amino acid sequence of said transport agent facilitating uptake of the active agent by a receptor-independent mechanism and being selected from the group consisting of SEQ ID NO: 21, SEQ ID NO: 26, SEQ ID NO: 31, SEQ ID NO: 44, SEQ ID NO: 45, SEQ ID NO: 46, SEQ ID NO: 47, and SEQ ID NO: 48, and; b) a pharmaceutically acceptable carrier. In one aspect of this embodiment, the carrier comprises a biological adhesive. In one aspect of this embodiment, the carrier comprises fibrin. In one aspect of this embodiment, the administration comprises injection. In one aspect of this embodiment, the amino acid sequence of the transport agent is at the carboxy-terminal end of said polypeptide and the amino acid sequence of the active agent is at the amino terminal end of said polypeptide.

In one aspect, a therapeutically effective amount of a polypeptide of this invention is an amount which will retard the progress of neovascularization proximal to the macula to a rate of at least 90%, preferably to a rate of at least 50%, more preferably to a rate of at least 10%, more preferably to a rate of at least 1%, and most preferably to a rate of at least 0.1% of the rate of neovascularization observed proximal to the macula in an untreated patient or in a patient treated with a control vehicle such as a carrier of a pharmaceutical composition of this invention which does not contain a polypeptide of this invention.

In another aspect, a therapeutically effective amount of a polypeptide of this invention is an amount which can retard or inhibit the rate of deposition of drusen in an eye of an average patient in a statistically relevant population of patients to produce a mean delay in the onset of vision loss that can result from said deposition, the mean delay of onset of vision loss being measured relative to the mean time of onset of vision loss that occurs in an average patient in the statistically relevant population of patients in the absence of said amount of polypeptide, the mean delay in the onset of vision loss comprising a period of at least 1 month, and more preferably a period of at least 6 months, and most preferably a period of greater than 6 months.

In another aspect, a therapeutically effective amount of a polypeptide of this invention is an amount which can retard or inhibit the progress (or rate) of photoreceptor cell death in an eye of an average patient in a statistically relevant population of patients to produce a mean delay in the onset of vision loss that can result from said cell death, the mean delay of onset of vision loss being measured relative to the mean time of onset of vision loss that occurs in an average patient in the statistically relevant population of patients in the absence of said amount of polypeptide, the mean delay in the onset of vision loss comprising a period of at least 1 month, and more preferably a period of at least 6 months, and most preferably a period of greater than 6 months.

In another aspect, a therapeutically effective amount of a polypeptide of this invention is an amount which can retard or inhibit the rate of deposition of drusen and retard or inhibit the progress (or rate) of cell death in an eye of an average patient in a statistically relevant population of patients to produce a mean delay in the onset of vision loss that can result from said deposition and said cell death, the mean delay of onset being measured relative to the mean time of onset of vision loss that occurs in an average patient in the statistically relevant population of patients in the absence of said amount of polypeptide, the mean delay in the onset of vision loss comprising a period of at least 1 month, and more preferably a period of at least 6 months, and most preferably a period of greater than 6 months.

A therapeutically effective amount or dose of a compound or composition of this invention can refer to that amount which will produce a desirable result upon administration. A therapeutically effective amount or dose can depend on a number of factors including the route of administration.

BRIEF DESCRIPTION OF THE FIGURES

FIG. 12 A illustrates the percentage of cells with neurites neurites longer than 1 cell body diameter (neurite outgrowth); FIG. 12 B illustrates the length of the longest neurite per cell (neurite length);

DETAILED DESCRIPTION

Figure 1:
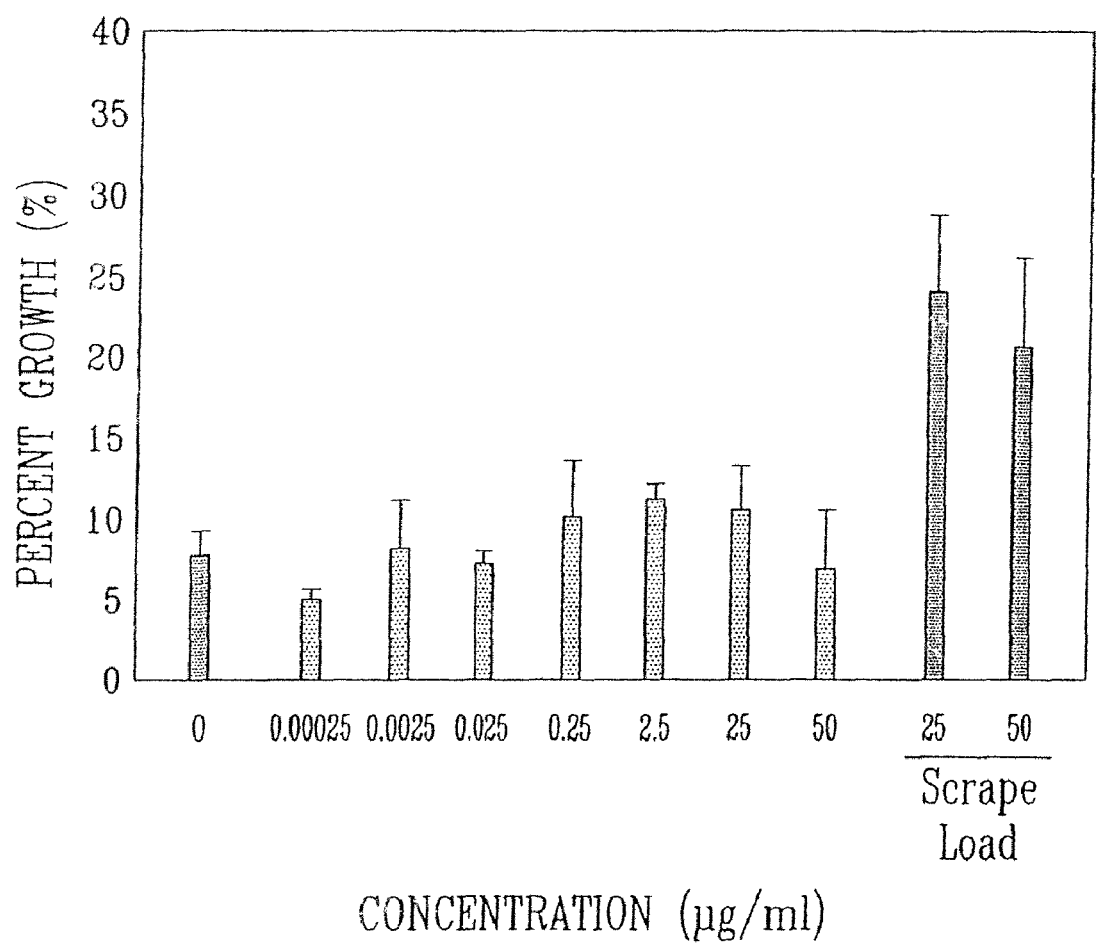
FIG. 1 illustrates the dose response of normal C3 with and without trituration.

Referring to FIG. 1, PC-12 cells were plated on inhibitory myelin substrates (0). Unmodified C3 added to the tissue culture medium at concentration from 0.00025-50 ug/ml did not significantly improve neurite outgrowth over the untreated control (grey bars). C3 was only effective in stimulating neurite outgrowth for cells plated on myelin substrates after scrape-loading (black bars). This Figure demonstrates the limited or no penetration in cells when passively added to the tissue culture medium. Please see Example 4 below for techniques.

Figure 2:
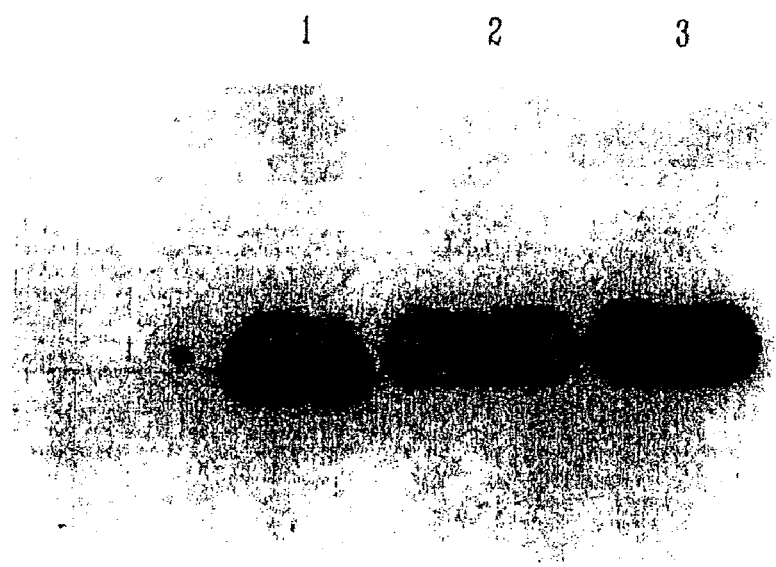
FIG. 2 illustrates ADP ribosylation by C3APLT and C3APS, but not C3 after passively adding the compounds to PC-12 cells, wherein lane 1 is a negative control showing C3 alone, lane 2 is a positive control showing scrape-loaded C3, and lane 3 shows addition of C3APLT.

Referring to FIG. 2, this Figure provides a demonstration that C3APLT and C3APS, ADP ribosylate Rho. Western blot showing RhoA in untreated cells (lane 1), and cells treated with C3APLT (lane 2) or C3APS (lane 3). When Rho is ADP ribosylated by C3 it undergoes a molecular weight shift (Lehmann et al supra), as observed for lanes 2 and 3. Please see Example 4 below for techniques.

Figure 3A:
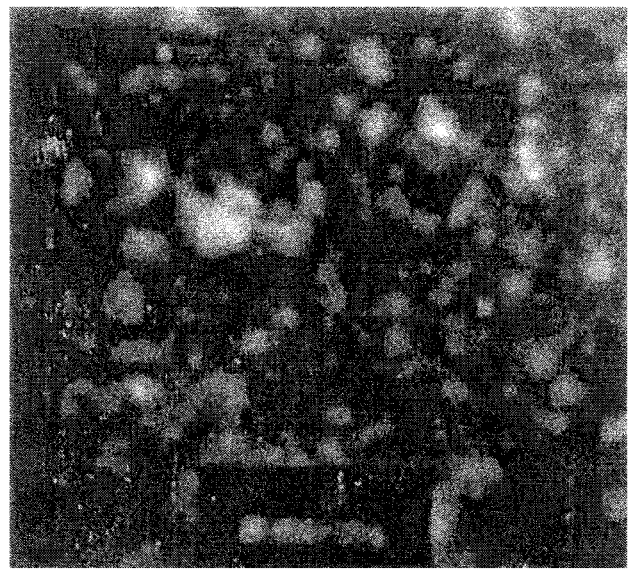
FIG. 3A illustrates that C3APLT penetrates cells.
Figure 3B:
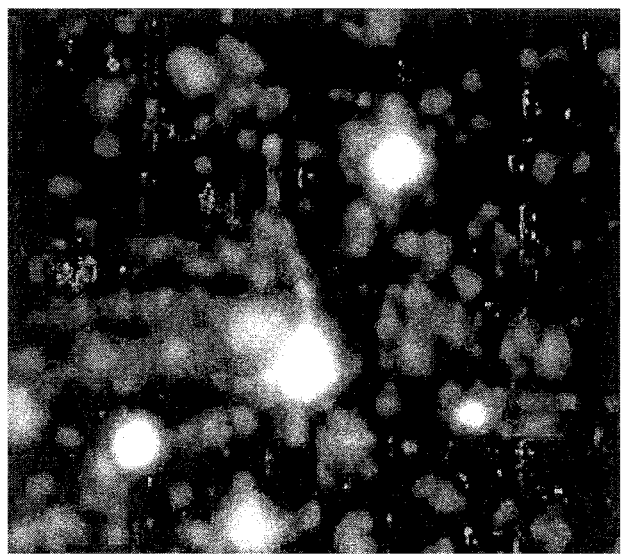
FIG. 3B illustrates a lower level of cell penetration by C3 as compared to FIG. 3A.

Referring to FIG. 3, this Figure shows intracellular activity after treatment with C3APLT. Detection that the new fusion C3 penetrates into the cells. Immunocytochemistry with anti-C3 antibody of PC-12 cells plated on myelin and treated with C3 (A) or C3APLT (13). Cells in A (FIG. 3A) are not immunoreactive because C3 has not penetrated into the cells. Cells in B (FIG. 3B) are immunoreactive and they are able to extend neurites on myelin substrates. Please see Example 4 below for techniques.

Figure 4:
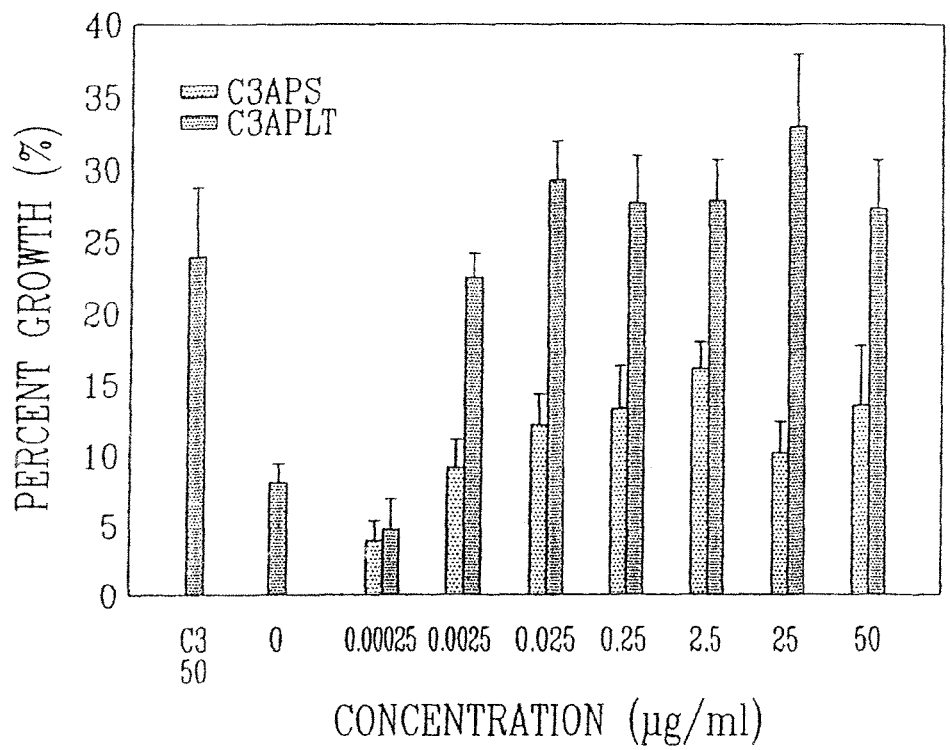
FIG. 4 illustrates the effectiveness of C3APLT and C3APS at low doses.

Turning to FIG. 4, this Figure shows that C3-antennapedia fusion proteins promote growth on inhibitory substrates. The percent of neurons that grow neurites was counted for each treatment. The dose response experiment shows that C3APLT and C3APS promote more neurite growth per cell than control PC-12 cells plated on myelin (0). PC-12 cells were plated on myelin and either scrape loaded with unmodified C3 (C3 50) left untreated (0) or treated with various concentrations of C3APLT. Compared to C3 used at 25 ug/ml, C3APS is effective at stimulating more cells to grow neurites at 0.0025 ug/ml, a dose 10,000× less. Please see Example 4 below for techniques.

Figure 5:
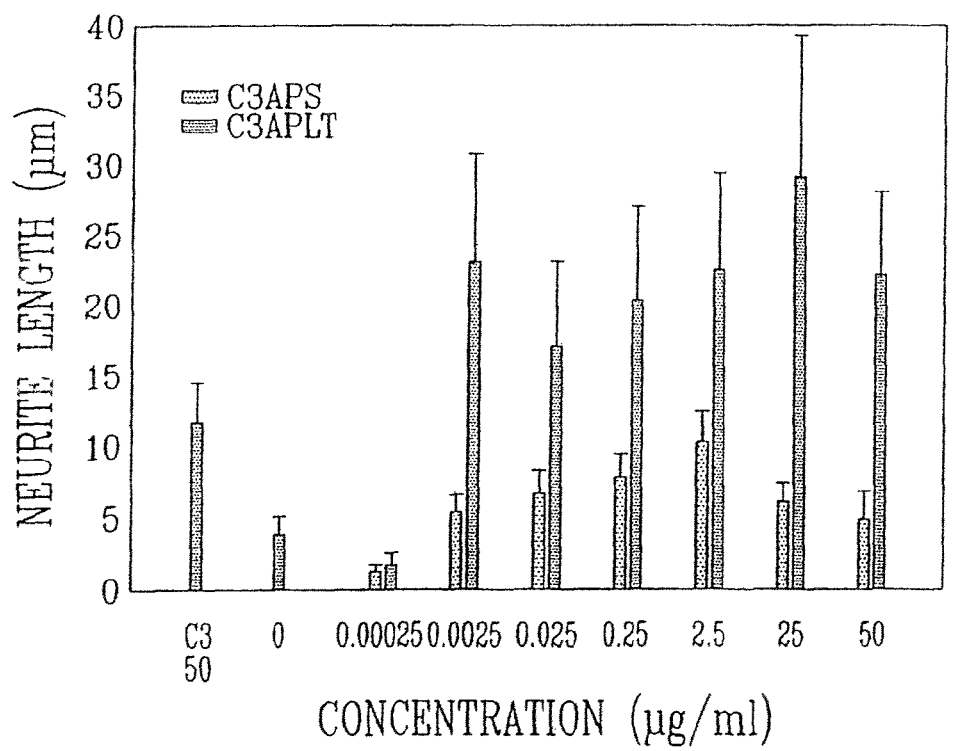
FIG. 5 illustrates the effectiveness of C3APLT and C3APS at low doses.

FIG. 5 shows a dose-response experiment showing that C3APLT and C3APS elicit long neurites to grow when cells are plated on inhibitory substrates. The length of neurites was measured for each treatment. PC-12 cells were plated on myelin and either scrape loaded with unmodified C3 (C3 50) left untreated (0) or treated with various concentrations of C3APLT. Compared to C3 used at 25 ug/ml, C3APS is effective at stimulating more cells to longer neurite growth at 0.0025 ug/ml, a dose 10,000.times. less. Please see Example 4 below for techniques.

Figure 6:
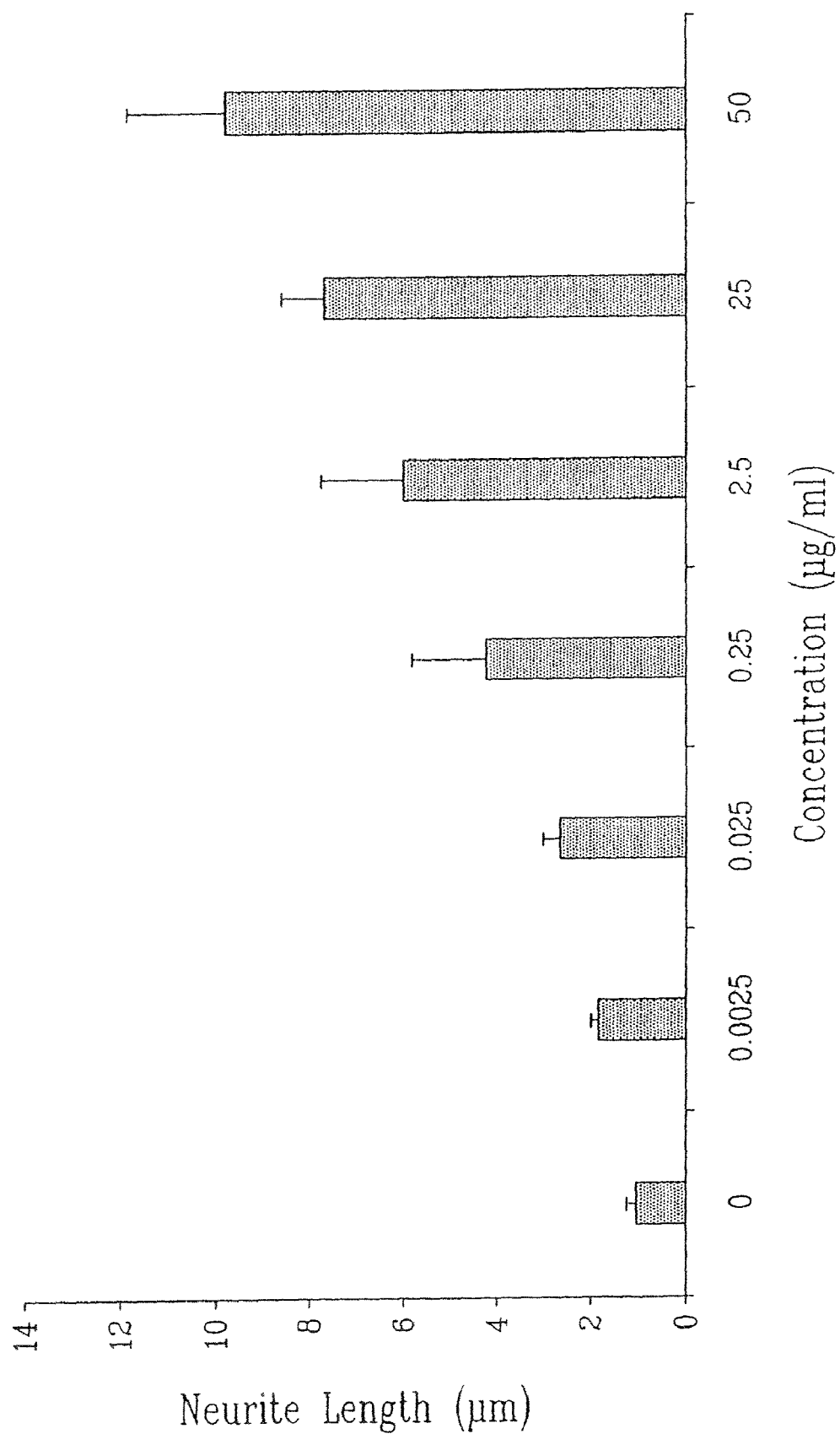
FIG. 6 illustrates the effectiveness of C3APLT to stimulate axon regeneration of primary neurons.

As may be seen FIG. 6 shows primary neurons growing on inhibitory substrates after treatment with C3APLT. Rat retinal ganglion cells were plated on myelin substrates and treated with different concentrations of C3APLT. Concentrations of 0.025 and above promoted significantly longer neurites. This dose is 1000.times. lower than that of C3 needed to promote growth on myelin.

Figure 7:
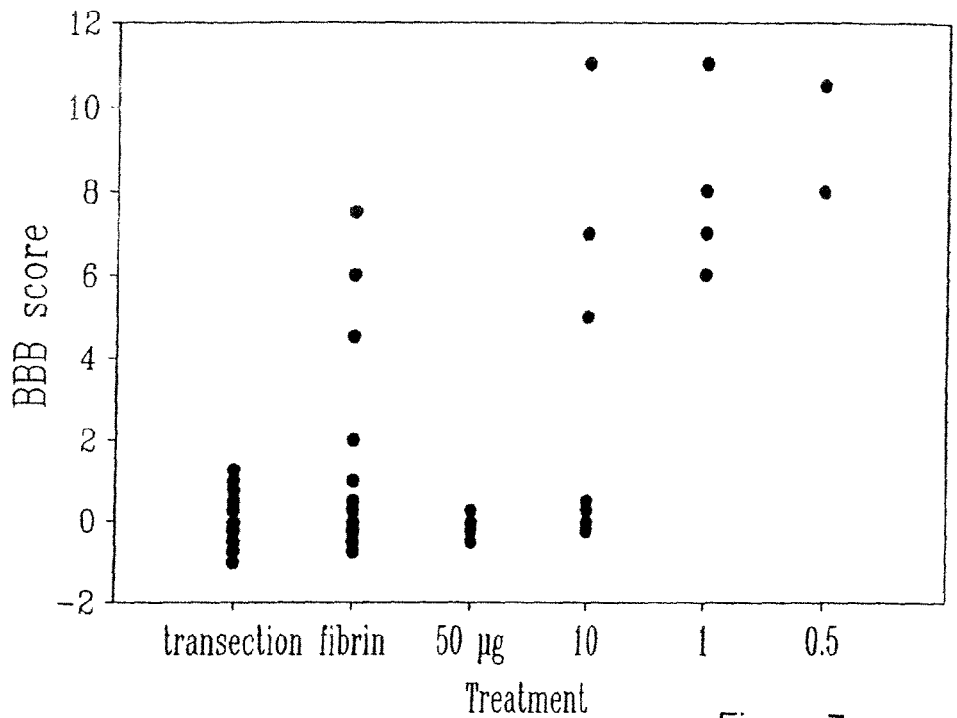
FIG. 7 illustrates the effectiveness of C3APLT to promote functional recovery after spinal cord injury.

Referring to FIG. 7, this Figure shows behavioral recovery after treatment of adult mice with C3APLT in a dose-response experiment. Mice received a dorsal hemisection of the spinal cord and were left untreated (transection), were treated with fibrin alone (fibrin) or were treated with fibrin plus C3APLT at the indicated concentrations given in ug/mouse. Each point represents one animal. The BBB score (see Example 6 for details) was assessed 24 hours after treatment. Animals treated with C3APLT exhibited a significant improvement in behavioral recovery compared to untreated animals. The effective dose of 0.5 µg is 100.times. less than unmodified C3 used (see previous experiment shown in Canadian patent application 2,325,842). Please see Example 6.

Figure 8:
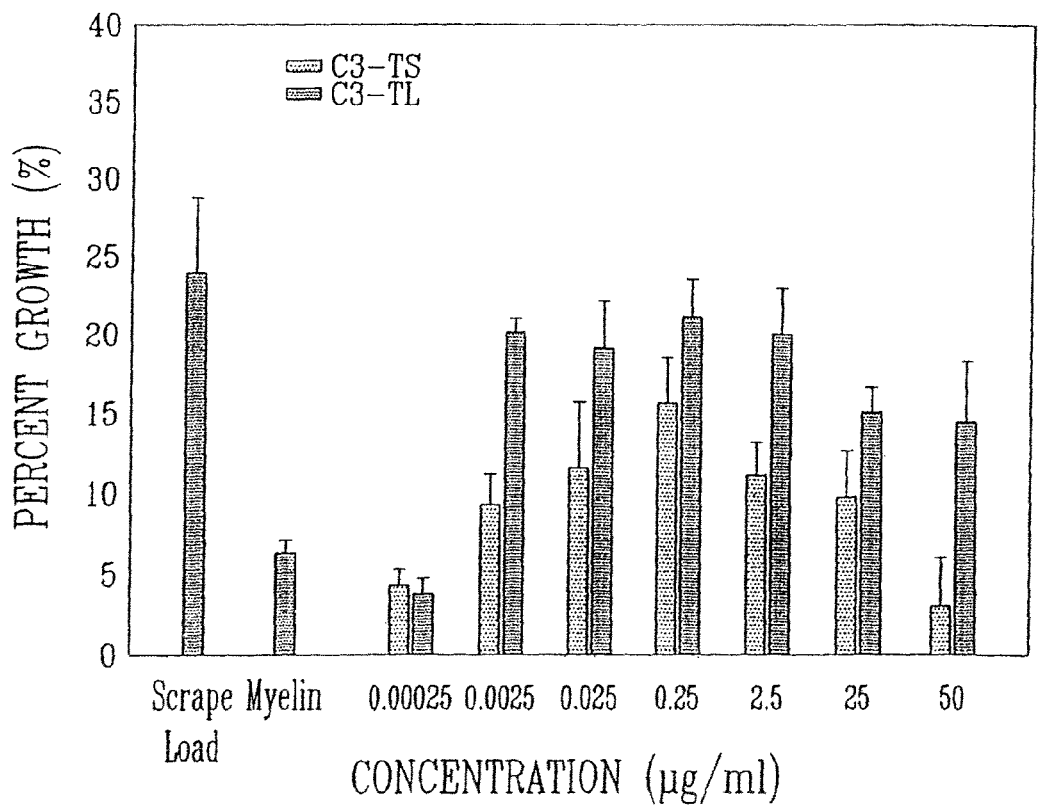
FIG. 8 illustrates effectiveness of Tat transport sequences to enhance growth as C3-Tat (C3-TL and C3-TS) chimeras.

Referring to FIG. 8, this Figure shows promotion of axon growth by C3-Tat chimeric proteins. The dose-response experiment shows that C3-TS and C3-TL promote more neurite growth per cell than control PC-12 cells plated on myelin. PC-12 cells were plated on myelin and either scrape loaded with unmodified C3 (scrape load) left untreated (myelin) or treated with various concentrations of C3-TS (grey bars) or C3-TL (black bars). Compared to C3 used at 25 ug/ml, C3-TL is effective at stimulating more cells to grow neurites at 0.0025 ug/ml, a dose 10,000.times. less than C3.

Figure 9B:
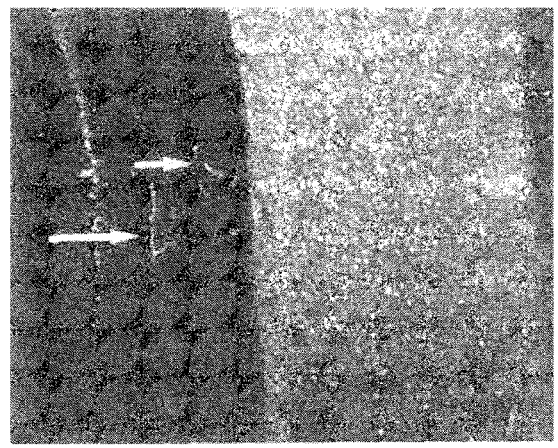
FIGS. 9A and 9B illustrate axon regeneration after spinal cord injury and treatment with C3APLT.
Figure 9A:

Referring to FIGS. 9A and 9B, these Figures show axon regeneration in injured spinal cord, i.e. anatomical regeneration after treatment with C3APLT. Section of the spinal cord after anterograde labeling with horseradish peroxidase conjugated to wheat germ agglutinin (WGA-HRP). A) Sprouting of cut axons into the dorsal white matter. Arrows show regenerating axons distal to the lesion. B) Same section 3 mm from the lesion site. Arrows show regenerating axons.

Figure 10:
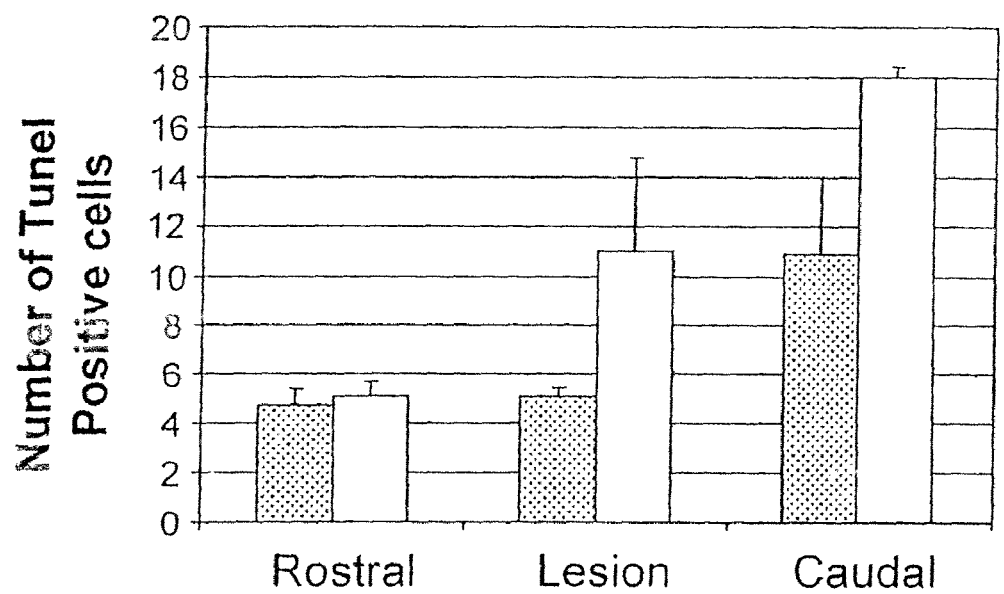
FIG. 10 illustrates effectiveness of C3APLT to prevent cell death after spinal cord injury, thereby showing that it is neuroprotective, wherein the stippled bars represent counts from spinal cord sections of rats that had a spinal cord injury and were treated with C3APLT, and the open bars show counts of cells from untreated rats with spinal cord injury.

Referring to FIG. 10, this Figure shows that C3-APLT protected neurons from cell death following spinal cord injury. Apoptotic (dying) cells were counted following TUNEL labeling (see Example 16) 2 mm rostral to the lesion (Rostral) at the lesion site (lesion) and 2 mm caudal to the lesion site (caudal). Bars show average counts of Tunel positive cells from 4 animals treated with fibrin only after spinal cord injury as control (white bars), or with C3APLT in fibrin at 1 µg (black bars). Treatment with C3APLT show significantly reduced numbers of Tunel-labeled cells (dying cells). Non-injured spinal cord samples were also processed and these spinal cords did not show Tunel labeling, as expected.

Figure 11:
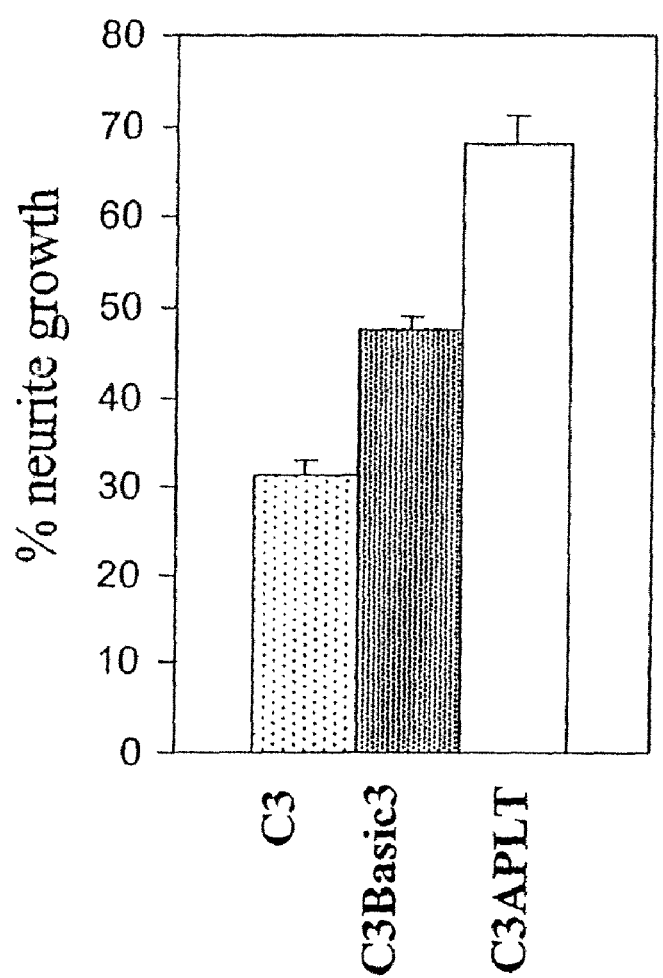
FIG. 11 illustrates a comparison of C3APLT and C3Basic3 to promote neurite outgrowth.

Referring to FIG. 11, this Figure shows that C3APLT and C3Basic3 promote rapid neurite outgrowth compared to untreated cells when cells are plated on plastic as part of a rapid bioassay (see Example 4).

Figure 12A:
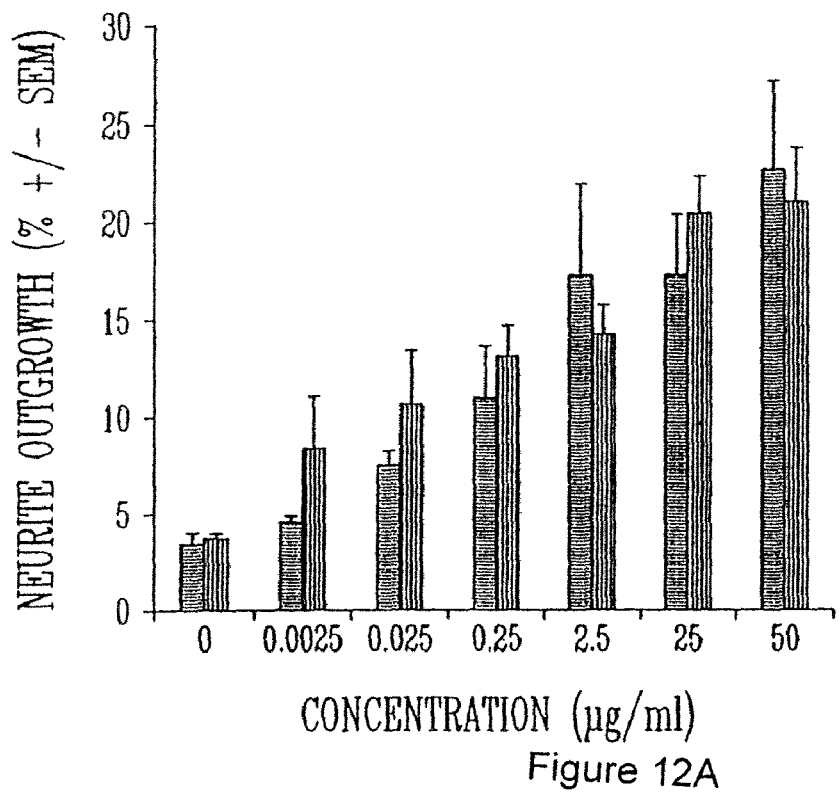
FIG. 12 illustrates that C3APLT promotes neurite outgrowth from retinal neurons plated on inhibitory myelin or CSPG substrates. Retinal neurons plated on myelin (dark bars) or CSPG (dotted bars) substrates and treated with C3-05.
Figure 12B:
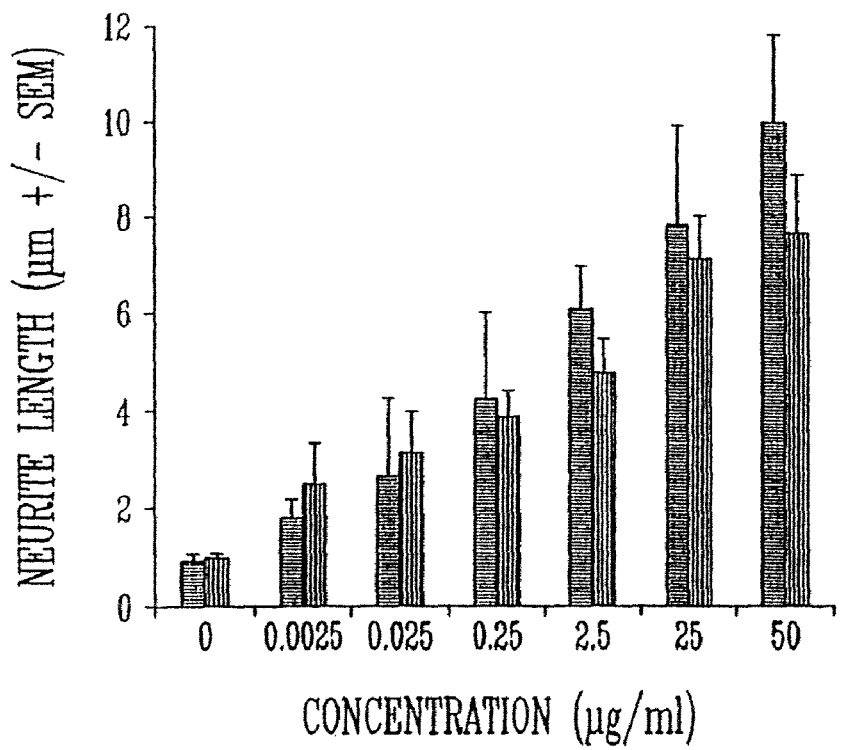

Referring to FIGS. 12A and 12B, to further support the ability of C3-like chimeric proteins to promote neurite outgrowth on inhibitory substrates, we examined the response of primary cultures plated on inhibitory substrates to C3APLT treatment. Purified retinal ganglion cells (RGCs) were plated on myelin, or CSPG substrates and treated with varying concentrations of C3APLT. During the RGC dissection great care was taken in order to try to limit the amount of mechanical manipulation of the cells, however, the isolation protocol requires that some triturating take place in order to dissociate and separate the cells. When RGCs are plated on inhibitory substrates, they maintained a similar round appearance to PC-12 cells plated on myelin. Treatment of RGCs with C3APLT promoted neurite outgrowth and increased neurite length on both myelin and CSPG substrates. In contrast to the wide range of concentrations shown to be effective in other PC-12 experiments a narrower range of C3APLT treatment, 0.025 ug/ml to 50 ug/ml promoted neurite outgrowth and increased neurite length on myelin. In the case of RGCs plated on CSPG substrates, effective concentration ranges of 0.0025 ug/ml to 50 ug/ml were observed.

Figure 13B:
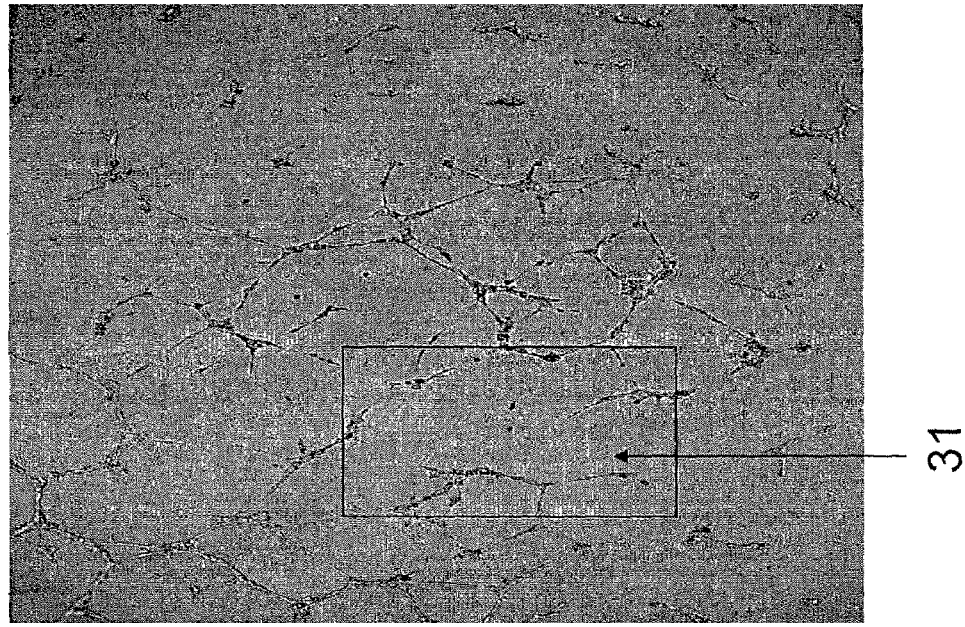
FIG. 13B illustrates a substantial reduction in tube formation of HUVEC endothelial cells cultured in a Matrigel™ matrix. Cultures treated with a composition of this invention comprising a fusion protein, C3APLT as SEQ ID 43, had fewer tubes (area 31) formed in the presence of the fusion protein, thereby demonstrating an inhibition of angiogenesis by administration of the fusion protein to the cells. This substantial reduction in tube formation can be a model for a substantial reduction in neovascularization.
Figure 13A:
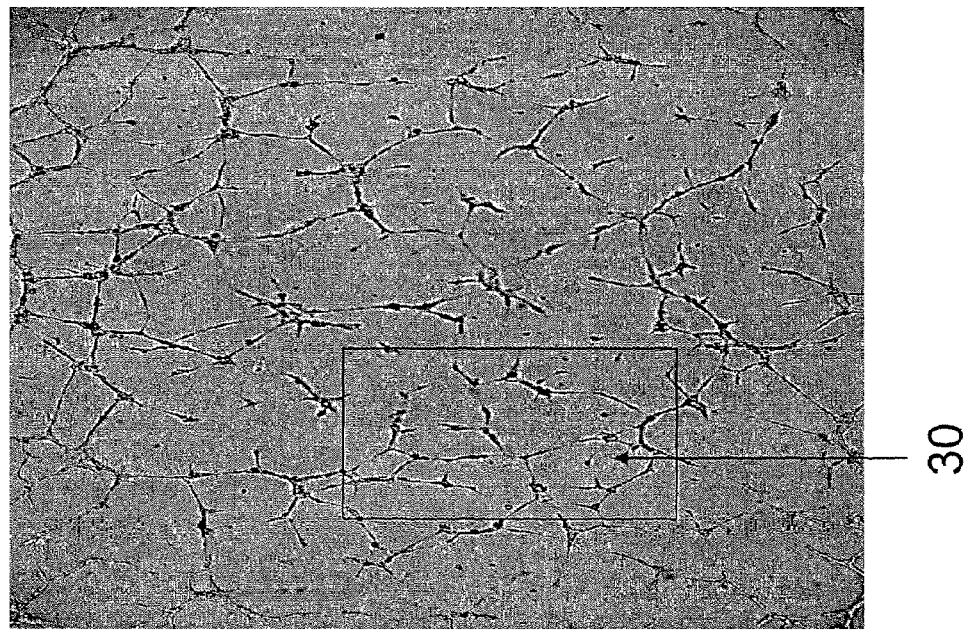
FIG. 13A illustrates tube formation by HUVEC endothelial cells cultured in a Matrigel™ matrix (BD Biosciences). This assay is a cell culture assay for antiogenesis. Tube formation (area 30) can be seen in the control HUVEC endothelial cell culture which does not contain a fusion protein of this invention. This tube formation can be a model for neovascularization.

Referring to FIG. 13, a fusion protein of this invention, C3APLT, can inhibit neovascularization represented by tube formation in an in vitro model comprising HUVEC endothelial cells in culture. In the absence of the fusion protein, extensive tube formation by HUVEC endothelial cells is observed (FIG. 13A, area 30) when the cells are cultured in a Matrigel™ matrix (BD Biosciences). This assay is a cell culture assay for antiogenesis. Tube formation in vitro can be a model for angiogenesis and neovascularization in vivo. However, in the presence of a fusion protein of this invention (e.g., C3APLT as SEQ ID 43 was administered to the cell culture in this example), a substantial reduction in the number and density of tubes formed by HUVEC endothelial cells when the cells are cultured in a Matrigel™ matrix is observed (FIG. 13B, area 31), demonstrating an inhibition of angiogenesis by the fusion protein. Reduction in tube formation can indicate inhibition of angiogenesis. Neovascularization in retinal diseases such as macular degeneration, retinitis pigmentosa, Stargardt's Disease, diabetic retinopathy, hypertensive retinopathy, and occlusive retinopathy, can be reduced or eliminated by inhibition of angiogenesis comprising administration of a fusion protein of this invention to the eye of a patient. Administration of a fusion protein of this invention can be useful to treat such diseases.

Thus, in one aspect, this invention comprises a method of treatment of a disease of the eye selected from the group consisting of macular degeneration, retinitis pigmentosa, Stargardt's Disease, diabetic retinopathy, hypertensive retinopathy, and occlusive retinopathy, the method comprising administration to a patient in need of such treatment a therapeutically effective amount of a pharmaceutical composition comprising:

a) a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating uptake of the active agent by a receptor-independent mechanism and being selected from the group consisting of a subdomain of HIV Tat protein, a homeodomain of antennapedia, and a Histidine tag, said polypeptide having ADP-ribosyl transferase activity, and;

b) a pharmaceutically acceptable carrier.

In another aspect, this invention comprises a method of inhibiting or substantially reducing the rate of subretinal neovascularization and proliferation of neovascular tissue in the eye of a mammalian host comprising administration to said host a therapeutically effective amount of a pharmaceutical composition comprising:

a) a) a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating uptake of the active agent by a receptor-independent mechanism and being selected from the group consisting of a subdomain of HIV Tat protein, a homeodomain of antennapedia, and a Histidine tag, said polypeptide having ADP-ribosyl transferase activity, and;

b) b) a pharmaceutically acceptable carrier.

Figure 14:
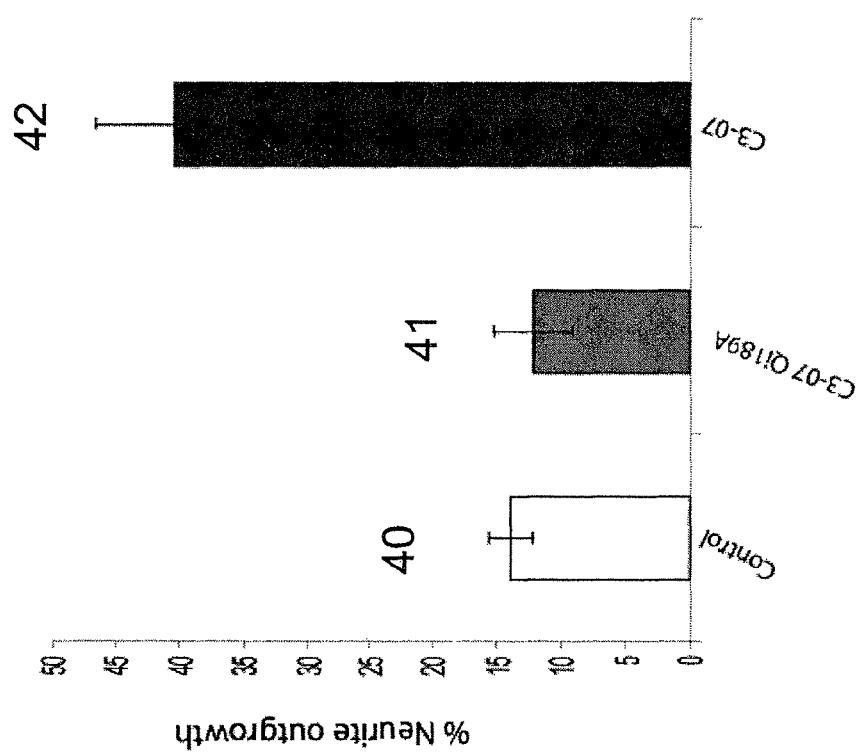
FIG. 14 illustrates activity of a fusion protein of the invention, C3-07, and lack of activity of an inactive mutant of the C3-07 fusion protein, C3-07Q189A, as assayed by bioassay with NG-108 cells. NG-108 cells cultured with fusion protein C3-07 exhibit accelerated neurite outgrowth (bar 42 in FIG. 14, which shows approximately 40% neurite outgrowth). Neurite outgrowth of NG-108 cells treated with C3-07A189A (bar 41, which shows approximately 12% neurite outgrowth) is similar to that of the control (bar 40, which shows approximately 14% neurite outgrowth) of untreated cells demonstrating that protein C3-07Q189A is not active as a fusion protein to induce accelerated neurite outgrowth.

Referring to FIG. 14, the intentional inactivity of a mutant of the C3-07 fusion protein, i.e., inactive C3-07Q189A, as assayed by a bioassay with NG-108 cells is illustrated. NG-108 cells cultured with an active fusion protein of this invention, C3-07, exhibit accelerated neurite outgrowth, which neurite outgrowth is the result of the presence of C3-07. However, neurite outgrowth of cells treated with intentionally inactive mutant C3-07A189A is similar to that of the control cells which are not treated with additional protein. The similarity to the control group demonstrates that the intentionally inactive mutant protein C3-07Q189A is inactive with respect to stimulation of neurite outgrowth.

Figure 15:
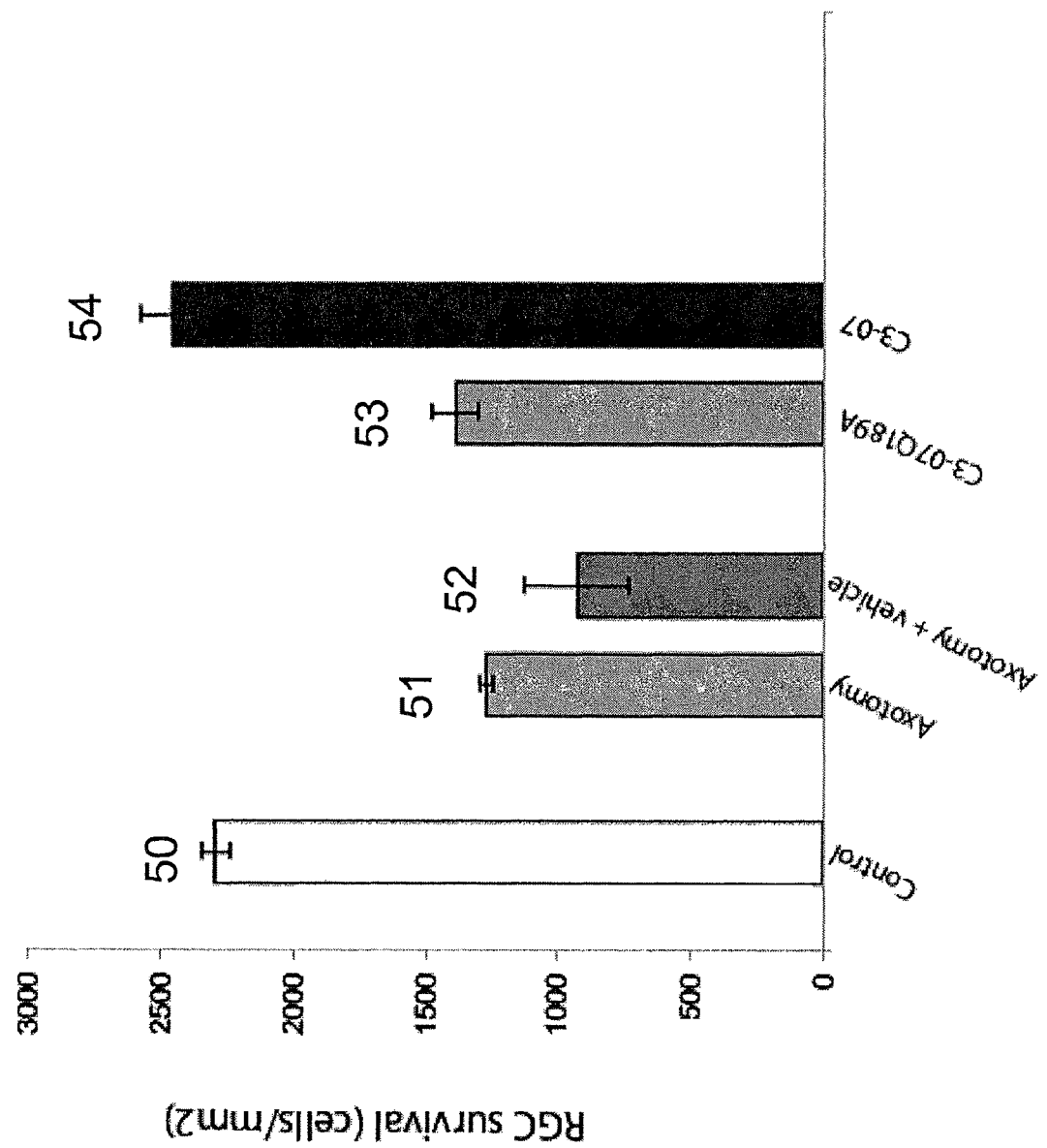
FIG. 15 illustrates that an injection of fusion protein C3-07 can prevent death of retinal ganglion cells (RGCs) induced by crush of the optic nerve following a single injection. After axotomy (bar 51) or axotomy with injection of vehicle (bar 52), where the vehicle is phosphate buffered saline, cells die after axotomy of the optic nerve. When C3-07Q189A, an inactive mutant of fusion protein C3-07, is injected into the eye it is not able to prevent death of the RGCs (bar 53). A single injection of C3-07 prevents cell death (bar 54) and the number of surviving cells is similar to that in control (bar 50), non-axotomized retinas. The results demonstrate that C3-07 can prevent death of retinal neurons, and the neuroprotective activity of C3-07 requires that the enzymatic activity of the C3 fusion protein is retained.

Referring to FIG. 15, an injection of a fusion protein of this invention, C3-07, can prevent (substantially reduce the observed rate of) death of retinal ganglion cells (RGCs) induced by crush of the optic nerve following a single injection. After axotomy or axotomy with injection of vehicle (phosphate buffered saline) cells die after axotomy of the optic nerve. When C3-07Q189A, an intentionally inactive mutant of C3-07, is injected into the eye it is not able to prevent death of the RGCs. A single injection of C3-07 prevents cell death and the number of surviving cells is similar to that in control, non-axotomized retinas. The results demonstrate that C3-07 as a fusion protein of this invention can prevent death of retinal neurons; the neuroprotective activity of C3-07 requires that the enzymatic activity of the C3 fusion protein is retained.

C3-07 exhibits ADP-ribosylation activity, whereas C3-07Q189A is intentionally inactive with respect to ADP-ribosylation activity.

Administration of a pharmaceutical composition comprising a fusion protein of this invention to a patient in need of treatment for a disease of the eye selected from the group consisting of macular degeneration, retinitis pigmentosa, Stargardt's Disease, diabetic retinopathy, hypertensive retinopathy, and occlusive retinopathy can substantially reduce or prevent angiogenesis associated with subretinal neovascularization, choroid neovascularization underlying the macula, and a proliferation of neovascular tissue in the subretinal choroid proximal to the macula in an eye in a mammalian host and comprises a method of treatment of a disease of the eye selected from the group consisting of macular degeneration, retinitis pigmentosa, Stargardt's Disease, diabetic retinopathy, hypertensive retinopathy, and occlusive retinopathy. In one aspect, the compositions of this invention are useful for inhibiting or substantially reducing the rate of subretinal neovascularization and proliferation of neovascular tissue related to a disease of the eye selected from the group consisting of macular degeneration, retinitis pigmentosa, Stargardt's Disease, diabetic retinopathy, hypertensive retinopathy, and occlusive retinopathy. The method can be useful as a prophylactic treatment to prevent further onset or progression of macular degeneration in an eye that exhibits symptoms of a disease of the eye selected from the group consisting of macular degeneration, retinitis pigmentosa, Stargardt's Disease, diabetic retinopathy, hypertensive retinopathy, and occlusive retinopathy. In another aspect, the method can be useful as a prophylactic treatment to prevent the deposition of drusen and the death of cells in the macula. In another aspect, the method can prevent the death of photoreceptor cells (which photoreceptor cells are also herein referred to as photoreceptors) in the eye of a patient by acting on intracellular mechanisms of the regulation of cell death. The method can also be useful to prevent onset or progression of macular degeneration in an eye that does not exhibit vision-obscuring symptoms of macular degeneration, especially in an eye of a patient whose other eye does exhibit vision-obscuring symptoms of macular degeneration.

In another aspect of this invention, a method of treatment of a disease of the eye selected from the group consisting of macular degeneration, retinitis pigmentosa, Stargardt's Disease, diabetic retinopathy, hypertensive retinopathy, and occlusive retinopathy comprises administration such as by injection or implantation into tissue proximal to the eye of a therapeutically effective amount of a polypeptide of this invention, or of a sterile pharmaceutical composition of this invention suitable for injectable administration and comprising a polypeptide of this invention and a carrier suitable for injectable use (e.g., sterile, sterilizable, and isotonic with blood), which polypeptide or pharmaceutical composition can prevent or delay the onset of angiogenesis associated with the group consisting of subretinal neovascularization, choroid neovascularization underlying the macula, and a proliferation of neovascular tissue in the subretinal choroid proximal to the macula in an eye of an average patient in a statistically relevant population of patients to produce a mean delay in the onset of vision loss that can result from said angiogenesis, the mean delay of onset being measured relative to the mean time of onset of vision loss that occurs in an average patient in the statistically relevant population of patients in the absence of said amount of polypeptide, the mean delay in the onset of vision loss comprising a period of at least 1 month, and more preferably a period of at least 6 months, and most preferably a period of greater than 6 months.

Inhibition of angiogenesis by a pharmaceutical composition comprising a fusion protein of this invention such as C3APLT can be evaluated in an in vitro system that can also be useful for the study of angiogenesis in the growth of a tumor, i.e., a system comprising cultivation of endothelial cells in the presence of an extract of basement membrane (Matrigel™) as a model for angiogenesis and for neovascularization and proliferation of neovascular tissue in the eye of a mammal. In the experimental observation conditions, capillary-like structures or tubules associated with angiogenesis or blood vessel capillary formation can be viewed under a microscope. The inhibitory effect of a fusion protein of this invention such as C3APLT on the progress of angiogenesis or on the formation of a tubular capillary network or on the disruption of the process or progress of tumor-associated angiogenesis can be observed by following the disappearance of tubular structures in a Matrigel assay.

Matrigel™ Matrix (BD Biosciences) is a solubulized basement membrane preparation extracted from EHS mouse sarcoma, a tumor rich in ECM proteins. Its major components are laminin, collagen IV, heparan sulfate proteoglycans, and entactin. At room temperature, BD Matrigel™ Matrix polymerizes to produce biologically active matrix material which can mimic mammalian cellular basement membrane, wherein cells can behave in vitro in a manner similar to in vivo conditions. Matrigel™ Matrix can provide a physiologically relevant environment for studies of cell morphology, biochemical function, migration or invasion, and gene expression.

In a Matrigel assay, Matrigel (about 12.5 mg/mL) is thawed at about 4° C. The matrix (about 50 microliters (uL)) is added to each well of a 96 well plate and allowed to solidify for about 10 min at about 37° C. The wells containing solid Matrigel are incubated for about 30 minutes with human umbilical vein endothelial cells (HUVEC cells) at a concentration of about 15,000 cells per well. When the cells are adhered, medium is removed and replaced by fresh medium supplemented with a fusion protein of this invention such as C3APLT and incubated at 37° C. for about 6 to about 8 hours. Control wells are incubated with medium alone. To analyze the growth, tube formation can be visualized by microscopy at, for example, about 50× magnification. The relative mean length, Yx, of an angiogenesis-derived capillary network observed in an evaluation of a pharmaceutical composition comprising a fusion protein, x, of this invention can be quantified using Northern Eclipse software according to the instructions.

Data from a typical Matrigel assay experiment, for example relating to the effect of a pharmaceutical composition comprising a fusion protein designated as C3APLT on length of an angiogenesis-derived capillary network are summarized in Table 3. These data show that the network formation was inhibited by approximately 13% to about 20% under the dose and formulation conditions used versus the inhibition produced by a control vehicle wherein zero inhibition provides 100% growth. This effect on angiogenesis can be enhanced by using higher doses of fusion protein and by preincubation of the HUVEC cells with fusion protein C3APLT prior to addition of the cells to Matrigel. The anti-angiogenesis effect of a composition comprising a polypeptide of this invention comprising an amino acid sequence of a transport agent covalently linked to an amino acid sequence of an active agent, wherein the amino acid sequence of the active agent retains an ADP-ribosyl transferase activity can be useful for inhibiting or substantially reducing the rate of subretinal neovascularization and proliferation of neovascular tissue in the eye of a mammalian host when the composition is administered to the mammal according to the methods of this invention.

TABLE 3

Anti-angiogenesis effect of a pharmaceutical composition comprising a fusion protein, C3APLT, on the mean length of a capillary network in a Matrigel matrix assay

| Mean length of a capillary network associated with angiogenesis | Relative mean length of a capillary network produced in the presence of a vehicle control | Relative mean length of a capillary network produced in the presence of a pharmaceutical composition comprising a fusion protein, C3APLT, at a concentration of 10 micrograms per milliter |
| --- | --- | --- |
| Y1 | 100 | 86.4 |
| Y2 | 100 | 78.2 |
| Y3 | 100 | 86.7 |

It is an advantage that the current invention provides compositions comprising a fusion protein of this invention, which fusion protein after administration to a mammal, preferably proximal to the eye or into a blood vessel that provides blood to the eye, has the ability to penetrate endothelial cells in the eye that in the absence of the fusion protein can form new blood vessels. Thus, when administered to the eye of a mammal, the compositions of this invention can inhibit or substantially reduce the rate of subretinal neovascularization and proliferation of neovascular tissue in the eye of the mammal.

Description of how to Measure Effect on Cell Death In Vivo

One system to examine the neuroprotective effect of fusion proteins in the eye is a model of optic nerve axotomy. In the visual system, retinal ganglion cells die after optic nerve injury, and the severity and rate of cell death depends on the proximity of axonal injury to the eye. In rats, transection of the optic nerve close to the eye causes a delayed RGC death, with cells beginning to die approximately 4 days after axotomy. It has been well demonstrated that intervention with factors that prevent cell death give partial and transient rescue of cells. Intraocular injection of growth factors that include BDNF, NT4, GDNF, CNTF and FGF can rescue RGCs from axotomy-induced cell death. Other ways to rescue cells are to interfere with enzymes that contribute to apoptotic cell death. Lens injury that induces macrophage activation and injection of zymosan from yeast cell walls promote survival of RGCs. To study the inactivation of Rho on RGC survival C3-07 was injected into the vitreous after axotomy: To separate effects of C3-07 on Rho activation from possible inflammatory responses induced by the intravitreal injection of a protein, we used an intentionally inactive mutant of C3-07 protein, i.e., C3-07Q189A, that lacks ADP-ribosylation activity but maintains normal glycohydrolysis activity. To our knowledge, this is the first in vivo study using a mutant C3 exoenzyme or C3-fusion proteins to study cell survival in the retina. We found that a single injection of C3-APLT or C3-07 promoted survival of RGCs equivalent to rates reported for BDNF, and that the effect of C3-07 is dependant on its ability to inactivate Rho.

Other animal models can be used to assess damage to and rescue of photoreceptor cells (e.g., reduction in the rate of death of photoreceptor cells). Useful are genetic models of retinal degeneration and other diseases of the eye in mice. The rescue of photoreceptors can be demonstrated in RCS rats that have an inherited retinal degeneration, or in transgenic lines of mice that express mutated forms of rhodopsin that cause retinitis pigmentosa in human. Such mice are commercially available from Jackson labs. Retinal detachment also leads to death of photoreceptor cells, and this provides another animal model to demonstrate neuroprotection (e.g., reduction in the rate of death of photoreceptor cells). To assess the effect of compounds on neovascularization that occurs in wet macular degeneration and related diseases, animal models are also used. Useful to model neovascularization of the retina are rodent models of oxygen-induced retinopathy of the neuroborn rodents, sometimes referred to as retinopathy of prematurity (ROP).

Method for Making the C3APL, C3APLT, and C3APS

C3APL is the name given to the protein made by ligating a cDNA encoding C3 (Dillon and Feig (1995) 256: 174-184) with cDNA encoding the antennapedia homeodomain (Bloch-Gallego (1993) 120: 485-492). The stop codon at the 3' end of the DNA was replaced with an EcoR I site by polymerase chain reaction (PCR) using the primers (oligonucleotides) 5'GAA TTC TTT AGG ATT GAT AGC TGT GCC 3' (SEQ ID NO: 1) and 5'GGT GGC GAC CAT CCT CCA AAA 3' (SEQ ID NO: 2). The PCR product was subcloned into a pSTBlue-1 vector (Novagen, city), then cloned into a pGEX-4T vector using BamH I and Not I restriction site. This vector was called pGEX-4T/C3. The antennapedia sequence used to add to the 3' end of C3 in pGEX-4T/C3 was created by PCR from the pET-3a vector (Bloch-Gallego (1993) 120: 485-492, Derossi (1994) 269: 10444-10450), subcloned into a pSTBlue-1 blunt vector, then cloned into the pGEX-4T/C3, using the restriction sites EcoR I and Sal I, creating pGEX-4T/C3APL. Another clone (C3APLT) with a frameshift mutation was selected, and the protein made and tested. When the cultures tested positive despite the mutation, the clone was resequenced by another company to confirm the mutation, and this clone was called C3APLT. To confirm the sequence of C3APLT, the coding sequence from both strands was sequenced. The sequence for this clone is given in Examples 16 and 17 (nucleotide sequence of C3APLT; SEQ ID NO: 42, amino acid sequence of C3APLT; SEQ ID NO: 43).

A shorter version of the Antennapedia (pGEX-4T/C3APS) was also made. This chimeric sequence was made by ligating oligonucleotides encoding the short antennapedia peptide (Maizel (1999) 126: 3183-3190) into the pGEX-4T/C3 vector cut with EcoR I and Sal I. The recombinant C3APLT and C3APS cDNAs were separately transformed into bacteria, and after the recombinant proteins were produced, a bacterial homogenate was obtained by sonication, and the homogenate cleared by centrifugation. Glutathione-agarose beads (Sigma) were added to the cleared lysate and placed on a rotating plate for 2-3 hours, then washed extensively. To remove the glutathione S transferase sequence from the recombinant protein, 20 U (unit) of Thrombin was added, the beads were left on a rotator overnight at 4° C. After cleavage with thrombin, the beads were loaded into an empty 20 ml column, and the proteins eluted with PBS (phosphate buffered saline). Aliquots containing recombinant protein were pooled and 100 µl p-aminobenzamidine agarose beads (Sigma) were added and left mixing for 45 minutes at 4° C. to remove thrombin, then recombinant protein was isolated from the beads by centrifugation. Purity of the sample was determined by sodium dodecyl sulfate polyacrylamide gel electrophoresis (SDS-PAGE), and bioactivity bioassay with PC-12 cells was performed (See Lehmann et al supra).

Other possible methods for making bioactive chimeric proteins include anion exchange chromatography. For this, the GST tag is not required and can be removed. The cDNA can then be cloned into a high expression bacterial vector, such as pET, as given in Example 16.

The Rho antagonist is a recombinant protein and can be made according to methods present in the art. The proteins of the present invention may be prepared from bacterial cell extracts, or through the use of recombinant techniques by transformation, transfection, or infection of a host cell with all or part of a C3-encoding DNA fragment with an antennapedia-derived transport sequence in a suitable expression vehicle. Those skilled in the field of molecular biology will understand that any of a wide variety of expression systems can be used to provide the recombinant protein. The precise host cell used is not critical to the invention.

Any fusion protein can be readily purified by utilizing either affinity purification techniques or more traditional column chromatography. Affinity techniques include, but are not restricted to GST (gluathionie-S-transferase), or the use of an antibody specific for the fusion protein being expressed, or the use of a histidine tag. Alternatively, recombinant protein can be fused to an immunoglobulin Fc domain. Such a fusion protein can be readily purified using a protein A column. It is envisioned that small molecule mimetics of the above-described antagonists are also encompassed by the invention.

Testing the Bioactivity of C3APLT, C3APS, C3-TL and C3-TS

To test the efficacy of C3APLT, C3APS, C3-TL and C3-TS a number of experiments were performed with PC-12 cells, a neural cell line, grown on growth inhibitory substrates (see Lehmann et al supra). PC-12 cells were plated on myelin substrates as described (Lehmann et al, supra). C3, C3APLT, C3APS, C3-TL or C3-TS were added at different concentrations without trituration (please refer to FIGS. 4, 5 and 8 for concentrations used). C3 added passively to the culture medium in this way was not able to promote neurite growth in the growth inhibitory substrates because cells must be triturated for C3 to enter the cells and be active (FIG. 1). Both C3APLT and C3APS were able to ADP ribosylate Rho to cause a shift in the molecular weight of RhoA (FIG. 2). Both C3APLT and C3APS were able to promote neurite growth and enter neurons after being added passively to the culture medium (FIG. 3, FIGS. 4 and 5). Dose-response experiment where concentrations of 0.25 ng/ml, 2.5 ng/ml, 25 ng/ml, 250 ng/ml and 2.5 µg/ml (2.5 microgram/milliliter) and 25 µg/ml (25 microgram/milliliter) were tested and showed that C3APLT and C3APS helped more neurons differentiate neurites at doses 10,000 fold less than C3 (FIG. 4). Dose response experiments where concentrations of 0.25 ng/ml, 2.5 ng/ml, 25 ng/ml, 250 ng/ml and 2.5 µg/ml (2.5 microgram/milliliter) and 25 µg/ml (25 microgram/milliliter) were tested and showed that C3APLT was able to promote long neurite growth when added at a minimum concentration of 0.0025 ug/ml (0.0025 microgram/milliliter) (FIG. 5). These concentrations of 2.5 ng/ml and 25 ng/ml for C3APLT and C3APS, represent 10,000 and 1,000 times less than the dose needed with C3, respectively. Moreover, at the highest concentration tested, 50 ug/ml (50 microgram/milliliter), these two new Rho antagonists did not exhibit toxic effects on PC-12 cells, and were able to stimulate neurite outgrowth on growth inhibitory substrates.

C3-TL and C3-TS also were tested at concentrations of 0.25 ng/ml, 2.5 ng/ml, 25 ng/ml, 250 ng/ml and 2.5 µg/ml (2.5 microgram/milliliter) and 25 µg/ml (25 microgram/milliliter) and were found to be able to promote neurite growth on myelin substrates at doses significantly less than C3 (FIG. 8). C3Basic3 was tested at 50 ug/ml in a fast growth assay (FIG. 11).

To verify the ability of C3APLT and C3APS to promote growth from primary neurons, primary retinal cultures were prepared, and the neurons were plated on myelin substrates as described with respect to Example 5. In the absence of treatment with C3APLT or C3APS, the cells remained round and were not able to grow neurites. When treated with C3APLT or C3APS, retinal neurons were able to extend long neurites on inhibitory myelin substrates (FIG. 6).

Next, was tested the ability of C3APLT and C3APS to promote growth on a different type of growth inhibitory substrate relevant to the type of growth inhibitory proteins found at glial scars. Chamber slides were coated with a mixture of chondroitin sulfate proteoglycans (Chemicon), and then plated with retinal neurons (results presented in FIG. 12). The neurons were not able to extend neurites on the proteoglycan substrates, but when treated with C3APLT or C3APS, they extended long neurites. These studies demonstrate that C3APLT and C3APS can be used to promote neurite growth on myelin and on proteoglycans, the major classes of inhibitory substrates that prevent repair after injury in the CNS.

Testing Ability of C3APLT to Promote Regeneration and Functional Recovery after Spinal Cord Injury To test if C3APLT could promote repair after spinal cord injury, fully adult mice were used (as described with respect to Example 6). A dorsal hemisection was made at T8 (thoracic spinal level 8), and mice were treated with different amounts (FIG. 7) of C3APLT in a fibrin glue as described (McKerracher, US patent pending (delivery patent)). In previous known experiments with C3, it was found that 40-50 µg was needed to promote anatomical regeneration in optic nerve (Lehmann et all supra). We tested different doses (see FIG. 7) of C3APLT ranging from 1 µg (1 microgram/milliliter) to 50 µg (50 microgram/milliliter) and assessed animals for behavioral recovery according the BBB scale (Basso (1995) 12: 1-21).

The day following surgery and application of C3APLT, behavioral testing began. The animals were placed in an open field environment that consisted of a rubber mat approximately 4' by 3' in size. The animals were left to move randomly, the movement of the animals were videotaped. For each test two observers scored the animals for ability to move ankle, knee and hip joints in the early phase of recovery. Previously C3 treatment of mice was seen to lead to functional recovery observable 24 hours after treatment. In mice treated with C3APLT, functional recovery could be observed as early as 24 hours after spinal cord injury (FIG. 7). Untreated mice exhibit a function recovery score according to the BBB scale averaging 0, whereas mice treated with C3 are able to walk and have a BBB score averaging 8 (FIG. 7). At higher concentrations of 50 ug, about 50% of the mice treated with C3APLT died within 24 hours. However, of the mice that survived, they exhibited good long-term functional recovery. These results demonstrate that C3APLT effectively promotes functional recovery early after spinal cord injury, and that it is effective at much lower doses than C3. However, at high concentrations, C3APLT appears to exhibit toxicity, and therefore careful doing will be required for clinical use.

Qualitative observations of the videotapes showed that only animals that received C3APLT reached the late phase of recovery after 30 days of treatment. Untreated control animals did not typically pass beyond the early phase of recovery. These results indicate that the application of C3APLT improved long-term functional recovery after spinal cord injury compared to no treatment, injury alone, or fibrin adhesive alone.

To test if the early recovery was due to neuroprotection, spinal cord sections were examined for apoptosis by Tunel labeling following manufacturer's instruction (Roche Diagnostic). C3APLT was able to reduce the number of dying cells observed at the lesion site. Therefore, C3APLT should be an effective neuroprotective agent for treatment of ischemia, such as follows stroke.

EXAMPLE 1

DNA and Protein Sequence Details of C3APL

Nucleotide Sequence of C3APL

It has been reported that the long version of antennapedia transport sequence can enhance neurite growth (Bloch-Gallego, E., LeRoux, I.-, Joliot, A. H., Volovitch, M., Henderson, C. E., Prochiantz, A. 1993. J. Cell Biol. 120:485). Therefore, this sequence is expected to enhance neurite growth. For the sequence given below, the start site, is in the GST sequence of the plasmid (not shown). The vector with the GST sequence is commercially available and thus the entire GST sequence including the start was not sequenced. It was desired to determine only the sequence located 3' to the thrombin cleavage site which releases C3 conjugate from the GST sequence. The GST sequence is cleaved with thrombin.

The APL transport sequence (SEQ ID NO.: 44) is as follows:

```
Val Met Glu Ser Arg Lys Arg Ala Arg Gln Thr Tyr
 1               5                   10

Thr Arg Tyr Gln Thr Leu Glu Leu Glu Lys Glu Phe
            15                  20

His Phe Asn Arg Tyr Leu Thr Arg Arg Arg Arg Ile
 25                  30                      35

Glu Ile Ala His Ala Leu Cys Leu Thr Glu Arg Gln
             40                  45

Ile Lys Ile Trp Phe Gln Asn Arg Arg Met Lys Trp
 50                      55                  60

Lys Lys Glu Asn
```

Nucleotide Sequence of C3APL (SEQ ID NO: 3)

```
ggatcctcta gagtcgacct gcaggcatgc aatgcttatt ccattaatca aaaggcttat    60
tcaaatactt accaggagtt tactaatatt gatcaagcaa aagcttgggg taatgctcag   120
tataaaaagt atggactaag caaatcagaa aaagaagcta tagtatcata tactaaaagc   180
gctagtgaaa taaatggaaa gctaagacaa aataagggag ttatcaatgg atttccttca   240
aatttaataa aacaagttga acttttagat aaatctttta ataaaatgaa gacccctgaa   300
aatattatgt tatttagagg cgacgaccct gcttatttag gaacagaatt tcaaaacact   360
cttcttaatt caaatggtac aattaataaa acggcttttg aaaaggctaa agctaagttt   420
ttaaataaag atagacttga atatggatat attagtactt cattaatgaa tgtctctcaa   480
tttgcaggaa gaccaattat tacacaattt aaagtagcaa aaggctcaaa ggcaggatat   540
attgacccta ttagtgcttt tcagggacaa cttgaaatgt tgcttcctag acatagtact   600
tatcatatag acgatatgag attgtcttct gatggtaaac aaataataat tacagcaaca   660
atgatgggca cagctatcaa tcctaaagaa ttcgtgatgg aatcccgcaa acgcgcaagg   720
cagacataca cccggtacca gactctagag ctagagaagg agtttcactt caatcgctac   780
ttgacccgtc ggcgaaggat cgagatcgcc cacgccctgt gcctcacgga gcgccagata   840
aagatttggt tccagaatcg gcgcatgaag tggaagaagg agaactga              888
```

Amino Acid Sequence of C3APL (SEQ ID NO: 4)

```
Gly Ser Ser Arg Val Asp Leu Gln Ala Cys Asn Ala Tyr Ser Ile Asn
 1               5                   10                  15

Gln Lys Ala Tyr Ser Asn Thr Tyr Gln Glu Phe Thr Asn Ile Asp Gln
             20                  25                  30

Ala Lys Ala Trp Gly Asn Ala Gln Tyr Lys Lys Tyr Gly Leu Ser Lys
             35                  40                  45

Ser Glu Lys Glu Ala Ile Val Ser Tyr Thr Lys Ser Ala Ser Glu Ile
 50                  55                      60
```

```
Asn Gly Lys Leu Arg Gln Asn Lys Gly Val Ile Asn Gly Phe Pro Ser
 65                  70                  75                  80

Asn Leu Ile Lys Gln Val Glu Leu Leu Asp Lys Ser Phe Asn Lys Met
                 85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
            115                 120                 125

Asn Lys Thr Ala Phe Glu Lys Ala Lys Ala Lys Phe Leu Asn Lys Asp
        130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
            195                 200                 205

Ser Ser Asp Gly Lys Gln Ile Ile Ile Thr Ala Thr Met Met Gly Thr
210                 215                 220

Ala Ile Asn Pro Lys Glu Phe Val Met Glu Ser Arg Lys Arg Ala Arg
225                 230                 235                 240

Gln Thr Tyr Thr Arg Tyr Gln Thr Leu Glu Leu Glu Lys Glu Phe His
                245                 250                 255

Phe Asn Arg Tyr Leu Thr Arg Arg Arg Ile Glu Ile Ala His Ala
            260                 265                 270

Leu Cys Leu Thr Glu Arg Gln Ile Lys Ile Trp Phe Gln Asn Arg Arg
        275                 280                 285

Met Lys Trp Lys Lys Glu Asn
    290                 295
```

Physical Characteristics of C3APL
Molecular Weight 34098.03 Daltons
295 Amino Acids
48 Strongly Basic(+) Amino Acids (K,R)
28 Strongly Acidic(−) Amino Acids (D,E)
89 Hydrophobic Amino Acids (A, I, L, F, W, V)
94 Polar Amino Acids (N, C, Q, S, T, Y)

9.847 Isolectric Point
20.524 Charge at PH 7.0
Davis, Botstein, Roth Melting Temp C. 79.48

EXAMPLE 2

DNA and Protein Sequence Details of C3APS

Nucleotide sequence of C3APS (SEQ ID NO: 5). The start site, is in the GST sequence of the plasmid, not shown here.

```
ggatcctcta gagtcgacct gcaggcatgc aatgcttatt ccattaatca aaaggcttat   60
tcaaatactt accaggagtt tactaatatt gatcaagcaa aagcttgggg taatgctcag  120
tataaaaagt atggactaag caaatcagaa aaagaagcta tagtatcata tactaaaagc  180
gctagtgaaa taaatggaaa gctaagacaa aataagggag ttatcaatgg atttccttca  240
aatttaataa aacaagttga acttttagat aaatctttta ataaaatgaa gaccccctgaa  300
aatattatgt tatttagagg cgacgaccct gcttatttag gaacagaatt tcaaaacact  360
cttcttaatt caaatggtac aattaataaa acggcttttg aaaaggctaa agctaagttt  420
ttaaataaag atagacttga atatggatat attagtactt cattaatgaa tgtctctcaa  480
tttgcaggaa gaccaattat tacacaattt aaagtagcaa aaggctcaaa ggcaggatat  540
attgacccta ttagtgcttt tcagggacaa cttgaaatgt tgcttcctag acatagtact  600
```

```
tatcatatag acgatatgag attgtcttct gatggtaaac aaataataat tacagcaaca    660
atgatgggca cagctatcaa tcctaaagaa ttccgccaga tcaagatttg gttccagaat    720
cgtcgcatga agtggaagaa ggtcgactcg agcggccgca tcgtgactga ctga         774
```

The APS transport sequence (SEQ ID NO.: 45) is as follows:

```
Arg Gln Ile Lys Ile Trp Phe Gln Asn Arg Arg Met
 1               5                  10

Lys Trp Lys Lys Val Asp Ser
            15
```

Amino Acid Sequence for C3APS (SEQ ID NO: 6)

Physical Characteristics of C3APS
Molecular Weight 29088.22 Daltons
257 Amino Acids
38 Strongly Basic(+) Amino Acids (K,R)
23 Strongly Acidic(−) Amino Acids (D,E)
79 Hydrophobic Amino Acids (A, I, L, F, W, V)
83 Polar Amino Acids (N, C, Q, S, T, Y)
9.745 Isolectric Point
15.211 Charge at PH 7.0
Davis, Botstein, Roth Melting Temp C. 78.34

```
Gly Ser Ser Arg Val Asp Leu Gln Ala Cys Asn Ala Tyr Ser Ile Asn
 1               5                  10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
            35                  40                  45

Ser Glu Lys Glu Ala Ile Val Ser Tyr Thr Lys Ser Ala Ser Glu Ile
        50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
                100                 105                 110

Leu Gly Thr Glu Phe Gln Asn Thr Leu Leu Asn Ser Asn Gly Thr Ile
            115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
            195                 200                 205

Ser Ser Asp Gly Lys Gln Ile Ile Ile Thr Ala Thr Met Met Gly Thr
    210                 215                 220

Ala Ile Asn Pro Lys Glu Phe Arg Gln Ile Lys Ile Trp Phe Gln Asn
225                 230                 235                 240

Arg Arg Met Lys Trp Lys Lys Val Asp Ser Ser Gly Arg Ile Val Thr
                245                 250                 255

Asp
```

EXAMPLE 3

Method for Making the C3APLT and C3APS Proteins

C3APL (amino acid sequence: SEQ ID NO.: 4) and C3APLT (amino acid sequence; SEQ ID NO: 37) are the names given to the proteins encoded by cDNAs made by ligating the functional domain of C3 transferase and the homeobox region of the transcription factor called antennapedia (Bloch-Gallego (1993) 120: 485-492) in the following way. A cDNA encoding C3 (Dillon and Feig (1995) 256: 174-184) cloned in the plasmid vector pGEX-2T was used for the C3 portion of the chimeric protein. The stop codon at the 3' end of the DNA was replaced with an EcoR I site by polymerase chain reaction using the primers 5'GAA TTC TTT AGG ATT GAT AGC TGT GCC 3' (SEQ ID NO: 1) and 5'GGT GGC GAC CAT CCT CCA AAA 3' (SEQ ID NO: 2). The PCR product was sub-cloned into a pSTBlue-1 vector (Novagen, city), then cloned into a pGEX-4T vector using BamH I and Not I restriction site. This vector was called pGEX-4T/C3. The pGEX-4T vector has a 5' glutathione S transferase (GST) sequence for use in affinity purification. The antennapedia sequence used to add to the 3' end of C3 in pGEX-4T/C3 was created by PCR from the pET-3a vector (Bloch-Gallego (1993) 120: 485-492, Derossi (1994) 269: 10444-10450). The primers used were 5'GAA TCC CGC AAA CGC GCA AGG CAG 3' (SEQ ID NO: 7) and 5'TCA GTT CTC CTT CTT CCA CTT CAT GCG 3' (SEQ ID NO: 8). The PCR product obtained from the reaction was sub-cloned into a pSTBlue-1 blunt vector, then cloned into the pGEX-4T/C3, using the restriction sites EcoR I and Sal I, creating pGEX-4T/C3APL and C3APLT. C3APLT was selected for the presence of a frameshift mutation giving a transport region moiety rich in prolines.

A shorter version of the antennapedia (pGEX-4T/C3AP-short) (amino acid sequence of C3APS; SEQ ID NO.: 6) was also made. This chimeric sequence was made by ligating oligonucleotides encoding the short antennapedia peptide (Maizel (1999) 126: 3183-3190) into the pGEX-4T/C3 vector cut with EcoR I and Sal I. For pGEX-4T/C3AP-short the sequences of the oligos made were 5'AAT TCC GCC AGA TCA AGA TTT GGT TCC AGA ATC GTC GCA TGA AGT GGA AGA AGG 3' (SEQ ID NO: 9) and 5'GGC GGT CTA GTT CTA AAC CAA GCT CTT AGC AGC GTA GTT CAC CTT CTT CCA GCT 3' (SEQ ID NO: 10). The two strands were annealed together by mixing equal amounts of the oligonucleotides, heating at 72° C. for 5 minutes and then leaving them at room temperature for 15 minutes. The oligonucleotides were ligated into the pGEX4T/C3 vector and clones were picked and analyzed.

To prepare recombinant C3APLT (SEQ ID NO.: 37) and C3APS (SEQ ID NO.: 6) proteins, the plasmids containing the corresponding cDNAs (pGEX-4T/C3APLT and pGEX-4T/C3AP-short) were transformed into bacteria, strain XL-1 blue competent *E. coli*. The bacteria were grown in L-broth (10 g/L Bacto-Tryptone, 5 g/L Yeast Extract, 10 g/L NaCl) with ampicillin at 50 ug/ml (BMC-Roche), in a shaking incubator for 1 hr at 37° C. and 300 rpm. Isopropyl .beta.-D-thiogalactopyranoside (IPTG), (Gibco) was added to a final concentration of 0.5 mM to induce the production of recombinant protein and the culture was grown for a further 6 hours at 37° C. and 250 rpm. Bacteria pellets were obtained by centrifugation in 250 ml centrifuge bottles at 7000 rpm for 6 minutes at 4° C. Each pellet was re-suspended in 10 ml of Buffer A (50 mM Tris, pH 7.5, 50 mM NaCl, 5 mM MgCl2, 1 mM DTT) plus 1 mM PMSF. All re-suspended pellets were pooled and transferred to a 100 ml plastic beaker on ice. The remaining Buffer A with PMSF was added to the pooled sample. The bacteria sample was sonicated 6.times.20 seconds using a Branson Sonifier 450 probe sonicator. Both the bacteria and probe were cooled on ice 1 minute between sonications. The sonicate was centrifuged in a Sorvall SS-34 rotor at 16,000 rpm for 12 minutes at 4° C. to clarify the supernatant. The supernatant was transferred into fresh SS-34 tubes and re-spun at 12,000 rpm for 12 minutes at 4° C. Up to 20 ml of Glutathione-agarose beads (Sigma) were added to the cleared lysate and placed on a rotating plate for 2-3 hours. The beads were washed 4 times with buffer B, (Buffer A, NaCl is 150 mM, no PSMF) then 2 times with Buffer C (Buffer B+2.5 mM CaCl2). The final wash was poured out till the beads created a thick slurry. To remove the glutathione S transferase sequence from the recombinant protein, 20 U of Thrombin (Bovine, Plasminogen-free, Calbiochem) was added, the beads were left on a rotator overnight at 4° C. After cleavage with thrombin the beads were loaded into an empty 20 ml column. Approximately 20 aliquots of 1 ml were collected by elution with PBS. Samples of each aliquot of 0.5 ul were spotted on nitrocellulose and stained with Amido Black to determine the protein peak. Aliquots containing fusion proteins were pooled and 100 □l (100 microliter) p-aminobenzamidine agarose beads (Sigma) were added and left mixing for 45 minutes at 4° C. This last step removed the thrombin from the recombinant protein sample. The recombinant protein was centrifuged to remove the beads and then concentrated using a centriprep-10 concentrator (Amicon). The concentrated recombinant protein was desalted with a PD-10 column (Pharmacia, containing Sephadex G-25M) and ten 0.5 ml aliquots were collected. A dot-blot was done on these samples to determine the protein peak, and the appropriate aliquots pooled, filter-sterilized, and stored at −80° C. A protein assay (DC assay, Biorad) was used to determine the concentration of recombinant protein. Purity of the sample was determined by SDS-PAGE, and bioactivity bioassay with PC-12 cells.

EXAMPLE 4

Testing of Efficacy of C3APLT and C3APS in Tissue Culture

To test the ability of C3APLT and C3APS to overcome growth inhibition, PC-12 cells were plated on myelin, a growth inhibitory substrate. The myelin was purified from bovine brain (Norton and Poduslo (1973) 21: 749-757). In some other experiments chondroitin sulfate proteoglycan (CSPG) substrates were made from a purchased protein composition (Chemicon). Before coating coverslips or wells of a 96 well plate, they were coated with poly-L-lysine (0.025 □g/ml; 0.025 microgram/milliliter) (Sigma, St. Louis, Mo.), washed with water and allowed to dry. Myelin stored as a 1 mg/ml solution at −80° C. was thawed at 37° C., and vortexed. The myelin was plated at 8 ug/well in a 8 well chamber Lab-Tek slides (Nuc, Naperville, Ill.). The myelin solution was left to dry overnight in a sterile tissue culture hood. The next morning the substrate was washed gently with phosphate buffered saline, and then cells in media were added to the substrate. PC-12 cells (Lehmann et al., 1999) were grown in DMEM with 10% horse serum (HS) and 5% fetal bovine serum (FBS). Two days prior to use the PC-12 cells were differentiated by 50 ng/ml of nerve growth factor (NGF). After the cells were primed, 5 ml of trypsin was added to the culture dish to detach the cells, the cells were pelleted and re-suspended in 2 ml of DMEM with 1% HS and 50 ng/ml of nerve growth factor. Approximately, 5000 to 7000 cells were then plated on 8 well chamber Lab-Tek slides (Nuc, Naperville, Ill.) coated myelin. The cells were placed on the test substrates at 37° C. for 3-4 hours to allow the cells to settle. The original media was carefully removed by aspiration, taking care not to disrupt the cells and replaced with DMEM with 1% HS, 50 ng/ml of NGF and varying amounts of the C3, C3APLT, or C3APS, depending on the dose desired. After two days, the cells were fixed (4% paraformaldehyde and 0.5% glutaraldehyde). For control experiments with unmodified C3, NGF primed PC-12 cells were trypsinized to detach them from the culture dish, the cells were washed once with scrape loading buffer (114 mM KCL, 15 mM NaCl, 5.5 mM MgCl2, and 10 mM Tris-HCL) and then the cells were scraped with a rubber policeman into 0.5 ml of scraping buffer in the presence of 25 or 50 □g/ml (microgram/milliliter) of C3. The cells were pelleted and resuspended in 2 ml of DMEM, 1% HS and 50 ng/ml nerve growth factor before plating. At least four experiments were analyzed for each treatment. For each well, twelve images were collected with a 20.times. objective using a Zeiss Axiovert microscope. For each image, the numbers of cells with and without neurites were counted and the lengths of the neurites were determined. Since myelin is phase dense, cells plated on myelin substrates were immuno-stained with anti-.beta.III tubulin antibody before analysis. Quantitative analysis of neurite outgrowth was with the aid of Northern Eclipse software (Empix Imaging, Mississauga, Ontario, Canada). Data analysis and statistics were with Microsoft Excel.

For a fast bioassay, the compounds were tested in tissue culture as described above, except that the cells were plated on the tissue culture plastic rather than on inhibitory substrates. For these experiments the plates were fixed and the neurites counted five hours after plating the cells. The test compounds (C3APLT and C3Basic3) were able to promote faster growth on tissue culture plastic than cells plated without treatment (FIG. 11).

To examine ADP ribosylation by C3, C3APLT, and C3APS, the compounds were added to PC-12 cell cultures, as described above. The cells were harvested by centrifugation, cell homogenates prepared and the proteins separated by SDS polyacrylamide gel electrophoresis. The proteins were then transferred to nitrocellulose and the Western blots probed with anti-RhoA antibody (Santa Cruz).

EXAMPLE 5

Testing Ability of C3APLT and C3APS to Override Inhibition of Multiple Growth Inhibitory Proteins Myelin substrates were made as described in Example 4 and plated on tissue culture chamber slides. P1 to P3 rat pups were decapitated, the heads washed in ethanol and the eye removed and placed in a petri dish with Hanks buffered saline solution (HBSS, from Gibco). A hole was cut in the cornea, the lens removed, and the retina squeezed out. Typically, four retinas per preparation were used. The retinas were removed to a 15 ml tube and the volume brought to 7 ml. A further 7 ml of dissociation enzymes and papain were added. The dissociation enzyme solution was made as follows: 30 mg DL cysteine was added to a 15 ml tube (Sigma DL cystein hydrochloride), and 70 ml HBSS, 280 ul of 10 mg/ml bovine serum albumin were added and the solution mixed and pH adjusted to 7 with 0.3 N NaOH. The dissociate solution was filter-sterilized and kept frozen in 7 ml aliquots, and before use 12.5 units papain per ml (Worthington) was added. After adding the dissociation solution to the retina, the tube was incubated for 30 minutes on a rocking tray at 37° C. The retinas were then gently triturated, centrifuged and washed with HBSS. The HBSS was replaced with growth medium (DMEM (Gibco), 10% fetal bovine serum, and 50 ng/ml brain derived neurotrophic factor (BDNF) vitamins, penicillin-streptomycin, in the presence or absence of C3APLT or C3APS. Cells were plated on test substrates of myelin or CSPG in chamber slides prepared as described in Example 4, above. A quantitative analysis was completed as described for Example 4 above. Neurons were visualized by fluorescent microscopy with anti-.beta.III tubulin antibody, which detects growing retinal ganglion cells (RGCs). Results are presented in FIG. 6.

EXAMPLE 6

Treatment of Injured Mouse Spinal Cord with C3APLT and Measurement of Recovery of Motor Function in Treated Mice Adult Balb-c mice were anaesthetized with 0.6 ml/kg hypnorm, 2.5 mg/kg diazepam and 35 mg/kg ketamine. This does gives about 30 minutes of anaesthetic, which is sufficient for the entire operation. A segment of the thoracic spinal column was exposed by removing the vertebrae and spinus process with microrongeurs (Fine Science Tools). A spinal cord lesion was then made dorsally, extending past the central canal with fine scissors, and the lesion was recut with a fine knife. This lesion renders all of the control animals paraplegic. The paravertebral muscle were closed with reabsorbable sutures, and the skin was closed with 2.0 silk sutures. After surgery, the bladder was manually voided every 8-10 hours until the animals regained control, typically 2-3 days. Food was placed in the cage for easy access, and sponge-water used for easy accessibility of water after surgery. Also, animals received subcutaneous injection Buprenorphine (0.05 to 0.1 mg/kg) every 8-12 hours for the first 3 days. Any animals that lost 15-20% of body weight were killed.

Rho antagonists (C3 or C3-like proteins) were delivered locally to the site of the lesion by a fibrin-based tissue adhesive delivery system (McKerracher, Canadian patent application No. 2,325,842). Recombinant C3APLT was mixed with fibrinogen and thrombin in the presence of CaCl2. Fibrinogen is cleaved by thrombin, and the resulting fibrin monomers polymerize into a three-dimensional matrix. We added C3APLT as part of a fibrin adhesive, which polymerized within about 10 seconds after being placed in the injured spinal cord. We tested C3APLT applied to the spinal cord lesion site after the lesion was made. For control we injected fibrin adhesive alone, or transected the cord without further treatment. For behavioral testing, the BBB scoring method was used to examine locomotion in an open field environment (Basso (1995) 12: 1-21). Results are presented in FIG. 7. The environment was a rubber mat approximately 4'.times.3' in size, and animals were placed on the mat and videotaped for about 4 minutes. Care was taken not to stimulate the peroneal region or touch the animals excessively during the taping session. The video tapes were digitized and observed by two observers to assign BBB scores. The BBB score, modified for mice, was as follows:

| Score | Description |
|---|---|
| 1 | No observable hindlimb (HL) movement. |
| 2 | Slight movement of one or two joints. |
| 3 | Extensive movement of one joint and/or slight movement of one other joint. |
| 4 | Extensive movement of two joints. |
| 5 | Slight movement of all three joints of the HL. |
| 6 | Slight movement of two joints and extensive movement of the third. |
| 7 | Extensive movement of two joints and slight movement of the third. |
| 8 | Extensive movement of all three joints of the HL walking with no weight support. |
| 9 | Extensive movement of all three joints, walking with weight support. |
| 10 | Frequent to consistent dorsal stepping with weight support. |
| 11 | Frequent plantar stepping with weight support. |
| 12 | Consistent plantar stepping with weight support, no coordination. |
| 13 | Consistent plantar stepping with consistent weight support, occasional FL-HL coordination. |
| 14 | Consistent plantar stepping with consistent weight support, frequent FL-HL coordination. |
| 15 | Consistent plantar stepping with consistent weight support, consistent FL-HL coordination; predominant paw position during locomotion is rotated internally or externally, or consistent FL-HL coordination with occasional dorsal stepping. |
| 16 | Consistent plantar stepping with consistent weight support, consistent FL-HL coordination; predominant paw position is parallel to the body; frequent to consistent toe drag, or curled toes, trunk instability. |
| 17 | Consistent plantar stepping with consistent weight support, consistent FL-HL coordination; predominant paw position is parallel to the body, no toe drag, some trunk instability. |
| 18 | Consistent plantar stepping with consistent weight support, consistent FL-HL coordination; predominant paw position is parallel to the body, no toe drag and consistent stability in the locomotion. |

EXAMPLE 7

Treatment of Injured Mouse Spinal Cord with C3APLT and Assessment of Anatomical Recovery Mice that received a spinal cord injury and treated as controls or with C3APLT, as described for Example 6 were assessed for morphological changes to the scar and for axon regeneration. To study axon regeneration, the corticospinal axons were identified by anterograde labeling. For anterograde labeling studies, the animals were anaesthetized as above, and the cranium over the motor cortex was removed. With the fine glass micropipetter (about 100 um in diameter) the cerebral cortex was injected with 2-4 ul of horse radish peroxidase conjugated to wheat germ agglutinin (2%), a marker that is taken up by nerve cells and transported anterogradely into the axon that extends into the spinal cord. After injection of the anterograde tracer, the cranium was replaced, and the skin closed with 5-0 silk sutures. The animals were sacrificed with chloral hydrate (4.9 mg/10 g) after 48 hours, and perfused with 4% paraformaldehyde in phosphate buffer as a fixative. The spinal cord was removed, cryoprotected with sucrose and cryostat sections placed on slides for histological examination.

EXAMPLE 8

DNA and Protein Sequence Details of C3-TL

The Tat coding sequence was obtained by polymerase chain reaction of the plasmid SVCMV-TAT (obtained form Dr. Eric Cohen, Universite de Montreal) that contains the entire HIV-1 Tat coding sequence. To isolate the transport sequence of the Tat protein, PCR was used. The first primer (5'GAATCCAAGCACCAGGAAGTCAGCC 3' (SEQ ID NO.: 11)) and the second primer (5' ACC AGCCACCACCT-TCTGATA 3' (SEQ ID NO.: 12)) used corresponded to amino acids 27 to 72 of the HIV Tat protein. Upon verification and purification, the PCR product was sub cloned into a pST-Blue-1 blunt vector. This transport segment of the Tat protein was then cloned into pGEX-4T/C3 at the 3' end of C3, using the restriction sites EcoR I and Sac I. The new C3-Tat fusion protein was called C3-TL. Recombinant protein was made as described in Example 3.

DNA Sequence of C3-TL (SEQ ID NO.: 13)

```
ggatcctcta gagtcgacct gcaggcatgc aatgcttatt ccattaatca aaaggcttat      60
tcaaatactt accaggagtt tactaatatt gatcaagcaa aagcttgggg taatgctcag     120
tataaaaagt atggactaag caaatcagaa aaagaagcta tagtatcata tactaaaagc     180
gctagtgaaa taaatggaaa gctaagacaa aataagggag ttatcaatgg atttccttca     240
aatttaataa aacaagttga acttttagat aaatctttta ataaaatgaa gaccccctgaa    300 aatattatgt tatttagagg cgacgaccct gcttatttag gaacagaatt tcaaaacact     360
cttcttaatt caaatggtac aattaataaa acggcttttg aaaaggctaa agctaagttt     420
ttaaataaag atagacttga atatggatat attagtactt cattaatgaa tgtctctcaa     480
tttgcaggaa gaccaattat tacacaattt aaagtagcaa aaggctcaaa ggcaggatat     540 attgaccctta ttagtgcttt tcagggacaa cttgaaatgt tgcttcctag acatagtact    600
tatcatatag acgatatgag attgtcttct gatggtaaac aaataataat tacagcaaca     660
atgatgggca cagctatcaa tcctaaagaa ttcaagcatc caggaagtca gcctaaaact     720
gcttgtacca attgctattg taaaaagtgt tgctttcatt gccaagtttg tttcataaca     780
aaagccttag gcatctccta tggcaggaag cggagacagc gacgaagagc tcatcagaac     840
agtcagactc atcaagcttc tctatcaaag cagtaa                               876
```

The TL transport peptide sequence by itself is as follows:
(SEQ ID NO.: 46)

```
Lys His Pro Gly Ser Gln Pro Lys Thr Ala Cys Thr
 1               5                  10
Asn Cys Tyr Cys Lys Lys Cys Cys Phe His Cys Gln
             15              20
Val Cys Phe Ile Thr Lys Ala Leu Gly Ile Ser Tyr
 25                  30                  35
Gly Arg Lys Arg Arg Gln Arg Arg Ala His Gln Asn
             40              45
Ser Gln Thr His Gln Ala Ser Leu Ser Lys Gln
 50                  55
```

Physical Characteristics
Molecular Weight 32721.40 Daltons
291 Amino Acids
43 Strongly Basic(+) Amino Acids (K,R)
21 Strongly Acidic(−) Amino Acids (D,E)
82 Hydrophobic Amino Acids (A, I, L, F, W, V)
104 Polar Amino Acids (N, C, Q, S, T, Y)
9.688 Isoelectric Point
22.655 Charge at PH 7.0
Total Number of Bases Translated is 876

| | |
|---|---|
| % A = 37.44 | [328] |
| % G = 17.58 | [154] |
| % T = 28.31 | [248] |
| % C = 16.67 | [146] |

The Protein Sequence of C3-TL (SEQ ID NO.: 14)

```
Gly Ser Ser Arg Val Asp Leu Gln Ala Cys Asn Ala Tyr Ser Ile Asn
 1               5                  10                  15
Gln Lys Ala Tyr Ser Asn Thr Tyr Gln Glu Phe Thr Asn Ile Asp Gln
             20                  25                  30
Ala Lys Ala Trp Gly Asn Ala Gln Tyr Lys Lys Tyr Gly Leu Ser Lys
             35                  40                  45
Ser Glu Lys Glu Ala Ile Val Ser Tyr Thr Lys Ser Ala Ser Glu Ile
 50                  55                  60
Asn Gly Lys Leu Arg Gln Asn Lys Gly Val Ile Asn Gly Phe Pro Ser
 65              70                  75                  80
Asn Leu Ile Lys Gln Val Glu Leu Leu Asp Lys Ser Phe Asn Lys Met
             85                  90                  95
Lys Thr Pro Glu Asn Ile Met Leu Phe Arg Gly Asp Asp Pro Ala Tyr
             100                 105                 110
Leu Gly Thr Glu Phe Gln Asn Thr Leu Leu Asn Ser Asn Gly Thr Ile
             115                 120                 125
Asn Lys Thr Ala Phe Glu Lys Ala Lys Ala Lys Phe Leu Asn Lys Asp
             130                 135                 140
Arg Leu Glu Tyr Gly Tyr Ile Ser Thr Ser Leu Met Asn Val Ser Gln
 145                 150                 155                 160
Phe Ala Gly Arg Pro Ile Ile Thr Gln Phe Lys Val Ala Lys Gly Ser
             165                 170                 175
Lys Ala Gly Tyr Ile Asp Pro Ile Ser Ala Phe Gln Gly Gln Leu Glu
             180                 185                 190
Met Leu Leu Pro Arg His Ser Thr Tyr His Ile Asp Asp Met Arg Leu
             195                 200                 205
Ser Ser Asp Gly Lys Gln Ile Ile Ile Thr Ala Thr Met Met Gly Thr
 210                 215                 220
Ala Ile Asn Pro Lys Glu Phe Lys His Pro Gly Ser Gln Pro Lys Thr
 225                 230                 235                 240
Ala Cys Thr Asn Cys Tyr Cys Lys Lys Cys Cys Phe His Cys Gln Val
             245                 250                 255
Cys Phe Ile Thr Lys Ala Leu Gly Ile Ser Tyr Gly Arg Lys Arg Arg
             260                 265                 270
Gln Arg Arg Ala His Gln Asn Ser Gln Thr His Gln Ala Ser Leu
             275                 280                 285
Ser Lys Gln
 290
```

EXAMPLE 9

DNA and Protein Sequence Details of C3-TS

A shorter Tat construct was also made (C3-TS). To make the shorter C3 Tat fusion protein the following oligonucleotides were 5'AAT TCT ATG GTC GTA AAA AAC GTC GTC AAC GTC GTC GTG 3' (SEQ ID NO.: 15) and 5' GAT ACC AGC ATT TTT TGC AGC AGT TGC AGC AGC ACA GCT 3' (SEQ ID NO.: 16). The two oligonucleotide strands were annealed together by combining equal amounts of the oligonucleotides, heating at 72° C. for 5 minutes and then letting the oligonucleotide solution cool at room temperature for 15 minutes. The oligonucleotides were ligated into the pGEX4T/C3 vector at the 3' end of C3. The construct was sequenced. All plasmids were transformed into XL-1 blue competent cells. Recombinant protein was made as described in Example 3.

Nucleotide Sequence of C3-TS (SEQ ID NO.: 17)

```
ggatcctcta gagtcgacct gcaggcatgc aatgcttatt ccattaatca aaaggcttat      60
tcaaatactt accaggagtt tactaatatt gatcaagcaa aagcttgggg taatgctcag     120
tataaaaagt atggactaag caaatcagaa aaagaagcta tagtatcata tactaaaagc     180
gctagtgaaa taaatggaaa gctaagacaa aataagggag ttatcaatgg atttccttca     240
aatttaataa aacaagttga acttttagat aaatctttta ataaaatgaa gaccccctgaa    300
aatattatgt tatttagagg cgacgaccct gcttatttag gaacagaatt tcaaaacact     360
cttcttaatt caaatggtac aattaataaa acggcttttg aaaaggctaa agctaagttt     420
ttaaataaag atagacttga atatggatat attagtactt cattaatgaa tgtctctcaa     480
tttgcaggaa gaccaattat tacacaattt aaagtagcaa aaggctcaaa ggcaggatat     540
attgacccta ttagtgcttt tcagggacaa cttgaaatgt tgcttcctag acatagtact     600
tatcatatag acgatatgag attgtcttct gatggtaaac aaataataat tacagcaaca     660
atgatgggca cagctatcaa tcctaaagaa ttctatggtg ctaaaaaacg tcgtcaacgt     720
cgtcgtgtcg actcgagcgg cccgcatcgt gactga                              756
```

The TS transport peptide sequence by itself is as follows: (SEQ ID NO.: 47)

```
Tyr Gly Ala Lys Lys Arg Arg Gln Arg Arg Arg Val
 1               5                   10

Asp Ser Ser Gly Pro His Arg Asp
            15                  20
```

The Protein Sequence of C3-TS (SEQ ID NO.: 18)

```
Gly Ser Ser Arg Val Asp Leu Gln Ala Cys Asn Ala Tyr Ser Ile Asn
 1               5                   10                  15

Gln Lys Ala Tyr Ser Asn Thr Tyr Gln Glu Phe Thr Asn Ile Asp Gln
                20                  25                  30

Ala Lys Ala Trp Gly Asn Ala Gln Tyr Lys Lys Tyr Gly Leu Ser Lys
            35                  40                  45

Ser Glu Lys Glu Ala Ile Val Ser Tyr Ile Lys Ser Ala Ser Glu Thr
        50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Pro Ala Tyr
            100                 105                 110

Leu Gly Thr Glu Phe Gln Asn Thr Leu Leu Asn Ser Asn Gly Thr Ile
            115                 120                 125

Asn Lys Thr Ala Phe Glu Lys Ala Lys Ala Lys Phe Leu Asn Lys Asp
            130                 135                 140
```

-continued

```
Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
            165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
        210                 215                 220

Ala Ile Asn Pro Lys Glu Phe Tyr Gly Ala Lys Lys Arg Arg Gln Arg
225                 230                 235                 240

Arg Arg Val Asp Ser Ser Gly Pro His Arg Asp
            245                 250
```

Physical Characteristics

Molecular Weight 26866.62 Daltons
238 Amino Acids
36 Strongly Basic(+) Amino Acids (K,R)
21 Strongly Acidic(−) Amino Acids (D,E)
71 Hydrophobic Amino Acids (A, I, L, F, W, V)
78 Polar Amino Acids (N, C, Q, S, T, Y)
9.802 Isoelectric Point
15.212 Charge at PH 7.0
Total Number of Bases Translated is 717

| | | |
|---|---|---|
| % A = 38.91 | [279] | |
| % G = 17.43 | [125] | |
| % T = 28.45 | [204] | |
| % C = 15.20 | [109] | |

EXAMPLE 10

The following example illustrates how a coding sequence can be modified without affecting the efficacy of the translated protein. The example shows modifications to C3Basic3 that would not affect the activity. Sequences may include the entire GST sequence, as shown here that includes the start site, which would not be removed enzymatically. Also, the transport sequence shown in this example has changes in amino acid composition surrounding the active sequence due to a difference in the cloning strategy, and the His tag has been omitted. However, the active region is: R R K Q R R K R R (SEQ ID NO:53). This sequence is contained in the C3Basic3, and is the active transport sequence in the sequence below. Also note that the C-terminal region of the protein after this active region differs from C3Basic3. That is because the cloning strategy was changed, the restriction sites differ, and therefore non-essential amino acids 3' terminal to the transport sequence are transplanted and included in the protein.

Nucleic Acid Sequence: (SEQ ID NO.: 19)
1413 base pairs
single strand
linear sequence

```
atgtccccta tactaggtta ttggaaaatt aagggccttg tgcaacccac tcgacttctt   60
ttggaatatc ttgaagaaaa atatgaagag catttgtatg agcgcgatga aggtgataaa  120
tggcgaaaca aaaagtttga attgggtttg gagtttccca atcttcctta ttatattgat  180
ggtgatgtta aattaacaca gtctatggcc atcatacgtt atatagctga caagcacaac  240
atgttgggtg gttgtccaaa agagcgtgca gagatttcaa tgcttgaagg agcggttttg  300
gatattagat acggtgtttc gagaattgca tatagtaaag actttgaaac tctcaaagtt  360
gattttctta gcaagctacc tgaaatgctg aaaatgttcg aagatcgttt atgtcataaa  420
acatatttaa atggtgatca tgtaacccat cctgacttca tgttgtatga cgctcttgat  480
gttgttttat acatggaccc aatgtgcctg gatgcgttcc caaaattagt ttgttttaaa  540
aaacgtattg aagctatccc acaaattgat aagtacttga atccagcaa gtatatagca  600
tggcctttgc agggctggca agccacgttt ggtggtggcg accatcctcc aaaatcggat  660
ctggttccgc gtggatcctc tagagtcgac ctgcaggcat gcaatgctta ttccattaat  720
caaaaggctt attcaaatac ttaccaggag tttactaata ttgatcaagc aaaagcttgg  780
ggtaatgctg agtataaaaa gtatggacta agcaaatcag aaaaagaagc tatagtatca  840
tatactaaaa gcgctagtga aataaatgga aagctaagac aaaataaggg agttatcaat  900
```

-continued

```
ggatttcctt caaatttaat aaaacaagtt gaacttttag ataaatcttt taataaaatg      960
aagacccctg aaaatattat gttatttaga ggcgaggagc ctgcttattt aggaacagaa     1020
tttcaaaaca ctcttcttaa ttcaaatggt acaattaata aaacggcttt tgaaaaggct     1080
aaagctaagt ttttaaataa agatagactt gaatatggat atattagtac ttcattaatg     1140
aatgtttctc aatttgcagg aagaccaatt attacaaaat ttaaagtagc aaaaggctca     1200
aaggcaggat atattgagcc tattagtgct tttcagggac aacttgaaat gttgcttcct     1260
agacatagta cttatcatat agacgatatg agattgtctt ctgatggtaa acaaataata     1320
attacagcaa caatgatggg cacagctatc aatcctaaag aattcagaag gaaacaaaga     1380
agaaaaagaa gactgcaggc ggccgcatcg tga                                  1413
```

Amino Acid Sequence (SEQ ID NO: 20)
479 amino acids
linear,
single strand

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Ser Arg Val Asp Leu Gln Ala Cys Asn Ala Tyr Ser Ile Asn
225                 230                 235                 240

Gln Lys Ala Tyr Ser Asn Thr Tyr Gln Glu Phe Thr Asn Thr Asp Gln
                245                 250                 255

Ala Lys Ala Trp Gly Asn Ala Gln Tyr Lys Lys Tyr Gly Leu Ser Lys
            260                 265                 270

Ser Glu Lys Glu Ala Ile Val Ser Tyr Thr Lys Ser Ala Ser Glu Thr
        275                 280                 285
```

-continued

```
Asn Gly Lys Leu Arg Gln Asn Lys Gly Val Ile Asn Gly Phe Pro Ser
    290                 295                 300

Asn Leu Ile Lys Gln Val Glu Leu Leu Asp Lys Ser Phe Asn Lys Met
305                 310                 315                 320

Lys Thr Pro Glu Asn Ile Met Leu Phe Arg Gly Asp Pro Ala Tyr
                325                 330                 335

Leu Gly Thr Glu Phe Gln Asn Thr Leu Leu Asn Ser Asn Gly Thr Ile
                340                 345                 350

Asn Lys Thr Ala Phe Glu Lys Ala Lys Ala Lys Phe Leu Asn Lys Asp
                355                 360                 365

Arg Leu Glu Tyr Gly Tyr Ile Ser Thr Ser Leu Met Asn Val Ser Gln
    370                 375                 380

Phe Ala Gly Arg Pro Ile Ile Thr Arg Phe Lys Val Ala Lys Gly Ser
385                 390                 395                 400

Lys Ala Gly Tyr Ile Asp Pro Ile Ser Ala Phe Gln Gly Gln Leu Glu
                405                 410                 415

Met Leu Leu Pro Arg His Ser Thr Tyr His Asp Asp Met Arg Leu Ser
                420                 425                 430

Ser Asp Gly Lys Gln Ile Ile Ile Thr Ala Thr Met Met Gly Thr Ala
                435                 440                 445

Ile Asn Pro Lys Glu Phe Arg Arg Lys Gln Arg Arg Lys Arg Arg Leu
    450                 455                 460

Gln Ala Ala Ala Ser
465
```

Physical Characteristics
Molecular Weight 53813.02 Daltons
470 Amino Acids
68 Strongly Basic(+) Amino Acids (K,R)
55 Strongly Acidic(−) Amino Acids (D,E)
149 Hydrophobic Amino Acids (A, I, L, F, W, V)
121 Polar Amino Acids (N, C, Q, S, T, Y)
9.137 Isolectric Point
14.106 Charge at PH 7.0
Total Number of Bases Translated is 1413

| | |
|---|---|
| % A = 34.61 | [489] |
| % G = 19.75 | [279] |
| % T = 29.51 | [417] |
| % C = 15.99 | [226] |
| % Ambiguous = 0.14 | [2] |
| % A + T = 64.12 | [906] |
| % C + G = 35.74 | [505] |

Davis, Botstein, Roth Melting Temp C. 79.20

EXAMPLE 11

Additional Chimeric C3 Proteins that would be Effective to Stimulate Repair in the CNS The following sequences could be added to the amino terminal or carboxy terminal of C3 or a truncated C3 that retains its enzymatic activity.

(1) Sequences of polyarginine as described (Wender, et al. (2000) 97: 13003-8.). These could be from 6 to 9 or more arginines.
(2) Sequences of poly-lysine
(3) Sequences of poly-histidine
(4) Sequences of arginine and lysine mixed.
(5) Basic stretches of amino acids containing non-basic amino acids stretch where the sequence added retains transport characteristics.
(6) Sequences of 5-15 amino acids containing at least 50% basic amino acids
(7) Sequences longer than 15-30 amino acids containing at least 30% basic amino acids.
(8) Sequences longer than 50 amino acids containing at least 18% basic amino acids.
(9) Any of the above where the amino acids are chemically modified, such as by addition of cyclohexyl side chains, other side chains, different alkyl spacers.
(10) Sequences that have proline residues with helix-breaking propensity to act as effective transporters.

EXAMPLE 12

Additional Chimeric C3 Proteins that would be Effective to Stimulate Repair in the CNS C3Basic1: C3 fused to a randomly designed basic tail
C3Basic2: C3 fused to a randomly designed basic tail
C3 Basic3: C3 fused to the reverse Tat sequence We have designed the following DNA encoding a chimeric C3 with membrane transport properties. The protein is designated C3Basic1. This sequence was designed with C3 fused to a random basic sequence. The construct was made to encode the peptide given below.

```
                                        (SEQ ID NO.: 21)
Lys Arg Arg Arg Arg Arg Pro Lys Lys Arg Arg Arg
 1              5                   10

Ala Lys Arg Arg
        15
```

The construct was made by synthesizing the two oligonucleotides given below, annealing them together, and ligating them into the pGEX-4T/C3 vector with an added histidine tag.

(SEQ ID NO: 22)
aagagaaggc gaagaagacc taagaagaga cgaagggcga    48
agaggaga (SEQ ID NO: 23)
ttctcttccg cttcttctgg attcttctct gcttcccgct    48
tctcctct DNA Sequence of C3Basic1 (SEQ ID NO: 24)

```
ggatcctcta gagtcgacct gcaggcatgc aatgcttatt ccattaatca aaaggcttat    60
tcaaatactt accaggagtt tactaatatt gatcaagcaa aagcttgggg taatgctcag   120
tataaaaagt atggactaag caaatcagaa aaagaagcta tagtatcata tactaaaagc   180
gctagtgaaa taaatggaaa gctaagacaa aataagggag ttatcaatgg atttccttca   240
aatttaataa aacaagttga acttttagat aaatctttta ataaaatgaa gaccctgaa    300
aatattatgt tatttagagg cgacgaccct gcttatttag aacagaatt tcaaaacact    360
cttcttaatt caaatggtac aattaataaa acggcttttg aaaaggctaa agctaagttt   420
ttaaataaag atagacttga atatggatat attagtactt cattaatgaa tgtttctcaa   480
tttgcaggaa gaccaattat tacaaaattt aaagtagcaa aaggctcaaa ggcaggatat   540
attgaccccta ttagtgcttt tcagggacaa cttgaaatgt tgcttcctag acatagtact   600
tatcatatag acgatatgag attgtcttct gatggtaaac aaataataat tacagcaaca   660
atgatgggca cagctatcaa tcctaaagaa ttcaagagaa ggcgaagaag acctaagaag   720
agacgaaggg cgaagaggag acaccaccac caccaccacg tcgactcgag cggccgcatc   780
gtgactgact ga                                                       792
```

Protein Sequence of C3Basic1 (SEQ ID NO: 25)

GSSRVDLQACNAYSTNQKAYSNTYQEFTNDQAKAWGNAQYKKYGLSKSEK

EAIVSYTKSASEINGKLRQNKGVINGFPSNUKQVELLDKSFNKMKTPENI

MLFRGDDPAYLGTEFQNTLLNSNGTINKTAFEKAKAKFLNKDRLEYGYIS

TSLMNVSQFAGRPIITKFKVAKGSKAGYDPISAFQGQLEMLLPRHSTYHD

DMRLSSDGKIIITATMMGTAINPKEFKRRRRRPKKRRRAKRRHHHHHVD

SSGRIVTD.

Physical Characteristics
Molecular Weight 29897.03 Daltons
263 Amino Acids
44 Strongly Basic(+) Amino Acids (K,R)
23 Strongly Acidic(−) Amino Acids (D,E)
75 Hydrophobic Amino Acids (A, I, L, F, W, V)
79 Polar Amino Acids (N, C, Q, S, T, Y)
10.024 Isoelectric Point
22.209 Charge at PH 7.0
Davis, Botstein, Roth Melting Temp C. 78.56

EXAMPLE 13

Additional Chimeric C3 Protein that would be Effective to Stimulate Repair in the CNS We have designed the following DNA encoding a chimeric C3 with membrane transport properties. The protein is designated C3Basic2. This sequence was designed with C3 fused to a random basic sequence. The construct was made to encode the peptide given below.

```
                                           (SEQ ID NO.:26)
Lys Arg Arg Arg Arg Lys Lys Arg Arg Gln Arg Arg
 1              5                  10

Arg
```

The construct was made by synthesizing the two oligonucleotides given below, annealing them together, and ligating them into the pGEX4T/C3 vector with an added histidine tag.

```
                                       (SEQ ID NO.: 27)
aagcgtcgac gtagaaagaa acgtagacag cgtagacgt   39

(SEQ ID NO.: 28)
ttcgcagctg catctttctt tgcatctgtc gcatctgca   39
```

DNA Sequence of C3Basic2 (SEQ ID NO.: 29)

```
5' GGA TCC TCT AGA GTC GAC CTG CAG GCA TGC AAT GCT
TAT TCC ATT AAT CAA AAG GCT TAT TCA AAT ACT TAC
CAG GAG TTT ACT AAT ATT GAT CAA GCA AAA GCT TGG
GGT AAT GCT CAG TAT AAA AAG TAT GGA CTA AGC AAA
TCA GAA AAA GPA GCT ATA GTA TCA TAT ACT AAA AGC
GCT AGT GAA ATA AAT GGA AAG CTA AGA CAA AAT AAG
GGA GTT ATC AAT GGA TTT CCT TCA AAT TTA ATA AAA
CAA GTT GAA CTT TTA GAT PAA TCT TTT AAT AAA ATG
AAG ACC CCT GAA AAT ATT ATG TTA TTT AGA GGC GAC
```

```
GAC CCT GCT TAT TTA GGA ACA GPA TTT CPA AAC ACT

CTT CTT AAT TCA AAT GGT ACA ATT AAT AAA ACG GCT

TTT GAA AAG GCT AAA GCT AAG TTT TTA AAT AAA GAT

AGA CTT GAA TAT GGA TAT ATT AGT ACT TCA TTA ATG

AAT GTT TCT CAA TTT GCA GGA AGA CCA ATT ATT ACA

AAA TTT AAA GTA GCA AAA GGC TCA AAG GCA GGA TAT

ATT GAC CCT ATT AGT GCT TTT CAG GGA CAA CTT GAA

ATG TTG CTT CCT AGA CAT AGT ACT TAT CAT ATA GAC

GAT ATG AGA TTG TCT TCT GAT GGT AAA CAA ATA ATA

ATT ACA GCA ACA ATG ATG GGC ACA GCT ATC AAT CCT

AAA GAA TTC AAG CGT CGA CGT AGA AAG AAA CGT AGA

CAG CGT AGA CGT CAC CAC CAC CAC CAC CAC GTC GAC

TCG AGC GGC CGC ATC GTG ACT GAC TGA 3'
```

Protein Sequence of C3Basic2 (SEQ ID NO.: 30)

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Asp Gln Ala
            20                  25                  30

Lys Ala Trp Gly Asn Ala Gln Tyr Lys Lys Tyr Gly Leu Ser Lys Ser
            35                  40                  45

Glu Lys Glu Ala Ile Val Ser Tyr Thr Lys Ser Ala Ser Glu Thr Asn
    50                  55                  60

Gly Lys Leu Arg Gln Asn Lys Gly Val Thr Asn Gly Phe Pro Ser Asn
65              70                  75                  80

Leu Ile Lys Gln Val Glu Leu Leu Asp Lys Ser Phe Asn Xaa Met Lys
                85                  90                  95

Thr Pro Glu Asn Thr Met Leu Phe Arg Gly Asp Pro Ala Tyr Leu
                100                 105                 110

Gly Thr Glu Phe Gln Asn Thr Leu Leu Asn Ser Asn Gly Thr Ile Asn
            115                 120                 125

Lys Thr Ala Phe Glu Lys Ala Lys Ala Lys Phe Leu Asn Lys Asp Arg
            130                 135                 140

Leu Glu Tyr Gly Tyr Ile Ser Thr Ser Leu Met Asn Val Ser Gln Phe
145                 150                 155                 160

Ala Gly Arg Pro Ile Ile Thr Lys Phe Lys Val Ala Lys Gly Ser Lys
                165                 170                 175

Ala Gly Tyr Ile Asp Pro Ile Ser Ala Phe Gln Gly Gln Leu Glu Met
                180                 185                 190

Leu Leu Pro Arg His Ser Thr Tyr His Thr Asp Asp Met Arg Leu Ser
            195                 200                 205

Ser Asp Gly Lys Gln Ile Ile Ile Thr Ala Thr Met Met Gly Thr Ala
    210                 215                 220

Thr Asn Pro Lys Glu Phe Lys Arg Arg Arg Lys Lys Arg Arg Gln
225                 230                 235                 240

Arg Arg Arg His His His His His His Val Asp Ser Ser Gly Arg Ile
                245                 250                 255

Val Thr Asp
```

Physical Characteristics
Molecular Weight 29572.61 Daltons
260 Amino Acids
42 Strongly Basic(+) Amino Acids (K,R)
23 Strongly Acidic(−) Amino Acids (D,E)
74 Hydrophobic Amino Acids (A, I, L, F, W, V)
80 Polar Amino Acids (N, C, Q, S, T, Y)
9.956 Isoelectric Point
20.210 Charge at PH 7.0
Davis, Botstein, Roth Melting Temp C. 78.45

EXAMPLE 14

Additional Chimeric C3 Protein that would be Effective to Stimulate Repair in the CNS We have designed the following DNA encoding a chimeric C3 with membrane transport properties. The protein is designated C3Basic3. This sequence was designed with C3 fused to a reverse Tat sequence. The construct was made to encode the peptide given below

```
Arg Arg Lys Gln Arg Arg Lys Arg Arg
1               5
```
(SEQ ID NO:31)

The construct was made by synthesizing the two oligo-nucleotides given below, annealing them together, and ligating them into the pGEX4T/C3 vector with an added histidine tag, then subcloning in pGEX-4T/C3.

```
agaaggaaac aaagaagaaa aagaaga     27  (SEQ ID NO.: 32)
tcttcctttg tttcttcttt tcttct      27  (SEQ ID NO.: 33)
```

DNA Sequence of C3Basic3 (SEQ ID NO.: 34)

```
ggatcctcta gagtcgacct gcaggcatgc aatgcttatt ccattaatca aaaggcttat   60
tcaaatactt accaggagtt tactaatatt gatcaagcaa aagcttgggg taatgctcag  120
tataaaaagt atggactaag caaatcagaa aaagaagcta tagtatcata tactaaaagc  180
gctagtgaaa taaatggaaa gctaagacaa aataagggag ttatcaatgg atttccttca  240
aatttaataa aacaagttga acttttagat aaatctttta ataaaatgaa gaccectgaa  300
aatattatgt tatttagagg cgacgaccct gcttatttag aacagaatt tcaaaacact  360
cttcttaatt caaatggtac aattaataaa acggcttttg aaaaggctaa agctaagttt  420
ttaaataaag atagacttga atatggatat attagtactt cattaatgaa tgtttctcaa  480
tttgcaggaa gaccaattat tacaaaattt aaagtagcaa aaggctcaaa ggcaggatat  540
attgacccta ttagtgcttt tcagggacaa cttgaaatgt tgcttcctag acatagtact  600
tatcatatag acgatatgag attgtcttct gatggtaaac aaataataat tacagcaaca  660
atgatgggca cagctatcaa tcctaaagaa ttcagaagga aacaaagaag aaaaagaaga  720
caccaccacc accaccacgt cgactcgagc ggccgcatcg tgactgactg a            771
```

Protein Sequence of C3Basic3 (SEQ ID NO.: 35)

```
Gly Ser Ser Arg Val Asp Leu Gln Ala Cys Asn Ala Tyr Ser Thr Asn
  1               5                  10                  15
Gln Lys Ala Tyr Ser Asn Thr Tyr Gln Glu Phe Thr Asn Ile Asp Gln
                 20                  25                  30
Ala Lys Ala Trp Gly Asn Ala Gln Tyr Lys Lys Tyr Gly Leu Ser Lys
             35                  40                  45
Ser Glu Lys Ile Glu Ala Ile Val Ser Tyr Thr Lys Ser Ala Ser Glu
         50                  55                  60
Ile Asn Gly Lys Leu Arg Gln Asn Lys Gly Val Ile Asn Gly Phe Pro
 65                  70                  75                  80
Ser Asn Ile Lys Gln Val Glu Leu Leu Asp Lys Ser Phe Asn Lys Met
                 85                  90                  95
Lys Thr Pro Glu Asn Ile Met Leu Phe Arg Gly Asp Asp Pro Ala Tyr
            100                 105                 110
Leu Gly Thr Glu Phe Gln Asn Thr Leu Leu Asn Ser Asn Gly Thr Thr
        115                 120                 125
Asn Lys Thr Ala Phe Glu Lys Ala Lys Ala Lys Phe Leu Asn Lys Asp
    130                 135                 140
Arg Leu Glu Tyr Gly Tyr Ile Ser Thr Ser Leu Met Asn Val Ser Gln
145                 150                 155                 160
Phe Ala Gly Arg Leu Pro Ile Ile Thr Arg Phe Lys Val Ala Lys Gly
                165                 170                 175
Ser Lys Ala Gly Tyr Ile Asp Pro Ile Ser Ala Phe Gln Gly Gln Leu
            180                 185                 190
Glu Met Leu Leu Ala Arg His Ser Thr Tyr His Ile Asp Asp Met Arg
        195                 200                 205
```

```
Leu Ser Ser Asp Gly Lys Gln Ile Ile Ile Thr Ala Thr Met Met Gly
    210                 215                 220

Thr Ala Ile Asn Pro Lys Glu Phe Arg Arg Lys Gln Arg Arg Lys Arg
225                 230                 235                 240

Arg His His His His His Val Asp Ser Ser Gly Arg Ile Val Thr
                    245                 250                 255

Asp
```

Physical Characteristics
Molecular Weight 29441.47 Daltons
260 Amino Acids
39 Strongly Basic(+) Amino Acids (K,R)
23 Strongly Acidic(−) Amino Acids (D,E)
76 Hydrophobic Amino Acids (A, I, L, F, W, V)
80 Polar Amino Acids (N, C, Q, S, T, Y)
9.833 Isoelectric Point
17.211 Charge at PH 7.0
Davis, Botstein, Roth Melting Temp C. 78.29

EXAMPLE 15

Sequences for C3APLT

One of the clones that was selected from the subcloning of C3APL into pGEX encoded a protein that was not the expected size but had good biological activity. This clone that had a frameshift mutation leading to a truncation, and this clone was called C3APLT. The clone was resequenced and the chromatograms analyzed to confirm the sequence. To confirm the sequences of C3APLT, the coding sequence from both strands of pGEX-4T/C3APLT were sequenced by double strand sequencing of the full length of the clone (BioS&T, Montreal, Quebec).

The DNA Sequence for C3APLT is as follows: (SEQ ID NO.: 36)

```
ggatcctcta gagtcgacct gcaggcatgc aatgcttatt ccattaatca aaaggcttat      60
tcaaatactt accaggagtt tactaatatt gatcaagcaa aagcttgggg taatgctcag     120
tataaaaagt atggactaag caaatcagaa aaagaagcta tagtatcata tactaaaagc     180
gctagtgaaa taaatggaaa gctaagacaa aataagggag ttatcaatgg atttccttca     240
aatttaataa aacaagttga acttttagat aaatctttta ataaaatgaa gaccctgaa      300 aatattatgt tatttagagg cgacgaccct gcttatttag gaacagaatt tcaaaacact     360
cttcttaatt caaatggtac aattaataaa acggcttttg aaaaggctaa agctaagttt     420
ttaaataaag atagacttga atatggatat attagtactt cattaatgaa tgtttctcaa     480
tttgcaggaa gaccaattat tacaaaattt aaagtagcaa aaggctcaaa ggcaggatat     540
attgacccta ttagtgcttt tgcaggacaa cttgaaatgt tgcttcctag acatagtact     600
tatcatatag acgatatgag attgtcttct gatggtaaac aaataataat tacagcaaca     660
atgatgggca cagctatcaa tcctaaagaa ttcgtgatga atcccgcaaa cgcgcaaggc     720
agacatacac ccggtaccag actctagagc tagagaagga gtttcacttc aatcgctact     780
tgacccgtcg gcgaaggatc gagatcgccc acgccctgtg cctcacggag cgccagataa     840
agatttggtt ccagaatcgg cgcatgaagt ggaagaagga gaactga                   887
```

The APLT transport peptide sequence by itself is as follows (SEQ ID NO.: 48):

```
Val Met Asn Pro Ala Asn Ala Gln Gly Arg His Thr
1               5                   10
Pro Gly Thr Arg Leu
            15
```

The Protein Sequence for C3APLT is as follows: (SEQ ID NO.: 37)

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
                20                  25                  30

Ala Lys Ala Trp Gly Asn Ala Gln Tyr Lys Lys Tyr Gly Leu Ser Lys
            35                  40                  45

Ser Glu Lys Ile Glu Ala Ile Val Ser Tyr Thr Lys Ser Ala Ser Glu
        50                  55                  60

Ile Asn Gly Lys Leu Arg Gln Asn Lys Gly Val Ile Asn Gly Phe Pro
65                  70                  75                  80

Ser Asn Leu Ile Lys Gln Val Glu Leu Leu Asp Lys Ser Phe Asn Lys
                85                  90                  95

Met Lys Thr Pro Glu Asn Ile Met Leu Phe Arg Gly Asp Asp Pro Ala
            100                 105                 110

Tyr Leu Gly Thr Glu Phe Gln Asn Thr Leu Leu Asn Ser Asn Gly Thr
        115                 120                 125

Ile Asn Lys Thr Ala Phe Glu Lys Ala Lys Ala Lys Phe Leu Asn Ile
        130                 135                 140

Lys Asp Arg Leu Glu Tyr Gly Tyr Ile Ser Thr Ser Leu Met Asn Val
145                 150                 155                 160

Ser Gln Phe Ala Gly Arg Pro Ile Ile Thr Lys Phe Lys Val Ala Lys
                165                 170                 175

Gly Ser Lys Ala Gly Tyr Ile Asp Pro Ile Ser Ala Phe Ala Gly Gln
            180                 185                 190

Leu Glu Met Leu Leu Pro Arg His Ser Thr Tyr His Ile Asp Asp Met
        195                 200                 205

Arg Leu Ser Ser Asp Gly Lys Gln Ile Ile Ile Thr Ala Thr Met Met
        210                 215                 220

Gly Thr Ala Thr Asn Pro Lys Glu Phe Val Met Asn Pro Ala Asn Ala
225                 230                 235                 240

Gln Gly Arg His Thr Pro Gly Thr Arg Leu
                245                 250
```

Physical Characteristics
Molecular Weight 27574.42 Daltons
248 Amino Acids
33 Strongly Basic(+) Amino Acids (K,R)
21 Strongly Acidic(−) Amino Acids (D,E)
76 Hydrophobic Amino Acids (A, I, L, F, W, V)
80 Polar Amino Acids (N, C, Q, S, T, Y)
9.636 Isoelectric Point
12.379 Charge at PH 7.0

EXAMPLE 16

Sequence for C3-07

Subcloning and Sequences for C3APLT in pET

C3 has been reported to be stably expressed in *E. coli* by both pGEX-series and pET-series vectors (e.g., Dillon and Feig, 1995 Meth. Enzymol. 256: 174-184. Small GTPases and Their Regulators. Part B. Rho Family. W. E. Balch, C. J. Der, and A. Hall, eds.; Lehmann et al., 1999 supra; Han et al., 2001. J. Mol. Biol. 395: 95-107). The fusion proteins were expressed well in the pGEX vector, for synthesis and testing. However, for large-scale production it is more efficient to synthesize recombinant proteins without an affinity tag that increases the size of the protein produced. Also, it is more economical to synthesize proteins in large scale by affinity chromatography using automated FPLC systems. The polymerase chain reaction was used to transfer recombinant construct C3APLT into the pET T7 polymerase based system *E. coli* expression system (reviewed by Studier et al., 1990. Meth. Enzymol. 185: 60-89. Gene Expression Technology. D. V. Goeddel, ed.). A similar PCR approach is suitable for others in the fusion protein series of C3-based constructs with transport sequences. The pET3a vector DNA was obtained from Dr. Jerry Pelletier, McGill University. PCR primers were obtained from Invitrogen. The upper (5') primer was 5'-GGA TCT GGT TCC GCG TCA TAT GTC TAG AGT CGA CCT G-3 (37 b) (SEQ ID NO.:38). Underlined is the Nde I site that was introduced into the primer to replace the BamHI site in pGEX4T-C3APLT. The lower primer was 5'-CGC GGA TCC ATT AGT TCT CCT TCT TCC ACT TC-3' (32 b) (SEQ ID NO.:39). This primer introduced two changes in the coding strand DNA of pGEX4T-C3APLT, replacing the EcoRI site from pGEX4T-C3APLT with a BamH I site (underlined) and replacing a TGA stop codon with the strong stop sequence TAAT (the italicized ATTA sequence in the complementary primer). Compared to pGEX4T-C3APLT, the predicted N-terminal sequence of pET3a-C3APLT is Met-Ser rather than Gly-Ser-Ser, a loss of one serine and a substitution of Met for Gly. There were no changes in amino acid sequence at the C-terminus of C3APLT.

The target C3APLT gene was amplified using Pfu polymerase (Invitrogen/Canadian Life Technologies) with buffer, DNA and deoxyribonucleotide concentrations recommended by the manufacturer. The PCR was carried out as follows: 95° C. for 5 minutes, 10 cycles of 94° C. for 2 minutes followed by 56° C. for 2 minutes then extension at 70° C. for 2 minutes, then 30 cycles of 94° C. for 2 minutes followed by 70° C. Completed reactions were stored at 4° C. The QIAEXII kit (Qiagen) was used to purify the agarose gel slice containing DNA band. The purified PCR product DNA and the vector were digested with BamH I and Nde I (both obtained from New England BioLabs) following the instructions of the manufacturer. The digestion products were separated from extraneous DNA by agarose gel electrophoresis and purified with the QIAEXII kit. The insert and vector DNA were incubated together overnight at 16° C. with T4 DNA ligase according to directions provided by the manufacturer (New England BioLabs). Competent E. coli (DH5.alpha., obtained from Invitrogen/Canadian Life Technologies) were transformed with the ligation mixture.

DNA was prepared from purified colonies using the Qiagen plasmid midi kit, and the entire insert and junction sequences were verified by double strand sequencing of the full length of the clone (BioS&T, Montreal, Quebec) with forward primer 5' AAA TTA ATA CGA CTC ACT ATA GGG 3' (24 bases) (SEQ ID NO.: 40) and reverse T7 terminator sequencing primer 5' GCT AGT TAT TGC TCAGCG G 3' (19 bases) (SEQ ID NO.: 41). The sequence of the C3APLT cDNA in pET is given in SEQ ID NO.: 42. The amino acid sequence is given in SEQ. ID NO.: 43.

EXAMPLE 17

Modifications of Sequences

Any of sequences given in Examples 1, 2, 8, 9, 10, 11, 12 and 13, 15 and 16 could be modified to retain C3 enzymatic activity and effective transport sequences. For example amino acids encoded from DNA at the 3' end of the sequence that represents the translation of the restriction sites used in cloning may be removed without affecting activity. Some of the amino terminal amino acids may also be removed without affecting activity. The minimal amount of sequence needed for biological activity of the C3 portion of the fusion protein is not known but could be easily determined by known techniques. For example, increasingly more of the 5' end of the cDNA encoding C3 could be removed, and the resulting proteins made and tested for biological activity. Similarly, increasing amounts of the 3' end could be removed and the fragments tested for biological activity. Next, fragments testing the central region could be tested for retention of C3 activity. Therefore, the C3 portion of the protein could be truncated to include just the amino acids needed for activity. Alternatively mutations could be made in the coding regions of C3, and the resulting proteins tested for activity. The transport sequences could be modified to add or remove one or more amino acids or to completely change the transport peptide, but retain the transport characteristics in terms of effective dose compared to C3 in our tissue culture bioassay (Example 4). New transport sequences could be tested for biological activity to improve the efficiency of C3 activity by plating neurons and testing them on inhibitory substrates, as described in Example 4.

As discussed previously, it has been determined in tissue culture studies, that the minimum amount of C3 that can be used to induce growth on inhibitory substrates is 25 ug/ml (Lehmann, et al. (1999) J. Neurosci. 19: 7537-7547; Morii, N and Narumiya, S. (1995) Methods in Enzymology, Vol 256 part B, pg. 196-206. If the cells are not triturated, even this dose is ineffective (FIG. 1). In the context of the present invention it has been determined, for example, that at least 40 □g (40 microgram) of C3/20 g mouse needs to be applied to injured mouse spinal cord or rat optic nerve (McKerracher, Canadian patent application No.: 2,325,842). Calculating doses that would be required to treat an adult human on an equivalent dose per weight scale up used for rat and mice experiments, it would be necessary to apply 120 mg/kg of C3 (i.e. alone) to the injured human spinal cord. This large amount of recombinant C3 protein needed, creates significant problems for manufacturing, due to the large-scale protein purification and cost. It also limits the dose ranging that can be tested because of the large amount of protein needed for minimal effective doses.

Fusion proteins of the present invention are much more effective than C3 (i.e., alone) in promoting neurite outgrowth on myelin substrate. For example, concentrations of C3APLT and C3APS, 10,000 and 1,000 times less than the concentration needed for C3 may be used with comparable (similar) effects without exhibiting toxic effects (e.g., on PC-12 cells). C3-TL and C3-TS are also able to promote neurite growth on myelin substrates at doses significantly less than C3. In vivo results also indicate that lower dose of the fusion proteins may be required to promote regeneration and functional recovery after spinal cord injury in mice. Thus, fusion proteins of the present invention represent a significant improvement and advantage over C3 in both manufacture cost and doses required for treatment.

EXAMPLE 18

General Method for Determination of Inhibition of Angiogenesis

The formation of new blood vessels can be studied in a cell culture model by growing endothelial cells in the presence of a matrix of basement membrane (Matigel). Human umbilical vein endothelial cells (HUVEC) are harvested from stock cultures by trypinization, and are resuspended in growth medial consisting of EBM-2 (Clonetics), FBS, hydrocortisone, hFGF, VEGF, R3-IGF-1, ascorbic acid, hEGF, GA-1000, heparin. Matrigel (12.5 mg/mL) is thawed at 4° C., and 50 mL of Matrigel is added to each well of a 96 well plate, and allowed to solidify for 10 min. at 37° C. Cells in growth medium at a concentration of 15,000 cells/well are added to each well, and are allowed to adhere for 6 hours. A fusion protein of this invention, e.g., C3APLT, in phosphate buffered saline (PBS) is added to the well at about 10 mg/ml, and in other wells PBS is added as control. The cultures are allowed to grow for a further 6 to 8 hours. The growth of tubes can be visualized by microscopy at a magnification of 50×, and the mean length of the capillary network is quantified using Northern Eclipse software. Treatment of the cells in the Matrigel assay with a fusion protein of this invention (e.g., C3APLT) reduces tube formation (see FIG. 13).

EXAMPLE 19

A Lyophilized Formulation

A solution comprising a unit dosage amount of a composition of this invention comprising a fusion protein such as C3APLT dissolved in an pharmaceutically acceptable isotonic aqueous medium comprising a pharmaceutically acceptable buffer salt and/or a readily water-soluble pharmaceutically acceptable carbohydrate (preferably a pharmaceutically acceptable non-reducing sugar or a cyclodextrin) is sterile-filtered (e.g. through a 0.2 micron filter) under aseptic conditions, the filtrate is placed in a sterilized vial, the filtrate is frozen, the frozen aqueous solution is lyophilized aseptically at reduced pressure in a pharmaceutically acceptable lyophilizer to leave a dried matrix comprising the fusion protein in the vial, the vial is returned to atmospheric pressure under a sterile inert atmosphere, the vial is sealed with a sterile stopper (e.g. together with a crimp cap). The sealed vial is labeled with its contents and dosage amount and placed in a kit together with a second sealed sterile vial which contains sterilized water for injection in an amount useful to transfer into the first vial containing the lyophilized fusion protein in order to reconstitute the fusion protein matrix to a solution as a unit dosage form. In another embodiment, the fusion protein can be dissolved in a starting volume of aqueous medium which comprises a hypertonic aqueous medium, the solution sterile filtered, the filtrate filled into a vial, and lyophilized to form a dried matrix. This dried matrix can be dissolved or reconstituted in a larger-than-original volume of sterile water, the larger volume sufficient to form an isotonic solution for injection such as by intravenous injection and/or infusion. Alternatively, a hypertonic solution can be used for administration by infusion into a drip bag containing a larger volume of isotonic aqueous medium such that the hypertonic solution is substantially diluted. Optionally, a vial containing a volume of sterile water in an amount suitable to reconstitute the matrix to a unit dosage form is distributed as a kit with the lyophilized protein. Preferably the reconstituted composition comprises an isotonic solution. The fusion protein can be used for intravenous delivery, and/or infusion, and/or direct injection into tissue of the eye or tissue proximal to the eye with this formulation.

EXAMPLE 20

Construction of an Inactive Mutant Variant of C3-07, C3-07Q189A

C3-07 is a derivative of C3APLT lacking the GST sequence. C3-07 was prepared by polymerase chain reaction and subcloned into pET9a vector to create C3-07. C3-07 differs from C3-05 by silent amino acid changes which can be described as a deletion of the terminal glycine in C3-05 which provides a truncated fragment of C3-05 terminating in a serine plus a mutation (i.e., substitution) of that terminal serine in the truncated fragment by a methione to provide C3-07. C3-07Q189A was made by intentionally producing a mutation in C3-07 near the ADP-ribosyl transferase catalytic site in the fusion protein, thereby substantially reducing ADP-ribosylation activity. Two oligonucleotides were designed to change the amino acid 189 glutamine at the active site (gln, Q, coded by CAA) to 189 alanine (ala, A, coded by GCA) by site-directed-mutagenesis using the QuikChange (Stratagene). Polymerase chain reaction was carried out in a thermo cycler using 50 ng of "pET9a-BA-207" which is sometimes also referred to as "pET9a-BA05", 133 ng of 41-mer mutant primer ZSM3, and 137 ng of 41-mer mutant primer ZSM4. The cycle program for the Q189A mutant was as follows: 95° C. for 30 sec, 18 cycles of 95° C. for 30 sec., 55° C. for 1 min., and 68° C. for 10 min., and hold at 4° C.

Primer ZSM3
5'- GCT TTT GCA GGA {GC}A CTT GAA ATG TTG CTT CCT AGA CAT AG'

Primer ZSM4
5'- CT ATG T CT A GG AAG CAA CAT TTC AAG T{GC} TCC TGC AAA AGC -3'

The bracketed bold letters in the above sequence denote the change from the C3-07 sequence.

The amino acid sequence of C3-07 is SEQ ID NO.: 43.
The cDNA sequence of C3-07 is SEQ ID NO.: 42.

DpnI digestion was done according to the manufacturer's instructions and 1 μL of this product was used to transform XL1-Blue competent cells. These plates were then incubated overnight at 37° C. Clones of Putative C3-07Q189A were selected and their plasmid DNA amplified and purified using the Qiagen Midi Kit. The purified plasmids were analyzed by restriction digestion analyses. The DNA from three candidate clones was sequenced at BioS&T (Lachine, Quebec) using the T7 and T7T primers. Mutant ZSMT2-2 was confirmed to contain the mutation and the DNA was used to transform BL21 (DE3) cells and prepare a research cell bank (RCB).

Purified C3-07Q189A was prepared from *E. coli*. First, a flask of 0.5 L Luria Broth with glucose was inoculated with 2 vials of research cell bank (RCB) of pET9a-C3-07Q189A and grown overnight. The starter culture was diluted 10-fold into 8 flasks each containing 500 mL growth medium. The flasks were incubated at 37° C. and after 1 hour 20 min, isopropylthio-B-D-galactoside (IPTG) was added to increase the expression of C3-07Q189A. After a further 4 hours, the cells were harvested by centrifugation and stored at –80° C. until required. A sample of the harvested culture was analyzed for C3-07Q189A content. Next, the cells were thawed and subjected to primary recovery, which in the research scale process for production of C3-07 is sonication in extraction buffer. The crude extract was treated with positively-charged polymer to remove nucleic acids and with ammonium sulfate to remove some proteins and reduce the volume. Excess salt was removed. The protein was further purified by passing over four chromatography columns. The final purification and isolation steps consisted of concentration of the resulting purified protein solution (ultrafiltration can be used), filtration of the protein solution (e.g., through a 0.2 micrometer filtration membrane which can be useful to sterilize the protein solution), dispensing of the solution into sterile tubes, freezing the protein solution, and lyophilization of the frozen solution to leaving the protein formulated in the form of a powder. After the C3-07Q189A was purified, the fusion protein was analyzed to determine the amount of protein which was produced, its purity, its potency and its biological activity (e.g., ADP-ribosyl transferase related activity for neurite outgrowth). Purity was measured by scanning densitometry of SDS-polyacrylamide gels stained with Coomassie Blue. The activity of C3-07Q189A was determined using an NG108 cell 4 hour neurite outgrowth bioassay. The procedure for the bioassay comprises incubation of h NG-108 cells for 4 hours with an aliquot of a buffered solution containing C3-07Q189A. A simultaneous and otherwise identical bioassay was run as a positive control, wherein C3APLT or C3-07 was used in place of C3-07Q189A. The cells were then fixed with paraformaldehyde, stained with cresyl violet, and the percentage of cells in each well that demonstrated neurites greater than one cell body in length was determined by counting under the microscope. Each data point was determined in triplicate.

The amino acid sequence of C3-07Q189A is as follows:

Protein sequence for C3-07Q189A

```
                                             (SEQ ID NO:55)
Met Ser Arg Val Asp Leu Gln Ala Cys Asn Ala Tyr
 1               5                  10

Ser Ile Asn Gln Lys Ala Tyr Ser Asn Thr Tyr Gln
            15                  20

Glu Phe Thr Asn Ile Asp Gln Ala Lys Ala Trp Gly
25                  30                  35

Asn Ala Gln Tyr Lys Lys Tyr Gly Leu Ser Lys Ser
                40                  45

Glu Lys Glu Ala Ile Val Ser Tyr Thr Lys Ser Ala
    50                  55                  60

Ser Glu Ile Asn Gly Lys Leu Arg Gln Asn Lys Gly
                65                  70

Val Ile Asn Gly Phe Pro Ser Asn Leu Ile Lys Gln
            75                  80

Val Glu Leu Leu Asp Lys Ser Phe Asn Lys Met Lys
85                  90                  95

Thr Pro Glu Asn Ile Met Leu Phe Arg Gly Asp Asp
            100                 105

Pro Ala Tyr Leu Gly Thr Glu Phe Gln Asn Thr Leu
    110                 115                 120

Leu Asn Ser Asn Gly Thr Ile Asn Lys Thr Ala Phe
                125                 130

Glu Lys Ala Lys Ala Lys Phe Leu Asn Lys Asp Arg
            135                 140

Leu Glu Tyr Gly Tyr Ile Ser Thr Ser Leu Met Asn
145                 150                 155

Val Ser Gln Phe Ala Gly Arg Pro Ile Ile Thr Gln
            160                 165

Phe Lys Val Ala Lys Gly Ser Lys Ala Gly Tyr Ile
    170                 175                 180

Asp Pro Ile Ser Ala Phe Gln Gly Ala Leu Glu Met
            185                 190

Leu Leu Pro Arg His Ser Thr Tyr His Ile Asp Asp
            195                 200

Met Arg Leu Ser Ser Asp Gly Lys Gln Ile Ile Ile
205                 210                 215

Thr Ala Thr Met Met Gly Thr Ala Ile Asn Pro Lys
                220                 225

Glu Phe Val Met Asn Pro Ala Asn Ala Gln Gly Arg
    230                 235                 240

His Thr Pro Gly Thr Arg Leu
            245
```

The cDNA sequence of C3-07Q189A is as follows:

cDNA sequence for C3-07Q189A

```
                                             (SEQ ID NO:54)
atgtctagag tcgacctgca ggcatgcaat gcttattcca ttaatcaaaa ggcttattca    60
aatacttacc aggagtttac taatattgat caagcaaaag cttggggtaa tgctcagtat   120
aaaaagtatg gactaagcaa atcagaaaaa gaagctatag tatcatatac taaaagcgct   180
agtgaaataa atggaaagct aagacaaaat aagggagtta tcaatggatt tccttcaaat   240
ttaataaaac aagttgaact tttagataaa tctttaata aaatgaagac ccctgaaaat   300
attatgttat ttagaggcga cgaccctgct tatttaggaa cagaatttca aaacactctt   360
cttaattcaa atggtacaat taataaaacg gcttttgaaa aggctaaagc taagtttta   420 aataaagata gacttgaata tggatatatt agtacttcat taatgaatgt ttctcaattt   480
gcaggaagac caattattac aaaatttaaa gtagcaaaag gctcaaaggc aggatatatt   540
gaccctatta gtgcttttgc aggagcactt gaaatgttgc ttcctagaca tagtacttat   600
catatagacg atatgagatt gtcttctgat ggtaaacaaa taataattac agcaacaatg   660
atgggcacag ctatcaatcc taagaattc gtgatgaatc ccgcaaacgc gcaaggcaga   720
catacacccg gtaccagact ctag                                          744
```

EXAMPLE 21

General Procedure to Determine the Relative Neuroprotection Ability in the Retina of a Fusion Protein of this Invention C3-APLT and C3-07 are examples of fusion proteins of this invention, each protein having ADP-riboysyl transferase activity and each having an ADP-riboysyl transferase active site.

In the visual system, retinal ganglion cells die after optic nerve injury. The severity (i.e., the number of cells which die) and rate of cell death depends on the proximity of axonal injury to the eye. To study the effects of inactivation of Rho on RGC survival we have made use of two cell-membrane penetrating (i.e., cell-membrane permeable) derivatives of C3 transferase: C3-APLT and C3-07.

Rats were anaesthetised under 2-3% isoflurane. RGCs were retrogradely labelled from the superior colliculus with Fluorogold (Fluorchrome Inc, Denver, Colo.). The right midbrain of a rat was exposed by making a small circular opening in the bone, followed by aspiration of cortex, and removal of the pia matter overlying the superior colliculi. A small piece of Gelfoam soaked in an aqueous medium comprising 2% fluorgold and 10% DMSO was applied to the surface of the right superior colliculus. Seven days after Fluorogold application, the left optic nerve was transected 1 mm from the eye. The optic nerve was accessed within the orbit by making an incision parasagitally in the skin covering the superior rim of the orbit bone, taking care to leave the supraorbital vein intact. Following partial resection or reflection of the lacrimal gland, the superior extraocular muscles were spread with a small retractor or 6-0 silk suture. The optic nerve was exposed, and the surrounding sheath was cut longitudinally to avoid cutting blood vessels while exposing the optic nerve. The pia mater of the optic nerve was nicked, the optic nerve moved gently to dislodge it, and then scissors were slipped tangentially under the optic nerve to give a clean cut 1 mm from the eye. In animals used for studies on cytokine levels, a microcrush lesion was used. For these studies the pia was left intact, and the optic nerve was lifted out from the sheath and crushed 1 mm from the globe by constriction with a 10.0 suture held for 60 seconds.

Anesthetised animals received single injections of C3APLT or C3-07 in aqueous buffer immediately after the optic nerve was cut, or 4 days later. Intraocular injections were made with a 10 μl syringe attached to a glass micropipette. A hole was made in the superior nasal retina approximately 4 mm from the optic disc with a 30 g needle before introduction of the glass pipette to inject 5 μl of fusion protein (e.g., C3-07) or buffer control. The needle was withdrawn slowly to allow diffusion of the solution into the vitreous spaces. The sclera was then sealed with tissue adhesive (Indermil, Tyco Heathcare, Mansfield, USA). Care was taken not to damage the lens during injection to avoid cataract formation and consequential increased survival of the RGCs. The skin was closed, and the integrity of the retinal vasculature was evaluated by a postoperative opthalmoscopic examination. Rats with compromised vasculature or rats that developed cataracts were not included in the experimental results.

Fluorogold labeled retinas were prepared for counting 7 or 14 days after axotomy. Animals were perfused with 4% paraformaldehyde (PFA), and their eyes were removed and postfixed in 4% PFA after puncture of the cornea. The eyes were then rinsed with phosphate buffered saline (PBS) for 1 hour. Incisions were made in each eye in the four retinal quadrants, and the retinas were removed and flat-mounted on glass slides. Excess vitreous was blotted away with paper wicks. Coverslips were placed on the slides over the mounted retinas, and RGCs were examined with an ultraviolet filter (365/420). Labeled RGCs were counted under the microscope at 20× magnification with the aid of a rectangle insert in one ocular field of view of the microscope to provide a rectangular field area of 0.375 mm×0.1125 mm. Four standard rectangular areas of retina were counted at 1 and 2 mm from the disc. The number of labeled cells in each area was divided by 0.04125 (rectangular area counted in $mm^2$), and the average density for each retina was calculated as $RGCs/mm^2$. Cells counts were conducted by the same investigator blind to the treatment. After axotomy, Fluorogold is also present in endothelial cells and microglial cells. These cells, identified by morphology were excluded from the counts of RGCs. Statistics were performed with Excel, and results from treated animals were compared with results from controls by T-test.

A single injection of FPLC-purified C3APLT was neuroprotective and rescued all RGCs at 7 days after axotomy, and a single injection of FPLC-purified C3-07 was neuroprotective and rescued all RGCs at 7 days after axotomy. To determine if RGC cell survival following C3-07 injection might be increased because of properties of C3-07 other than its Rho ribosylation activity, we tested the effect of C3-07Q189A on RGC cell survival. The mutant protein, C3-07Q189A, was purified by FPLC, and 1 ug was injected immediately after axotomy in the manner used for C3-07. Cell survival following administration of C3-07Q189A was not significantly different from cell survival following axotomy alone, and was significantly different from the effect of C3-07 (FIG. 14). Therefore, the neuroprotective activity of C3-07 is due to the presence of ADP-ribosyl transferase in the fusion protein and thus inactivation of Rho, not from other effects.

Ischemia can be produced in the retina of the albino Lewis rat by raising intraocular pressure by intraocular injection of saline (Unoki and LaVail, Invest Opthalmol Vis. Sci. 35:907, 1994). The survival of RGCs can be assessed by counting RGCs retrogradely labeled with Florogold in retinal wholemounts, as described above.

EXAMPLE 22

Procedure to Measure Efficacy to Prevent Photoreceptor Cell Death in Rat Models of Photoreceptor Degeneration The rescue of photoreceptor cells can be demonstrated in Royal College of Surgeons (RCS) rats, which rats have an inherited retinal degeneration (Faktorovich et al., Nature 347: 83, 1990). Intraocular injections of C3APLT in aqueous buffer are made with a 10 μl syringe attached to a glass micropipette. A hole is made in the superior nasal retina approximately 4 mm from the optic disc using a 30 g needle before introduction of the glass pipette to inject 5 μl of 1 ug C3-APLT or buffer control. The needle is withdrawn slowly to allow diffusion of the solution into the vitreous spaces, and the sclera is sealed with tissue adhesive. Care is taken not to damage the lens during injection because lens damage can lead to cataract formation and consequent increases in survival of the RGCs. The skin is closed, and the integrity of the retinal vasculature is evaluated by a postoperative opthalmoscopic examination. Rats with compromised vasculature or rats that develop cataracts are not included in the experimental results.

A histological analysis useful to assess photoreceptor survival in therapeutically treated or untreated RCS rats comprises the steps of vascular perfusion of an anesthetized animal, embedding of the animal's eye in paraffin, and staining of 6 micron thick sections with hemotoxyline and eosin or with toluidine blue. In the eyes of untreated RCS rats at 53 days after birth (P53) the outer nuclear layer, which contains the photoreceptor cells, is reduced in thickness to only a few rows of cells (approximately 20% of the thickness found in normal rats at the same age). A therapeutically effective dose of C3APLT administered by intravitreal administration (e.g., a single injection comprising one microgram of protein) can restore the thickness of the outer nuclear layer, and hence rescue photoreceptor cells.

Alternatively, rescue of photoreceptor cells can be demonstrated using 2-to-3 month old male Sprague-Dawley rats in a model of exposure to constant light (115-200 foot-candles) for 1 week following the procedures of LaVail et al., PNAS USA 89:11249, 1992, the disclosure of which is incorporated herein by reference. An aqueous buffer solution of C3APLT can be injected (1 ug of protein) into the subretinal space or into the vitreous humor 48 hours prior to the onset of continuous illumination. Histological examination and analysis of retinas following a fixed recovery period (usually 10 days) is used to assess the death or damage to and the rescue or survival of photoreceptor cells.

Retinal detachment also leads to the death of photoreceptor cells. An animal model described by Erickson et al., J Struct. Biol. 108:148, 1992, the disclosure of which is incorporated herein by reference, can demonstrate the effect of administration of C3APLT to enhance survival of retinal cells in vitro relative to administration of buffer control, a protein mutated to eliminate ADP-ribosylation activity, and to untreated controls.

EXAMPLE 23

Procedure to Measure Efficacy of a Fusion Protein of the Invention to Prevent Photoreceptor Cell Death in Transgenic Mouse Models of Photoreceptor Degeneration Several mouse genetic models of photoreceptor degeneration (e.g., rd-mutant of b subunit of cGMP phosphodiesterasel rds-mutant of peripherin) can be employed using the modes of administration described above to demonstrate fusion protein-related (e.g., C3APLT-related) photoreceptor cell enhanced survival effects in vivo.

Rd-mutant mice and rds-mutant mice exhibit retinal degeneration within a few weeks after birth. Following intravitreal injection of a fusion protein (e.g., C3APLT) as described above, tissues are analysed by histological methods described above.

Retinal explants from rd-mutant mice cultured in a C3APLT-containing medium can be assayed for thickness of the outer nuclear layer using methods described in Caffe et al., Curr. Eye Res. 12:719, 1993, the disclosure of which is hereby incorporated by reference. Thus, mouse pups are enucleated 48 hours after birth and treated with proteinase K. After this enzyme treatment, the neural retina with the retinal pigmented epithelium (RPE) attached is recovered, placed into a multi-well culture dish, and incubated in 1.2 ml culture medium (e.g., R16) for up to 4 weeks at 37° C. with 5% CO2. Immunocytochemical staining for opsin of fixed (e.g., 4% paraformaldehyde) sections is used to assess the degeneration and rescue of photoreceptor cells. In the rd-mutant mouse the outer nuclear layer (photoreceptor cells) degenerate after 2-to-4 weeks in culture. The media can be supplemented with a dose range of C3APLT to achieve an effect on retinal cell function, such as rescue of the outer nuclear layer from degeneration. Survival effects can also be shown using the TUNEL method on sections of retina analysed in the models described above.

EXAMPLE 24

Procedure to Determine Efficacy of a Fusion Protein to Prevent Neovascularization of the Retina Uncontrolled retinal angiogenesis can contribute to the pathology of a number of diseases of the retina such as wet macular degeneration, retinitis pigmentosa, Stargardt's Disease, diabetic retinopathy, hypertensive retinopathy, and occlusive retinopathy. Vascular endothelial growth factor (VEGF) production is increased by hypoxia in the retina, and neovascularization of the retina is thereby induced.

A mouse model of ischemia-induced retinal neovascularization employs newborn C57BL/6J mice which are exposed to 75% O2 from postnatal day (P) 7 to P12, along with their nursing mothers, followed by a return to room air. To accomplish this, the mice are weighed and placed at day P7 in a plexiglass box which serves as an oxygen chamber together with enough food and water for 5 days to P12. An oxygen flow rate of 1.5 L/min is maintained through the box for 5 days. The flow rate is checked twice daily with a Beckman oxygen analyzer (model D2, Irvine Calif.). The chamber is not opened during the 5 days of hyperoxia. An intraocular injection of a fusion protein (e.g., C3APLT) is performed at day P12 and the mice are removed to ambient air thereby inducing hypoxia. At day P17 the mice are sacrificed by cardiac perfusion with saline followed by 4% paraformaldehyde (PF), and their eyes are removed and fixed in PF overnight. The eyes are then rinsed, brought through a graded alcohol series, and then radial sections 6 um thick are cut. Sections through the optic nerve head are stained with periodic acid/Schiff reagent and hematoxylin. Sections 30 um apart are evaluated for a span of 300 um through the retina. All retinal vascular nuclei anterior to the internal limiting membrane are counted in each section. The mean of 10 counted sections is determined to give the average number of neovascular nuclei per section per eye. No vascular cell nuclei anterior to the limiting membrane are observed in normal, unmanipulated animals. The administration of a fusion protein substantially reduces the number of retinal vascular nuclei relative to the number observed in the absence of fusion protein.

What is claimed is:

1. A method of treatment of a disease of the eye selected from the group consisting of macular degeneration, retinitis pigmentosa, Stargardt's Disease, diabetic retinopathy, hypertensive retinopathy, and occlusive retinopathy, the method comprising administration to a patient in need of such treatment a therapeutically effective amount of a pharmaceutical composition comprising:
a) a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating uptake of the active agent by a receptor-independent mechanism and being the sequence set forth in SEQ ID NO: 48, said polypeptide having ADP-ribosyl transferase activity, and;
b) a pharmaceutically acceptable carrier.

2. The method of claim 1, wherein the amino acid sequence of the transport agent is at the carboxy-terminal end of said polypeptide and the amino acid sequence of the active agent is at the amino terminal end of said polypeptide.

3. The method of claim 1, wherein the carrier comprises a biological adhesive.

4. The method of claim 1, wherein the carrier comprises fibrin.

5. The method of claim 1, wherein the administration comprises injection.

6. A method of treatment of a disease of the eye selected from the group consisting of macular degeneration, retinitis pigmentosa, Stargardt's Disease, diabetic retinopathy, hypertensive retinopathy, and occlusive retinopathy, the method comprising administration to a patient in need of such treatment a therapeutically effective amount of a pharmaceutical composition comprising:
a polypeptide comprising an amino acid sequence of a transport agent covalently linked to an amino acid sequence of an active agent, said polypeptide comprising an amino acid sequence having at least 90% sequence identity with the amino acid sequence of SEQ ID NO: 43 and retaining ADP-ribosyl transferase activity, said amino acid sequence of said transport agent facilitating uptake of the active agent by a receptor-independent mechanism; and
b) a pharmaceutically acceptable carrier.

7. The method of claim 6, wherein the carrier comprises a biological adhesive.

8. The method of claim 6, wherein the carrier comprises fibrin.

9. The method of claim 6, wherein the administration comprises injection.

10. The method of claim 6, wherein the amino acid sequence of the transport agent is at the carboxy-terminal end of said polypeptide and the amino acid sequence of the active agent is at the amino terminal end of said polypeptide.

11. A method of inhibiting or reducing the rate of subretinal neovascularization and proliferation of neovascular tissue in the eye of a mammalian host in need thereof comprising administration to said host a therapeutically effective amount of a pharmaceutical composition comprising:
a) a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating uptake of the active agent by a receptor-independent mechanism and being the sequence set forth in SEQ ID NO: 48, said polypeptide having ADP-ribosyl transferase activity, and;

b) a pharmaceutically acceptable carrier;

wherein the mammalian host has a disease of the eye selected from the group consisting of macular degeneration, retinitis pigmentosa, Stargardt's Disease, diabetic retinopathy, hypertensive retinopathy, and occlusive retinopathy.

12. The method of claim 11, wherein the amino acid sequence of the transport agent is at the carboxy-terminal end of said polypeptide and the amino acid sequence of the active agent is at the amino terminal end of said polypeptide.

13. The method of claim 11, wherein the carrier comprises a biological adhesive.

14. The method of claim 11, wherein the carrier comprises fibrin.

15. The method of claim 11 wherein the administration comprises injection.

16. A method of inhibiting or reducing the rate of subretinal neovascularization and proliferation of neovascular tissue in the eye of a mammalian host in need thereof comprising administration to said host a therapeutically effective amount of a pharmaceutical composition comprising:

a polypeptide comprising an amino acid sequence of a transport agent covalently linked to an amino acid sequence of an active agent, said polypeptide comprising an amino acid sequence having at least 90% sequence identity with the amino acid sequence of SEQ ID NO: 43 and retaining ADP-ribosyl transferase activity, said amino acid sequence of said transport agent facilitating uptake of the active agent by a receptor-independent mechanism; and b) a pharmaceutically acceptable carrier;

wherein the mammalian host has a disease of the eye selected from the group consisting of macular degeneration, retinitis pigmentosa, Stargardt's Disease, diabetic retinopathy, hypertensive retinopathy, and occlusive retinopathy.

17. The method of claim 16, wherein the carrier comprises a biological adhesive.

18. The method of claim 16, wherein the carrier comprises fibrin.

19. The method of claim 16, wherein the administration comprises injection.

20. The method of claim 16, wherein the amino acid sequence of the transport agent is at the carboxy-terminal end of said polypeptide and the amino acid sequence of the active agent is at the amino terminal end of said polypeptide.

* * * * *

SEQUENCE LISTING

<160> NUMBER OF SEQ ID NOS: 55

<210> SEQ ID NO 1
<211> LENGTH: 27
<212> TYPE: DNA
<213> ORGANISM: Artificial Sequence

```
<220> FEATURE:
<223> OTHER INFORMATION: Oligonucleotide used to remove the stop codon
      from ADP-ribosyl transferase C3 (Clostridium botulinum) cDNA.

<400> SEQUENCE: 1
gaattcttta ggattgatag ctgtgcc                                         27

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide used to remove the stop codon
      from ADP-ribosyl transferase C3 (Clostridium botulinum) cDNA.

<400> SEQUENCE: 2
ggtggcgacc atcctccaaa a                                               21

<210> SEQ ID NO 3
<211> LENGTH: 888
<212> TYPE: DNA
<213> ORGANISM: Artificial Sequence
<220> FEATURE:
<223> OTHER INFORMATION: Sequence of C3APL: includes  ADP-ribosyl
      transferase C3 (Clostridium botulinum) and  Antennapedia
      sequence.
<220> FEATURE:
<221> NAME/KEY: CDS
<222> LOCATION: (1)..(888)
<223> OTHER INFORMATION:

<400> SEQUENCE: 3 gga tcc tct aga gtc gac ctg cag gca tgc aat gct tat tcc att aat       48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa       96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa      144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata      192
Ser Glu Lys Glu Ala Ile Val Ser Tyr Thr Lys Ser Ala Ser Glu Ile
50                  55                  60 aat gga aag cta aga caa aat aag gga gtt atc aat gga ttt cct tca      240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg      288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat      336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att      384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat      432
Asn Lys Thr Ala Phe Glu Lys Ala Lys Ala Lys Phe Leu Asn Lys Asp
130                 135                 140 aga ctt gaa tat gga tat att agt act tca tta atg aat gtc tct caa      480
Arg Leu Glu Tyr Gly Tyr Ile Ser Thr Ser Leu Met Asn Val Ser Gln
145                 150                 155                 160 ttt gca gga aga cca att att aca caa ttt aaa gta gca aaa ggc tca      528
Phe Ala Gly Arg Pro Ile Ile Thr Gln Phe Lys Val Ala Lys Gly Ser
                165                 170                 175
```

```
aag gca gga tat att gac cct att agt gct ttt cag gga caa ctt gaa    576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg    624
Met Leu Leu Pro Arg His Ser Thr Tyr His Ile Asp Asp Met Arg Leu
        195                 200                 205 tct tct gat ggt aaa caa ata ata att aca gca aca atg atg ggc aca    672
Ser Ser Asp Gly Lys Gln Ile Ile Ile Thr Ala Thr Met Met Gly Thr
    210                 215                 220 gct atc aat cct aaa gaa ttc gtg atg gaa tcc cgc aaa cgc gca agg    720
Ala Ile Asn Pro Lys Glu Phe Val Met Glu Ser Arg Lys Arg Ala Arg
225                 230                 235                 240 cag aca tac acc cgg tac cag act cta gag cta gag aag gag ttt cac    768
Gln Thr Tyr Thr Arg Tyr Gln Thr Leu Glu Leu Glu Lys Glu Phe His
                245                 250                 255 ttc aat cgc tac ttg acc cgt cgg cga agg atc gag atc gcc cac gcc    816
Phe Asn Arg Tyr Leu Thr Arg Arg Arg Ile Glu Ile Ala His Ala
            260                 265                 270 ctg tgc ctc acg gag cgc cag ata aag att tgg ttc cag aat cgg cgc    864
Leu Cys Leu Thr Glu Arg Gln Ile Lys Ile Trp Phe Gln Asn Arg Arg
        275                 280                 285 atg aag tgg aag aag gag aac tga                                    888
Met Lys Trp Lys Lys Glu Asn
    290                 295

<210> SEQ ID NO 4
<211> LENGTH: 295
<212> TYPE: PRT
<213> ORGANISM: Artificial Sequence
<220> FEATURE:
<223> OTHER INFORMATION: Sequence of C3APL: includes  ADP-ribosyl
      transferase C3 (Clostridium botulinum) and Antennapedia
      sequence.

<400> SEQUENCE: 4

Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190
```

```
Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Val Met Glu Ser Arg Lys Arg Ala Arg
225                 230                 235                 240

Gln Thr Tyr Thr Arg Tyr Gln Thr Leu Glu Leu Glu Lys Glu Phe His
                245                 250                 255

Phe Asn Arg Tyr Leu Thr Arg Arg Arg Ile Glu Ile Ala His Ala
                260                 265                 270

Leu Cys Leu Thr Glu Arg Gln Ile Lys Ile Trp Phe Gln Asn Arg Arg
        275                 280                 285

Met Lys Trp Lys Lys Glu Asn
        290                 295

<210> SEQ ID NO 5
<211> LENGTH: 774
<212> TYPE: DNA
<213> ORGANISM: Artificial Sequence
<220> FEATURE:
<223> OTHER INFORMATION: Sequence of C3APS: Includes  ADP-ribosyl
      transferase C3 (Clostridium botulinum) and Antennapedia
      sequence.
<220> FEATURE:
<221> NAME/KEY: CDS
<222> LOCATION: (1)..(774)
<223> OTHER INFORMATION:

<400> SEQUENCE: 5 gga tcc tct aga gtc gac ctg cag gca tgc aat gct tat tcc att aat        48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa        96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa       144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata       192
Ser Glu Lys Glu Ala Ile Val Ser Tyr Thr Lys Ser Ala Ser Glu Ile
    50                  55                  60 aat gga aag cta aga caa aat aag gga gtt atc aat gga ttt cct tca       240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg       288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat       336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att       384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat       432
Asn Lys Thr Ala Phe Glu Lys Ala Lys Ala Lys Phe Leu Asn Lys Asp
    130                 135                 140 aga ctt gaa tat gga tat att agt act tca tta atg aat gtc tct caa       480
Arg Leu Glu Tyr Gly Tyr Ile Ser Thr Ser Leu Met Asn Val Ser Gln
145                 150                 155                 160 ttt gca gga aga cca att att aca caa ttt aaa gta gca aaa ggc tca       528
Phe Ala Gly Arg Pro Ile Ile Thr Gln Phe Lys Val Ala Lys Gly Ser
```

```
                  165                 170                 175
aag gca gga tat att gac cct att agt gct ttt cag gga caa ctt gaa    576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg    624
Met Leu Leu Pro Arg His Ser Thr Tyr His Ile Asp Asp Met Arg Leu
        195                 200                 205 tct tct gat ggt aaa caa ata ata att aca gca aca atg atg ggc aca    672
Ser Ser Asp Gly Lys Gln Ile Ile Ile Thr Ala Thr Met Met Gly Thr
    210                 215                 220 gct atc aat cct aaa gaa ttc cgc cag atc aag att tgg ttc cag aat    720
Ala Ile Asn Pro Lys Glu Phe Arg Gln Ile Lys Ile Trp Phe Gln Asn
225                 230                 235                 240 cgt cgc atg aag tgg aag aag gtc gac tcg agc ggc cgc atc gtg act    768
Arg Arg Met Lys Trp Lys Lys Val Asp Ser Ser Gly Arg Ile Val Thr
                245                 250                 255 gac tga                                                             774
Asp

<210> SEQ ID NO 6
<211> LENGTH: 257
<212> TYPE: PRT
<213> ORGANISM: Artificial Sequence
<220> FEATURE:
<223> OTHER INFORMATION: Sequence of C3APS: Includes  ADP-ribosyl
      transferase C3 (Clostridium botulinum) and Antennapedia
      sequence.

<400> SEQUENCE: 6

Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Arg Gln Ile Lys Ile Trp Phe Gln Asn
```

```
225                 230                 235                 240
Arg Arg Met Lys Trp Lys Lys Val Asp Ser Ser Gly Arg Ile Val Thr
                245                 250                 255
Asp

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide used in the amplification of
      Antennapedia sequence

<400> SEQUENCE: 7
gaatcccgca aacgcgcaag gcag                                              24

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide used in the amplification of
      Antennapedia sequence

<400> SEQUENCE: 8
tcagttctcc ttcttccact tcatgcg                                           27

<210> SEQ ID NO 9
<211> LENGTH: 54
<212> TYPE: DNA
<213> ORGANISM: Artificial Sequence
<220> FEATURE:
<223> OTHER INFORMATION: Oligonucleotide used in the cloning of
      sequences from Antennapedia

<400> SEQUENCE: 9
aattccgcca gatcaagatt tggttccaga atcgtcgcat gaagtggaag aagg             54

<210> SEQ ID NO 10
<211> LENGTH: 54
<212> TYPE: DNA
<213> ORGANISM: Artificial Sequence
<220> FEATURE:
<223> OTHER INFORMATION: Oligonucleotide used in the cloning of
      sequences from Antennapedia

<400> SEQUENCE: 10
ggcggtctag ttctaaacca agctcttagc agcgtagttc accttcttcc agct             54

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide used inthe amplification of a
      sequence corresponding to amino acid 27-72 of HIV-1 Tat

<400> SEQUENCE: 11
gaatccaagc atccaggaag tcagcc                                            26

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide used inthe amplification of a
      sequence corresponding to amino acid 27-72 of HIV-1 Tat
```

```
<400> SEQUENCE: 12
accagccacc accttctgat a                                              21

<210> SEQ ID NO 13
<211> LENGTH: 876
<212> TYPE: DNA
<213> ORGANISM: Artificial Sequence
<220> FEATURE:
<223> OTHER INFORMATION: Sequence of C3-TL: Includes  ADP-ribosyl
      transferase C3 (Clostridium botulinum) and HIV-1 Tat sequence.
<220> FEATURE:
<221> NAME/KEY: CDS
<222> LOCATION: (1)..(876)
<223> OTHER INFORMATION:

<400> SEQUENCE: 13
```

| | | | | | | | | | | | | | | | | |
|---|---|---|---|---|---|---|---|---|---|---|---|---|---|---|---|---|
| gga | tcc | tct | aga | gtc | gac | ctg | cag | gca | tgc | aat | gct | tat | tcc | att | aat | 48 |
| Gly | Ser | Ser | Arg | Val | Asp | Leu | Gln | Ala | Cys | Asn | Ala | Tyr | Ser | Ile | Asn | |
| 1 | | | | 5 | | | | | 10 | | | | | 15 | | |
| caa | aag | gct | tat | tca | aat | act | tac | cag | gag | ttt | act | aat | att | gat | caa | 96 |
| Gln | Lys | Ala | Tyr | Ser | Asn | Thr | Tyr | Gln | Glu | Phe | Thr | Asn | Ile | Asp | Gln | |
| | | | 20 | | | | | 25 | | | | | 30 | | | |
| gca | aaa | gct | tgg | ggt | aat | gct | cag | tat | aaa | aag | tat | gga | cta | agc | aaa | 144 |
| Ala | Lys | Ala | Trp | Gly | Asn | Ala | Gln | Tyr | Lys | Lys | Tyr | Gly | Leu | Ser | Lys | |
| | 35 | | | | | 40 | | | | | 45 | | | | | |
| tca | gaa | aaa | gaa | gct | ata | gta | tca | tat | act | aaa | agc | gct | agt | gaa | ata | 192 |
| Ser | Glu | Lys | Glu | Ala | Ile | Val | Ser | Tyr | Thr | Lys | Ser | Ala | Ser | Glu | Ile | |
| 50 | | | | | 55 | | | | | 60 | | | | | | |
| aat | gga | aag | cta | aga | caa | aat | aag | gga | gtt | atc | aat | gga | ttt | cct | tca | 240 |
| Asn | Gly | Lys | Leu | Arg | Gln | Asn | Lys | Gly | Val | Ile | Asn | Gly | Phe | Pro | Ser | |
| 65 | | | | | 70 | | | | | 75 | | | | | 80 | |
| aat | tta | ata | aaa | caa | gtt | gaa | ctt | tta | gat | aaa | tct | ttt | aat | aaa | atg | 288 |
| Asn | Leu | Ile | Lys | Gln | Val | Glu | Leu | Leu | Asp | Lys | Ser | Phe | Asn | Lys | Met | |
| | | | | 85 | | | | | 90 | | | | | 95 | | |
| aag | acc | cct | gaa | aat | att | atg | tta | ttt | aga | ggc | gac | gac | cct | gct | tat | 336 |
| Lys | Thr | Pro | Glu | Asn | Ile | Met | Leu | Phe | Arg | Gly | Asp | Asp | Pro | Ala | Tyr | |
| | | | 100 | | | | | 105 | | | | | 110 | | | |
| tta | gga | aca | gaa | ttt | caa | aac | act | ctt | ctt | aat | tca | aat | ggt | aca | att | 384 |
| Leu | Gly | Thr | Glu | Phe | Gln | Asn | Thr | Leu | Leu | Asn | Ser | Asn | Gly | Thr | Ile | |
| | 115 | | | | | 120 | | | | | 125 | | | | | |
| aat | aaa | acg | gct | ttt | gaa | aag | gct | aaa | gct | aag | ttt | tta | aat | aaa | gat | 432 |
| Asn | Lys | Thr | Ala | Phe | Glu | Lys | Ala | Lys | Ala | Lys | Phe | Leu | Asn | Lys | Asp | |
| 130 | | | | | 135 | | | | | 140 | | | | | | |
| aga | ctt | gaa | tat | gga | tat | att | agt | act | tca | tta | atg | aat | gtc | tct | caa | 480 |
| Arg | Leu | Glu | Tyr | Gly | Tyr | Ile | Ser | Thr | Ser | Leu | Met | Asn | Val | Ser | Gln | |
| 145 | | | | | 150 | | | | | 155 | | | | | 160 | |
| ttt | gca | gga | aga | cca | att | att | aca | caa | ttt | aaa | gta | gca | aaa | ggc | tca | 528 |
| Phe | Ala | Gly | Arg | Pro | Ile | Ile | Thr | Gln | Phe | Lys | Val | Ala | Lys | Gly | Ser | |
| | | | | 165 | | | | | 170 | | | | | 175 | | |
| aag | gca | gga | tat | att | gac | cct | att | agt | gct | ttt | cag | gga | caa | ctt | gaa | 576 |
| Lys | Ala | Gly | Tyr | Ile | Asp | Pro | Ile | Ser | Ala | Phe | Gln | Gly | Gln | Leu | Glu | |
| | | | 180 | | | | | 185 | | | | | 190 | | | |
| atg | ttg | ctt | cct | aga | cat | agt | act | tat | cat | ata | gac | gat | atg | aga | ttg | 624 |
| Met | Leu | Leu | Pro | Arg | His | Ser | Thr | Tyr | His | Ile | Asp | Asp | Met | Arg | Leu | |
| | 195 | | | | | 200 | | | | | 205 | | | | | |
| tct | tct | gat | ggt | aaa | caa | ata | ata | att | aca | gca | aca | atg | atg | ggc | aca | 672 |
| Ser | Ser | Asp | Gly | Lys | Gln | Ile | Ile | Ile | Thr | Ala | Thr | Met | Met | Gly | Thr | |
| 210 | | | | | 215 | | | | | 220 | | | | | | |
| gct | atc | aat | cct | aaa | gaa | ttc | aag | cat | cca | gga | agt | cag | cct | aaa | act | 720 |
| Ala | Ile | Asn | Pro | Lys | Glu | Phe | Lys | His | Pro | Gly | Ser | Gln | Pro | Lys | Thr | |
| 225 | | | | | 230 | | | | | 235 | | | | | 240 | |

```
gct tgt acc aat tgc tat tgt aaa aag tgt tgc ttt cat tgc caa gtt       768
Ala Cys Thr Asn Cys Tyr Cys Lys Lys Cys Cys Phe His Cys Gln Val
            245                 250                 255 tgt ttc ata aca aaa gcc tta ggc atc tcc tat ggc agg aag cgg aga       816
Cys Phe Ile Thr Lys Ala Leu Gly Ile Ser Tyr Gly Arg Lys Arg Arg
        260                 265                 270 cag cga cga aga gct cat cag aac agt cag act cat caa gct tct cta       864
Gln Arg Arg Arg Ala His Gln Asn Ser Gln Thr His Gln Ala Ser Leu
        275                 280                 285 tca aag cag taa                                                       876
Ser Lys Gln
    290

<210> SEQ ID NO 14
<211> LENGTH: 291
<212> TYPE: PRT
<213> ORGANISM: Artificial Sequence
<220> FEATURE:
<223> OTHER INFORMATION: Sequence of C3-TL: Includes  ADP-ribosyl
      transferase C3 (Clostridium botulinum) and HIV-1 Tat sequence.

<400> SEQUENCE: 14

Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Lys His Pro Gly Ser Gln Pro Lys Thr
225                 230                 235                 240

Ala Cys Thr Asn Cys Tyr Cys Lys Lys Cys Cys Phe His Cys Gln Val
                245                 250                 255

Cys Phe Ile Thr Lys Ala Leu Gly Ile Ser Tyr Gly Arg Lys Arg Arg
            260                 265                 270

Gln Arg Arg Arg Ala His Gln Asn Ser Gln Thr His Gln Ala Ser Leu
        275                 280                 285
```

Ser Lys Gln
    290

<210> SEQ ID NO 15
<211> LENGTH: 39
<212> TYPE: DNA
<213> ORGANISM: Artificial Sequence
<220> FEATURE:
<223> OTHER INFORMATION: Oligonucleotide used in the cloning of
      sequences from HIV-1 Tat

<400> SEQUENCE: 15
aattctatgg tcgtaaaaaa cgtcgtcaac gtcgtcgtg                              39

<210> SEQ ID NO 16
<211> LENGTH: 39
<212> TYPE: DNA
<213> ORGANISM: Artificial Sequence
<220> FEATURE:
<223> OTHER INFORMATION: Oligonucleotide used in the cloning of
      sequences from HIV-1 Tat

<400> SEQUENCE: 16
gataccagca tttttgcag cagttgcagc agcacagct                               39

<210> SEQ ID NO 17
<211> LENGTH: 756
<212> TYPE: DNA
<213> ORGANISM: Artificial Sequence
<220> FEATURE:
<223> OTHER INFORMATION: Sequence of C3-TS: Includes  ADP-ribosyl
      transferase C3 (Clostridium botulinum) and HIV-1 Tat sequence.
<220> FEATURE:
<221> NAME/KEY: CDS
<222> LOCATION: (1)..(756)
<223> OTHER INFORMATION:

<400> SEQUENCE: 17

```
gga tcc tct aga gtc gac ctg cag gca tgc aat gct tat tcc att aat        48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa        96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa       144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata       192
Ser Glu Lys Glu Ala Ile Val Ser Tyr Thr Lys Ser Ala Ser Glu Ile
    50                  55                  60 aat gga aag cta aga caa aat aag gga gtt atc aat gga ttt cct tca       240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg       288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat       336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att       384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat       432
Asn Lys Thr Ala Phe Glu Lys Ala Lys Ala Lys Phe Leu Asn Lys Asp
    130                 135                 140
```

```
aga ctt gaa tat gga tat att agt act tca tta atg aat gtc tct caa    480
Arg Leu Glu Tyr Gly Tyr Ile Ser Thr Ser Leu Met Asn Val Ser Gln
145                 150                 155                 160 ttt gca gga aga cca att att aca caa ttt aaa gta gca aaa ggc tca    528
Phe Ala Gly Arg Pro Ile Ile Thr Gln Phe Lys Val Ala Lys Gly Ser
            165                 170                 175 aag gca gga tat att gac cct att agt gct ttt cag gga caa ctt gaa    576
Lys Ala Gly Tyr Ile Asp Pro Ile Ser Ala Phe Gln Gly Gln Leu Glu
        180                 185                 190 atg ttg ctt cct aga cat agt act tat cat ata gac gat atg aga ttg    624
Met Leu Leu Pro Arg His Ser Thr Tyr His Ile Asp Asp Met Arg Leu
    195                 200                 205 tct tct gat ggt aaa caa ata ata att aca gca aca atg atg ggc aca    672
Ser Ser Asp Gly Lys Gln Ile Ile Ile Thr Ala Thr Met Met Gly Thr
210                 215                 220 gct atc aat cct aaa gaa ttc tat ggt gct aaa aaa cgt cgt caa cgt    720
Ala Ile Asn Pro Lys Glu Phe Tyr Gly Ala Lys Lys Arg Arg Gln Arg
225                 230                 235                 240 cgt cgt gtc gac tcg agc ggc ccg cat cgt gac tga                    756
Arg Arg Val Asp Ser Ser Gly Pro His Arg Asp
                245                 250
```

<210> SEQ ID NO 18
<211> LENGTH: 251
<212> TYPE: PRT
<213> ORGANISM: Artificial Sequence
<220> FEATURE:
<223> OTHER INFORMATION: Sequence of C3-TS: Includes ADP-ribosyl
      transferase C3 (Clostridium botulinum) and HIV-1 Tat sequence.

<400> SEQUENCE: 18

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Gly Thr Ile
        115                 120                 125

Asn Lys Thr Ala Phe Glu Lys Ala Lys Ala Lys Phe Leu Asn Lys Asp
130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
            165                 170                 175

Lys Ala Gly Tyr Ile Asp Pro Ile Ser Ala Phe Gln Gly Gln Leu Glu
        180                 185                 190

Met Leu Leu Pro Arg His Ser Thr Tyr His Ile Asp Asp Met Arg Leu
    195                 200                 205

Ser Ser Asp Gly Lys Gln Ile Ile Ile Thr Ala Thr Met Met Gly Thr
```

```
                    210                 215                 220
Ala Ile Asn Pro Lys Glu Phe Tyr Gly Ala Lys Lys Arg Arg Gln Arg
225                 230                 235                 240

Arg Arg Val Asp Ser Ser Gly Pro His Arg Asp
                245                 250

<210> SEQ ID NO 19
<211> LENGTH: 1413
<212> TYPE: DNA
<213> ORGANISM: Artificial Sequence
<220> FEATURE:
<223> OTHER INFORMATION: Includes GST sequences, ADP-ribosyl
      transferase C3 (C. botulinum) sequence and a random basic amino
      acid sequence.
<220> FEATURE:
<221> NAME/KEY: CDS
<222> LOCATION: (1)..(1413)
<223> OTHER INFORMATION:

<400> SEQUENCE: 19 atg tcc cct ata cta ggt tat tgg aaa att aag ggc ctt gtg caa ccc        48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg        96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg       144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa       192
Gly Leu Glu Phe Pro Asn Leu Pro Tyr Tyr Ile Asp Gly Asp Val Lys
    50                  55                  60 tta aca cag tct atg gcc atc cgt tat ata gct gac aag cac aac           240
Leu Thr Gln Ser Met Ala Ile Arg Tyr Ile Ala Asp Lys His Asn
65              70                  75                  80 atg ttg ggt ggt tgt cca aaa gag cgt gca gag att tca atg ctt gaa       288
Met Leu Gly Gly Cys Pro Lys Glu Arg Ala Glu Ile Ser Met Leu Glu
            85                  90                  95 gga gcg gtt ttg gat att aga tac ggt gtt tcg aga att gca tat agt       336
Gly Ala Val Leu Asp Ile Arg Tyr Gly Val Ser Arg Ile Ala Tyr Ser
        100                 105                 110 aaa gac ttt gaa act ctc aaa gtt gat ttt ctt agc aag cta cct gaa       384
Lys Asp Phe Glu Thr Leu Lys Val Asp Phe Leu Ser Lys Leu Pro Glu
    115                 120                 125 atg ctg aaa atg ttc gaa gat cgt tta tgt cat aaa aca tat tta aat       432
Met Leu Lys Met Phe Glu Asp Arg Leu Cys His Lys Thr Tyr Leu Asn
130                 135                 140 ggt gat cat gta acc cat cct gac ttc atg ttg tat gac gct ctt gat       480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta       528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac       576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc       624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt       672
Thr Phe Gly Gly Gly Asp His Pro Pro Lys Ser Asp Leu Val Pro Arg
    210                 215                 220
```

```
gga tcc tct aga gtc gac ctg cag gca tgc aat gct tat tcc att aat    720
Gly Ser Ser Arg Val Asp Leu Gln Ala Cys Asn Ala Tyr Ser Ile Asn
225             230                 235                 240 caa aag gct tat tca aat act tac cag gag ttt act aat att gat caa    768
Gln Lys Ala Tyr Ser Asn Thr Tyr Gln Glu Phe Thr Asn Ile Asp Gln
            245                 250                 255 gca aaa gct tgg ggt aat gct cag tat aaa aag tat gga cta agc aaa    816
Ala Lys Ala Trp Gly Asn Ala Gln Tyr Lys Lys Tyr Gly Leu Ser Lys
        260                 265                 270 tca gaa aaa gaa gct ata gta tca tat act aaa agc gct agt gaa ata    864
Ser Glu Lys Glu Ala Ile Val Ser Tyr Thr Lys Ser Ala Ser Glu Ile
    275                 280                 285 aat gga aag cta aga caa aat aag gga gtt atc aat gga ttt cct tca    912
Asn Gly Lys Leu Arg Gln Asn Lys Gly Val Ile Asn Gly Phe Pro Ser
290                 295                 300 aat tta ata aaa caa gtt gaa ctt tta gat aaa tct ttt aat aaa atg    960
Asn Leu Ile Lys Gln Val Glu Leu Leu Asp Lys Ser Phe Asn Lys Met
305                 310                 315                 320 aag acc cct gaa aat att atg tta ttt aga ggc gac gac cct gct tat   1008
Lys Thr Pro Glu Asn Ile Met Leu Phe Arg Gly Asp Asp Pro Ala Tyr
            325                 330                 335 tta gga aca gaa ttt caa aac act ctt ctt aat tca aat ggt aca att   1056
Leu Gly Thr Glu Phe Gln Asn Thr Leu Leu Asn Ser Asn Gly Thr Ile
        340                 345                 350 aat aaa acg gct ttt gaa aag gct aaa gct aag ttt tta aat aaa gat   1104
Asn Lys Thr Ala Phe Glu Lys Ala Lys Ala Lys Phe Leu Asn Lys Asp
    355                 360                 365 aga ctt gaa tat gga tat att agt act tca tta atg aat gtt tct caa   1152
Arg Leu Glu Tyr Gly Tyr Ile Ser Thr Ser Leu Met Asn Val Ser Gln
370                 375                 380 ttt gca gga aga cca att att aca aaa ttt aaa gta gca aaa ggc tca   1200
Phe Ala Gly Arg Pro Ile Ile Thr Lys Phe Lys Val Ala Lys Gly Ser
385                 390                 395                 400 aag gca gga tat att gac cct att agt gct ttt cag gga caa ctt gaa   1248
Lys Ala Gly Tyr Ile Asp Pro Ile Ser Ala Phe Gln Gly Gln Leu Glu
            405                 410                 415 atg ttg ctt cct aga cat agt act tat cat ata gac gat atg aga ttg   1296
Met Leu Leu Pro Arg His Ser Thr Tyr His Ile Asp Asp Met Arg Leu
        420                 425                 430 tct tct gat ggt aaa caa ata ata att aca gca aca atg atg ggc aca   1344
Ser Ser Asp Gly Lys Gln Ile Ile Ile Thr Ala Thr Met Met Gly Thr
    435                 440                 445 gct atc aat cct aaa gaa ttc aga agg aaa caa aga aga aaa aga aga   1392
Ala Ile Asn Pro Lys Glu Phe Arg Arg Lys Gln Arg Arg Lys Arg Arg
450                 455                 460 ctg cag gcg gcc gca tcg tga                                        1413
Leu Gln Ala Ala Ala Ser
465                 470

<210> SEQ ID NO 20
<211> LENGTH: 470
<212> TYPE: PRT
<213> ORGANISM: Artificial Sequence
<220> FEATURE:
<223> OTHER INFORMATION: Includes GST sequences, ADP-ribosyl
      transferase C3 (C. botulinum) sequence and a random basic amino
      acid sequence.

<400> SEQUENCE: 20

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
```

```
                     20                  25                  30
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
        50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
Gly Ser Ser Arg Val Asp Leu Gln Ala Cys Asn Ala Tyr Ser Ile Asn
225                 230                 235                 240
Gln Lys Ala Tyr Ser Asn Thr Tyr Gln Glu Phe Thr Asn Ile Asp Gln
                245                 250                 255
Ala Lys Ala Trp Gly Asn Ala Gly Tyr Lys Lys Tyr Gly Leu Ser Lys
            260                 265                 270
Ser Glu Lys Glu Ala Ile Val Ser Tyr Thr Lys Ser Ala Ser Glu Ile
        275                 280                 285
Asn Gly Lys Leu Arg Gln Asn Lys Gly Val Ile Asn Gly Phe Pro Ser
290                 295                 300
Asn Leu Ile Lys Gln Val Glu Leu Leu Asp Lys Ser Phe Asn Lys Met
305                 310                 315                 320
Lys Thr Pro Glu Asn Ile Met Leu Phe Arg Gly Asp Asp Pro Ala Tyr
                325                 330                 335
Leu Gly Thr Glu Phe Gln Asn Thr Leu Leu Asn Ser Asn Gly Thr Ile
            340                 345                 350
Asn Lys Thr Ala Phe Glu Lys Ala Lys Ala Lys Phe Leu Asn Lys Asp
        355                 360                 365
Arg Leu Glu Tyr Gly Tyr Ile Ser Thr Ser Leu Met Asn Val Ser Gln
    370                 375                 380
Phe Ala Gly Arg Pro Ile Ile Thr Lys Phe Lys Val Ala Lys Gly Ser
385                 390                 395                 400
Lys Ala Gly Tyr Ile Asp Pro Ile Ser Ala Phe Gln Gly Gln Leu Glu
                405                 410                 415
Met Leu Leu Pro Arg His Ser Thr Tyr His Ile Asp Asp Met Arg Leu
            420                 425                 430
Ser Ser Asp Gly Lys Gln Ile Ile Ile Thr Ala Thr Met Met Gly Thr
        435                 440                 445
```

Ala Ile Asn Pro Lys Glu Phe Arg Arg Lys Gln Arg Lys Arg Arg
    450                 455                 460

Leu Gln Ala Ala Ala Ser
465                 470

<210> SEQ ID NO 21
<211> LENGTH: 16
<212> TYPE: PRT
<213> ORGANISM: Artificial Sequence
<220> FEATURE:
<223> OTHER INFORMATION: Random basic amino acid sequence of C3Basic1

<400> SEQUENCE: 21

Lys Arg Arg Arg Arg Arg Pro Lys Lys Arg Arg Arg Ala Lys Arg Arg
1               5                   10                  15

<210> SEQ ID NO 22
<211> LENGTH: 48
<212> TYPE: DNA
<213> ORGANISM: Artificial Sequence
<220> FEATURE:
<223> OTHER INFORMATION: Oligonucleotide used in the cloning of a
      random basic amino acid sequence in C3Basic1

<400> SEQUENCE: 22
aagagaaggc gaagaagacc taagaagaga cgaagggcga agaggaga                48

<210> SEQ ID NO 23
<211> LENGTH: 48
<212> TYPE: DNA
<213> ORGANISM: Artificial Sequence
<220> FEATURE:
<223> OTHER INFORMATION: Oligonucleotide used in the cloning of a
      random basic amino acid sequence in C3Basic1

<400> SEQUENCE: 23
ttctcttccg cttcttctgg attcttctct gcttcccgct tctcctct                48

<210> SEQ ID NO 24
<211> LENGTH: 792
<212> TYPE: DNA
<213> ORGANISM: Artificial Sequence
<220> FEATURE:
<223> OTHER INFORMATION: Sequence of C3Basic1:  includes ADP-ribosyl
      transferase C3 (Clostridium botulinum) sequence and a sequence
      encoding a random basic amino acid sequence and a Histidine tag.
<220> FEATURE:
<221> NAME/KEY: CDS
<222> LOCATION: (1)..(792)
<223> OTHER INFORMATION:

<400> SEQUENCE: 24 gga tcc tct aga gtc gac ctg cag gca tgc aat gct tat tcc att aat    48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa    96
Gln Lys Ala Tyr Ser Asn Thr Tyr Gln Glu Phe Thr Asn Ile Asp Gln
                20                  25                  30 gca aaa gct tgg ggt aat gct cag tat aaa aag tat gga cta agc aaa   144
Ala Lys Ala Trp Gly Asn Ala Gln Tyr Lys Lys Tyr Gly Leu Ser Lys
            35                  40                  45 tca gaa aaa gaa gct ata gta tca tat act aaa agc gct agt gaa ata   192
Ser Glu Lys Glu Ala Ile Val Ser Tyr Thr Lys Ser Ala Ser Glu Ile
        50                  55                  60 aat gga aag cta aga caa aat aag gga gtt atc aat gga ttt cct tca   240
Asn Gly Lys Leu Arg Gln Asn Lys Gly Val Ile Asn Gly Phe Pro Ser
65                  70                  75                  80

```
aat tta ata aaa caa gtt gaa ctt tta gat aaa tct ttt aat aaa atg       288
Asn Leu Ile Lys Gln Val Glu Leu Leu Asp Lys Ser Phe Asn Lys Met
            85                  90                  95 aag acc cct gaa aat att atg tta ttt aga ggc gac gac cct gct tat       336
Lys Thr Pro Glu Asn Ile Met Leu Phe Arg Gly Asp Asp Pro Ala Tyr
        100                 105                 110 tta gga aca gaa ttt caa aac act ctt ctt aat tca aat ggt aca att       384
Leu Gly Thr Glu Phe Gln Asn Thr Leu Leu Asn Ser Asn Gly Thr Ile
            115                 120                 125 aat aaa acg gct ttt gaa aag gct aaa gct aag ttt tta aat aaa gat       432
Asn Lys Thr Ala Phe Glu Lys Ala Lys Ala Lys Phe Leu Asn Lys Asp
        130                 135                 140 aga ctt gaa tat gga tat att agt act tca tta atg aat gtt tct caa       480
Arg Leu Glu Tyr Gly Tyr Ile Ser Thr Ser Leu Met Asn Val Ser Gln
145                 150                 155                 160 ttt gca gga aga cca att att aca aaa ttt aaa gta gca aaa ggc tca       528
Phe Ala Gly Arg Pro Ile Ile Thr Lys Phe Lys Val Ala Lys Gly Ser
                165                 170                 175 aag gca gga tat att gac cct att agt gct ttt cag gga caa ctt gaa       576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg       624
Met Leu Leu Pro Arg His Ser Thr Tyr His Ile Asp Asp Met Arg Leu
        195                 200                 205 tct tct gat ggt aaa caa ata ata att aca gca aca atg atg ggc aca       672
Ser Ser Asp Gly Lys Gln Ile Ile Ile Thr Ala Thr Met Met Gly Thr
            210                 215                 220 gct atc aat cct aaa gaa ttc aag aga agg cga aga aga cct aag aag       720
Ala Ile Asn Pro Lys Glu Phe Lys Arg Arg Arg Arg Arg Pro Lys Lys
225                 230                 235                 240 aga cga agg gcg aag agg aga cac cac cac cac cac cac gtc gac tcg       768
Arg Arg Arg Ala Lys Arg Arg His His His His His His Val Asp Ser
                245                 250                 255 agc ggc cgc atc gtg act gac tga                                       792
Ser Gly Arg Ile Val Thr Asp
            260
```

<210> SEQ ID NO 25
<211> LENGTH: 263
<212> TYPE: PRT
<213> ORGANISM: Artificial Sequence
<220> FEATURE:
<223> OTHER INFORMATION: Sequence of C3Basic1: includes ADP-ribosyl
      transferase C3 (Clostridium botulinum) sequence and a sequence
      encoding a random basic amino acid sequence and a Histidine tag.

<400> SEQUENCE: 25

Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr

```
                    100                 105                 110
Leu Gly Thr Glu Phe Gln Asn Thr Leu Leu Asn Ser Asn Gly Thr Ile
            115                 120                 125
Asn Lys Thr Ala Phe Glu Lys Ala Lys Ala Lys Phe Leu Asn Lys Asp
        130                 135                 140
Arg Leu Glu Tyr Gly Tyr Ile Ser Thr Ser Leu Met Asn Val Ser Gln
145                 150                 155                 160
Phe Ala Gly Arg Pro Ile Ile Thr Lys Phe Lys Val Ala Lys Gly Ser
                165                 170                 175
Lys Ala Gly Tyr Ile Asp Pro Ile Ser Ala Phe Gln Gly Gln Leu Glu
            180                 185                 190
Met Leu Leu Pro Arg His Ser Thr Tyr His Ile Asp Asp Met Arg Leu
        195                 200                 205
Ser Ser Asp Gly Lys Gln Ile Ile Ile Thr Ala Thr Met Met Gly Thr
    210                 215                 220
Ala Ile Asn Pro Lys Glu Phe Lys Arg Arg Arg Arg Pro Lys Lys
225                 230                 235                 240
Arg Arg Arg Ala Lys Arg Arg His His His His His Val Asp Ser
                245                 250                 255
Ser Gly Arg Ile Val Thr Asp
            260

<210> SEQ ID NO 26
<211> LENGTH: 13
<212> TYPE: PRT
<213> ORGANISM: Artificial Sequence
<220> FEATURE:
<223> OTHER INFORMATION: Random amino acid sequence of C3Basic2

<400> SEQUENCE: 26

Lys Arg Arg Arg Arg Lys Lys Arg Arg Gln Arg Arg Arg
1               5                   10

<210> SEQ ID NO 27
<211> LENGTH: 39
<212> TYPE: DNA
<213> ORGANISM: Artificial Sequence
<220> FEATURE:
<223> OTHER INFORMATION: Oligonucleotide used in the cloning of a
      random basic amino acid sequence in C3Basic2

<400> SEQUENCE: 27
aagcgtcgac gtagaaagaa acgtagacag cgtagacgt                          39

<210> SEQ ID NO 28
<211> LENGTH: 39
<212> TYPE: DNA
<213> ORGANISM: Artificial Sequence
<220> FEATURE:
<223> OTHER INFORMATION: Oligonucleotide used in the cloning of a
      random basic amino acid sequence in C3Basic2

<400> SEQUENCE: 28
ttcgcagctg catctttctt tgcatctgtc gcatctgca                          39

<210> SEQ ID NO 29
<211> LENGTH: 783
<212> TYPE: DNA
<213> ORGANISM: Artificial Sequence
<220> FEATURE:
<223> OTHER INFORMATION: Sequence of C3Basic2: includes sequences
      from ADP-ribosyl-transferase C3 (Clostridium botulinum) and a
      sequence encoding a random basic amino acid sequence and a
```

```
                    histidine tag.
<220> FEATURE:
<221> NAME/KEY: CDS
<222> LOCATION: (1)..(783)
<223> OTHER INFORMATION:

<400> SEQUENCE: 29 gga tcc tct aga gtc gac ctg cag gca tgc aat gct tat tcc att aat      48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa      96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa     144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata     192
Ser Glu Lys Glu Ala Ile Val Ser Tyr Thr Lys Ser Ala Ser Glu Ile
50                  55                  60 aat gga aag cta aga caa aat aag gga gtt atc aat gga ttt cct tca     240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg     288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat     336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att     384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat     432
Asn Lys Thr Ala Phe Glu Lys Ala Lys Ala Lys Phe Leu Asn Lys Asp
130                 135                 140 aga ctt gaa tat gga tat att agt act tca tta atg aat gtt tct caa     480
Arg Leu Glu Tyr Gly Tyr Ile Ser Thr Ser Leu Met Asn Val Ser Gln
145                 150                 155                 160 ttt gca gga aga cca att att aca aaa ttt aaa gta gca aaa ggc tca     528
Phe Ala Gly Arg Pro Ile Ile Thr Lys Phe Lys Val Ala Lys Gly Ser
                165                 170                 175 aag gca gga tat att gac cct att agt gct ttt cag gga caa ctt gaa     576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg     624
Met Leu Leu Pro Arg His Ser Thr Tyr His Ile Asp Asp Met Arg Leu
        195                 200                 205 tct tct gat ggt aaa caa ata ata att aca gca aca atg atg ggc aca     672
Ser Ser Asp Gly Lys Gln Ile Ile Ile Thr Ala Thr Met Met Gly Thr
210                 215                 220 gct atc aat cct aaa gaa ttc aag cgt cga cgt aga aag aaa cgt aga     720
Ala Ile Asn Pro Lys Glu Phe Lys Arg Arg Arg Arg Lys Lys Arg Arg
225                 230                 235                 240 cag cgt aga cgt cac cac cac cac cac cac gtc gac tcg agc ggc cgc     768
Gln Arg Arg Arg His His His His His His Val Asp Ser Ser Gly Arg
                245                 250                 255 atc gtg act gac tga                                                  783
Ile Val Thr Asp
            260

<210> SEQ ID NO 30
<211> LENGTH: 260
<212> TYPE: PRT
```

<213> ORGANISM: Artificial Sequence
<220> FEATURE:
<223> OTHER INFORMATION: Sequence of C3Basic2: includes sequences
      from ADP-ribosyl-transferase C3 (Clostridium botulinum) and a
      sequence encoding a random basic amino acid sequence and a
      histidine tag.

<400> SEQUENCE: 30

```
Gly Ser Ser Arg Val Asp Leu Gln Ala Cys Asn Ala Tyr Ser Ile Asn
1               5                   10                  15
Gln Lys Ala Tyr Ser Asn Thr Tyr Gln Glu Phe Thr Asn Ile Asp Gln
            20                  25                  30
Ala Lys Ala Trp Gly Asn Ala Gln Tyr Lys Lys Tyr Gly Leu Ser Lys
        35                  40                  45
Ser Glu Lys Glu Ala Ile Val Ser Tyr Thr Lys Ser Ala Ser Glu Ile
    50                  55                  60
Asn Gly Lys Leu Arg Gln Asn Lys Gly Val Ile Asn Gly Phe Pro Ser
65                  70                  75                  80
Asn Leu Ile Lys Gln Val Glu Leu Leu Asp Lys Ser Phe Asn Lys Met
                85                  90                  95
Lys Thr Pro Glu Asn Ile Met Leu Phe Arg Gly Asp Asp Pro Ala Tyr
            100                 105                 110
Leu Gly Thr Glu Phe Gln Asn Thr Leu Leu Asn Ser Asn Gly Thr Ile
        115                 120                 125
Asn Lys Thr Ala Phe Glu Lys Ala Lys Ala Lys Phe Leu Asn Lys Asp
    130                 135                 140
Arg Leu Glu Tyr Gly Tyr Ile Ser Thr Ser Leu Met Asn Val Ser Gln
145                 150                 155                 160
Phe Ala Gly Arg Pro Ile Ile Thr Lys Phe Lys Val Ala Lys Gly Ser
                165                 170                 175
Lys Ala Gly Tyr Ile Asp Pro Ile Ser Ala Phe Gln Gly Gln Leu Glu
            180                 185                 190
Met Leu Leu Pro Arg His Ser Thr Tyr His Ile Asp Asp Met Arg Leu
        195                 200                 205
Ser Ser Asp Gly Lys Gln Ile Ile Ile Thr Ala Thr Met Met Gly Thr
    210                 215                 220
Ala Ile Asn Pro Lys Glu Phe Lys Arg Arg Arg Lys Lys Arg
225                 230                 235                 240
Gln Arg Arg Arg His His His His His Val Asp Ser Ser Gly Arg
                245                 250                 255
Ile Val Thr Asp
            260
```

<210> SEQ ID NO 31
<211> LENGTH: 9
<212> TYPE: PRT
<213> ORGANISM: Artificial Sequence
<220> FEATURE:
<223> OTHER INFORMATION: Reverse HIV-1 Tat amino acid sequence of
      C3Basic3

<400> SEQUENCE: 31

```
Arg Arg Lys Gln Arg Arg Lys Arg Arg
1               5
```

<210> SEQ ID NO 32
<211> LENGTH: 27
<212> TYPE: DNA
<213> ORGANISM: Artificial Sequence
<220> FEATURE:

-continued

<223> OTHER INFORMATION: Oligonucleotide used in the cloning of
      a reverse HIV Tat sequence in C3Basic3

<400> SEQUENCE: 32
agaaggaaac aaagaagaaa aagaaga                                       27

<210> SEQ ID NO 33
<211> LENGTH: 27
<212> TYPE: DNA
<213> ORGANISM: Artificial Sequence
<220> FEATURE:
<223> OTHER INFORMATION: Oligonucleotide used in the cloning of a
      reverse HIV Tat sequence in C3Basic3

<400> SEQUENCE: 33
tcttcctttg tttcttcttt ttcttct                                       27

<210> SEQ ID NO 34
<211> LENGTH: 771
<212> TYPE: DNA
<213> ORGANISM: Artificial Sequence
<220> FEATURE:
<223> OTHER INFORMATION: Sequence of C3Basic3: includes sequences from
      ADP-ribosyl tranferase C3 (C. botulinum) and a sequence encoding
      a reverse HIV-1 Tat amino acid sequence and a Histidine tag
<220> FEATURE:
<221> NAME/KEY: CDS
<222> LOCATION: (1)..(771)
<223> OTHER INFORMATION:

<400> SEQUENCE: 34

```
gga tcc tct aga gtc gac ctg cag gca tgc aat gct tat tcc att aat         48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa         96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa        144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata        192
Ser Glu Lys Glu Ala Ile Val Ser Tyr Thr Lys Ser Ala Ser Glu Ile
    50                  55                  60 aat gga aag cta aga caa aat aag gga gtt atc aat gga ttt cct tca        240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg        288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat        336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att        384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat        432
Asn Lys Thr Ala Phe Glu Lys Ala Lys Ala Lys Phe Leu Asn Lys Asp
    130                 135                 140 aga ctt gaa tat gga tat att agt act tca tta atg aat gtt tct caa        480
Arg Leu Glu Tyr Gly Tyr Ile Ser Thr Ser Leu Met Asn Val Ser Gln
145                 150                 155                 160 ttt gca gga aga cca att att aca aaa ttt aaa gta gca aaa ggc tca        528
Phe Ala Gly Arg Pro Ile Ile Thr Lys Phe Lys Val Ala Lys Gly Ser
                165                 170                 175
```

```
aag gca gga tat att gac cct att agt gct ttt cag gga caa ctt gaa      576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg      624
Met Leu Leu Pro Arg His Ser Thr Tyr His Ile Asp Asp Met Arg Leu
    195                 200                 205 tct tct gat ggt aaa caa ata ata att aca gca aca atg atg ggc aca      672
Ser Ser Asp Gly Lys Gln Ile Ile Ile Thr Ala Thr Met Met Gly Thr
210                 215                 220 gct atc aat cct aaa gaa ttc aga agg aaa caa aga aga aaa aga aga      720
Ala Ile Asn Pro Lys Glu Phe Arg Arg Lys Gln Arg Arg Lys Arg Arg
225                 230                 235                 240 cac cac cac cac cac cac gtc gac tcg agc ggc cgc atc gtg act gac      768
His His His His His His Val Asp Ser Ser Gly Arg Ile Val Thr Asp
                245                 250                 255 tga                                                                   771
```

<210> SEQ ID NO 35
<211> LENGTH: 256
<212> TYPE: PRT
<213> ORGANISM: Artificial Sequence
<220> FEATURE:
<223> OTHER INFORMATION: Sequence of C3Basic3: includes sequences from
    ADP-ribosyl tranferase C3 (C. botulinum) and a sequence encoding
    a reverse HIV-1 Tat amino acid sequence and a Histidine tag

<400> SEQUENCE: 35

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Arg Arg Lys Gln Arg Arg Lys Arg Arg
225                 230                 235                 240

His His His His His His Val Asp Ser Ser Gly Arg Ile Val Thr Asp
```

<210> SEQ ID NO 36
<211> LENGTH: 887
<212> TYPE: DNA
<213> ORGANISM: Artificial Sequence
<220> FEATURE:
<223> OTHER INFORMATION: Sequence of C3APLT: includes sequences from ADP-ribosyl transferase C3 (Clostridium botulinum) and a sequence encoding a proline rich region.
<220> FEATURE:
<221> NAME/KEY: CDS
<222> LOCATION: (1)..(747)
<223> OTHER INFORMATION:

<400> SEQUENCE: 36

```
gga tcc tct aga gtc gac ctg cag gca tgc aat gct tat tcc att aat      48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa      96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa     144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata     192
Ser Glu Lys Glu Ala Ile Val Ser Tyr Thr Lys Ser Ala Ser Glu Ile
50                  55                  60 aat gga aag cta aga caa aat aag gga gtt atc aat gga ttt cct tca     240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg     288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat     336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att     384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat     432
Asn Lys Thr Ala Phe Glu Lys Ala Lys Ala Lys Phe Leu Asn Lys Asp
130                 135                 140 aga ctt gaa tat gga tat att agt act tca tta atg aat gtt tct caa     480
Arg Leu Glu Tyr Gly Tyr Ile Ser Thr Ser Leu Met Asn Val Ser Gln
145                 150                 155                 160 ttt gca gga aga cca att att aca aaa ttt aaa gta gca aaa ggc tca     528
Phe Ala Gly Arg Pro Ile Ile Thr Lys Phe Lys Val Ala Lys Gly Ser
                165                 170                 175 aag gca gga tat att gac cct att agt gct ttt gca gga caa ctt gaa     576
Lys Ala Gly Tyr Ile Asp Pro Ile Ser Ala Phe Ala Gly Gln Leu Glu
            180                 185                 190 atg ttg ctt cct aga cat agt act tat cat ata gac gat atg aga ttg     624
Met Leu Leu Pro Arg His Ser Thr Tyr His Ile Asp Asp Met Arg Leu
        195                 200                 205 tct tct gat ggt aaa caa ata ata att aca gca aca atg atg ggc aca     672
Ser Ser Asp Gly Lys Gln Ile Ile Ile Thr Ala Thr Met Met Gly Thr
210                 215                 220 gct atc aat cct aaa gaa ttc gtg atg aat ccc gca aac gcg caa ggc     720
Ala Ile Asn Pro Lys Glu Phe Val Met Asn Pro Ala Asn Ala Gln Gly
225                 230                 235                 240 aga cat aca ccc ggt acc aga ctc tag agctagagaa ggagtttcac            767
Arg His Thr Pro Gly Thr Arg Leu
```

-continued

```
                                   245 ttcaatcgct acttgacccg tcggcgaagg atcgagatcg cccacgccct gtgcctcacg      827 gagcgccaga taaagatttg gttccagaat cggcgcatga agtggaagaa ggagaactga      887
```

<210> SEQ ID NO 37
<211> LENGTH: 248
<212> TYPE: PRT
<213> ORGANISM: Artificial Sequence
<220> FEATURE:
<223> OTHER INFORMATION: Sequence of C3APLT:   includes sequences from
      ADP-ribosyl transferase C3 (Clostridium botulinum) and a
      sequence encoding a proline rich region.

<400> SEQUENCE: 37

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175

Lys Ala Gly Tyr Ile Asp Pro Ile Ser Ala Phe Ala Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Val Met Asn Pro Ala Asn Ala Gln Gly
225                 230                 235                 240

Arg His Thr Pro Gly Thr Arg Leu
                245
```

<210> SEQ ID NO 38
<211> LENGTH: 37
<212> TYPE: DNA
<213> ORGANISM: Artificial Sequence
<220> FEATURE:
<223> OTHER INFORMATION: Oligonucleotide used in the cloning of C3APLT
      in pET vector

<400> SEQUENCE: 38

```
ggatctggtt ccgcgtcata tgtctagagt cgacctg                               37
```

```
<210> SEQ ID NO 39
<211> LENGTH: 32
<212> TYPE: DNA
<213> ORGANISM: Artificial Sequence
<220> FEATURE:
<223> OTHER INFORMATION: Oligonucleotide used in the cloning of C3APLT
      in pET vector

<400> SEQUENCE: 39
cgcggatcca ttagttctcc ttcttccact tc                                    32

<210> SEQ ID NO 40
<211> LENGTH: 24
<212> TYPE: DNA
<213> ORGANISM: Artificial Sequence
<220> FEATURE:
<223> OTHER INFORMATION: Oligonucleotide used in the sequencing of
      C3APLT

<400> SEQUENCE: 40
aaattaatac gactcactat aggg                                             24

<210> SEQ ID NO 41
<211> LENGTH: 19
<212> TYPE: DNA
<213> ORGANISM: Artificial Sequence
<220> FEATURE:
<223> OTHER INFORMATION: Oligonucleotide used in the sequencing of
      C3APLT

<400> SEQUENCE: 41
gctagttatt gctcagcgg                                                   19

<210> SEQ ID NO 42
<211> LENGTH: 888
<212> TYPE: DNA
<213> ORGANISM: Artificial Sequence
<220> FEATURE:
<223> OTHER INFORMATION: Sequence of C3APLT in a pET vector:
      includes sequences from ADP-ribosyl transferase C3
      (Clostridium botulinum) and a sequence encoding a proline rich
      region.
<220> FEATURE:
<221> NAME/KEY: CDS
<222> LOCATION: (1)..(744)
<223> OTHER INFORMATION:

<400> SEQUENCE: 42 atg tct aga gtc gca ctg cag gca tgc aat gct tat tcc att aat caa      48
Met Ser Arg Val Ala Leu Gln Ala Cys Asn Ala Tyr Ser Ile Asn Gln
1               5                  10                  15 aag gct tat tca aat act tac cag gag ttt act aat att gat caa gca      96
Lys Ala Tyr Ser Asn Thr Tyr Gln Glu Phe Thr Asn Ile Asp Gln Ala
            20                  25                  30 aaa gct tgg ggt aat gct cag tat aaa aag tat gga cta agc aaa tca     144
Lys Ala Trp Gly Asn Ala Gln Tyr Lys Lys Tyr Gly Leu Ser Lys Ser
        35                  40                  45 gaa aaa gaa gct ata gta tca tat act aaa agc gct agt gaa ata aat     192
Glu Lys Glu Ala Ile Val Ser Tyr Thr Lys Ser Ala Ser Glu Ile Asn
    50                  55                  60 gga aag cta aga caa aat aag gga gtt atc aat gga ttt cct tca aat     240
Gly Lys Leu Arg Gln Asn Lys Gly Val Ile Asn Gly Phe Pro Ser Asn
65                  70                  75                  80 tta ata aaa caa gtt gaa ctt tta gat aaa tct ttt aat aaa atg aag     288
Leu Ile Lys Gln Val Glu Leu Leu Asp Lys Ser Phe Asn Lys Met Lys
                85                  90                  95 acc cct gaa aat att atg tta ttt aga ggc gac gac cct gct tat tta     336
```

```
Thr Pro Glu Asn Ile Met Leu Phe Arg Gly Asp Asp Pro Ala Tyr Leu
              100                 105                 110 gga aca gaa ttt caa aac act ctt ctt aat tca aat ggt aca att aat      384
Gly Thr Glu Phe Gln Asn Thr Leu Leu Asn Ser Asn Gly Thr Ile Asn
            115                 120                 125 aaa acg gct ttt gaa aag gct aaa gct aag ttt tta aat aaa gat aga      432
Lys Thr Ala Phe Glu Lys Ala Lys Ala Lys Phe Leu Asn Lys Asp Arg
        130                 135                 140 ctt gaa tat gga tat att agt act tca tta atg aat gtt tct caa ttt      480
Leu Glu Tyr Gly Tyr Ile Ser Thr Ser Leu Met Asn Val Ser Gln Phe
145                 150                 155                 160 gca gga aga cca att att aca aaa ttt aaa gta gca aaa ggc tca aag      528
Ala Gly Arg Pro Ile Ile Thr Lys Phe Lys Val Ala Lys Gly Ser Lys
                165                 170                 175 gca gga tat att gac cct att agt gct ttt gca gga caa ctt gaa atg      576
Ala Gly Tyr Ile Asp Pro Ile Ser Ala Phe Ala Gly Gln Leu Glu Met
            180                 185                 190 ttg ctt cct aga cat agt act tat cat ata gac gat atg aga ttg tct      624
Leu Leu Pro Arg His Ser Thr Tyr His Ile Asp Asp Met Arg Leu Ser
        195                 200                 205 tct gat ggt aaa caa ata ata att aca gca aca atg atg ggc aca gct      672
Ser Asp Gly Lys Gln Ile Ile Ile Thr Ala Thr Met Met Gly Thr Ala
    210                 215                 220 atc aat cct aaa gaa ttc gtg atg aat ccc gca aac gcg caa ggc aga      720
Ile Asn Pro Lys Glu Phe Val Met Asn Pro Ala Asn Ala Gln Gly Arg
225                 230                 235                 240 cat aca ccc ggt acc aga ctc tag agctagagaa ggagtttcac ttcaatcgct    774
His Thr Pro Gly Thr Arg Leu
                245 acttgacccg tcggcgaagg atcgagatcg cccacgccct gtgcctcacg gagcgccaga   834 taaagatttg gttccagaat cggcgcatga agtggaagaa ggaggactaa ctga         888

<210> SEQ ID NO 43
<211> LENGTH: 247
<212> TYPE: PRT
<213> ORGANISM: Artificial Sequence
<220> FEATURE:
<223> OTHER INFORMATION: Sequence of C3APLT in a pET vector: includes
      sequences from ADP-ribosyl transferase C3 (Clostridium botulinum)
      and a sequence encoding a proline rich region.

<400> SEQUENCE: 43

Met Ser Arg Val Ala Leu Gln Ala Cys Asn Ala Tyr Ser Ile Asn Gln
1               5                   10                  15

Lys Ala Tyr Ser Asn Thr Tyr Gln Glu Phe Thr Asn Ile Asp Gln Ala
            20                  25                  30

Lys Ala Trp Gly Asn Ala Gln Tyr Lys Lys Tyr Gly Leu Ser Lys Ser
        35                  40                  45

Glu Lys Glu Ala Ile Val Ser Tyr Thr Lys Ser Ala Ser Glu Ile Asn
    50                  55                  60

Gly Lys Leu Arg Gln Asn Lys Gly Val Ile Asn Gly Phe Pro Ser Asn
65                  70                  75                  80

Leu Ile Lys Gln Val Glu Leu Leu Asp Lys Ser Phe Asn Lys Met Lys
                85                  90                  95

Thr Pro Glu Asn Ile Met Leu Phe Arg Gly Asp Asp Pro Ala Tyr Leu
            100                 105                 110

Gly Thr Glu Phe Gln Asn Thr Leu Leu Asn Ser Asn Gly Thr Ile Asn
        115                 120                 125

Lys Thr Ala Phe Glu Lys Ala Lys Ala Lys Phe Leu Asn Lys Asp Arg
```

```
                    130                 135                 140
Leu Glu Tyr Gly Tyr Ile Ser Thr Ser Leu Met Asn Val Ser Gln Phe
145                 150                 155                 160

Ala Gly Arg Pro Ile Ile Thr Lys Phe Lys Val Ala Lys Gly Ser Lys
                165                 170                 175

Ala Gly Tyr Ile Asp Pro Ile Ser Ala Phe Ala Gly Gln Leu Glu Met
            180                 185                 190

Leu Leu Pro Arg His Ser Thr Tyr His Ile Asp Asp Met Arg Leu Ser
                195                 200                 205

Ser Asp Gly Lys Gln Ile Ile Ile Thr Ala Thr Met Met Gly Thr Ala
            210                 215                 220

Ile Asn Pro Lys Glu Phe Val Met Asn Pro Ala Asn Ala Gln Gly Arg
225                 230                 235                 240

His Thr Pro Gly Thr Arg Leu
                245

<210> SEQ ID NO 44
<211> LENGTH: 64
<212> TYPE: PRT
<213> ORGANISM: Artificial Sequence
<220> FEATURE:
<223> OTHER INFORMATION: Amino acid sequence of Antennapedia from
      C3APL

<400> SEQUENCE: 44

Val Met Glu Ser Arg Lys Arg Ala Arg Gln Thr Tyr Thr Arg Tyr Gln
1               5                   10                  15

Thr Leu Glu Leu Glu Lys Glu Phe His Phe Asn Arg Tyr Leu Thr Arg
                20                  25                  30

Arg Arg Arg Ile Glu Ile Ala His Ala Leu Cys Leu Thr Glu Arg Gln
            35                  40                  45

Ile Lys Ile Trp Phe Gln Asn Arg Arg Met Lys Trp Lys Lys Glu Asn
        50                  55                  60

<210> SEQ ID NO 45
<211> LENGTH: 19
<212> TYPE: PRT
<213> ORGANISM: Artificial Sequence
<220> FEATURE:
<223> OTHER INFORMATION: Amino acid sequence of Antennapedia from
      C3APS

<400> SEQUENCE: 45

Arg Gln Ile Lys Ile Trp Phe Gln Asn Arg Arg Met Lys Trp Lys Lys
1               5                   10                  15

Val Asp Ser

<210> SEQ ID NO 46
<211> LENGTH: 60
<212> TYPE: PRT
<213> ORGANISM: Artificial Sequence
<220> FEATURE:
<223> OTHER INFORMATION: Amino acid sequence of HIV-1 Tat from C3-TL

<400> SEQUENCE: 46

Lys His Pro Gly Ser Gln Pro Lys Thr Ala Cys Thr Asn Cys Tyr Cys
1               5                   10                  15

Lys Lys Cys Cys Phe His Cys Gln Val Cys Phe Ile Thr Lys Ala Leu
                20                  25                  30

Gly Ile Ser Tyr Gly Arg Lys Arg Arg Gln Arg Arg Ala His Gln
            35                  40                  45
```

```
Asn Ser Gln Thr His Gln Ala Ser Leu Ser Lys Gln
    50                  55                  60

<210> SEQ ID NO 47
<211> LENGTH: 20
<212> TYPE: PRT
<213> ORGANISM: Artificial Sequence
<220> FEATURE:
<223> OTHER INFORMATION: Amino acid sequence of HIV-1 Tat from C3-TS

<400> SEQUENCE: 47

Tyr Gly Ala Lys Lys Arg Arg Gln Arg Arg Val Asp Ser Ser Gly
1               5                   10                  15

Pro His Arg Asp
            20

<210> SEQ ID NO 48
<211> LENGTH: 17
<212> TYPE: PRT
<213> ORGANISM: Artificial Sequence
<220> FEATURE:
<223> OTHER INFORMATION: Amino acid sequence of the proline rich
      region of C3APLT

<400> SEQUENCE: 48

Val Met Asn Pro Ala Asn Ala Gln Gly Arg His Thr Pro Gly Thr Arg
1               5                   10                  15

Leu

<210> SEQ ID NO 49
<211> LENGTH: 10
<212> TYPE: PRT
<213> ORGANISM: Artificial Sequence
<220> FEATURE:
<223> OTHER INFORMATION: Amino acid sequence fused to C3 protein to
      created C3 Tat-short

<400> SEQUENCE: 49

Tyr Gly Arg Lys Arg Arg Gln Arg Arg Arg
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Reverse sequence of Tat amino acids fused to
      C3 protein to created C3Basic3

<400> SEQUENCE: 50

Arg Arg Gln Arg Arg Lys Lys Arg
1               5

<210> SEQ ID NO 51
<211> LENGTH: 12
<212> TYPE: PRT
<213> ORGANISM: Artificial Sequence
<220> FEATURE:
<223> OTHER INFORMATION: transport peptide rich in Proline

<400> SEQUENCE: 51

Ala Ala Val Leu Leu Pro Val Leu Leu Ala Ala Pro
1               5                   10

<210> SEQ ID NO 52
<211> LENGTH: 24
```

```
<212> TYPE: PRT
<213> ORGANISM: Artificial Sequence
<220> FEATURE:
<223> OTHER INFORMATION: Sperm fertiline alpha peptide

<400> SEQUENCE: 52

His Pro Ile Gln Ile Ala Ala Phe Leu Ala Arg Ile Pro Pro Ile Ser
  1               5                  10                  15

Ser Ile Gly Thr Cys Ile Leu Lys
            20

<210> SEQ ID NO 53
<211> LENGTH: 9
<212> TYPE: PRT
<213> ORGANISM: Artificial Sequence
<220> FEATURE:
<223> OTHER INFORMATION: Amino acid sequence from the C3Basic3

<400> SEQUENCE: 53

Arg Arg Lys Gln Arg Arg Lys Arg Arg
  1               5

<210> SEQ ID NO 54
<211> LENGTH: 744
<212> TYPE: DNA
<213> ORGANISM: Artificial Sequence
<220> FEATURE:
<223> OTHER INFORMATION: Sequence of C3-07Q189A

<400> SEQUENCE: 54
atgtctagag tcgacctgca ggcatgcaat gcttattcca ttaatcaaaa ggcttattca      60
aatacttacc aggagtttac taatattgat caagcaaaag cttggggtaa tgctcagtat     120
aaaaagtatg gactaagcaa atcagaaaaa gaagctatag tatcatatac taaaagcgct     180
agtgaaataa atggaaagct aagacaaaat aagggagtta tcaatggatt tccttcaaat     240
ttaataaaac aagttgaact tttagataaa tcttttaata aaatgaagac ccctgaaaat     300
attatgttat ttagaggcga cgaccctgct tatttaggaa cagaatttca aaacactctt     360
cttaattcaa atggtacaat taataaaacg cttttgaaa aggctaaagc taagttttta     420
aataaagata gacttgaata tggatatatt agtacttcat taatgaatgt ttctcaattt     480
gcaggaagac caattattac aaaatttaaa gtagcaaaag gctcaaaggc aggatatatt     540
gaccctatta gtgcttttgc aggagcactt gaaatgttgc ttcctagaca tagtacttat     600
catatagacg atatgagatt gtcttctgat ggtaaacaaa taataattac agcaacaatg     660
atgggcacag ctatcaatcc taaagaattc gtgatgaatc ccgcaaacgc gcaaggcaga     720
catacacccg gtaccagact ctag                                            744

<210> SEQ ID NO 55
<211> LENGTH: 247
<212> TYPE: PRT
<213> ORGANISM: Artificial Sequence
<220> FEATURE:
<223> OTHER INFORMATION: Amino acid sequence of C3-07Q189A

<400> SEQUENCE: 55

Met Ser Arg Val Asp Leu Gln Ala Cys Asn Ala Tyr Ser Ile Asn Gln
  1               5                  10                  15

Lys Ala Tyr Ser Asn Thr Tyr Gln Glu Phe Thr Asn Ile Asp Gln Ala
             20                  25                  30

Lys Ala Trp Gly Asn Ala Gln Tyr Lys Lys Tyr Gly Leu Ser Lys Ser
         35                  40                  45
```

```
Glu Lys Glu Ala Ile Val Ser Tyr Thr Lys Ser Ala Ser Glu Ile Asn
    50              55                  60
Gly Lys Leu Arg Gln Asn Lys Gly Val Ile Asn Gly Phe Pro Ser Asn
65              70                  75                  80
Leu Ile Lys Gln Val Glu Leu Leu Asp Lys Ser Phe Asn Lys Met Lys
                85                  90                  95
Thr Pro Glu Asn Ile Met Leu Phe Arg Gly Asp Asp Pro Ala Tyr Leu
            100             105                 110
Gly Thr Glu Phe Gln Asn Thr Leu Leu Asn Ser Asn Gly Thr Ile Asn
            115             120                 125
Lys Thr Ala Phe Glu Lys Ala Lys Ala Lys Phe Leu Asn Lys Asp Arg
    130             135             140
Leu Glu Tyr Gly Tyr Ile Ser Thr Ser Leu Met Asn Val Ser Gln Phe
145             150                 155                 160
Ala Gly Arg Pro Ile Ile Thr Gln Phe Lys Val Ala Lys Gly Ser Lys
            165             170                 175
Ala Gly Tyr Ile Asp Pro Ile Ser Ala Phe Gln Gly Ala Leu Glu Met
            180             185                 190
Leu Leu Pro Arg His Ser Thr Tyr His Ile Asp Asp Met Arg Leu Ser
        195             200                 205
Ser Asp Gly Lys Gln Ile Ile Ile Thr Ala Thr Met Met Gly Thr Ala
    210             215                 220
Ile Asn Pro Lys Glu Phe Val Met Asn Pro Ala Asn Ala Gln Gly Arg
225             230                 235                 240
His Thr Pro Gly Thr Arg Leu
            245
```